US012733846B2

(12) United States Patent
LaTour et al.

(10) Patent No.: US 12,733,846 B2
(45) Date of Patent: Sep. 15, 2026

(54) ANALYTE SENSORS WITH METAL-CONTAINING REDOX MEDIATORS AND METHODS OF USING THE SAME

(71) Applicant: ABBOTT DIABETES CARE INC., Alameda, CA (US)

(72) Inventors: John V. LaTour, Alameda, CA (US); Kevin P. Wallis, Castro Valley, CA (US); Phu Le, Dublin, CA (US); Udo Hoss, San Ramon, CA (US)

(73) Assignee: ABBOTT DIABETES CARE INC., Alameda, CA (US)

(*) Notice: Subject to any disclaimer, the term of this patent is extended or adjusted under 35 U.S.C. 154(b) by 913 days.

(21) Appl. No.: 17/567,589

(22) Filed: Jan. 3, 2022

(65) Prior Publication Data

US 2022/0202326 A1 Jun. 30, 2022

Related U.S. Application Data

(60) Provisional application No. 63/188,765, filed on May 14, 2021, provisional application No. 63/132,901, filed on Dec. 31, 2020.

(51) Int. Cl.

| | |
|---|---|
| ***A61B 5/1486*** | (2006.01) |
| ***A61B 5/145*** | (2006.01) |
| ***C07F 15/00*** | (2006.01) |

(52) U.S. Cl.

CPC ...... *A61B 5/14865* (2013.01); *A61B 5/14532* (2013.01); *C07F 15/0026* (2013.01)

(58) Field of Classification Search

None

See application file for complete search history.

(56) References Cited

U.S. PATENT DOCUMENTS

| | | | | |
|---|---|---|---|---|
| 5,695,947 | A * | 12/1997 | Guo | C12Q 1/004 435/11 |
| 6,605,200 | B1 | 8/2003 | Mao et al. | |
| 6,605,201 | B1 | 8/2003 | Mao et al. | |
| 8,268,143 | B2 | 9/2012 | Liu et al. | |
| 8,444,834 | B2 | 5/2013 | Liu et al. | |
| 2004/0138543 | A1* | 7/2004 | Russell | A61B 5/150358 600/345 |
| 2005/0049313 | A1 | 3/2005 | Nishizawa et al. | |
| 2006/0118415 | A1* | 6/2006 | Say | A61B 5/14735 204/403.01 |

(Continued)

FOREIGN PATENT DOCUMENTS

| | | | |
|---|---|---|---|
| CN | 112 795 243 | A | 5/2021 |
| CN | 202280008621.7 | | 6/2026 |

(Continued)

OTHER PUBLICATIONS

JP, 2023-540061 Office Action, Dec. 16, 2025.

(Continued)

*Primary Examiner* — J. Christopher Ball

(74) *Attorney, Agent, or Firm* — ONE LLP

(57) ABSTRACT

The present disclosure provides redox mediators having two tridentate ligands and analyte sensors comprising such redox mediators. The present disclosure further provides methods of using such analyte sensors for detecting one or more analytes present in a biological sample of a subject.

34 Claims, 51 Drawing Sheets

(56) References Cited

U.S. PATENT DOCUMENTS

| | | | | |
|---|---|---|---|---|
| 2007/0193019 | A1* | 8/2007 | Feldman | C12Q 1/001 73/514.32 |
| 2008/0319294 | A1* | 12/2008 | Taub | A61B 5/4356 600/365 |
| 2010/0230285 | A1 | 9/2010 | Hoss et al. | |
| 2011/0094882 | A1 | 4/2011 | Macfie et al. | |
| 2013/0150691 | A1 | 6/2013 | Pace et al. | |
| 2014/0171771 | A1 | 6/2014 | Feldman et al. | |
| 2016/0331283 | A1 | 11/2016 | Rao et al. | |
| 2018/0235520 | A1 | 8/2018 | Rao et al. | |
| 2019/0274598 | A1 | 9/2019 | Scott et al. | |
| 2020/0196919 | A1 | 6/2020 | Rao et al. | |

FOREIGN PATENT DOCUMENTS

| | | | |
|---|---|---|---|
| JP | 9-159643 | S | 6/1997 |
| JP | 2011-13072 | A | 1/2011 |
| JP | 2023-540061 | | 6/2026 |
| WO | WO 00/202626 | A1 | 4/2000 |
| WO | WO 2010/030912 | A1 | 3/2010 |
| WO | WO 2018/136898 | A1 | 7/2018 |
| WO | WO 2019/236850 | A1 | 12/2019 |
| WO | WO 2019/236859 | A1 | 12/2019 |
| WO | WO 2019/236876 | A1 | 12/2019 |

OTHER PUBLICATIONS

Kohmoto et al., "Controlling the Adsorption of Ruthenium Complexes on Carbon Surfaces through Noncovalent Bonding with Pyrene Anchors: An Electrochemical Study," Langmuir, 32(17), 4141-4152 (2016), XP055336094.

International Search Report corresponding to PCT/US2022/011026 dated Apr. 25, 2022.

Nikitina et al., "Bi -enzyme biosensor based on NAD+- and glutathione-dependent recombinant formaldehyde dehydrogenase and diaphorase for formaldehyde assay," Sensors and Actuators B: Chemical, 125(1), 1-9 (2007) XP022143803.

* cited by examiner

6000

Group 3=

ANALYTE SENSORS WITH METAL-CONTAINING REDOX MEDIATORS AND METHODS OF USING THE SAME

CROSS-REFERENCE TO RELATED APPLICATIONS

This application claims priority to U.S. Provisional Application No. 63/132,901, filed Dec. 31, 2020, and U.S. Provisional Application No. 63/188,765, filed May 14, 2021, the contents of each of which are incorporated herein by reference in their entireties, and to each of which priority is claimed.

FIELD

The subject matter described herein relates to analyte sensors that include one or more redox mediators and methods of using the same.

BACKGROUND

The detection of various analytes within an individual can sometimes be vital for monitoring the condition of their health as deviations from normal analyte levels can be indicative of a physiological condition. For example, monitoring glucose levels can enable people suffering from diabetes to take appropriate corrective action including administration of medicine or consumption of particular food or beverage products to avoid significant physiological harm. Other analytes can be desirable to monitor for other physiological conditions. In certain instances, it can be desirable to monitor more than one analyte to monitor multiple physiological conditions, particularly if a person is suffering from comorbid conditions that result in simultaneous dysregulation of two or more analytes in combination with one another.

Many analytes represent intriguing targets for physiological analyses, provided that a suitable detection chemistry can be identified. To this end, enzyme-based amperometric sensors configured for assaying glucose continuously in vivo have been developed and refined over recent years to aid in monitoring the health of diabetic individuals. Other analytes commonly subject to concurrent dysregulation with glucose in diabetic individuals include, for example, lactate, oxygen, A1c, ketones, and the like. It can also be desirable to monitor these and other analytes independent of glucose dysregulation as well. Analyte sensors configured for detecting analytes other than glucose in vivo are known but are considerably less refined at present. For example, poor sensitivity for low-abundance analytes can be especially problematic.

Analyte monitoring in an individual can take place periodically or continuously over a period of time. Periodic analyte monitoring can take place by withdrawing a sample of bodily fluid, such as blood or urine, at set time intervals and analyzing ex vivo. Periodic, ex vivo analyte monitoring can be sufficient to determine the physiological condition of many individuals. However, ex vivo analyte monitoring can be inconvenient or painful in some instances. Moreover, there is no way to recover lost data if an analyte measurement is not obtained at an appropriate time. Continuous analyte monitoring can be conducted using one or more sensors that remain at least partially implanted within a tissue of an individual, such as dermally, subcutaneously or intravenously, so that analyses may be conducted in vivo. Implanted sensors can collect analyte data on-demand, at a set schedule, or continuously, depending on an individual's particular health needs and/or previously measured analyte levels. Analyte monitoring with an in vivo implanted sensor can be a more desirable approach for individuals having severe analyte dysregulation and/or rapidly fluctuating analyte levels, although it can also be beneficial for other individuals as well. Since implanted analyte sensors often remain within a tissue of an individual for an extended period of time, it can be highly desirable for such analyte sensors to be made from stable materials exhibiting a high degree of biocompatibility.

Analyte sensors such as electrochemical sensors used to measure various analytes in fluids can include two or more electrodes, e.g., including at least one working (or measuring) electrode and one reference electrode. The electrodes are connected through a circuit, such as a potentiostat. Upon passage of a current through the working electrode, a redox enzyme is electrooxidized or electroreduced. The redox enzyme is specific to the analyte to be detected, or to a product of the analyte. The turnover rate of the enzyme is typically related to the concentration of the analyte itself, or to its product, in a fluid. Electrooxidation or electroreduction of the enzyme can be facilitated by the presence of a redox mediator. The redox mediator assists in the electrical communication between the working electrode and the enzyme. Analyte sensors can be made, for example, by coating an electrode with a film that includes a redox mediator and an enzyme where the enzyme is catalytically specific to the desired analyte, or its product. When the substrate of the enzyme is electrooxidized, the redox mediator transports electrons from the substrate-reduced enzyme to the electrode; and when the substrate is electroreduced, the redox mediator transports electrons from the electrode to the substrate-oxidized enzyme.

Various redox mediators, such as monomeric ferrocenes, quinoid compounds including quinines (e.g., benzoquinones), nickel cyclamates, and ruthenium amines have been explored. However, these compounds often show insufficient stability and, therefore, contribute to limiting the lifetime of a sensor. As such, there is a need in the field to develop analyte sensors that not only have the desired electrochemical properties (e.g., enable rapid electron exchange), but also exhibit chemical, light, thermal, and/or pH stability.

SUMMARY

The purpose and advantages of the disclosed subject matter will be set forth in and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

To achieve these and other advantages and in accordance with the purpose of the disclosed subject matter, as embodied and broadly described, the disclosed subject matter includes an analyte sensor, which includes a sensor tail including at least a first working electrode and a first active area disposed upon a surface of the first working electrode and responsive to a first analyte, wherein the first active area includes a first polymer, a first redox mediator covalently bonded to the first polymer, and at least one enzyme responsive to the first analyte covalently bonded to the first polymer. In certain embodiments, the first redox mediator has a structure of:

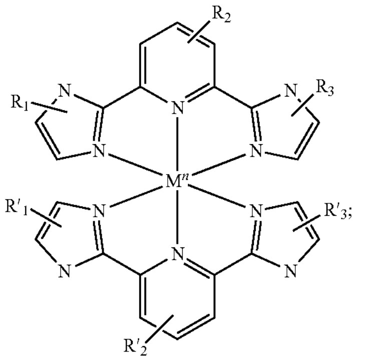

wherein M is iron, ruthenium, osmium, cobalt, or vanadium, wherein n is I, II, II, IV or V, wherein $R_1$, $R_3$, $R'_1$, and $R'_3$ are independently selected from H, an alkylamido group, alkylamino group, an alkoxy or an alkyl group, wherein $R_2$ and $R'_2$ are independently selected from H, an electron donating group or a linking group. In certain embodiments, the linking group covalently bonds the first redox mediator to the first polymer. In certain embodiments, the analyte sensor also includes a mass transport limiting membrane permeable to the first analyte that overcoats at least the first active area.

In certain embodiments of the present disclosure, the at least one enzyme includes an enzyme system including multiple enzymes that are collectively responsive to the first analyte.

In certain embodiments, the first analyte includes glucose.

In certain embodiments, the mass transport limiting membrane of the analyte sensors disclosed herein includes a membrane polymer crosslinked with a branched crosslinker including two or more or three or more crosslinkable groups. In certain embodiments, the mass transport limiting membrane comprises a polyvinylpyridine-based polymer, a polyvinylimidazole, a polyacrylate, a polyurethane, a polyether urethane, a silicone or a combination thereof. In certain embodiments, the mass transport limiting membrane includes a polyvinylpyridine or a polyvinylimidazole. In certain embodiments, wherein the mass transport limiting membrane includes a copolymer of vinylpyridine and styrene. In certain embodiments, the branched crosslinker includes polyethylene glycol diglycidyl ether or polyethylene glycol tetraglycidyl ether.

In certain embodiments, the M of a redox mediator of the analyte sensors disclosed herein is osmium (Os).

In certain embodiments, when the redox mediator includes a linking group, the linking group includes an amide linkage.

In certain embodiments, the analyte sensor disclosure herein further includes a second working electrode, and a second active area disposed upon a surface of the second working electrode and responsive to a second analyte differing from the first analyte, wherein the second active area including a second polymer, a second redox mediator differing from the first redox mediator covalently bonded to the second polymer, and at least one enzyme responsive to the second analyte covalently bonded to the second polymer, wherein a second portion of the mass transport limiting membrane overcoats the second active area.

In certain embodiments, the at least one enzyme responsive to the second analyte includes an enzyme system comprising multiple enzymes that are collectively responsive to the second analyte.

In certain embodiments, the second analyte includes a ketone.

In certain embodiments, the first active area of the analyte sensor disclosure herein is responsive to the first analyte at a potential above an oxidation-reduction potential of the first redox mediator and below about −80 mV relative to an Ag/AgCl reference.

Certain other aspects of the present disclosure include a method including providing an analyte sensor including (a) a sensor tail including at least a first working electrode, (b) sensor tail including at least a first working electrode responsive to the first analyte, wherein the first active area includes a first polymer, a first redox mediator covalently bonded to the first polymer, and at least one enzyme responsive to the first analyte covalently bonded to the first polymer, wherein the first redox mediator has a structure of:

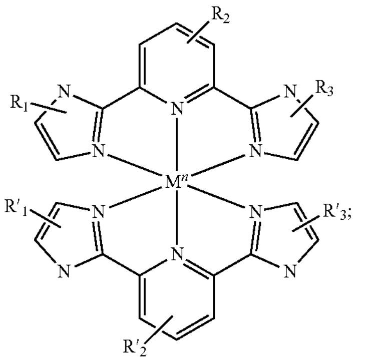

wherein M is iron, ruthenium, osmium, cobalt, or vanadium, wherein n is I, II, III, IV, or V, wherein $R_1$, $R_3$, $R'_1$, and $R'_3$ are independently selected from H, an alkylamido group, alkylamino group, an alkoxy or an alkyl group, wherein $R_2$ and $R'_2$ are independently selected from H, an electron donating group or a linking group, wherein the linking group covalently bonds the first redox mediator to the first polymer; and (c) a mass transport limiting membrane permeable to the first analyte that overcoats at least the first active area, wherein the method further includes applying a potential to the first working electrode, obtaining a first signal at or above an oxidation-reduction potential of the first active area, the first signal being proportional to a concentration of a first analyte in a fluid contacting the first active area, and correlating the first signal to the concentration of the first analyte in the fluid.

In certain embodiments, the at least one enzyme includes an enzyme system including multiple enzymes that are collectively responsive to the first analyte.

In certain embodiments, the first analyte includes glucose.

In certain embodiments, the transport limiting membrane of the analyte sensors used in the methods disclosure herein includes a membrane polymer crosslinked with a branched crosslinker including two or more or three or more crosslinkable groups. In certain embodiments, the mass transport limiting membrane comprises a polyvinylpyridine-based polymer, a polyvinylimidazole, a polyacrylate, a polyurethane, a polyether urethane, a silicone or a combination thereof. In certain embodiments, the mass transport limiting membrane includes a polyvinylpyridine or a polyvinylimidazole. In certain embodiments, the mass transport limiting membrane includes a copolymer of vinylpyridine and styrene. In certain embodiments, the branched crosslinker includes polyethylene glycol diglycidyl ether or polyethylene glycol tetraglycidyl ether.

In certain embodiments, the potential of the first active area of the analyte sensor used in the methods disclosed herein is above the oxidation-reduction potential of the first redox mediator and below about −80 mV relative to an Ag/AgCl reference.

In certain embodiments, the analyte sensor used in the methods disclosed herein includes (d) a second working electrode, and a second active area disposed upon a surface of the second working electrode and responsive to a second analyte differing from the first analyte, wherein the second active area including a second polymer, a second redox mediator differing from the first redox mediator covalently bonded to the second polymer, and at least one enzyme responsive to the second analyte covalently bonded to the second polymer, wherein a second portion of the mass transport limiting membrane overcoats the second active area.

In certain embodiments, the at least one enzyme responsive to the second analyte includes an enzyme system including multiple enzymes that are collectively responsive to the second analyte.

In certain embodiments, the second analyte includes a ketone.

In certain embodiments, the first redox mediator of the analyte sensors disclosed herein has a structure of:

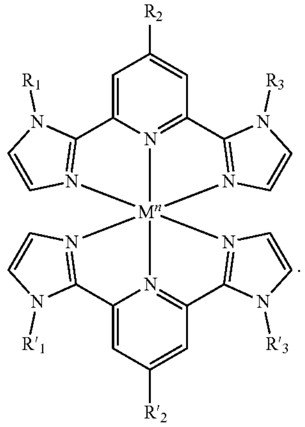

In certain embodiments, the first redox mediator of the analyte sensors disclosed herein has a structure of:

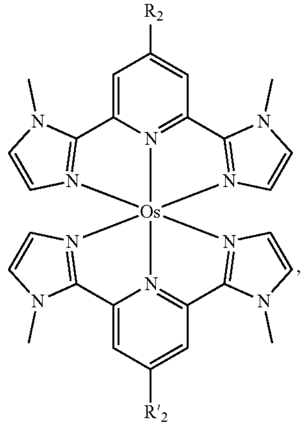

wherein n is II or III.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
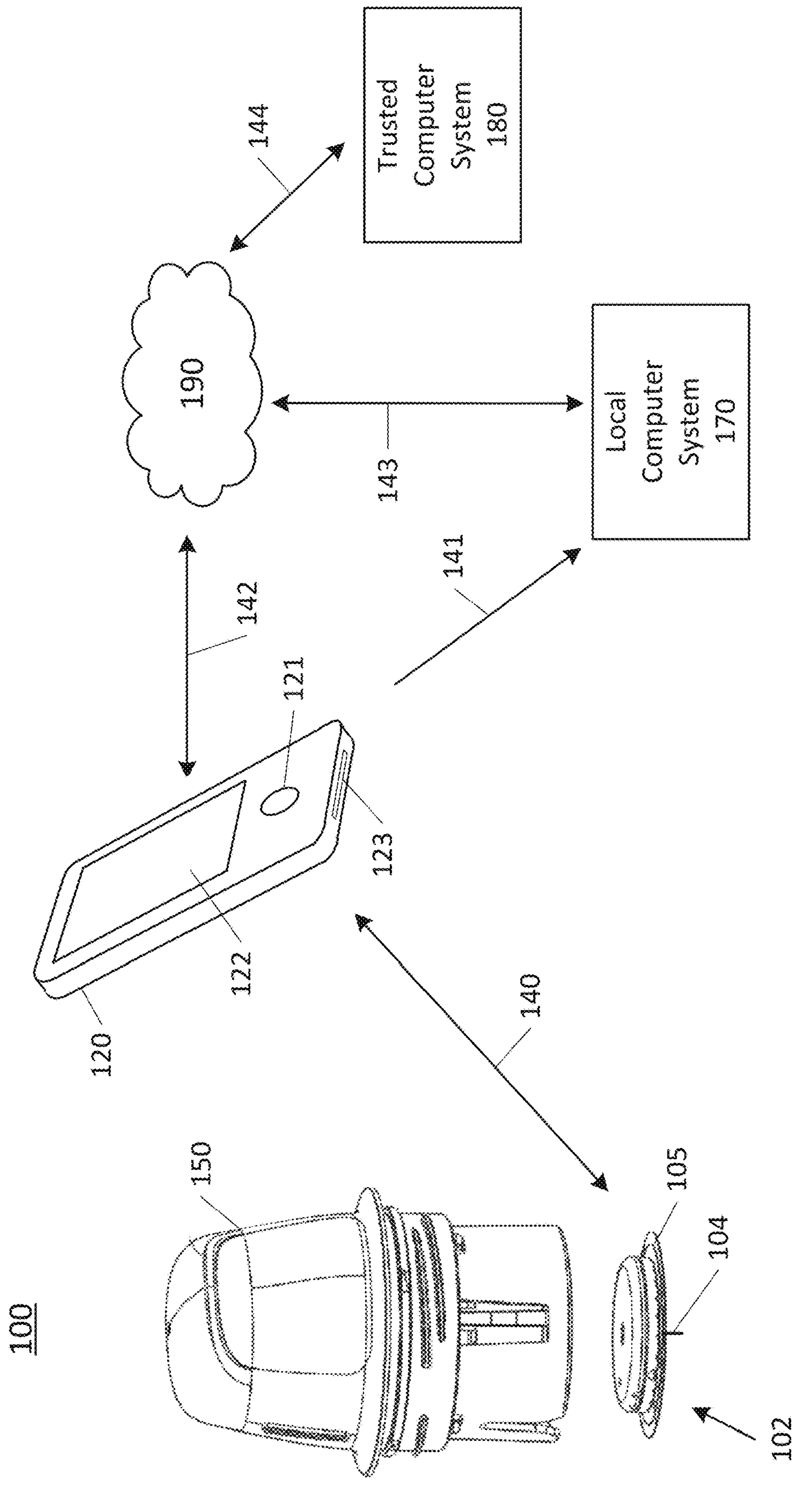
FIG. 1A is a system overview of a sensor applicator, reader device, monitoring system, network and remote system.
FIG. 1B is a diagram illustrating an operating environment of an example analyte monitoring system for use with the techniques described herein.

The present disclosure provides transition metal complexes and the use of such complexes as redox mediators in analyte sensors. The present disclosure generally describes analyte sensors suitable for in vivo use and, more specifically, analyte sensors comprising a redox mediator disclosed herein. Depending on sensor configuration, the analyte sensors of the present disclosure can be configured to detect one analyte or multiple analytes simultaneously or near simultaneously.

Various analyte sensor components can cause certain difficulties during monitoring of some analytes or combinations of analytes. Redox mediators used to promote electron transfer to a working electrode can require operation of an analyte sensor at relatively high potentials, which can lead to electrochemical side reactions that can complicate detection of some low-abundance analytes. In addition, operation of an analyte sensor under certain conditions, such as extended use, can result in the decomposition of the redox mediator and affect the sensitivity of the analyte sensor.

To address the foregoing needs, the present disclosure provides redox mediators for promoting electron transfer at lower working electrode potentials than are commonly used. Commonly used working electrode potentials typically range from 0 to 300 mV relative to an Ag/AgCl reference. Use of such "low-potential" redox mediators can reduce the occurrence of electrochemical side reactions and enable detection of analytes low-abundance analytes, such as ketones, more readily than would otherwise be possible at higher working electrode potentials. Such low-potential redox mediators can also be advantageous when used in conjunction with detecting multiple analytes, as discussed further hereinbelow. In addition, the redox mediators disclosed herein comprise a transition metal surrounded by two tridentate ligands, which provide increased structural stability to the redox mediator. Increased stability can result in extending the wear time of an analyte sensor comprising a redox mediator of the present disclosure.

In certain embodiments, analyte sensors incorporating one or more redox mediators of the present disclosure are capable of operation at a wide range of potentials, ranging from about −300 mV to about +200 mV as measured relative to an Ag/AgCl reference, e.g., from about −270 mV to about +130 mV. In certain embodiments, analyte sensors that incorporate one or more redox mediators of the present disclosure are capable of low potential operation. As used herein, the term "low potential" refers to a potential above the oxidation-reduction potential of the first redox mediator and below about +200 mV, as measured relative to an Ag/AgCl reference, including below about +100 mV, below about −50 mV, below about −80 mV or below about −100 mV. In certain embodiments, oxidation-reduction potentials of the first redox mediator that can facilitate operation at such working electrode potentials can be below about −200 mV, such as about −400 mV to about −200 mV, or from about −350 mV to about −250 mV, or from about −300 mV to about −250 mV, as measured relative to an Ag/AgCl reference.

For clarity, but not by way of limitation, the detailed description of the presently disclosed subject matter is divided into the following subsections:

I. Definitions;
II. Analyte sensors;
1. General Structure of Analyte Sensor Systems;
2. Redox Mediators;
3. Polymeric Backbone;
4. Enzymes;
5. Mass Transport Limiting Membrane;
6. Interference Domain;
III. Methods of Use; and
IV. Exemplary Embodiments.

I. DEFINITIONS

The terms used in this specification generally have their ordinary meanings in the art, within the context of this disclosure and in the specific context where each term is used. Certain terms are discussed below, or elsewhere in the specification, to provide additional guidance to the practitioner in describing the compositions and methods of the present disclosure and how to make and use them.

As used herein, the use of the word "a" or "an" when used in conjunction with the term "comprising" in the claims and/or the specification can mean "one," but it is also consistent with the meaning of "one or more," "at least one," and "one or more than one."

The terms "comprise(s)," "include(s)," "having," "has," "can," "contain(s)," and variants thereof, as used herein, are intended to be open-ended transitional phrases, terms or words that do not preclude additional acts or structures. The present disclosure also contemplates other embodiments "comprising," "consisting of" and "consisting essentially of," the embodiments or elements presented herein, whether explicitly set forth or not.

The term "about" or "approximately" means within an acceptable error range for the particular value as determined by one of ordinary skill in the art, which depends in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

The term "alkyl," as used herein, refers to linear or branched, saturated aliphatic hydrocarbons. Examples of alkyl groups include but are not limited to methyl, ethyl, n-propyl, isopropyl, n-butyl, tert-butyl, and the like. Unless otherwise noted, the term "alkyl" includes both alkyl and cycloalkyl groups.

The term "alkoxy," as used herein, refers to an alkyl group joined to the remainder of a structure by an oxygen atom. Examples of alkoxy groups include, but are not limited to methoxy, ethoxy, n-propoxy, isopropoxy, butoxy, tert-butoxy, and the like. In addition, unless otherwise noted, the term "alkoxy" includes both alkoxy and cycloalkoxy groups.

The term "alkenyl," as used herein, refers to an unsaturated, linear or branched aliphatic hydrocarbon having at least one carbon-carbon double bond. Non-limiting examples of alkenyl groups include ethenyl, 1-propenyl, 2-propenyl, 1-butenyl, 2-methyl-1-propenyl, and the like.

As used herein, "analyte sensor" or "sensor" can refer to any device capable of receiving sensor information from a user, including for purpose of illustration but not limited to, body temperature sensors, blood pressure sensors, pulse or heart-rate sensors, glucose level sensors, analyte sensors, physical activity sensors, body movement sensors, or any other sensors for collecting physical or biological information. Analytes measured by the analyte sensors can include, by way of example and not limitation, glutamate, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, aspartate, asparagine, magnesium, oxygen, pH, phosphorus, potassium, sodium, total protein, uric acid, etc.

The term a "reactive group," as used herein refers to a functional group of a molecule that is capable of reacting with another compound to couple at least a portion of that other compound to the molecule. Non-limiting examples of reactive groups include carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxylamine, alkyl halide, imidazole, pyridine, phenol, alkyl sulfonate, halotriazine, imido ester, maleimide, hydrazide, hydroxy, and photo-reactive azido aryl groups. Activated esters, as used herein and understood in the art, include but are not limited to esters of succinimidyl, benzotriazolyl, or aryl substituted by electron-withdrawing groups such as sulfo, nitro, cyano, or halo groups; or carboxylic acids activated by carbodiimides.

The term "substituted functional group" (e.g., substituted alkyl, alkenyl, or alkoxy group) as used herein, includes but is not limited to at least one substituent selected from the following: halogen, alkoxy, mercapto, aryl, alkoxycarbonyl, alkylaminocarbonyl, dialkylaminocarbonyl, —OH, —$NH_2$, alkylamino, dialkylamino, trialkylammonium, alkanoylamino, arylcarboxamido, hydrazino, alkylthio, alkenyl, and reactive groups.

The term "biological fluid," as used herein, refers to any bodily fluid or bodily fluid derivative in which the analyte can be measured. Non-limiting examples of a biological fluid include dermal fluid, interstitial fluid, plasma, blood, lymph, synovial fluid, cerebrospinal fluid, saliva, bronchoalveolar lavage, amniotic fluid, sweat, tears, or the like. In certain embodiments, the biological fluid is dermal fluid or interstitial fluid.

As used herein, the term "polyvinylpyridine-based polymer" refers to a polymer or copolymer that comprises polyvinylpyridine (e.g., poly(2-vinylpyridine) or poly(4-vinylpyridine)) or a derivative thereof.

As used herein, the term "redox mediator" refers to an electron transfer agent for carrying electrons between an analyte or an analyte-reduced or analyte oxidized enzyme and an electrode, either directly, or via one or more additional electron transfer agents. In certain embodiments, redox mediators that include a polymeric backbone can also be referred to as "redox polymers."

The term "electrolysis," as used herein, refers to electrooxidation or electroreduction of a compound either directly at an electrode or via one or more electron transfer agents (e.g., redox mediators or enzymes).

The term "reference electrode" as used herein, can refer to either reference electrodes or electrodes that function as both, a reference and a counter electrode. Similarly, the term "counter electrode," as used herein, can refer to both, a counter electrode and a counter electrode that also functions as a reference electrode.

The term "tridentate ligand," as used herein, refers to a ligand with three donor atoms that are capable of forming coordination bonds to a central metal atom or ion.

As used herein, the term "multi-component membrane" refers to a membrane comprising two or more types of membrane polymers.

As used herein, the term "single-component membrane" refers to a membrane comprising one type of membrane polymer.

II. ANALYTE SENSORS

1. General Structure of Analyte Sensor Systems

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

Generally, embodiments of the present disclosure include systems, devices and methods for the use of analyte sensor insertion applicators for use with in vivo analyte monitoring systems. An applicator can be provided to the user in a sterile package with an electronics housing of the sensor control device contained therein. According to some embodiments, a structure separate from the applicator, such as a container, can also be provided to the user as a sterile package with a sensor module and a sharp module contained therein. The user can couple the sensor module to the electronics housing, and can couple the sharp to the applicator with an assembly process that involves the insertion of the applicator into the container in a specified manner. In other embodiments, the applicator, sensor control device, sensor module, and sharp module can be provided in a single package. The applicator can be used to position the sensor control device on a human body with a sensor in contact with the wearer's bodily fluid. The embodiments provided herein are improvements to reduce the likelihood that a sensor is improperly inserted or damaged, or elicits an adverse physiological response. Other improvements and advantages are provided as well. The various configurations of these devices are described in detail by way of the embodiments which are only examples.

Furthermore, many embodiments include in vivo analyte sensors structurally configured so that at least a portion of the sensor is, or can be, positioned in the body of a user to obtain information about at least one analyte of the body. It should be noted, however, that the embodiments disclosed herein can be used with in vivo analyte monitoring systems that incorporate in vitro capability, as well as purely in vitro or ex vivo analyte monitoring systems, including systems that are entirely non-invasive.

Furthermore, for each and every embodiment of a method disclosed herein, systems and devices capable of performing each of those embodiments are covered within the scope of the present disclosure. For example, embodiments of sensor control devices are disclosed and these devices can have one or more sensors, analyte monitoring circuits (e.g., an analog circuit), memories (e.g., for storing instructions), power sources, communication circuits, transmitters, receivers, processors and/or controllers (e.g., for executing instructions) that can perform any and all method steps or facilitate the execution of any and all method steps. These sensor control device embodiments can be used and can be capable of use to implement those steps performed by a sensor control device from any and all of the methods described herein.

Furthermore, the systems and methods presented herein can be used for operations of a sensor used in an analyte monitoring system, such as but not limited to wellness, fitness, dietary, research, information or any purposes involving analyte sensing over time. As used herein, "analyte sensor" or "sensor" can refer to any device capable of receiving sensor information from a user, including for purpose of illustration but not limited to, body temperature sensors, blood pressure sensors, pulse or heart-rate sensors, glucose level sensors, analyte sensors, physical activity sensors, body movement sensors, or any other sensors for collecting physical or biological information. In certain embodiments, an analyte sensor of the present disclosure can further measure analytes including, but not limited to, glutamate, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, magnesium, oxygen, pH, phosphorus, potassium, sodium, total protein, uric acid, etc.

As mentioned, a number of embodiments of systems, devices, and methods are described herein that provide for the improved assembly and use of dermal sensor insertion devices for use with in vivo analyte monitoring systems. In particular, several embodiments of the present disclosure are designed to improve the method of sensor insertion with respect to in vivo analyte monitoring systems and, in particular, to prevent the premature retraction of an insertion sharp during a sensor insertion process. Some embodiments, for example, include a dermal sensor insertion mechanism with an increased firing velocity and a delayed sharp retraction. In other embodiments, the sharp retraction mechanism can be motion-actuated such that the sharp is not retracted until the user pulls the applicator away from the skin. Consequently, these embodiments can reduce the likelihood of prematurely withdrawing an insertion sharp during a sensor insertion process; decrease the likelihood of improper sensor insertion; and decrease the likelihood of damaging a sensor during the sensor insertion process, to name a few advantages. Several embodiments of the present disclosure also provide for improved insertion sharp modules to account for the small scale of dermal sensors and the relatively shallow insertion path present in a subject's dermal layer. In addition, several embodiments of the present disclosure are designed to prevent undesirable axial and/or rotational movement of applicator components during sensor insertion. Accordingly, these embodiments can reduce the likelihood of instability of a positioned dermal sensor, irritation at the insertion site, damage to surrounding tissue, and breakage of capillary blood vessels resulting in fouling of the dermal fluid with blood, to name a few advantages. In addition, to mitigate inaccurate sensor readings which can be caused by trauma at the insertion site, several embodiments of the present disclosure can reduce the end-depth penetration of the needle relative to the sensor tip during insertion.

Before describing these aspects of the embodiments in detail, however, it is first desirable to describe examples of devices that can be present within, for example, an in vivo analyte monitoring system, as well as examples of their operation, all of which can be used with the embodiments described herein.

There are various types of in vivo analyte monitoring systems. "Continuous Analyte Monitoring" systems (or "Continuous Glucose Monitoring" systems), for example, can transmit data from a sensor control device to a reader device continuously without prompting, e.g., automatically according to a schedule. "Flash Analyte Monitoring" systems (or "Flash Glucose Monitoring" systems or simply "Flash" systems), as another example, can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

In vivo analyte monitoring systems can be differentiated from "in vitro" systems that contact a biological sample outside of the body (or "ex vivo") and that typically include a meter device that has a port for receiving an analyte test strip carrying bodily fluid of the user, which can be analyzed to determine the user's blood analyte level.

In vivo monitoring systems can include a sensor that, while positioned in vivo, makes contact with the bodily fluid of the user and senses the analyte levels contained therein. The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include a device that receives sensed analyte data from the sensor control device and processes and/or displays that sensed analyte data, in any number of forms, to the user. This device, and variations thereof, can be referred to as a "handheld reader device," "reader device" (or simply a "reader"), "handheld electronics" (or simply a "handheld"), a "portable data processing" device or unit, a "data receiver," a "receiver" device or unit (or simply a "receiver"), or a "remote" device or unit, to name a few. Other devices such as personal computers have also been utilized with or incorporated into in vivo and in vitro monitoring systems.

A. Exemplary In Vivo Analyte Monitoring System

FIG. 1A is a conceptual diagram depicting an example embodiment of an analyte monitoring system 100 that includes a sensor applicator 150, a sensor control device 102, and a reader device 120. Here, sensor applicator 150 can be used to deliver sensor control device 102 to a monitoring location on a user's skin where a sensor 104 is maintained in position for a period of time by an adhesive patch 105. Sensor control device 102 is further described in FIGS. 2B and 2C, and can communicate with reader device 120 via a communication path or link 140 using a wired or wireless, uni- or bi-directional, and encrypted or non-encrypted technique. Example wireless protocols include Bluetooth, Bluetooth Low Energy (BLE, BTLE, Bluetooth SMART, etc.), Near Field Communication (NFC) and others. Users can monitor applications installed in memory on reader device 120 using screen 122 and input 121 and the device battery can be recharged using power port 123. More detail about reader device 120 is set forth with respect to FIG. 2A below. Reader device 120 can constitute an output medium for viewing analyte concentrations and alerts or notifications determined by sensor 104 or a processor associated therewith, as well as allowing for one or more user inputs, according to certain embodiments. Reader device 120 can be a multi-purpose smartphone or a dedicated electronic reader instrument. While only one reader device 120 is shown, multiple reader devices 120 can be present in certain instances.

Reader device 120 can communicate with local computer system 170 via a communication path 141, which also can be wired or wireless, uni- or bi-directional, and encrypted or non-encrypted. Local computer system 170 can include one or more of a laptop, desktop, tablet, phablet, smartphone, set-top box, video game console, remote terminal or other computing device and wireless communication can include any of a number of applicable wireless networking protocols including Bluetooth, Bluetooth Low Energy (BTLE), Wi-Fi or others. Local computer system 170 can communicate via communications path 143 with a network 190 similar to how reader device 120 can communicate via a communications path 142 with network 190, by wired or wireless technique as described previously. Network 190 can be any of a number of networks, such as private networks and public networks, local area or wide area networks, and so forth. A trusted computer system 180 can include a server and can provide authentication services and secured data storage and can communicate via communications path 144 with network 190 by wired or wireless technique. Local computer system 170 and/or trusted computer system 180 can be accessible, according to certain embodiments, by individuals other than a primary user who have an interest in the user's analyte levels. Reader device 120 can include display 122 and optional input component 121. Display 122 can include a touch-screen interface, according to certain embodiments.

Sensor control device 102 includes sensor housing, which can house circuitry and a power source for operating sensor 104. Optionally, the power source and/or active circuitry can be omitted. A processor (not shown) can be communicatively coupled to sensor 104, with the processor being physically located within the sensor housing or reader device 120. Sensor 104 protrudes from the underside of the sensor housing and extends through adhesive layer 105, which is adapted for adhering the sensor housing to a tissue surface, such as skin, according to certain embodiments.

Figure 1B:
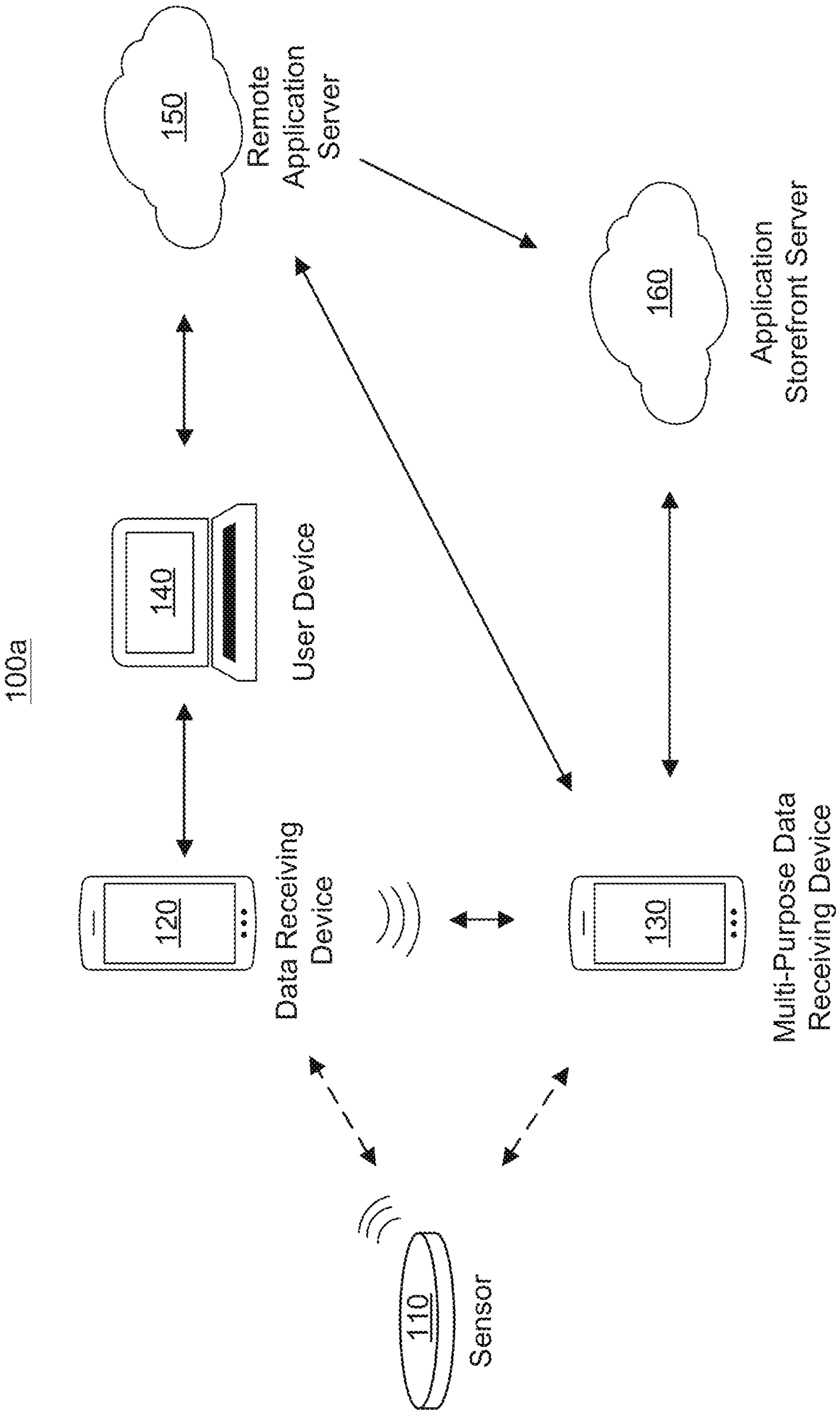

FIG. 1B illustrates an operating environment of an analyte monitoring system 100_a_ capable of embodying the techniques described herein. The analyte monitoring system 100_a_ can include a system of components designed to provide monitoring of parameters, such as analyte levels, of a human or animal body or can provide for other operations based on the configurations of the various components. As embodied herein, the system can include a low-power analyte sensor 110, or simply "sensor" worn by the user or attached to the body for which information is being collected. As embodied herein, the analyte sensor 110 can be a sealed, disposable device with a predetermined active use lifetime (e.g., 1 day, 14 days, 30 days, etc.). Sensors 110 can be applied to the skin of the user body and remain adhered over the duration of the sensor lifetime or can be designed to be selectively removed and remain functional when reapplied. The low-power analyte monitoring system 100*a* can further include a data reading device 120 or multi-purpose data receiving device 130 configured as described herein to facilitate retrieval and delivery of data, including analyte data, from the analyte sensor 110.

As embodied herein, the analyte monitoring system 100*a* can include a software or firmware library or application provided, for example via a remote application server 150 or application storefront server 160, to a third-party and incorporated into a multi-purpose hardware device 130 such as a mobile phone, tablet, personal computing device, or other similar computing device capable of communicating with the analyte sensor 110 over a communication link. Multi-purpose hardware can further include embedded devices, including, but not limited to insulin pumps or insulin pens, having an embedded library configured to communicate with the analyte sensor 110. Although the illustrated embodiments of the analyte monitoring system 100*a* include only one of each of the illustrated devices, this disclosure contemplates the analyte monitoring system 100*a* incorporate multiples of each components interacting throughout the system. For example and without limitation, as embodied herein, data reading device 120 and/or multi-purpose data receiving device 130 can include multiples of each. As embodied herein, multiple data receiving devices 130 can communicate directly with sensor 110 as described herein. Additionally or alternatively, a data receiving device 130 can communicate with secondary data receiving devices 130 to provide analyte data, or visualization or analysis of the data, for secondary display to the user or other authorized parties.

Sensor 104 of FIG. 1A is adapted to be at least partially inserted into a tissue of interest, such as within the dermal or subcutaneous layer of the skin. Sensor 104 can include a sensor tail of sufficient length for insertion to a desired depth in a given tissue. The sensor tail can include at least one working electrode. In certain configurations, the sensor tail can include an active area for detecting an analyte, which can include a low-potential redox mediator in certain instances, as discussed further herein. A counter electrode can be present in combination with the at least one working electrode. Particular electrode configurations upon the sensor tail are described in more detail below. One or more mass transport limiting membranes can overcoat the active area, as also described in further detail below.

The active area can be configured for detecting a particular analyte described herein. For example, but not by way of the limitation, the analyte can include glutamate, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, asparagine, aspartate, phosphorus, potassium, sodium, total protein, uric acid, etc. In certain embodiments, an active area of a presently disclosed sensor is configured to detect glucose. In certain embodiments, an active area of a presently disclosed sensor is configured to detect lactate. In certain embodiments, an active area of a presently disclosed sensor is configured to detect alcohol. In certain embodiments, an active area of a presently disclosed sensor is configured to detect ketones. For example, but not by way of limitation, a glucose-responsive active area can include a glucose-responsive enzyme, a lactate-responsive active area can include a lactate-responsive enzyme, and a ketones-responsive active area can include an enzyme system including at least two enzymes that are capable of acting in concert to facilitate detection of ketones. Suitable enzyme systems for detecting ketones are further described below in reference to FIGS. 22A-22C. In certain embodiments, an active area of a presently disclosed sensor is configured to detect creatinine. In certain embodiments, an active area of a presently disclosed sensor is configured to detect an alcohol, e.g., ethanol, e.g., by including an alcohol-responsive enzyme. In certain embodiments, an active area of a presently disclosed sensor is configured to detect glutamate, e.g., by including a glutamate-responsive enzyme. In certain embodiments, an active area of a presently disclosed sensor is configured to detect aspartate, e.g., by including an aspartate-responsive enzyme. In certain embodiments, an active area of a presently disclosed sensor is configured to detect asparagine, e.g., by including an asparagine-responsive enzyme. Each active area can include a polymer to which at least some of the enzymes are covalently bonded, according to various embodiments.

In certain embodiments of the present disclosure, one or more analytes can be monitored in any biological fluid of interest such as dermal fluid, interstitial fluid, plasma, blood, lymph, synovial fluid, cerebrospinal fluid, saliva, bronchoalveolar lavage, amniotic fluid, or the like. In certain particular embodiments, analyte sensors of the present disclosure can be adapted for assaying dermal fluid or interstitial fluid to determine a concentration of one or more analytes in vivo. In certain embodiments, the biological fluid is interstitial fluid.

An introducer can be present transiently to promote introduction of sensor 104 into a tissue. In certain illustrative embodiments, the introducer can include a needle or similar sharp. As would be readily recognized by a person skilled in the art, other types of introducers, such as sheaths or blades, can be present in alternative embodiments. More specifically, the needle or other introducer can transiently reside in proximity to sensor 104 prior to tissue insertion and then be withdrawn afterward. While present, the needle or other introducer can facilitate insertion of sensor 104 into a tissue by opening an access pathway for sensor 104 to follow. For example, and not by the way of limitation, the needle can facilitate penetration of the epidermis as an access pathway to the dermis to allow implantation of sensor 104 to take place, according to one or more embodiments. After opening the access pathway, the needle or other introducer can be withdrawn so that it does not represent a sharps hazard. In certain embodiments, suitable needles can be solid or hollow, beveled or non-beveled, and/or circular or non-circular in cross-section. In more particular embodiments, suitable needles can be comparable in cross-sectional diameter and/or tip design to an acupuncture needle, which can have a cross-sectional diameter of about 250 microns. However, suitable needles can have a larger or smaller cross-sectional diameter if needed for certain particular applications.

In certain embodiments, a tip of the needle (while present) can be angled over the terminus of sensor 104, such that the needle penetrates a tissue first and opens an access pathway for sensor 104. In certain embodiments, sensor 104 can reside within a lumen or groove of the needle, with the needle similarly opening an access pathway for sensor 104. In either case, the needle is subsequently withdrawn after facilitating sensor insertion.

B. Exemplary Reader Device

Figure 2A:
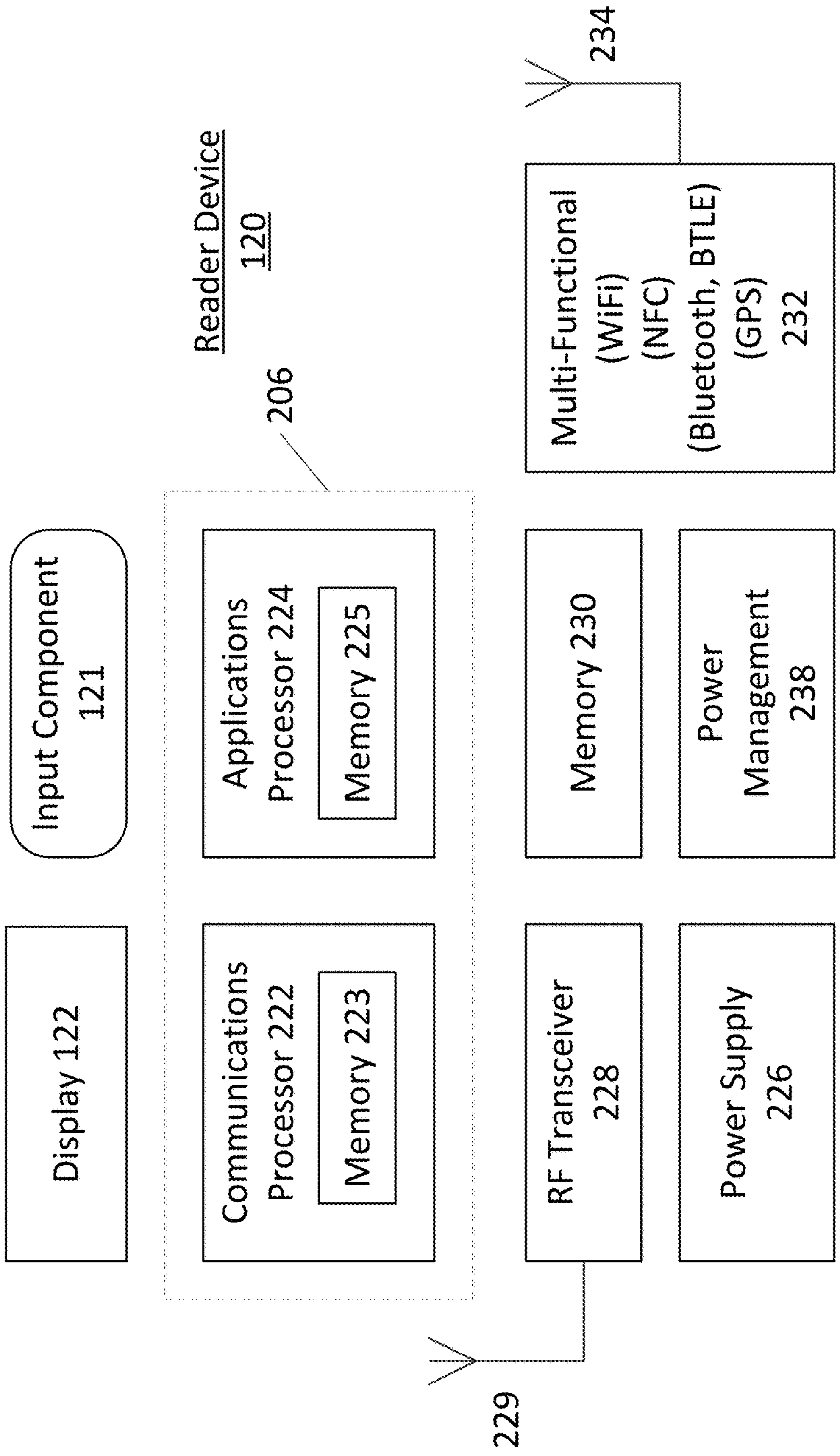
FIG. 2A is a block diagram depicting an example embodiment of a reader device.

FIG. 2A is a block diagram depicting an example embodiment of a reader device configured as a smartphone. Here, reader device 120 can include a display 122, input component 121, and a processing core 206 including a communications processor 222 coupled with memory 223 and an applications processor 224 coupled with memory 225. Also included can be separate memory 230, RF transceiver 228 with antenna 229, and power supply 226 with power management module 238. Further included can be a multifunctional transceiver 232 which can communicate over Wi-Fi, NFC, Bluetooth, BTLE, and GPS with an antenna 234. As understood by one of skill in the art, these components are electrically and communicatively coupled in a manner to make a functional device.

C. Exemplary Data Receiving Device Architecture

Figure 2B:
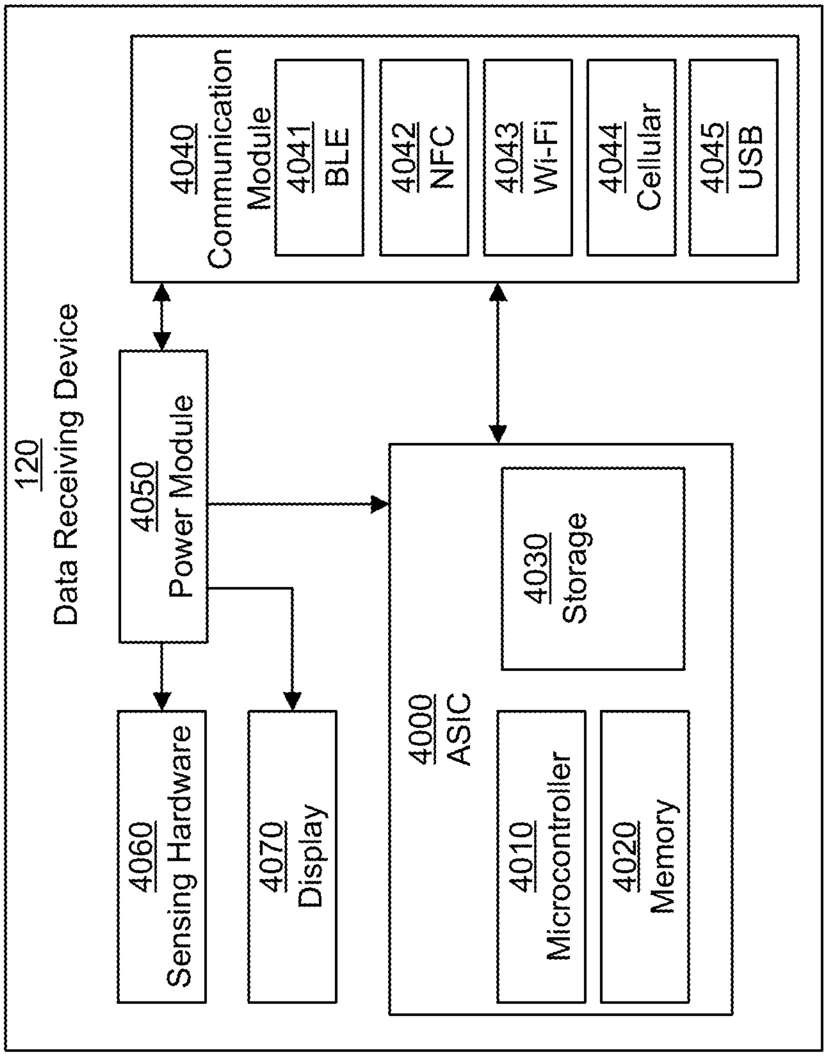
FIG. 2B is a block diagram illustrating an example data receiving device for communicating with the sensor according to exemplary embodiments of the disclosed subject matter.

For purpose of illustration and not limitation, reference is made to the exemplary embodiment of a data receiving device 120 for use with the disclosed subject matter as shown in FIG. 2B. The data receiving device 120, and the related multi-purpose data receiving device 130, includes components germane to the discussion of the analyte sensor 110 and its operations and additional components can be included. In particular embodiments, the data receiving device 120 and multi-purpose data receiving device 130 can be or include components provided by a third party and are not necessarily restricted to include devices made by the same manufacturer as the sensor 110.

As illustrated in FIG. 2B, the data receiving device 120 includes an ASIC 4000 including a microcontroller 4010, memory 4020, and storage 4030 and communicatively coupled with a communication module 4040. Power for the components of the data receiving device 120 can be delivered by a power module 4050, which as embodied herein can include a rechargeable battery. The data receiving device 120 can further include a display 4070 for facilitating review of analyte data received from an analyte sensor 110 or other device (e.g., user device 140 or remote application server 150). The data receiving device 120 can include separate user interface components (e.g., physical keys, light sensors, microphones, etc.).

The communication module 4040 can include a BLE module 4041 and an NFC module 4042. The data receiving device 120 can be configured to wirelessly couple with the analyte sensor 110 and transmit commands to and receive data from the analyte sensor 110. As embodied herein, the data receiving device 120 can be configured to operate, with respect to the analyte sensor 110 as described herein, as an NFC scanner and a BLE end point via specific modules (e.g., BLE module 4042 or NFC module 4043) of the communication module 4040. For example, the data receiving device 120 can issue commands (e.g., activation commands for a data broadcast mode of the sensor; pairing commands to identify the data receiving device 120) to the analyte sensor 110 using a first module of the communication module 4040 and receive data from and transmit data to the analyte sensor 110 using a second module of the communication module 4040. The data receiving device 120 can be configured for communication with a user device 140 via a Universal Serial Bus (USB) module 4045 of the communication module 4040.

As another example, the communication module 4040 can include, for example, a cellular radio module 4044. The cellular radio module 4044 can include one or more radio transceivers for communicating using broadband cellular networks, including, but not limited to third generation (3G), fourth generation (4G), and fifth generation (5G) networks. Additionally, the communication module 4040 of the data receiving device 120 can include a Wi-Fi radio module 4043 for communication using a wireless local area network according to one or more of the IEEE 802.11 standards (e.g., 802.11a, 802.11b, 802.11g, 802.11n (aka Wi-Fi 4), 802.11ac (aka Wi-Fi 5), 802.11ax (aka Wi-Fi 6)). Using the cellular radio module 4044 or Wi-Fi radio module 4043, the data receiving device 120 can communicate with the remote application server 150 to receive analyte data or provide updates or input received from a user (e.g., through one or more user interfaces). Although not illustrated, the communication module 5040 of the analyte sensor 120 can similarly include a cellular radio module or Wi-Fi radio module.

As embodied herein, the on-board storage 4030 of the data receiving device 120 can store analyte data received from the analyte sensor 110. Further, the data receiving device 120, multi-purpose data receiving device 130, or a user device 140 can be configured to communicate with a remote application server 150 via a wide area network. As embodied herein, the analyte sensor 110 can provide data to the data receiving device 120 or multi-purpose data receiving device 130. The data receiving device 120 can transmit the data to the user computing device 140. The user computing device 140 (or the multi-purpose data receiving device 130) can in turn transmit that data to a remote application server 150 for processing and analysis.

As embodied herein, the data receiving device 120 can further include sensing hardware 4060 similar to, or expanded from, the sensing hardware 5060 of the analyte sensor 110. In particular embodiments, the data receiving device 120 can be configured to operate in coordination with the analyte sensor 110 and based on analyte data received from the analyte sensor 110. As an example, where the analyte sensor 110 glucose sensor, the data receiving device 120 can be or include an insulin pump or insulin injection pen. In coordination, the compatible device 130 can adjust an insulin dosage for a user based on glucose values received from the analyte sensor.

D. Exemplary Sensor Control Devices

Figure 2C:
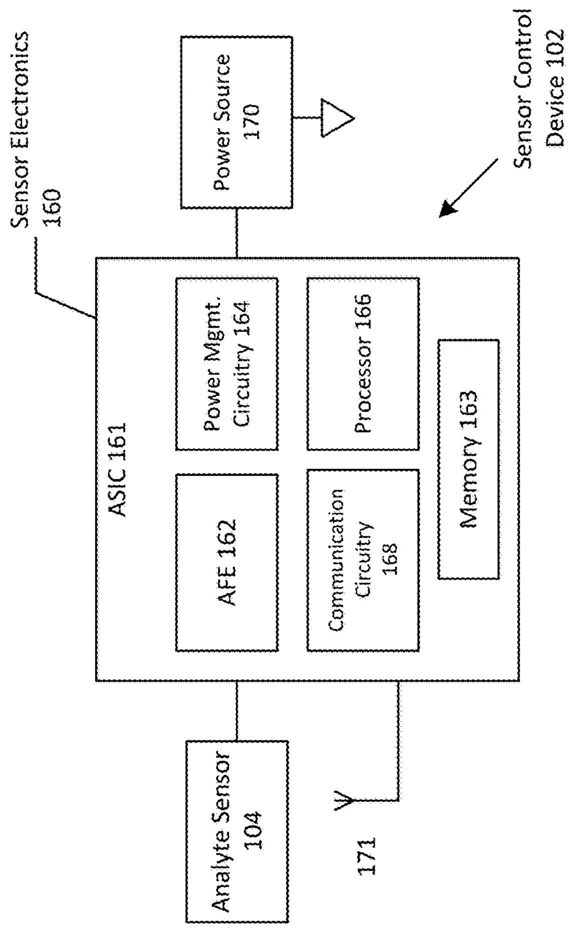
FIGS. 2C and 2D are block diagrams depicting example embodiments of sensor control devices.
Figure 2D:
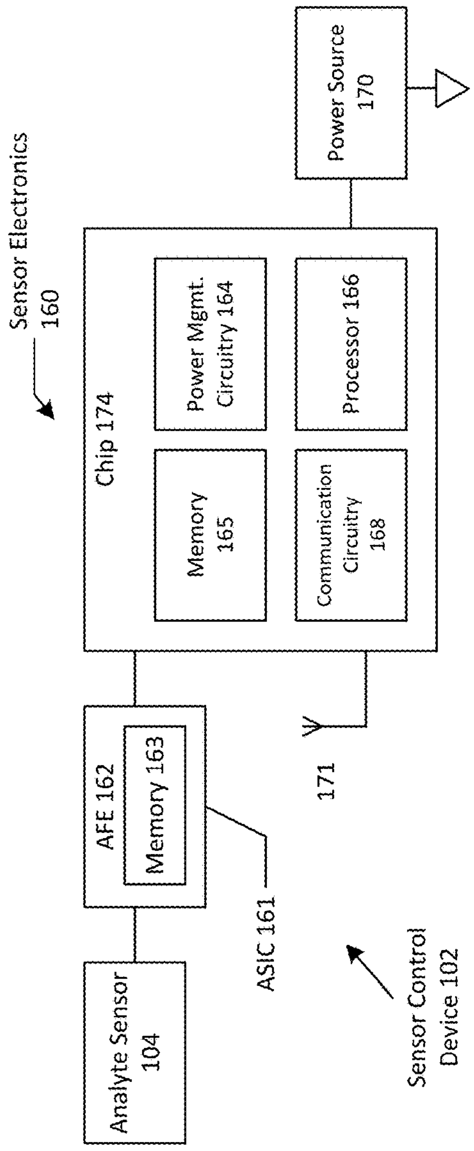

FIGS. 2C and 2D are block diagrams depicting example embodiments of sensor control device 102 having analyte sensor 104 and sensor electronics 160 (including analyte monitoring circuitry) that can have the majority of the processing capability for rendering end-result data suitable for display to the user. In FIG. 2C, a single semiconductor chip 161 is depicted that can be a custom application specific integrated circuit (ASIC). Shown within ASIC 161 are certain high-level functional units, including an analog front end (AFE) 162, power management (or control) circuitry 164, processor 166, and communication circuitry 168 (which can be implemented as a transmitter, receiver, transceiver, passive circuit, or otherwise according to the communication protocol). In this embodiment, both AFE 162 and processor 166 are used as analyte monitoring circuitry, but in other embodiments either circuit can perform the analyte monitoring function. Processor 166 can include one or more processors, microprocessors, controllers, and/or microcontrollers, each of which can be a discrete chip or distributed amongst (and a portion of) a number of different chips.

A memory 163 is also included within ASIC 161 and can be shared by the various functional units present within ASIC 161, or can be distributed amongst two or more of them. Memory 163 can also be a separate chip. Memory 163 can be volatile and/or non-volatile memory. In this embodiment, ASIC 161 is coupled with power source 170, which can be a coin cell battery, or the like. AFE 162 interfaces with in vivo analyte sensor 104 and receives measurement data therefrom and outputs the data to processor 166 in digital form, which in turn processes the data to arrive at the end-result glucose discrete and trend values, etc. This data can then be provided to communication circuitry 168 for sending, by way of antenna 171, to reader device 120 (not shown), for example, where minimal further processing is needed by the resident software application to display the data.

FIG. 2D is similar to FIG. 2C but instead includes two discrete semiconductor chips 162 and 174, which can be packaged together or separately. Here, AFE 162 is resident on ASIC 161. Processor 166 is integrated with power management circuitry 164 and communication circuitry 168 on chip 174. AFE 162 includes memory 163 and chip 174 includes memory 165, which can be isolated or distributed within. In one example embodiment, AFE 162 is combined with power management circuitry 164 and processor 166 on one chip, while communication circuitry 168 is on a separate chip. In another example embodiment, both AFE 162 and communication circuitry 168 are on one chip, and processor 166 and power management circuitry 164 are on another chip. It should be noted that other chip combinations are possible, including three or more chips, each bearing responsibility for the separate functions described, or sharing one or more functions for fail-safe redundancy.

Figure 2E:
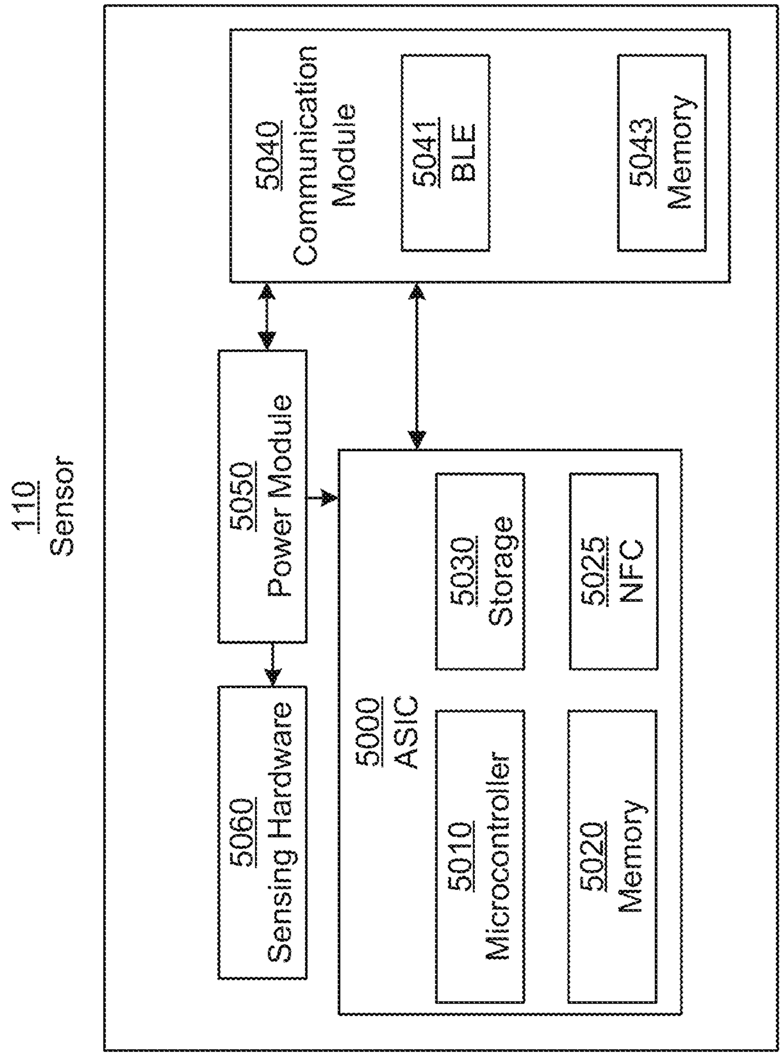
FIG. 2E is a block diagram illustrating an example analyte sensor according to exemplary embodiments of the disclosed subject matter.

For purpose of illustration and not limitation, reference is made to the exemplary embodiment of an analyte sensor 110 for use with the disclosed subject matter as shown in FIG. 2E. FIG. 2E illustrates a block diagram of an example analyte sensor 110 according to exemplary embodiments compatible with the security architecture and communication schemes described herein.

As embodied herein, the analyte sensor 110 can include an Application-Specific Integrated Circuit ("ASIC") 5000 communicatively coupled with a communication module 5040. The ASIC 5000 can include a microcontroller core 5010, on-board memory 5020, and storage memory 5030. The storage memory 5030 can store data used in an authentication and encryption security architecture. The storage memory 5030 can store programming instructions for the sensor 110. As embodied herein, certain communication chipsets can be embedded in the ASIC 5000 (e.g., an NFC transceiver 5025). The ASIC 5000 can receive power from a power module 5050, such as an on-board battery or from an NFC pulse. The storage memory 5030 of the ASIC 5000 can be programmed to include information such as an identifier for the sensor 110 for identification and tracking purposes. The storage memory 5030 can also be programmed with configuration or calibration parameters for use by the sensor 110 and its various components. The storage memory 5030 can include rewritable or one-time programming (OTP) memory. The storage memory 5030 can be updated using techniques described herein to extend the usefulness of the sensor 110.

As embodied herein, the communication module 5040 of the sensor 100 can be or include one or more modules to support the analyte sensor 110 communicating with other devices of the analyte monitoring system 100. As an example only and not by way of limitation, example communication modules 5040 can include a Bluetooth Low-Energy ("BLE") module 5041 As used throughout this disclosure, Bluetooth Low Energy ("BLE") refers to a short-range communication protocol optimized to make pairing of Bluetooth devices simple for end users. The communication module 5040 can transmit and receive data and commands via interaction with similarly-capable communication modules of a data receiving device 120 or user device 140. The communication module 5040 can include additional or alternative chipsets for use with similar short-range communication schemes, such as a personal area network according to IEEE 802.15 protocols, IEEE 802.11 protocols, infrared communications according to the Infrared Data Association standards (IrDA), etc.

To perform its functionalities, the sensor 100 can further include suitable sensing hardware 5060 appropriate to its function. As embodied herein, the sensing hardware 5060 can include an analyte sensor transcutaneously or subcutaneously positioned in contact with a bodily fluid of a subject. The analyte sensor can generate sensor data containing values corresponding to levels of one or more analytes within the bodily fluid.

E. Exemplary Assembly Processes for Sensor Control Devices

The components of sensor control device 102 can be acquired by a user in multiple packages requiring final assembly by the user before delivery to an appropriate user location. FIGS. 3A-3D depict an example embodiment of an assembly process for sensor control device 102 by a user, including preparation of separate components before coupling the components in order to ready the sensor for delivery. FIGS. 3E-3F depict an example embodiment of delivery of sensor control device 102 to an appropriate user location by selecting the appropriate delivery location and applying device 102 to the location.

Figure 3A:
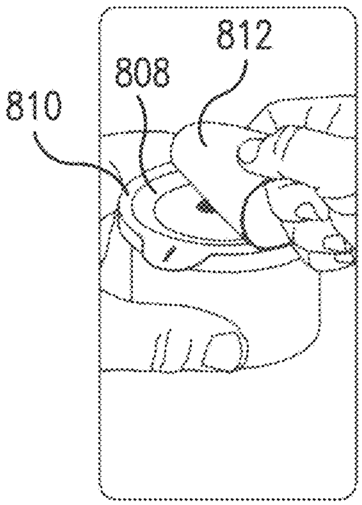
FIG. 3A is a proximal perspective view depicting an example embodiment of a user preparing a tray for an assembly.

FIG. 3A is a proximal perspective view depicting an example embodiment of a user preparing a container 810, configured here as a tray (although other packages can be used), for an assembly process. The user can accomplish this preparation by removing lid 812 from tray 810 to expose platform 808, for instance by peeling a non-adhered portion of lid 812 away from tray 810 such that adhered portions of lid 812 are removed. Removal of lid 812 can be appropriate in various embodiments so long as platform 808 is adequately exposed within tray 810. Lid 812 can then be placed aside.

Figure 3B:
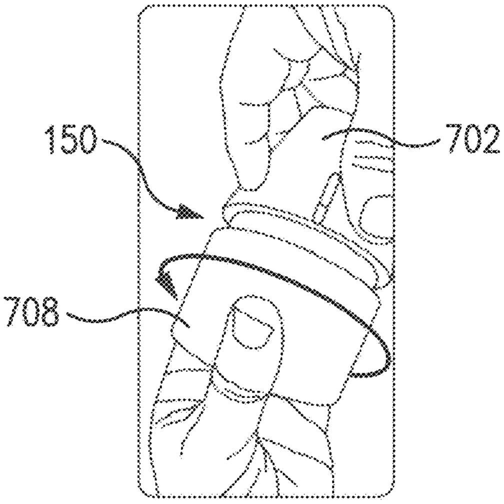
FIG. 3B is a side view depicting an example embodiment of a user preparing an applicator device for an assembly.
Figure 3C:
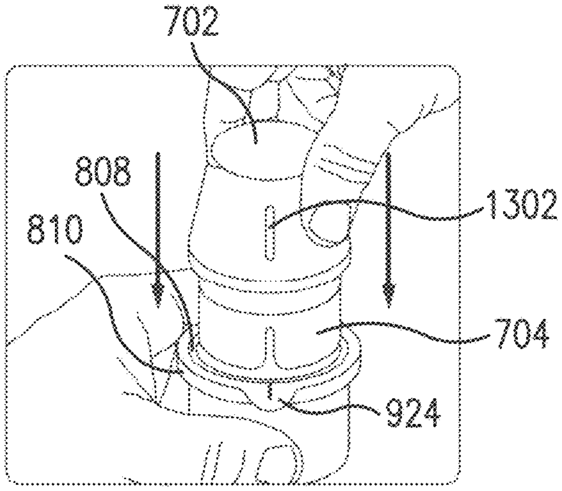
FIG. 3C is a proximal perspective view depicting an example embodiment of a user inserting an applicator device into a tray during an assembly.

FIG. 3B is a side view depicting an example embodiment of a user preparing an applicator device 150 for assembly. Applicator device 150 can be provided in a sterile package sealed by a cap 708. Preparation of applicator device 150 can include uncoupling housing 702 from cap 708 to expose sheath 704 (FIG. 3C). This can be accomplished by unscrewing (or otherwise uncoupling) cap 708 from housing 702. Cap 708 can then be placed aside.

FIG. 3C is a proximal perspective view depicting an example embodiment of a user inserting an applicator device 150 into a tray 810 during an assembly. Initially, the user can insert sheath 704 into platform 808 inside tray 810 after aligning housing orienting feature 1302 (or slot or recess) and tray orienting feature 924 (an abutment or detent). Inserting sheath 704 into platform 808 temporarily unlocks sheath 704 relative to housing 702 and also temporarily unlocks platform 808 relative to tray 810. At this stage, removal of applicator device 150 from tray 810 will result in the same state prior to initial insertion of applicator device 150 into tray 810 (i.e., the process can be reversed or aborted at this point and then repeated without consequence).

Sheath 704 can maintain position within platform 808 with respect to housing 702 while housing 702 is distally advanced, coupling with platform 808 to distally advance platform 808 with respect to tray 810. This step unlocks and collapses platform 808 within tray 810. Sheath 704 can contact and disengage locking features (not shown) within tray 810 that unlock sheath 704 with respect to housing 702 and prevent sheath 704 from moving (relatively) while housing 702 continues to distally advance platform 808. At the end of advancement of housing 702 and platform 808, sheath 704 is permanently unlocked relative to housing 702.

A sharp and sensor (not shown) within tray 810 can be coupled with an electronics housing (not shown) within housing 702 at the end of the distal advancement of housing 702. Operation and interaction of the applicator device 150 and tray 810 are further described below.

Figure 3D:
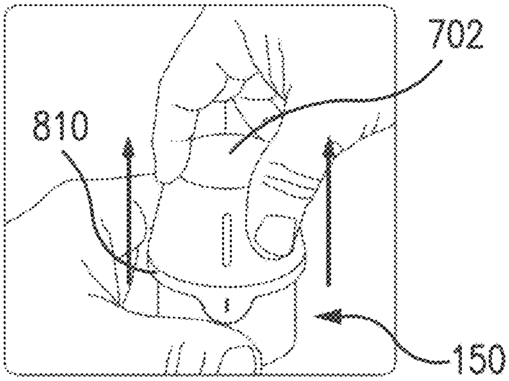
FIG. 3D is a proximal perspective view depicting an example embodiment of a user removing an applicator device from a tray during an assembly.
Figure 3E:
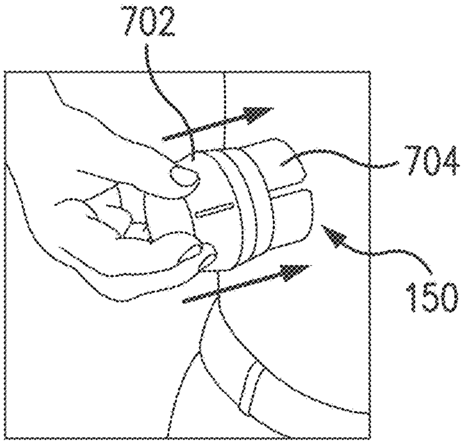
FIG. 3E is a proximal perspective view depicting an example embodiment of a patient applying a sensor using an applicator device.
Figure 3F:
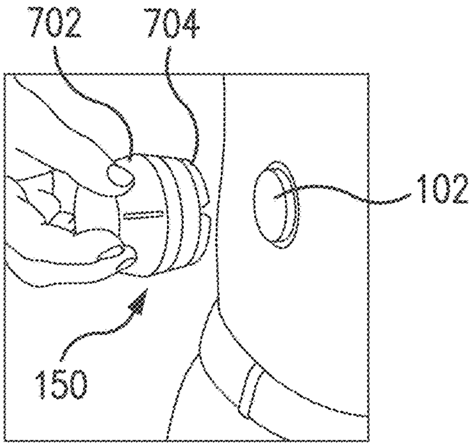
FIG. 3F is a proximal perspective view depicting an example embodiment of a patient with an applied sensor and a used applicator device.

FIG. 3D is a proximal perspective view depicting an example embodiment of a user removing an applicator device 150 from a tray 810 during an assembly. A user can remove applicator 150 from tray 810 by proximally advancing housing 702 with respect to tray 810 or other motions having the same end effect of uncoupling applicator 150 and tray 810. The applicator device 150 is removed with sensor control device 102 (not shown) fully assembled (sharp, sensor, electronics) therein and positioned for delivery.

FIG. 3E is a proximal perspective view depicting an example embodiment of a patient applying sensor control device 102 using applicator device 150 to a target area of skin, for instance, on an abdomen or other appropriate location. Advancing housing 702 distally collapses sheath 704 within housing 702 and applies the sensor to the target location such that an adhesive layer on the bottom side of sensor control device 102 adheres to the skin. The sharp is automatically retracted when housing 702 is fully advanced, while the sensor (not shown) is left in position to measure analyte levels.

FIG. 3F is a proximal perspective view depicting an example embodiment of a patient with sensor control device 102 in an applied position. The user can then remove applicator 150 from the application site.

System 100, described with respect to FIGS. 3A-3F and elsewhere herein, can provide a reduced or eliminated chance of accidental breakage, permanent deformation, or incorrect assembly of applicator components compared to prior art systems. Since applicator housing 702 directly engages platform 808 while sheath 704 unlocks, rather than indirect engagement via sheath 704, relative angularity between sheath 704 and housing 702 will not result in breakage or permanent deformation of the arms or other components. The potential for relatively high forces (such as in conventional devices) during assembly will be reduced, which in turn reduces the chance of unsuccessful user assembly.

F. Exemplary Sensor Applicator Devices

Figure 4C:
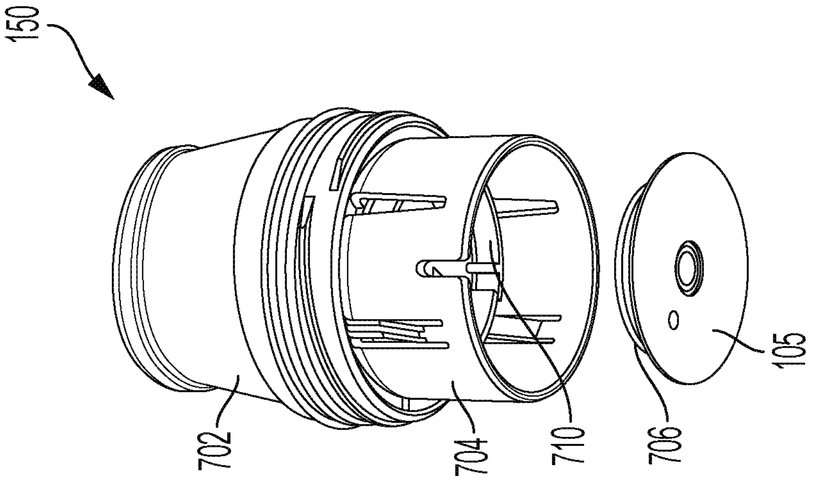
FIG. 4C is a perspective view depicting an example embodiment of a distal end of an applicator device and electronics housing.
Figure 4B:
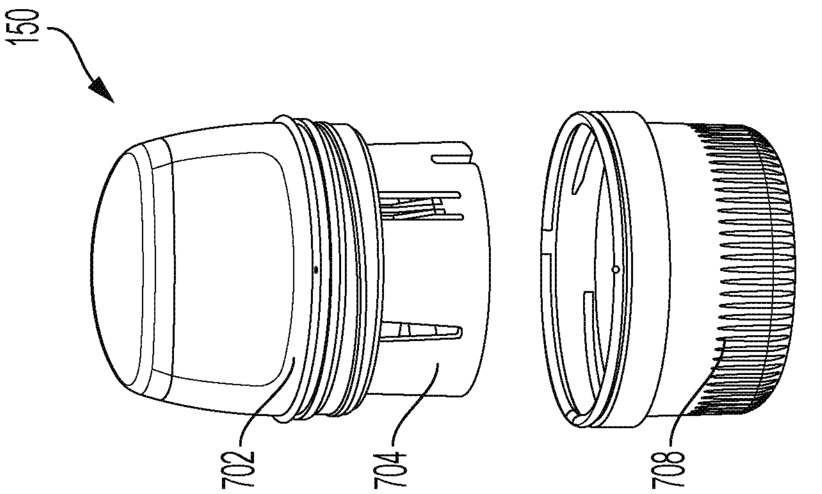
FIG. 4B is a side perspective view depicting an example embodiment of an applicator device and cap decoupled.
Figure 4A:
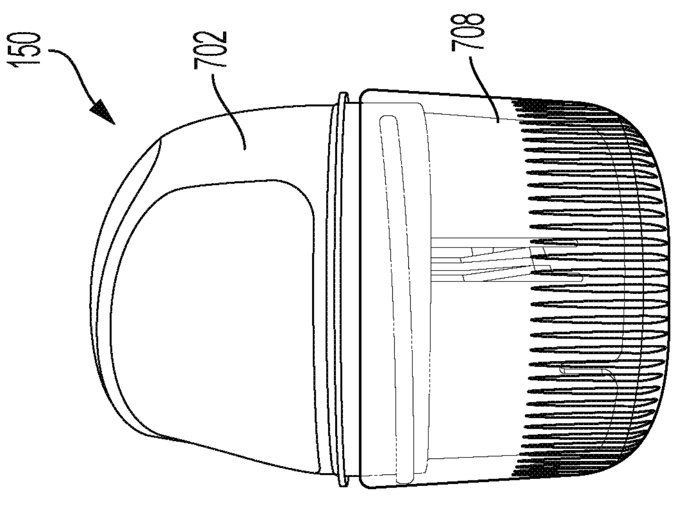
FIG. 4A is a side view depicting an example embodiment of an applicator device coupled with a cap.

FIG. 4A is a side view depicting an example embodiment of an applicator device 150 coupled with screw cap 708. This is an example of how applicator 150 is shipped to and received by a user, prior to assembly by the user with a sensor. FIG. 4B is a side perspective view depicting applicator 150 and cap 708 after being decoupled. FIG. 4C is a perspective view depicting an example embodiment of a distal end of an applicator device 150 with electronics housing 706 and adhesive patch 105 removed from the position they would have retained within sensor carrier 710 of sheath 704, when cap 708 is in place.

Figure 4E:
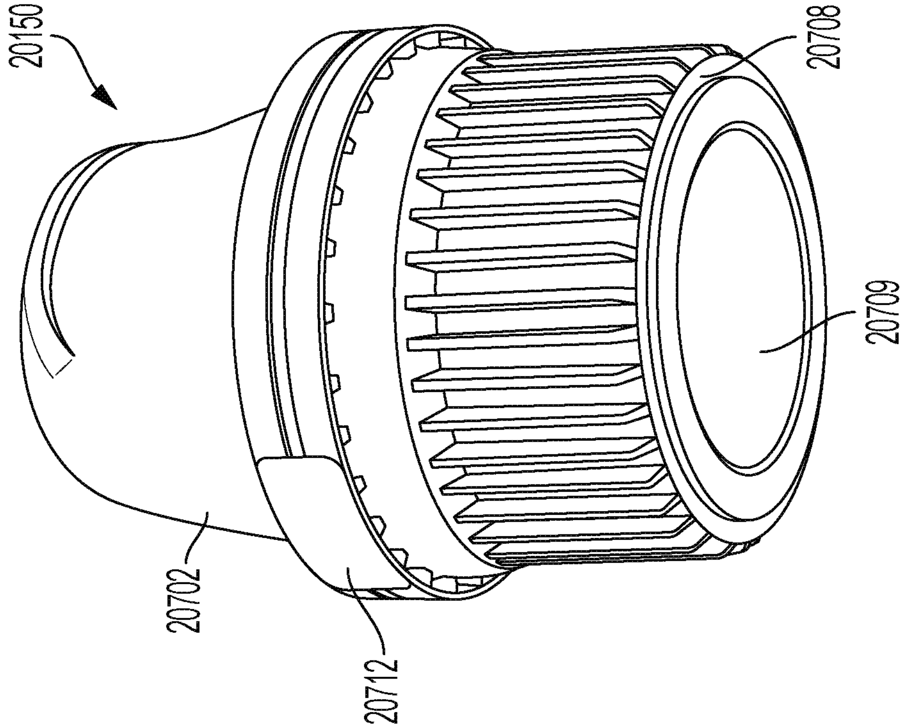
FIG. 4E is a bottom perspective view of the applicator device of FIG. 4D.
Figure 4D:
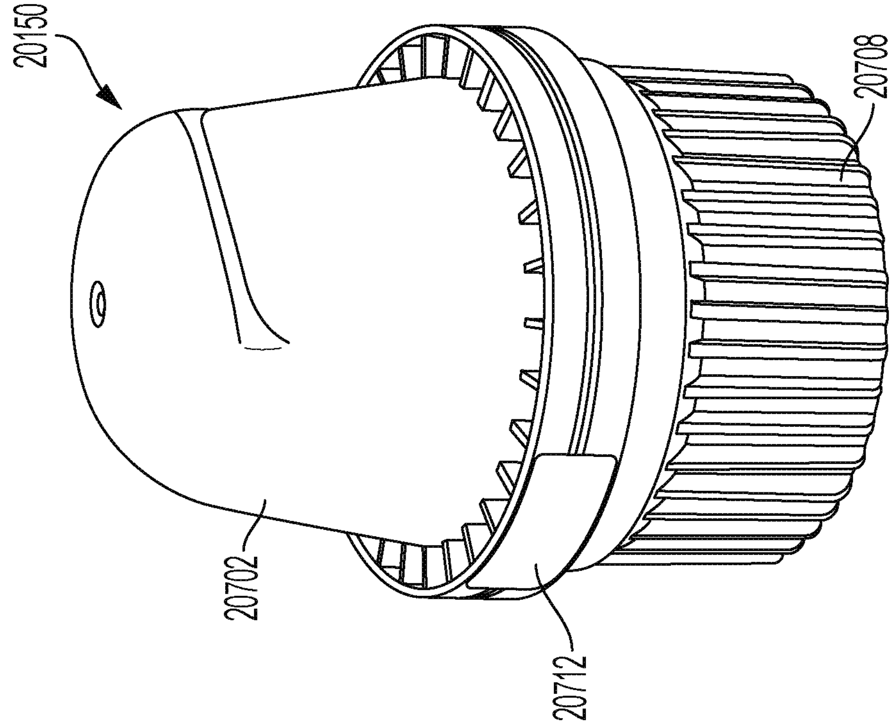
FIG. 4D is a top perspective view of an exemplary applicator device in accordance with the disclosed subject matter.
Figure 4F:
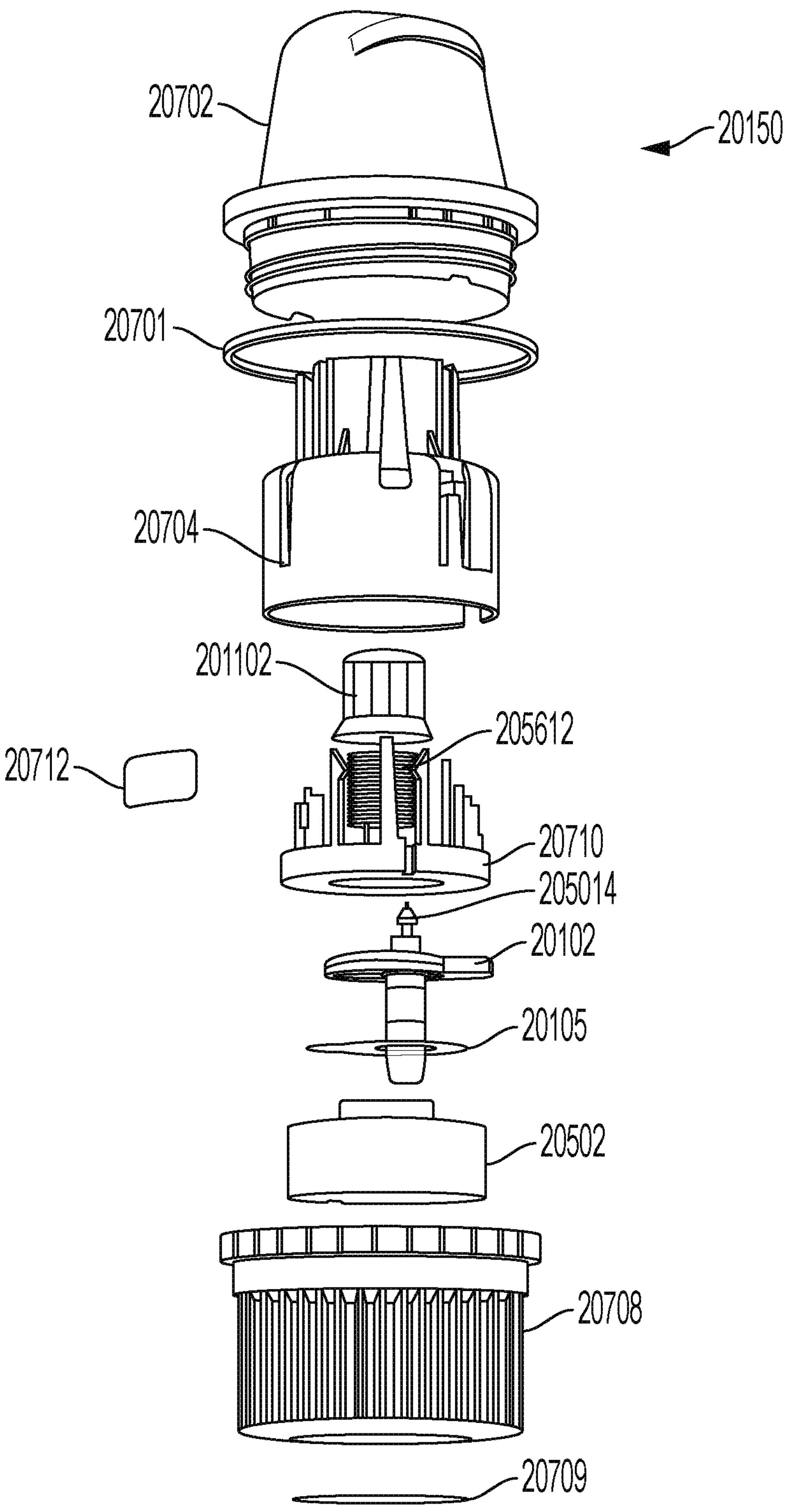
FIG. 4F is an exploded view of the applicator device of FIG. 4D.
Figure 4G:
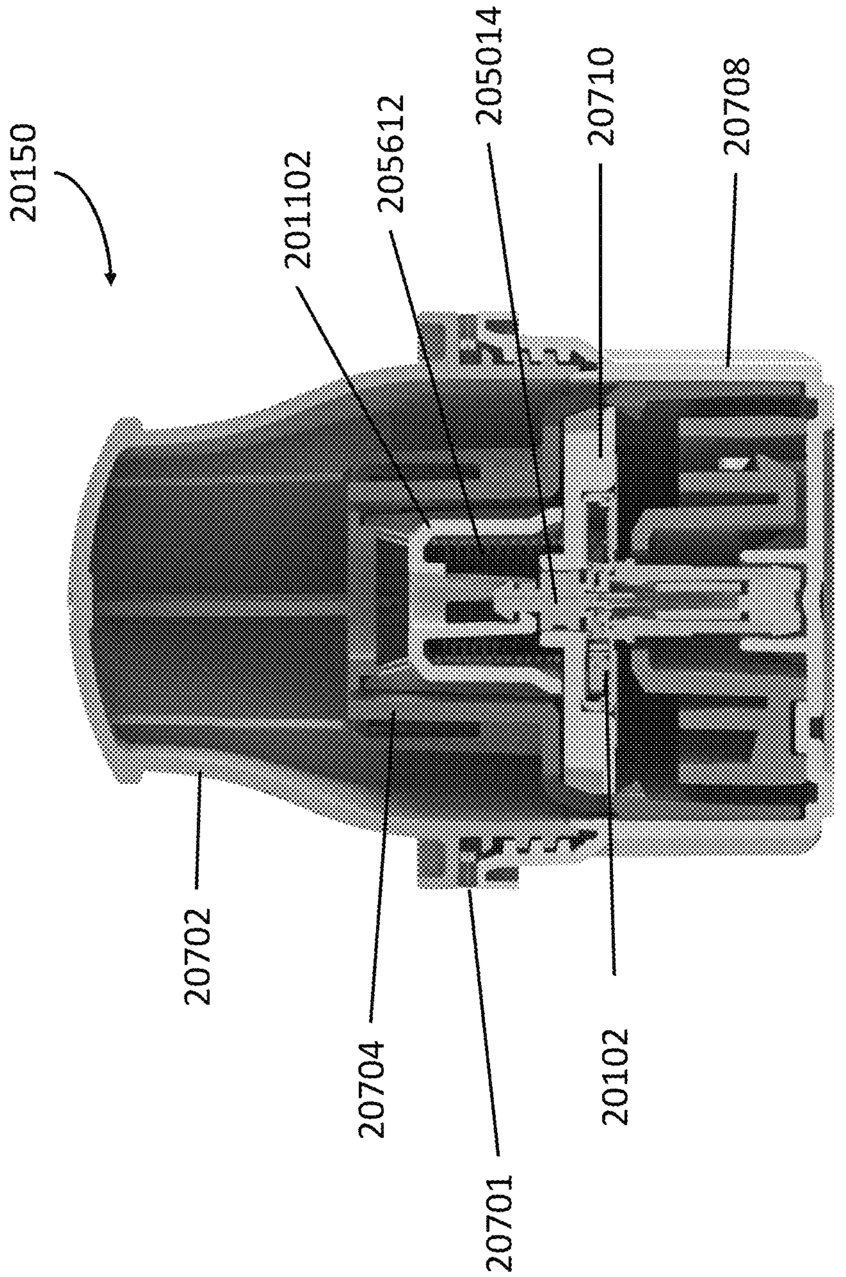
FIG. 4G is a side cutaway view of the applicator device of FIG. 4D.

Referring to FIG. 4D-G for purpose of illustration and not limitation, the applicator device 20150 can be provided to a user as a single integrated assembly. FIGS. 4D and 4E provide perspective top and bottom views, respectively, of the applicator device 20150, FIG. 4F provides an exploded view of the applicator device 20150 and FIG. 4G provides a side cut-away view. The perspective views illustrate how applicator 20150 is shipped to and received by a user. The exploded and cut-away views illustrate the components of the applicator device 20150. The applicator device 20150 can include a housing 20702, gasket 20701, sheath 20704, sharp carrier 201102, spring 205612, sensor carrier 20710 (also referred to as a "puck carrier"), sharp hub 205014, sensor control device (also referred to as a "puck") 20102, adhesive patch 20105, desiccant 20502, cap 20708, serial label 20709, and tamper evidence feature 20712. As received by a user, only the housing 20702, cap 20708, tamper evidence feature 20712, and label 20709 are visible. The tamper evidence feature 20712 can be, for example, a sticker coupled to each of the housing 20702 and the cap 20708, and tamper evidence feature 20712 can be damaged, for example, irreparably, by uncoupling housing 20702 and cap 20708, thereby indicating to a user that the housing 20702 and cap 20708 have been previously uncoupled. These features are described in greater detail below.

G. Exemplary Tray and Sensor Module Assembly

Figure 5:
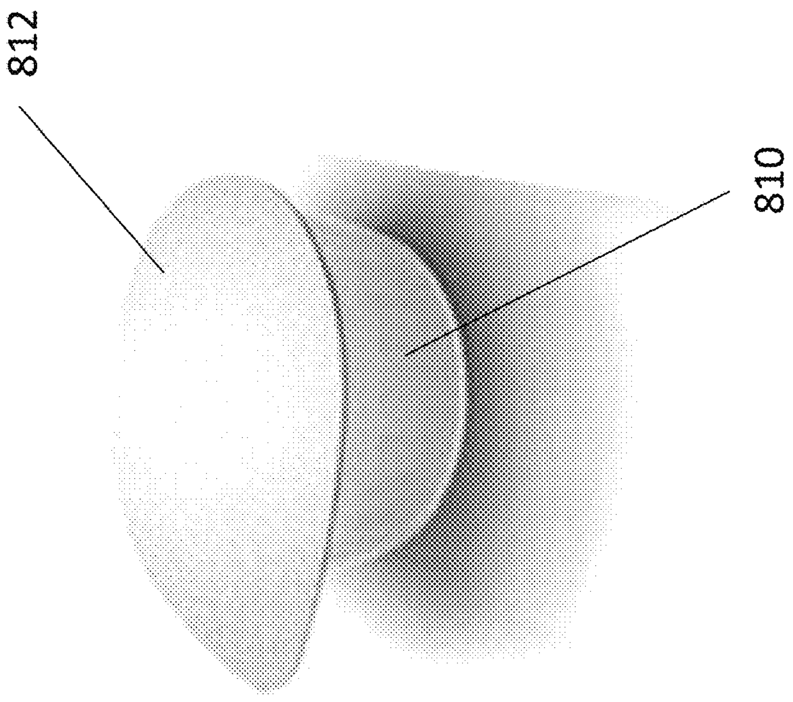
FIG. 5 is a proximal perspective view depicting an example embodiment of a tray with sterilization lid coupled.

FIG. 5 is a proximal perspective view depicting an example embodiment of a tray 810 with sterilization lid 812 removably coupled thereto, which may be representative of how the package is shipped to and received by a user prior to assembly.

Figure 6A:
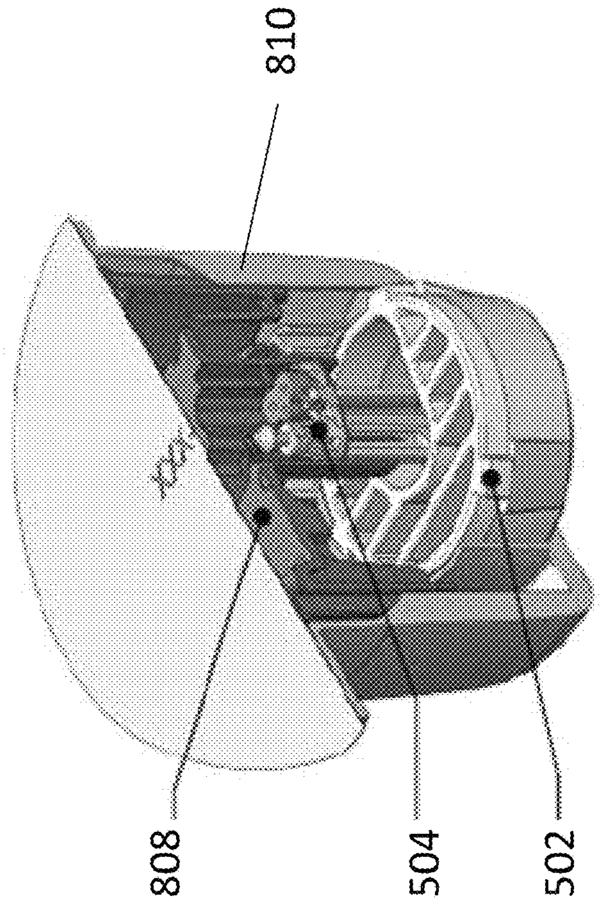
FIG. 6A is a proximal perspective cutaway view depicting an example embodiment of a tray with sensor delivery components.

FIG. 6A is a proximal perspective cutaway view depicting sensor delivery components within tray 810. Platform 808 is slidably coupled within tray 810. Desiccant 502 is stationary with respect to tray 810. Sensor module 504 is mounted within tray 810.

Figure 6B:
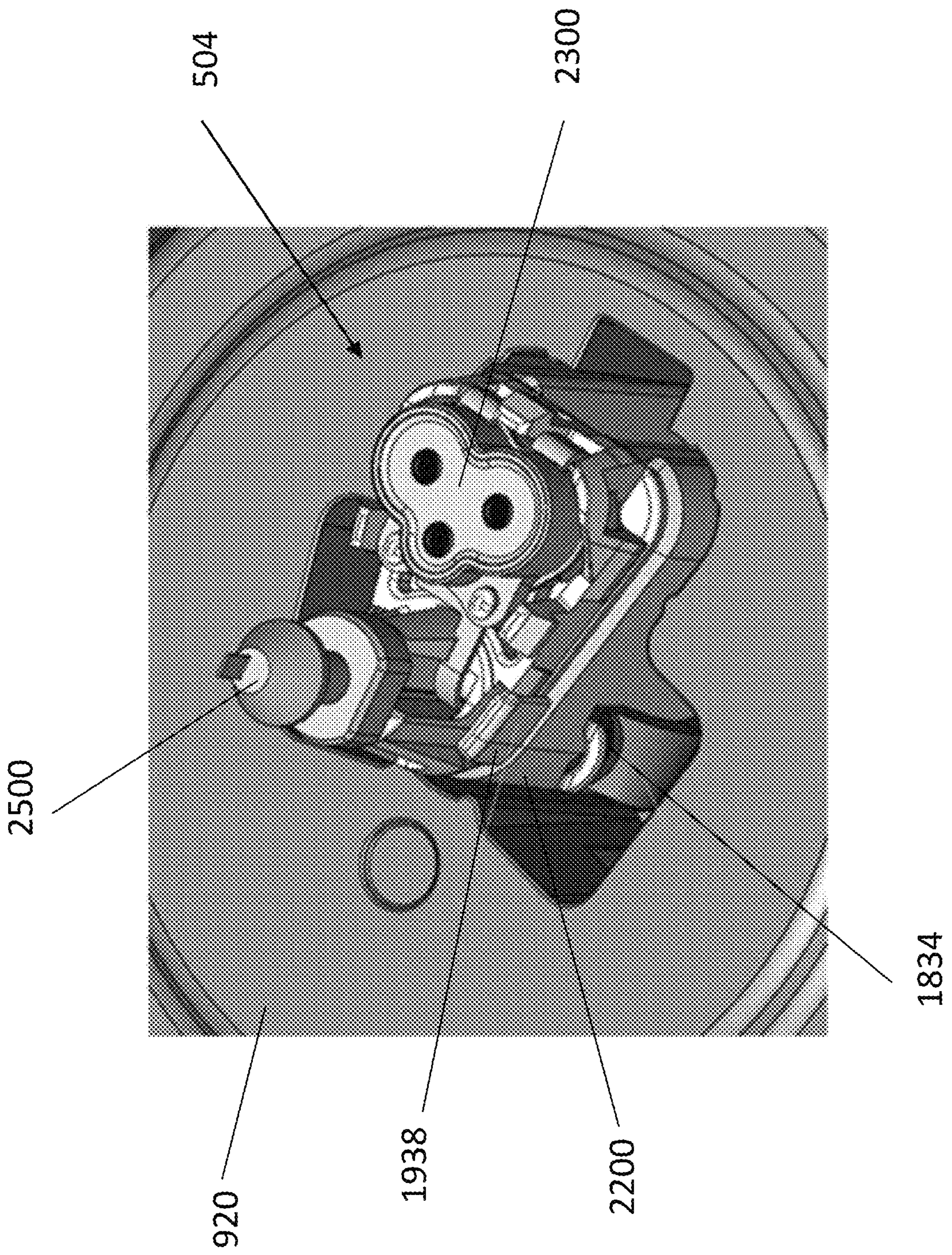
FIG. 6B is a proximal perspective view depicting sensor delivery components.

FIG. 6B is a proximal perspective view depicting sensor module 504 in greater detail. Here, retention arm extensions 1834 of platform 808 releasably secure sensor module 504 in position. Module 2200 is coupled with connector 2300, sharp module 2500 and sensor (not shown) such that during assembly they can be removed together as sensor module 504.

H. Exemplary Applicators and Sensor Control Devices for One Piece Architectures

Referring briefly again to FIGS. 1A and 3A-3G, for the two-piece architecture system, the sensor tray 202 and the sensor applicator 102 are provided to the user as separate packages, thus requiring the user to open each package and finally assemble the system. In some applications, the discrete, sealed packages allow the sensor tray 202 and the sensor applicator 102 to be sterilized in separate sterilization processes unique to the contents of each package and otherwise incompatible with the contents of the other. More specifically, the sensor tray 202, which includes the plug assembly 207, including the sensor 110 and the sharp 220, may be sterilized using radiation sterilization, such as electron beam (or "e-beam") irradiation. Suitable radiation sterilization processes include, but are not limited to, electron beam (e-beam) irradiation, gamma ray irradiation, X-ray irradiation, or any combination thereof. Radiation sterilization, however, can damage the electrical components arranged within the electronics housing of the sensor control device 102. Consequently, if the sensor applicator 102, which contains the electronics housing of the sensor control device 102, needs to be sterilized, it may be sterilized via another method, such as gaseous chemical sterilization using, for example, ethylene oxide. Gaseous chemical sterilization, however, can damage the enzymes or other chemistry and biologics included on the sensor 110. Because of this sterilization incompatibility, the sensor tray 202 and the sensor applicator 102 are commonly sterilized in separate sterilization processes and subsequently packaged separately, which requires the user to finally assemble the components for use.

Figure 7A:
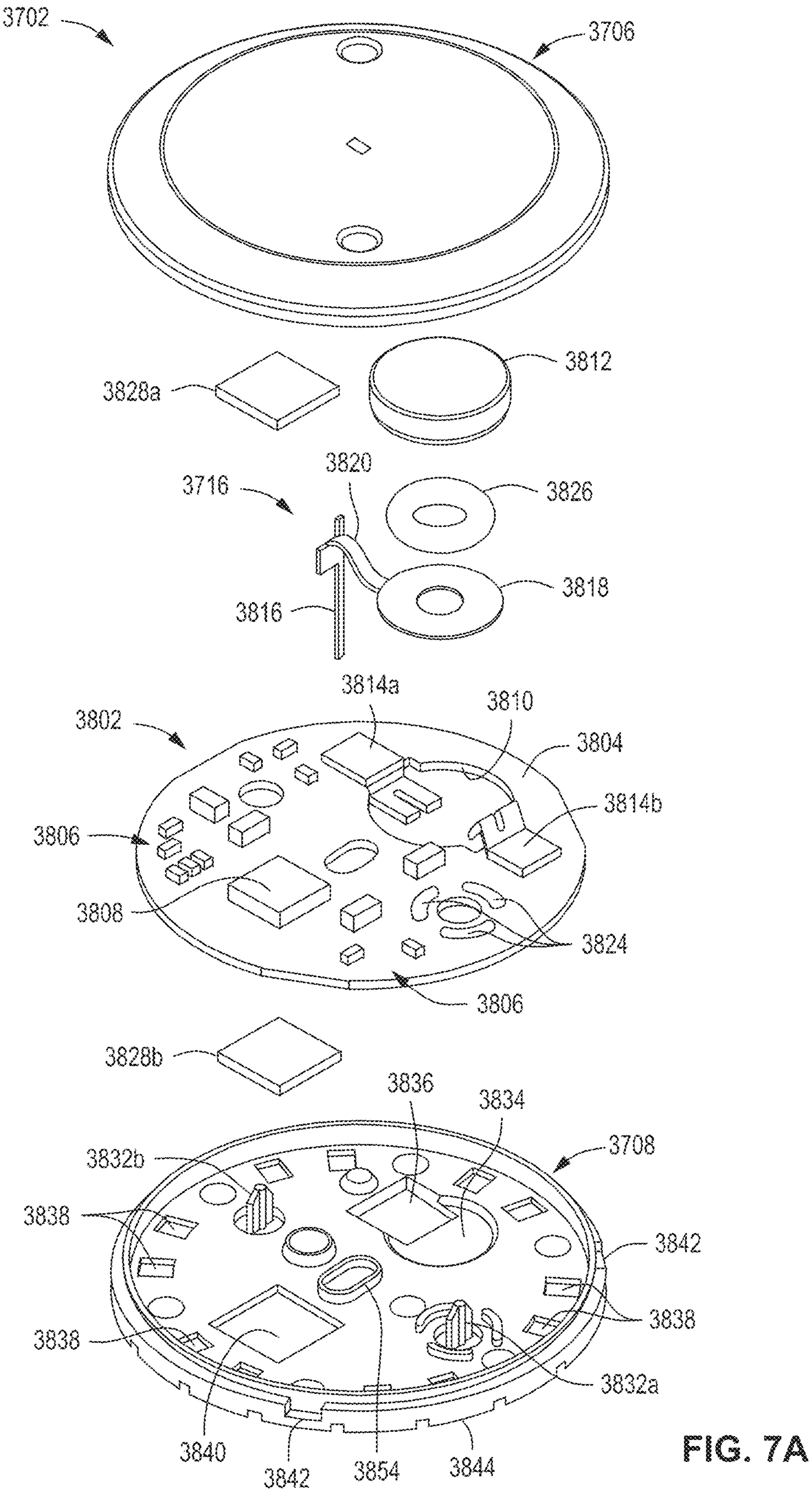
FIGS. 7A and 7B are isometric exploded top and bottom views, respectively, of an exemplary sensor control device.
Figure 7B:
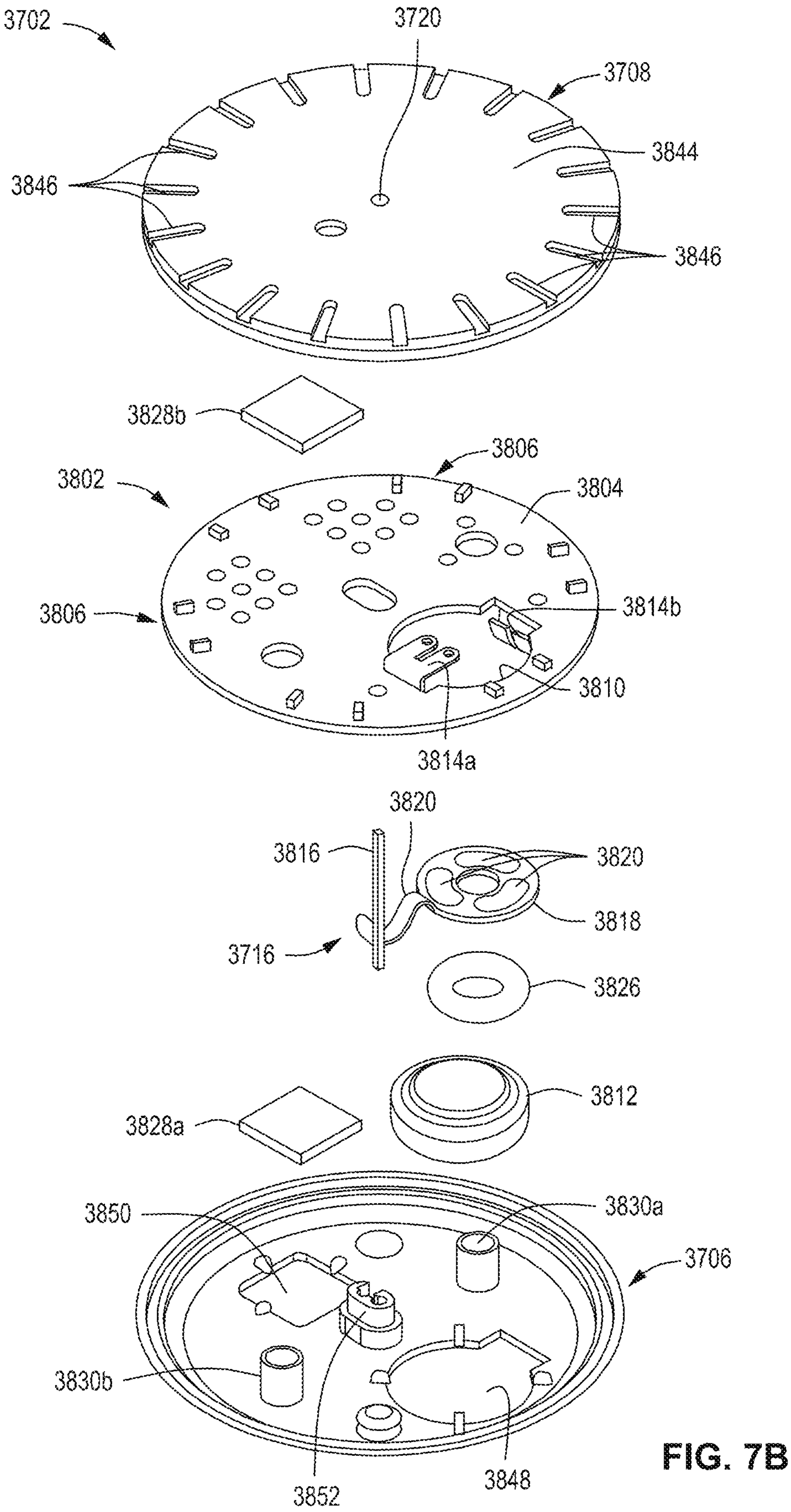

FIGS. 7A and 7B are exploded top and bottom views, respectively, of the sensor control device 3702, according to one or more embodiments. The shell 3706 and the mount 3708 operate as opposing clamshell halves that enclose or otherwise substantially encapsulate the various electronic components of the sensor control device 3702. As illustrated, the sensor control device 3702 may include a printed circuit board assembly (PCBA) 3802 that includes a printed circuit board (PCB) 3804 having a plurality of electronic modules 3806 coupled thereto. Example electronic modules 3806 include, but are not limited to, resistors, transistors, capacitors, inductors, diodes, and switches. Prior sensor control devices commonly stack PCB components on only one side of the PCB. In contrast, the PCB components 3806 in the sensor control device 3702 can be dispersed about the surface area of both sides (i.e., top and bottom surfaces) of the PCB 3804.

Besides the electronic modules 3806, the PCBA 3802 may also include a data processing unit 3808 mounted to the PCB 3804. The data processing unit 3808 may comprise, for example, an application specific integrated circuit (ASIC) configured to implement one or more functions or routines associated with operation of the sensor control device 3702. More specifically, the data processing unit 3808 may be configured to perform data processing functions, where such functions may include but are not limited to, filtering and encoding of data signals, each of which corresponds to a sampled analyte level of the user. The data processing unit 3808 may also include or otherwise communicate with an antenna for communicating with the reader device 106 (FIG. 1A).

A battery aperture 3810 may be defined in the PCB 3804 and sized to receive and seat a battery 3812 configured to power the sensor control device 3702. An axial battery contact 3814*a* and a radial battery contact 3814*b* may be coupled to the PCB 3804 and extend into the battery aperture 3810 to facilitate transmission of electrical power from the battery 3812 to the PCB 3804. As their names suggest, the axial battery contact 3814*a* may be configured to provide an axial contact for the battery 3812, while the radial battery contact 3814*b* may provide a radial contact for the battery 3812. Locating the battery 3812 within the battery aperture 3810 with the battery contacts 3814*a,b* helps reduce the height H of the sensor control device 3702, which allows the PCB 3804 to be located centrally and its components to be dispersed on both sides (i.e., top and bottom surfaces). This also helps facilitate the chamfer 3718 provided on the electronics housing 3704.

The sensor 3716 may be centrally located relative to the PCB 3804 and include a tail 3816, a flag 3818, and a neck 3820 that interconnects the tail 3816 and the flag 3818. The tail 3816 may be configured to extend through the central aperture 3720 of the mount 3708 to be transcutaneously received beneath a user's skin. Moreover, the tail 3816 may have an enzyme or other chemistry included thereon to help facilitate analyte monitoring.

The flag 3818 may include a generally planar surface having one or more sensor contacts 3822 (three shown in FIG. 7B) arranged thereon. The sensor contact(s) 3822 may be configured to align with and engage a corresponding one or more circuitry contacts 3824 (three shown in FIG. 7A) provided on the PCB 3804. In some embodiments, the sensor contact(s) 3822 may comprise a carbon impregnated polymer printed or otherwise digitally applied to the flag 3818. Prior sensor control devices typically include a connector made of silicone rubber that encapsulates one or more compliant carbon impregnated polymer modules that serve as electrical conductive contacts between the sensor and the PCB. In contrast, the presently disclosed sensor contacts(s) 3822 provide a direct connection between the sensor 3716 and the PCB 3804 connection, which eliminates the need for the prior art connector and advantageously reduces the height H. Moreover, eliminating the compliant carbon impregnated polymer modules eliminates a significant circuit resistance and therefor improves circuit conductivity.

The sensor control device 3702 may further include a compliant member 3826, which may be arranged to interpose the flag 3818 and the inner surface of the shell 3706. More specifically, when the shell 3706 and the mount 3708 are assembled to one another, the compliant member 3826 may be configured to provide a passive biasing load against the flag 3818 that forces the sensor contact(s) 3822 into continuous engagement with the corresponding circuitry contact(s) 3824. In the illustrated embodiment, the compliant member 3826 is an elastomeric O-ring, but could alternatively comprise any other type of biasing device or mechanism, such as a compression spring or the like, without departing from the scope of the disclosure.

The sensor control device 3702 may further include one or more electromagnetic shields, shown as a first shield 3828*a* and a second shield The shell 3706 may provide or otherwise define a first clocking receptacle 3830*a* (FIG. 7B) and a second clocking receptacle 3830*b* (FIG. 7B), and the mount 3708 may provide or otherwise define a first clocking post 3832*a* (FIG. 7A) and a second clocking post 3832*b* (FIG. 7A). Mating the first and second clocking receptacles 3830*a,b* with the first and second clocking posts 3832*a,b*, respectively, will properly align the shell 3706 to the mount 3708.

Referring specifically to FIG. 7A, the inner surface of the mount 3708 may provide or otherwise define a plurality of pockets or depressions configured to accommodate various component parts of the sensor control device 3702 when the shell 3706 is mated to the mount 3708. For example, the inner surface of the mount 3708 may define a battery locator 3834 configured to accommodate a portion of the battery 3812 when the sensor control device 3702 is assembled. An adjacent contact pocket 3836 may be configured to accommodate a portion of the axial contact 3814*a*.

Moreover, a plurality of module pockets 3838 may be defined in the inner surface of the mount 3708 to accommodate the various electronic modules 3806 arranged on the bottom of the PCB 3804. Furthermore, a shield locator 3840 may be defined in the inner surface of the mount 3708 to accommodate at least a portion of the second shield 3828*b* when the sensor control device 3702 is assembled. The battery locator 3834, the contact pocket 3836, the module pockets 3838, and the shield locator 3840 all extend a short distance into the inner surface of the mount 3708 and, as a result, the overall height H of the sensor control device 3702 may be reduced as compared to prior sensor control devices. The module pockets 3838 may also help minimize the diameter of the PCB 3804 by allowing PCB components to be arranged on both sides (i.e., top and bottom surfaces).

Still referring to FIG. 7A, the mount 3708 may further include a plurality of carrier grip features 3842 (two shown) defined about the outer periphery of the mount 3708. The carrier grip features 3842 are axially offset from the bottom 3844 of the mount 3708, where a transfer adhesive (not shown) may be applied during assembly. In contrast to prior sensor control devices, which commonly include conical carrier grip features that intersect with the bottom of the mount, the presently disclosed carrier grip features 3842 are offset from the plane (i.e., the bottom 3844) where the transfer adhesive is applied. This may prove advantageous in helping ensure that the delivery system does not inadvertently stick to the transfer adhesive during assembly. Moreover, the presently disclosed carrier grip features 3842 eliminate the need for a scalloped transfer adhesive, which simplifies the manufacture of the transfer adhesive and eliminates the need to accurately clock the transfer adhesive relative to the mount 3708. This also increases the bond area and, therefore, the bond strength.

Referring to FIG. 7B, the bottom 3844 of the mount 3708 may provide or otherwise define a plurality of grooves 3846, which may be defined at or near the outer periphery of the mount 3708 and equidistantly spaced from each other. A transfer adhesive (not shown) may be coupled to the bottom 3844 and the grooves 3846 may be configured to help convey (transfer) moisture away from the sensor control device 3702 and toward the periphery of the mount 3708 during use. In some embodiments, the spacing of the grooves 3846 may interpose the module pockets 3838 (FIG. 7A) defined on the opposing side (inner surface) of the mount 3708. As will be appreciated, alternating the position of the grooves 3846 and the module pockets 3838 ensures that the opposing features on either side of the mount 3708 do not extend into each other. This may help maximize usage of the material for the mount 3708 and thereby help maintain a minimal height H of the sensor control device 3702. The module pockets 3838 may also significantly reduce mold sink, and improve the flatness of the bottom 3844 that the transfer adhesive bonds to.

Still referring to FIG. 7B, the inner surface of the shell 3706 may also provide or otherwise define a plurality of pockets or depressions configured to accommodate various component parts of the sensor control device 3702 when the shell 3706 is mated to the mount 3708. For example, the inner surface of the shell 3706 may define an opposing battery locator 3848 arrangeable opposite the battery locator 3834 (FIG. 7A) of the mount 3708 and configured to accommodate a portion of the battery 3812 when the sensor control device 3702 is assembled. The opposing battery locator 3848 extends a short distance into the inner surface of the shell 3706, which helps reduce the overall height H of the sensor control device 3702.

A sharp and sensor locator 3852 may also be provided by or otherwise defined on the inner surface of the shell 3706. The sharp and sensor locator 3852 may be configured to receive both the sharp (not shown) and a portion of the sensor 3716. Moreover, the sharp and sensor locator 3852 may be configured to align and/or mate with a corresponding sharp and sensor locator 2054 (FIG. 7A) provided on the inner surface of the mount 3708.

Figure 8A:
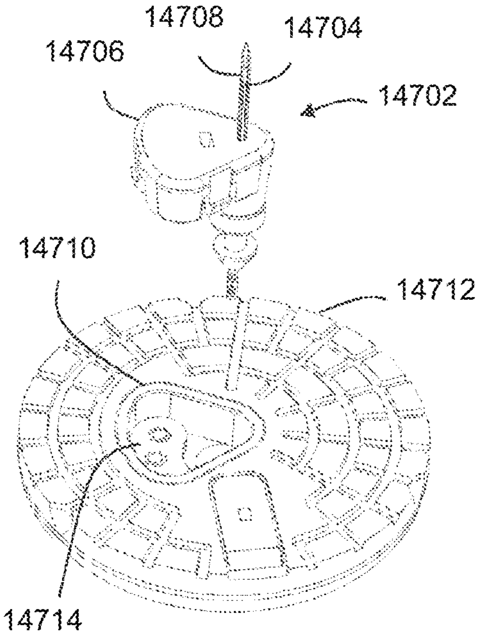
FIG. 8A-8C are assembly and cross-sectional views of an on-body device including an integrated connector for the sensor assembly.
Figure 8B:
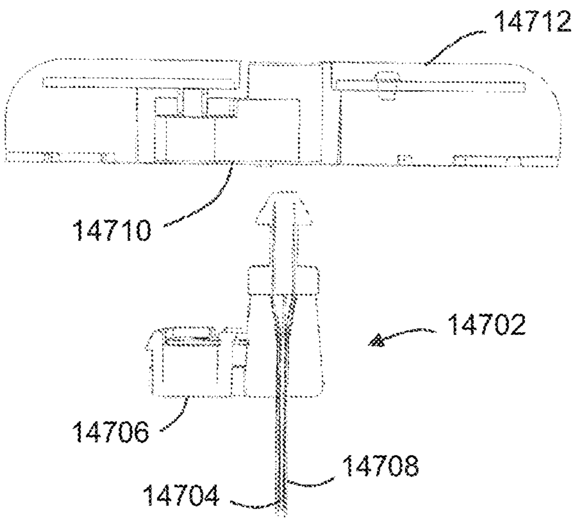
Figure 8C:
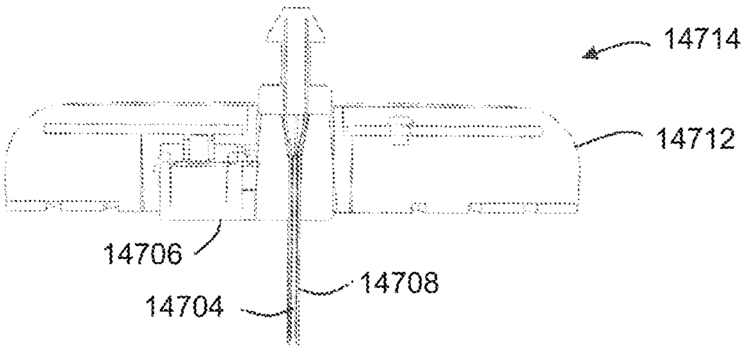

According to embodiments of the present disclosure, an alternative sensor assembly/electronics assembly connection approach is illustrated in FIGS. 8A to 8C. As shown, the sensor assembly 14702 includes sensor 14704, connector support 14706, and sharp 14708. Notably, a recess or receptacle 14710 may be defined in the bottom of the mount of the electronics assembly 14712 and provide a location where the sensor assembly 14702 may be received and coupled to the electronics assembly 14712, and thereby fully assemble the sensor control device. The profile of the sensor assembly 14702 may match or be shaped in complementary fashion to the receptacle 14710, which includes an elastomeric sealing member 14714 (including conductive material coupled to the circuit board and aligned with the electrical contacts of the sensor 14704). Thus, when the sensor assembly 14702 is snap fit or otherwise adhered to the electronics assembly 14712 by driving the sensor assembly 14702 into the integrally formed recess 14710 in the electronics assembly 14712, the on-body device 14714 depicted in FIG. 8C is formed. This embodiment provides an integrated connector for the sensor assembly 14702 within the electronics assembly 14712.

Additional information regarding sensor assemblies is provided in U.S. Publication No. 2013/0150691 and U.S. Publication No. 2021/0204841, each of which is incorporated by reference herein in its entirety.

According to embodiments of the present disclosure, the sensor control device 102 may be modified to provide a one-piece architecture that may be subjected to sterilization techniques specifically designed for a one-piece architecture sensor control device. A one-piece architecture allows the sensor applicator 150 and the sensor control device 102 to be shipped to the user in a single, sealed package that does not require any final user assembly steps. Rather, the user need only open one package and subsequently deliver the sensor control device 102 to the target monitoring location. The one-piece system architecture described herein may prove advantageous in eliminating component parts, various fabrication process steps, and user assembly steps. As a result, packaging and waste are reduced, and the potential for user error or contamination to the system is mitigated.

Figure 9B:
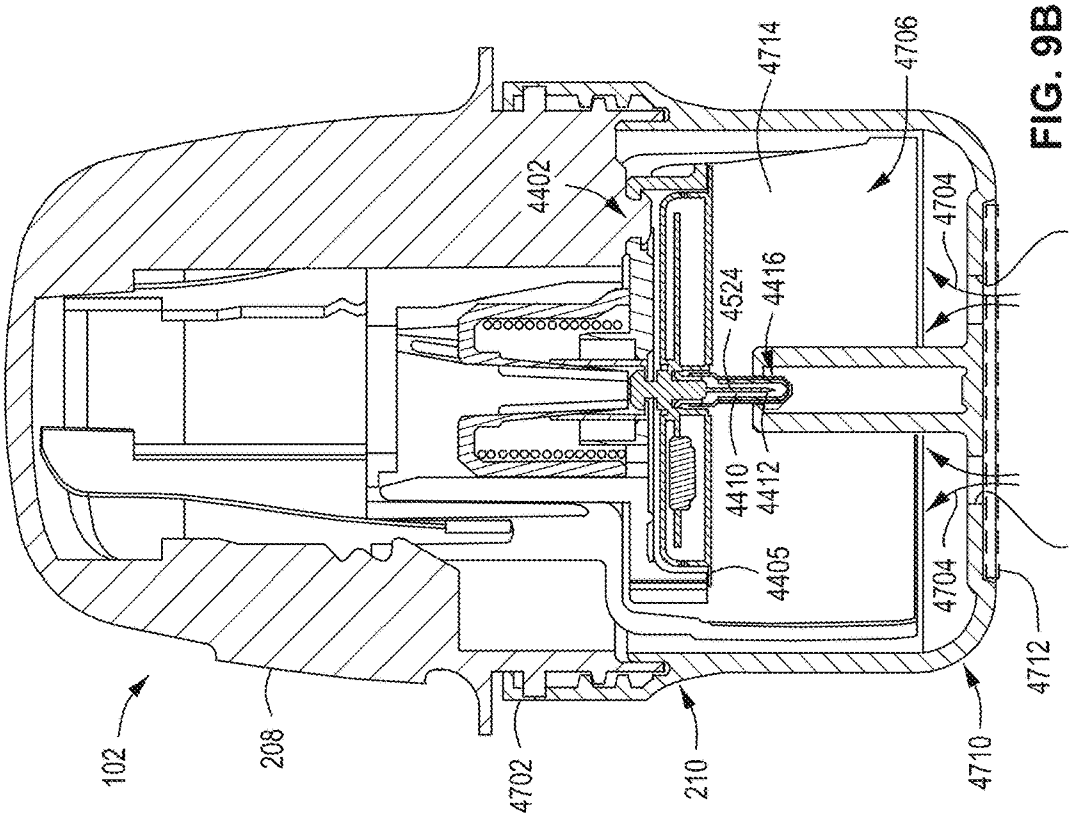
FIGS. 9A and 9B are side and cross-sectional side views, respectively, of an example embodiment of the sensor applicator of FIG. 1A with the cap of FIG. 2C coupled thereto.
Figure 9A:
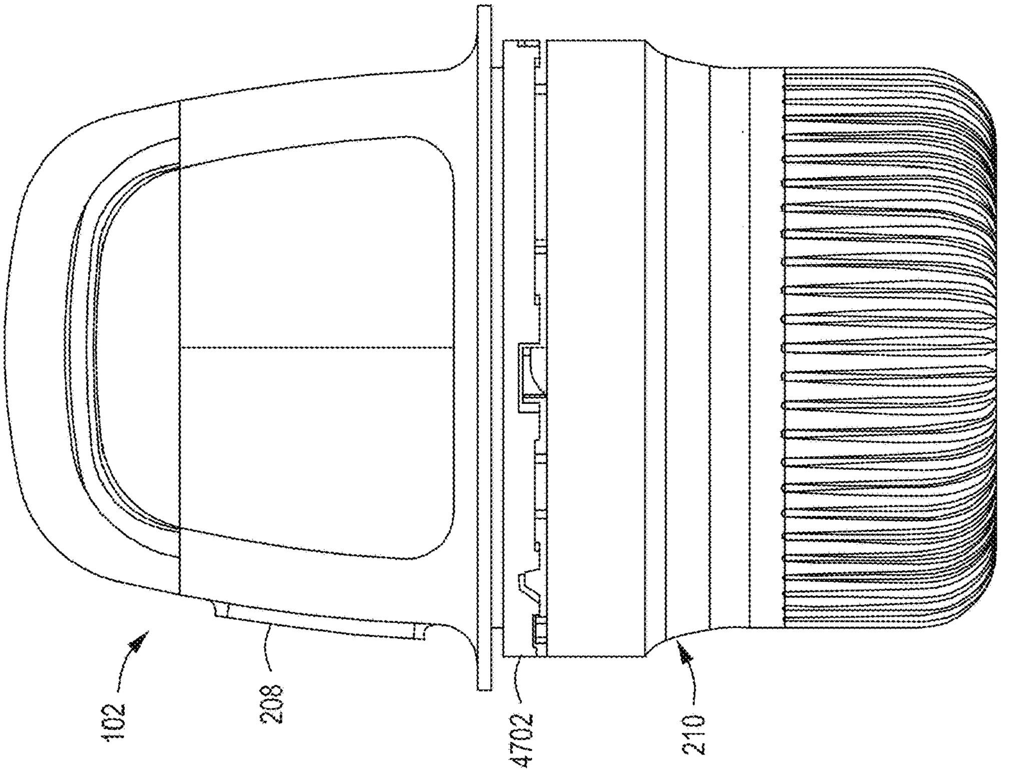

FIGS. 9A and 9B are side and cross-sectional side views, respectively, of an example embodiment of the sensor applicator 102 with the applicator cap 210 coupled thereto. More specifically, FIG. 9A depicts how the sensor applicator 102 might be shipped to and received by a user, and FIG. 9B depicts the sensor control device 4402 arranged within the sensor applicator 102. Accordingly, the fully assembled sensor control device 4402 may already be assembled and installed within the sensor applicator 102 prior to being delivered to the user, thus removing any additional assembly steps that a user would otherwise have to perform.

The fully assembled sensor control device 4402 may be loaded into the sensor applicator 102, and the applicator cap 210 may subsequently be coupled to the sensor applicator 102. In some embodiments, the applicator cap 210 may be threaded to the housing 208 and include a tamper ring 4702. Upon rotating (e.g., unscrewing) the applicator cap 210 relative to the housing 208, the tamper ring 4702 may shear and thereby free the applicator cap 210 from the sensor applicator 102.

According to the present disclosure, while loaded in the sensor applicator 102, the sensor control device 4402 may be subjected to gaseous chemical sterilization 4704 configured to sterilize the electronics housing 4404 and any other exposed portions of the sensor control device 4402. To accomplish this, a chemical may be injected into a sterilization chamber 4706 cooperatively defined by the sensor applicator 102 and the interconnected cap 210. In some applications, the chemical may be injected into the sterilization chamber 4706 via one or more vents 4708 defined in the applicator cap 210 at its proximal end 610. Example chemicals that may be used for the gaseous chemical sterilization 4704 include, but are not limited to, ethylene oxide, vaporized hydrogen peroxide, nitrogen oxide (e.g., nitrous oxide, nitrogen dioxide, etc.), and steam.

Since the distal portions of the sensor 4410 and the sharp 4412 are sealed within the sensor cap 4416, the chemicals used during the gaseous chemical sterilization process do not interact with the enzymes, chemistry, and biologics provided on the tail 4524 and other sensor components, such as membrane coatings that regulate analyte influx.

Once a desired sterility assurance level has been achieved within the sterilization chamber 4706, the gaseous solution may be removed and the sterilization chamber 4706 may be aerated. Aeration may be achieved by a series of vacuums and subsequently circulating a gas (e.g., nitrogen) or filtered air through the sterilization chamber 4706. Once the sterilization chamber 4706 is properly aerated, the vents 4708 may be occluded with a seal 4712 (shown in dashed lines).

In some embodiments, the seal 4712 may comprise two or more layers of different materials. The first layer may be made of a synthetic material (e.g., a flash-spun high-density polyethylene fiber), such as Tyvek® available from DuPont®. Tyvek® is highly durable and puncture resistant and allows the permeation of vapors. The Tyvek® layer can be applied before the gaseous chemical sterilization process, and following the gaseous chemical sterilization process, a foil or other vapor and moisture resistant material layer may be sealed (e.g., heat sealed) over the Tyvek® layer to prevent the ingress of contaminants and moisture into the sterilization chamber 4706. In other embodiments, the seal 4712 may comprise only a single protective layer applied to the applicator cap 210. In such embodiments, the single layer may be gas permeable for the sterilization process, but may also be capable of protection against moisture and other harmful elements once the sterilization process is complete.

With the seal 4712 in place, the applicator cap 210 provides a barrier against outside contamination, and thereby maintains a sterile environment for the assembled sensor control device 4402 until the user removes (unthreads) the applicator cap 210. The applicator cap 210 may also create a dust-free environment during shipping and storage that prevents the adhesive patch 4714 from becoming dirty.

Figure 10A:
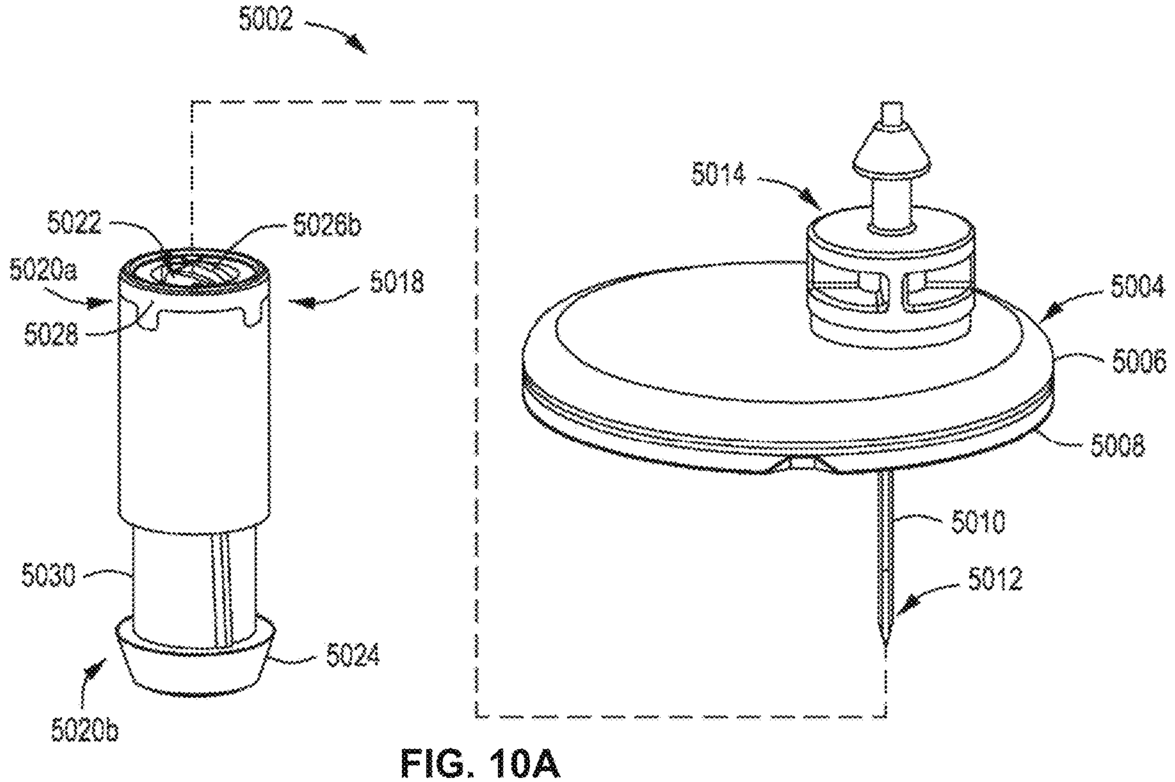
FIGS. 10A and 10B are isometric and side views, respectively, of another example sensor control device.
Figure 10B:
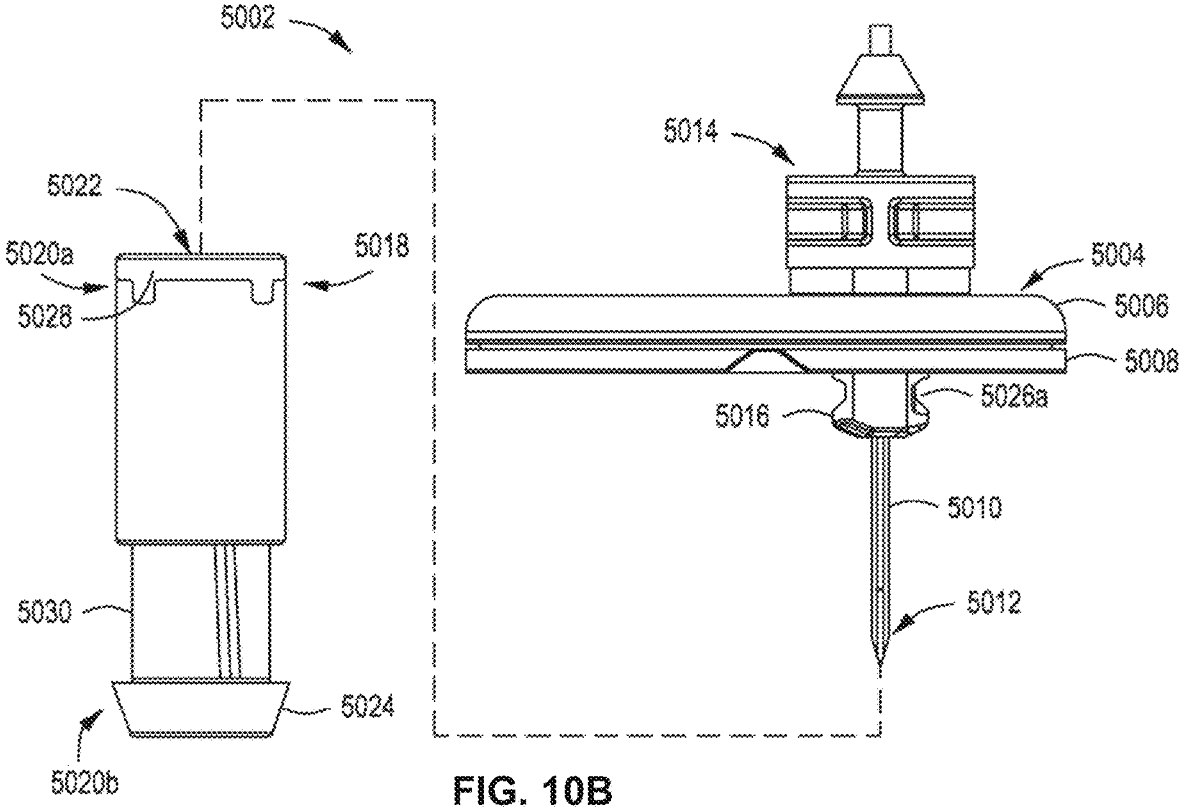

FIGS. 10A and 10B are isometric and side views, respectively, of another example sensor control device 5002, according to one or more embodiments of the present disclosure. The sensor control device 5002 may be similar in some respects to the sensor control device 102 of FIG. 1A and therefore may be best understood with reference thereto. Moreover, the sensor control device 5002 may replace the sensor control device 102 of FIG. 1A and, therefore, may be used in conjunction with the sensor applicator 102 of FIG. 1A, which may deliver the sensor control device 5002 to a target monitoring location on a user's skin.

Unlike the sensor control device 102 of FIG. 1A, however, the sensor control device 5002 may comprise a one-piece system architecture not requiring a user to open multiple packages and finally assemble the sensor control device 5002 prior to application. Rather, upon receipt by the user, the sensor control device 5002 may already be fully assembled and properly positioned within the sensor applicator 150 (FIG. 1A). To use the sensor control device 5002, the user need only open one barrier (e.g., the applicator cap 708 of FIG. 3B) before promptly delivering the sensor control device 5002 to the target monitoring location for use.

As illustrated, the sensor control device 5002 includes an electronics housing 5004 that is generally disc-shaped and may have a circular cross-section. In other embodiments, however, the electronics housing 5004 may exhibit other cross-sectional shapes, such as ovoid or polygonal, without departing from the scope of the disclosure. The electronics housing 5004 may be configured to house or otherwise contain various electrical components used to operate the sensor control device 5002. In at least one embodiment, an adhesive patch (not shown) may be arranged at the bottom of the electronics housing 5004. The adhesive patch may be similar to the adhesive patch 105 of FIG. 1A, and may thus help adhere the sensor control device 5002 to the user's skin for use.

As illustrated, the sensor control device 5002 includes an electronics housing 5004 that includes a shell 5006 and a mount 5008 that is matable with the shell 5006. The shell 5006 may be secured to the mount 5008 via a variety of ways, such as a snap fit engagement, an interference fit, sonic welding, one or more mechanical fasteners (e.g., screws), a gasket, an adhesive, or any combination thereof. In some cases, the shell 5006 may be secured to the mount 5008 such that a sealed interface is generated therebetween.

The sensor control device 5002 may further include a sensor 5010 (partially visible) and a sharp 5012 (partially visible), used to help deliver the sensor 5010 transcutaneously under a user's skin during application of the sensor control device 5002. As illustrated, corresponding portions of the sensor 5010 and the sharp 5012 extend distally from the bottom of the electronics housing 5004 (e.g., the mount 5008). The sharp 5012 may include a sharp hub 5014 configured to secure and carry the sharp 5012. As best seen in FIG. 10B, the sharp hub 5014 may include or otherwise define a mating member 5016. To couple the sharp 5012 to the sensor control device 5002, the sharp 5012 may be advanced axially through the electronics housing 5004 until the sharp hub 5014 engages an upper surface of the shell 5006 and the mating member 5016 extends distally from the bottom of the mount 5008. As the sharp 5012 penetrates the electronics housing 5004, the exposed portion of the sensor 5010 may be received within a hollow or recessed (arcuate) portion of the sharp 5012. The remaining portion of the sensor 5010 is arranged within the interior of the electronics housing 5004.

The sensor control device 5002 may further include a sensor cap 5018, shown exploded or detached from the electronics housing 5004 in FIGS. 10A-10B. The sensor cap 5016 may be removably coupled to the sensor control device 5002 (e.g., the electronics housing 5004) at or near the bottom of the mount 5008. The sensor cap 5018 may help provide a sealed barrier that surrounds and protects the exposed portions of the sensor 5010 and the sharp 5012 from gaseous chemical sterilization. As illustrated, the sensor cap 5018 may comprise a generally cylindrical body having a first end 5020*a* and a second end 5020*b* opposite the first end 5020*a*. The first end 5020*a* may be open to provide access into an inner chamber 5022 defined within the body. In contrast, the second end 5020*b* may be closed and may provide or otherwise define an engagement feature 5024. As described herein, the engagement feature 5024 may help mate the sensor cap 5018 to the cap (e.g., the applicator cap 708 of FIG. 3B) of a sensor applicator (e.g., the sensor applicator 150 of FIGS. 1A and 3A-3G), and may help remove the sensor cap 5018 from the sensor control device 5002 upon removing the cap from the sensor applicator.

The sensor cap 5018 may be removably coupled to the electronics housing 5004 at or near the bottom of the mount 5008. More specifically, the sensor cap 5018 may be removably coupled to the mating member 5016, which extends distally from the bottom of the mount 5008. In at least one embodiment, for example, the mating member 5016 may define a set of external threads 5026*a* (FIG. 10B) matable with a set of internal threads 5026*b* (FIG. 10A) defined by the sensor cap 5018. In some embodiments, the external and internal threads 5026*a, b* may comprise a flat thread design (e.g., lack of helical curvature), which may prove advantageous in molding the parts. Alternatively, the external and internal threads 5026*a,b* may comprise a helical threaded engagement. Accordingly, the sensor cap 5018 may be threadably coupled to the sensor control device 5002 at the mating member 5016 of the sharp hub 5014. In other embodiments, the sensor cap 5018 may be removably coupled to the mating member 5016 via other types of engagements including, but not limited to, an interference or friction fit, or a frangible member or substance that may be broken with minimal separation force (e.g., axial or rotational force).

In some embodiments, the sensor cap 5018 may comprise a monolithic (singular) structure extending between the first and second ends 5020*a, b*. In other embodiments, however, the sensor cap 5018 may comprise two or more component parts. In the illustrated embodiment, for example, the sensor cap 5018 may include a seal ring 5028 positioned at the first end 5020*a* and a desiccant cap 5030 arranged at the second end 5020*b*. The seal ring 5028 may be configured to help seal the inner chamber 5022, as described in more detail below. In at least one embodiment, the seal ring 5028 may comprise an elastomeric O-ring. The desiccant cap 5030 may house or comprise a desiccant to help maintain preferred humidity levels within the inner chamber 5022. The desiccant cap 5030 may also define or otherwise provide the engagement feature 5024 of the sensor cap 5018.

Figure 11B:
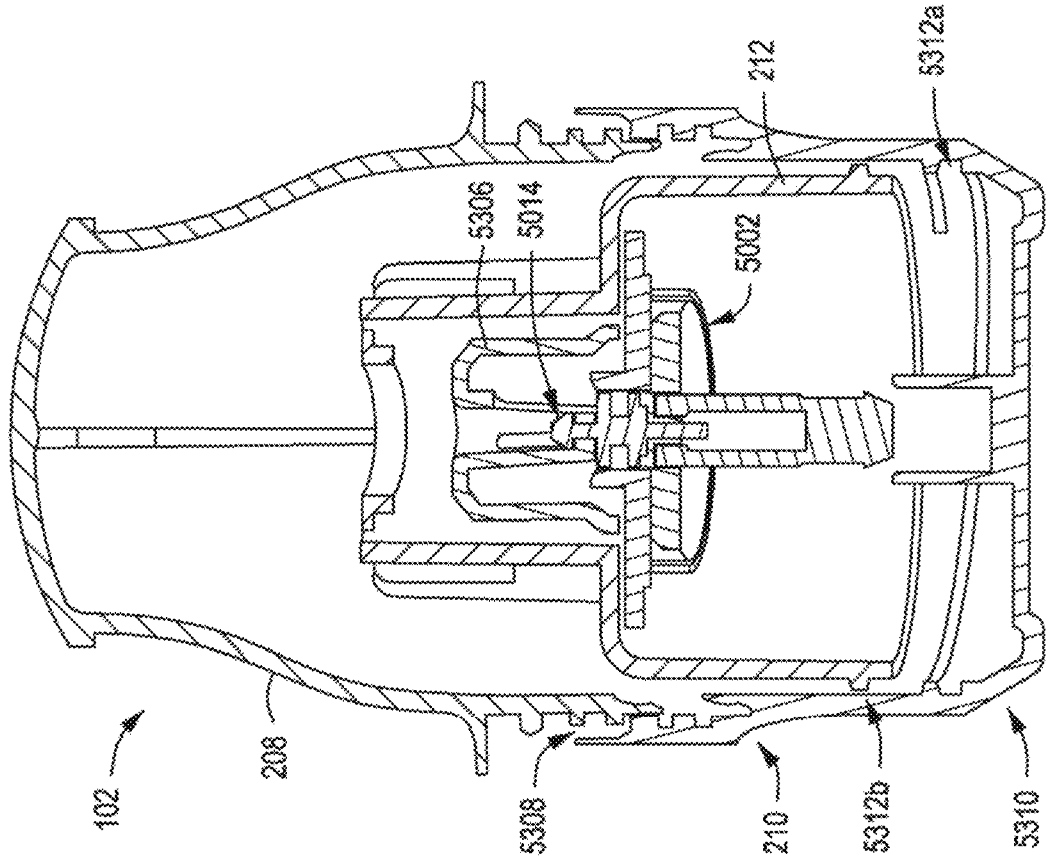
FIGS. 11A-11C are progressive cross-sectional side views showing assembly of the sensor applicator with the sensor control device of FIGS. 10A-10B.
Figure 11A:
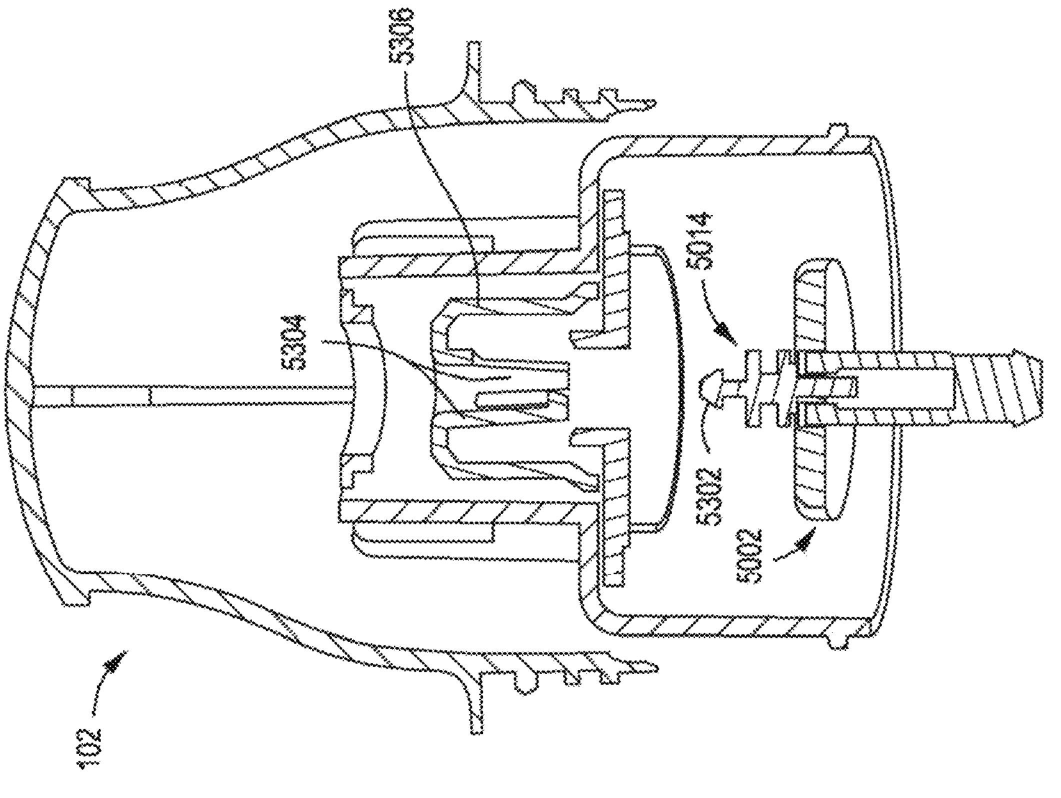
Figure 11C:
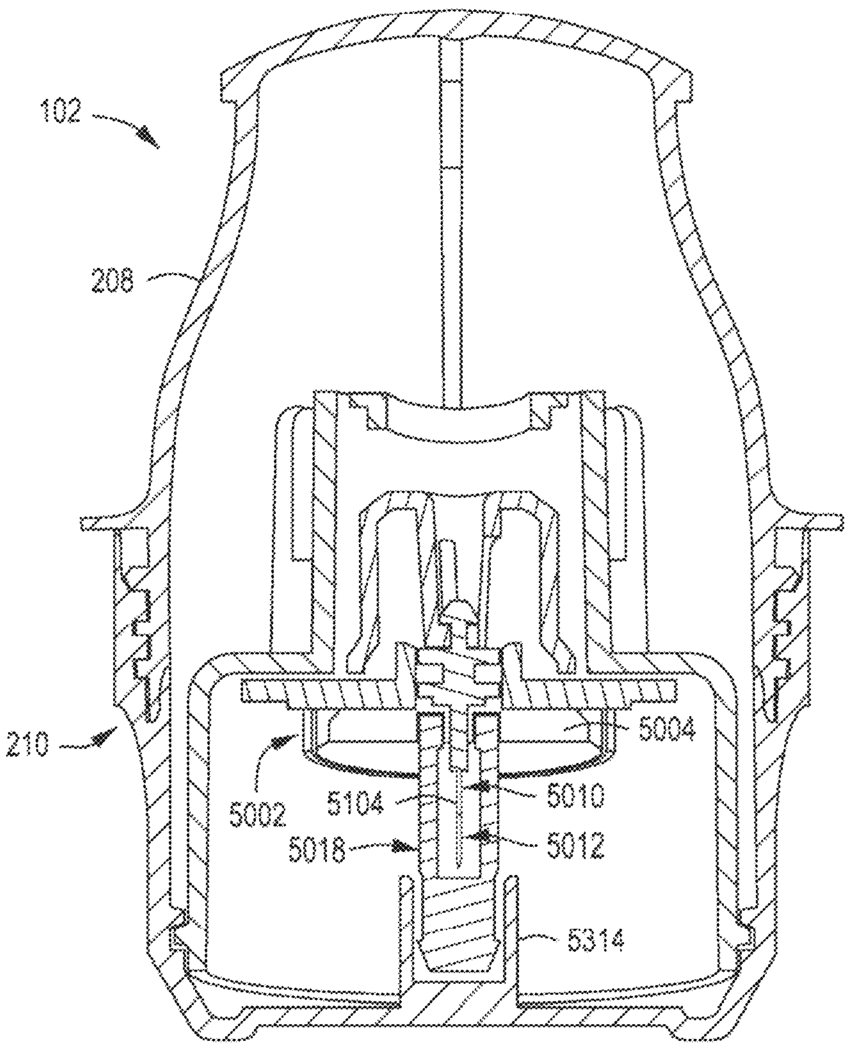

FIGS. 11A-11C are progressive cross-sectional side views showing assembly of the sensor applicator 102 with the sensor control device 5002, according to one or more embodiments. Once the sensor control device 5002 is fully assembled, it may then be loaded into the sensor applicator 102. With reference to FIG. 11A, the sharp hub 5014 may include or otherwise define a hub snap pawl 5302 configured to help couple the sensor control device 5002 to the sensor applicator 102. More specifically, the sensor control device 5002 may be advanced into the interior of the sensor applicator 102 and the hub snap pawl 5302 may be received by corresponding arms 5304 of a sharp carrier 5306 positioned within the sensor applicator 102.

In FIG. 11B, the sensor control device 5002 is shown received by the sharp carrier 5306 and, therefore, secured within the sensor applicator 102. Once the sensor control device 5002 is loaded into the sensor applicator 102, the applicator cap 210 may be coupled to the sensor applicator 102. In some embodiments, the applicator cap 210 and the housing 208 may have opposing, matable sets of threads 5308 that enable the applicator cap 210 to be screwed onto the housing 208 in a clockwise (or counter-clockwise) direction and thereby secure the applicator cap 210 to the sensor applicator 102.

As illustrated, the sheath 212 is also positioned within the sensor applicator 102, and the sensor applicator 102 may include a sheath locking mechanism 5310 configured to ensure that the sheath 212 does not prematurely collapse during a shock event. In the illustrated embodiment, the sheath locking mechanism 5310 may comprise a threaded engagement between the applicator cap 210 and the sheath 212. More specifically, one or more internal threads 5312*a* may be defined or otherwise provided on the inner surface of the applicator cap 210, and one or more external threads 5312*b* may be defined or otherwise provided on the sheath 212. The internal and external threads 5312*a,b* may be configured to threadably mate as the applicator cap 210 is threaded to the sensor applicator 102 at the threads 5308. The internal and external threads 5312*a,b* may have the same thread pitch as the threads 5308 that enable the applicator cap 210 to be screwed onto the housing 208.

In FIG. 11C, the applicator cap 210 is shown fully threaded (coupled) to the housing 208. As illustrated, the applicator cap 210 may further provide and otherwise define a cap post 5314 centrally located within the interior of the applicator cap 210 and extending proximally from the bottom thereof. The cap post 5314 may be configured to receive at least a portion of the sensor cap 5018 as the applicator cap 210 is screwed onto the housing 208.

With the sensor control device 5002 loaded within the sensor applicator 102 and the applicator cap 210 properly secured, the sensor control device 5002 may then be subjected to a gaseous chemical sterilization configured to sterilize the electronics housing 5004 and any other exposed portions of the sensor control device 5002. Since the distal portions of the sensor 5010 and the sharp 5012 are sealed within the sensor cap 5018, the chemicals used during the gaseous chemical sterilization process are unable to interact with the enzymes, chemistry, and biologics provided on the tail 5104, and other sensor components, such as membrane coatings that regulate analyte influx.

Figure 12B:
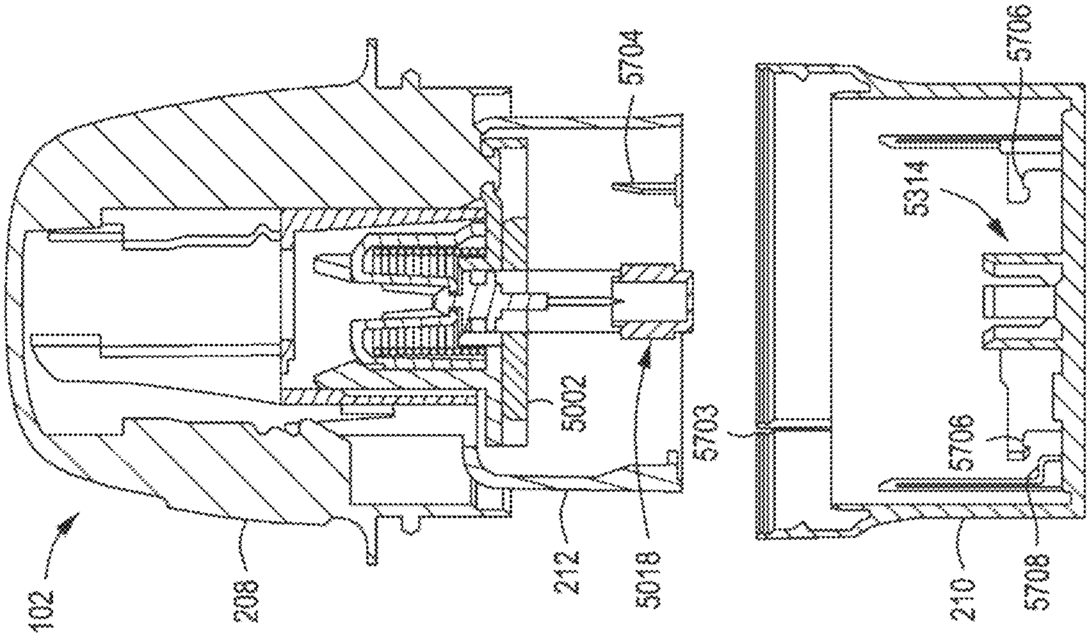
FIGS. 12A-12C are progressive cross-sectional side views showing assembly and disassembly of an example embodiment of the sensor applicator with the sensor control device of FIGS. 10A-10B.
Figure 12A:
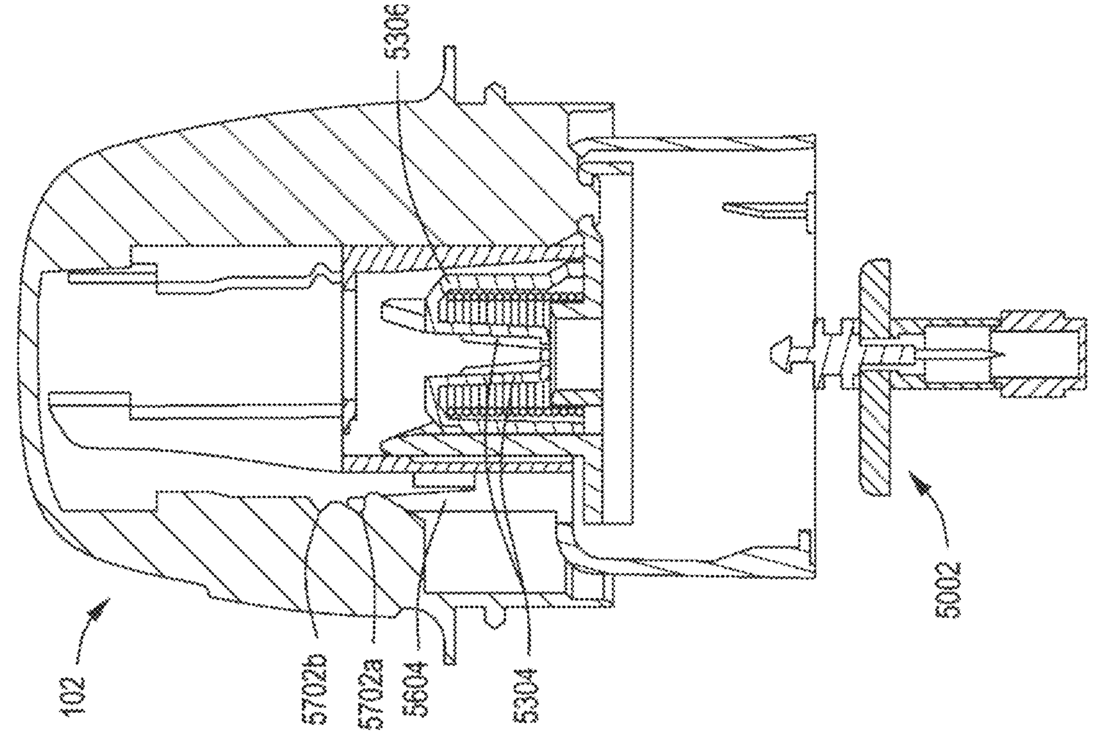
Figure 12C:
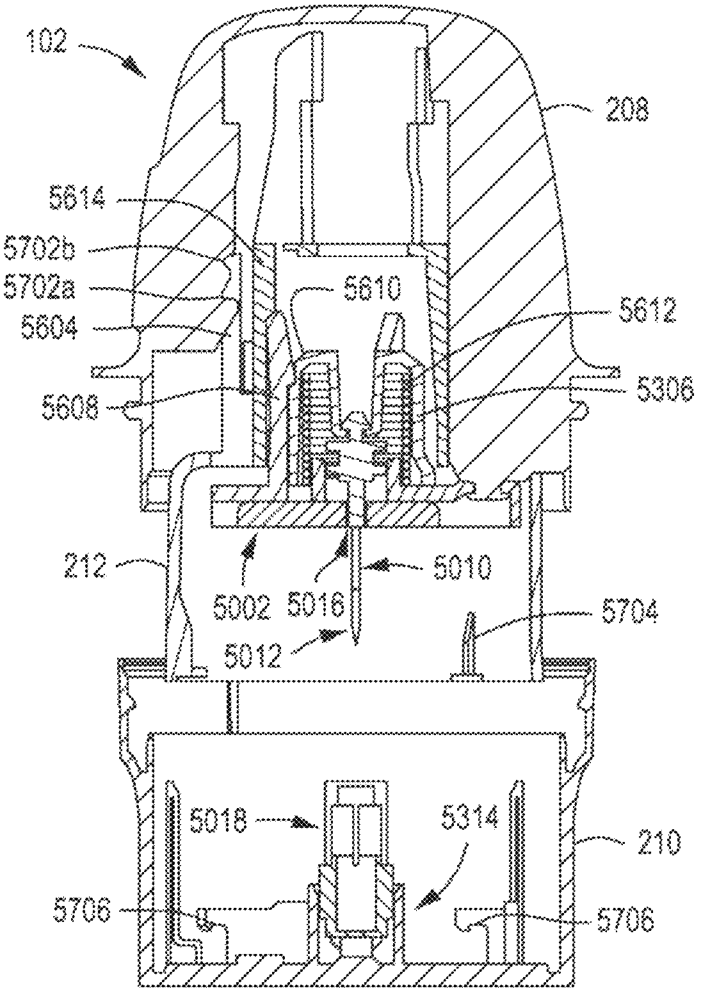

FIGS. 12A-12C are progressive cross-sectional side views showing assembly and disassembly of an alternative embodiment of the sensor applicator 102 with the sensor control device 5002, according to one or more additional embodiments. A fully assembled sensor control device 5002 may be loaded into the sensor applicator 102 by coupling the hub snap pawl 5302 into the arms 5304 of the sharp carrier 5306 positioned within the sensor applicator 102, as generally described above.

In the illustrated embodiment, the sheath arms 5604 of the sheath 212 may be configured to interact with a first detent 5702*a* and a second detent 5702*b* defined within the interior of the housing 208. The first detent 5702*a* may alternately be referred to a "locking" detent, and the second detent 5702*b* may alternately be referred to as a "firing" detent. When the sensor control device 5002 is initially installed in the sensor applicator 102, the sheath arms 5604 may be received within the first detent 5702*a*. As discussed below, the sheath 212 may be actuated to move the sheath arms 5604 to the second detent 5702*b*, which places the sensor applicator 102 in firing position.

In FIG. 12B, the applicator cap 210 is aligned with the housing 208 and advanced toward the housing 208 so that the sheath 212 is received within the applicator cap 210. Instead of rotating the applicator cap 210 relative to the housing 208, the threads of the applicator cap 210 may be snapped onto the corresponding threads of the housing 208 to couple the applicator cap 210 to the housing 208. Axial cuts or slots 5703 (one shown) defined in the applicator cap 210 may allow portions of the applicator cap 210 near its threading to flex outward to be snapped into engagement with the threading of the housing 208. As the applicator cap 210 is snapped to the housing 208, the sensor cap 5018 may correspondingly be snapped into the cap post 5314.

Similar to the embodiment of FIGS. 11A-11C, the sensor applicator 102 may include a sheath locking mechanism configured to ensure that the sheath 212 does not prematurely collapse during a shock event. In the illustrated embodiment, the sheath locking mechanism includes one or more ribs 5704 (one shown) defined near the base of the sheath 212 and configured to interact with one or more ribs 5706 (two shown) and a shoulder 5708 defined near the base of the applicator cap 210. The ribs 5704 may be configured to inter-lock between the ribs 5706 and the shoulder 5708 while attaching the applicator cap 210 to the housing 208. More specifically, once the applicator cap 210 is snapped onto the housing 208, the applicator cap 210 may be rotated (e.g., clockwise), which locates the ribs 5704 of the sheath 212 between the ribs 5706 and the shoulder 5708 of the applicator cap 210 and thereby "locks" the applicator cap 210 in place until the user reverse rotates the applicator cap 210 to remove the applicator cap 210 for use. Engagement of the ribs 5704 between the ribs 5706 and the shoulder 5708 of the applicator cap 210 may also prevent the sheath 212 from collapsing prematurely.

In FIG. 12C, the applicator cap 210 is removed from the housing 208. As with the embodiment of FIGS. 12A-12C, the applicator cap 210 can be removed by reverse rotating the applicator cap 210, which correspondingly rotates the cap post 5314 in the same direction and causes sensor cap 5018 to unthread from the mating member 5016, as generally described above. Moreover, detaching the sensor cap 5018 from the sensor control device 5002 exposes the distal portions of the sensor 5010 and the sharp 5012.

As the applicator cap 210 is unscrewed from the housing 208, the ribs 5704 defined on the sheath 212 may slidingly engage the tops of the ribs 5706 defined on the applicator cap 210. The tops of the ribs 5706 may provide corresponding ramped surfaces that result in an upward displacement of the sheath 212 as the applicator cap 210 is rotated, and moving the sheath 212 upward causes the sheath arms 5604 to flex out of engagement with the first detent 5702*a* to be received within the second detent 5702*b*. As the sheath 212 moves to the second detent 5702*b*, the radial shoulder 5614 moves out of radial engagement with the carrier arm(s) 5608, which allows the passive spring force of the spring 5612 to push upward on the sharp carrier 5306 and force the carrier arm(s) 5608 out of engagement with the groove(s) 5610. As the sharp carrier 5306 moves upward within the housing 208, the mating member 5016 may correspondingly retract until it becomes flush, substantially flush, or sub-flush with the bottom of the sensor control device 5002. At this point, the sensor applicator 102 in firing position. Accordingly, in this embodiment, removing the applicator cap 210 correspondingly causes the mating member 5016 to retract.

I. Exemplary Firing Mechanism of One-Piece and Two-Piece Applicators

FIGS. 13A-13F illustrate example details of embodiments of the internal device mechanics of "firing" the applicator 216 to apply sensor control device 222 to a user and including retracting sharp 1030 safely back into used applicator 216. All together, these drawings represent an example sequence of driving sharp 1030 (supporting a sensor coupled to sensor control device 222) into the skin of a user, withdrawing the sharp while leaving the sensor behind in operative contact with interstitial fluid of the user, and adhering the sensor control device to the skin of the user with an adhesive. Modification of such activity for use with the alternative applicator assembly embodiments and components can be appreciated in reference to the same by those with skill in the art. Moreover, applicator 216 may be a sensor applicator having one-piece architecture or a two-piece architecture as disclosed herein.

Figure 13A:
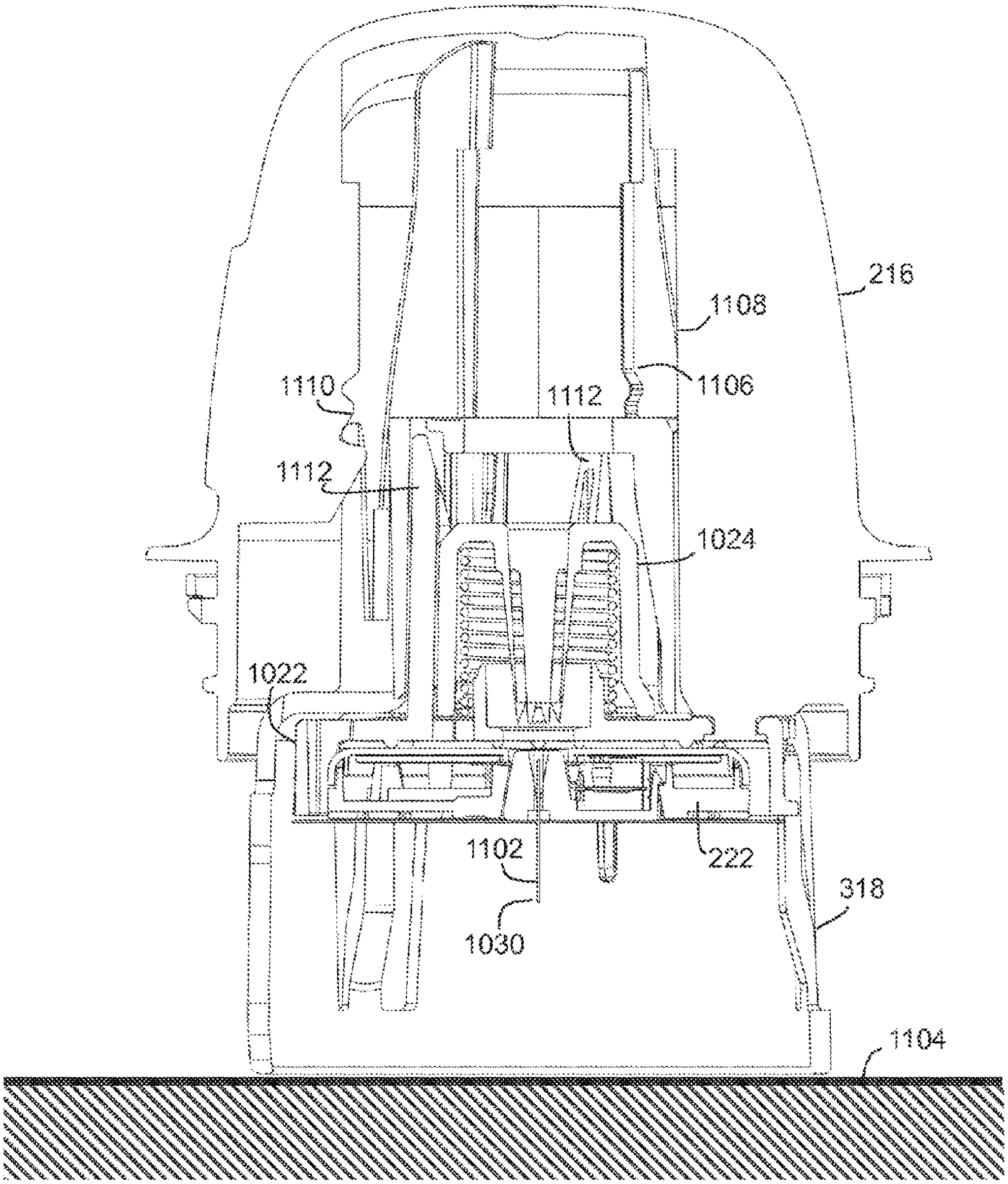
FIGS. 13A-13F illustrate cross-sectional views depicting an example embodiment of an applicator during a stage of deployment.

Turning now to FIG. 13A, a sensor 1102 is supported within sharp 1030, just above the skin 1104 of the user. Rails 1106 (optionally three of them) of an upper guide section 1108 may be provided to control applicator 216 motion relative to sheath 318. The sheath 318 is held by detent features 1110 within the applicator 216 such that appropriate downward force along the longitudinal axis of the applicator 216 will cause the resistance provided by the detent features 1110 to be overcome so that sharp 1030 and sensor control device 222 can translate along the longitudinal axis into (and onto) skin 1104 of the user. In addition, catch arms 1112 of sensor carrier 1022 engage the sharp retraction assembly 1024 to maintain the sharp 1030 in a position relative to the sensor control device 222.

Figure 13B:
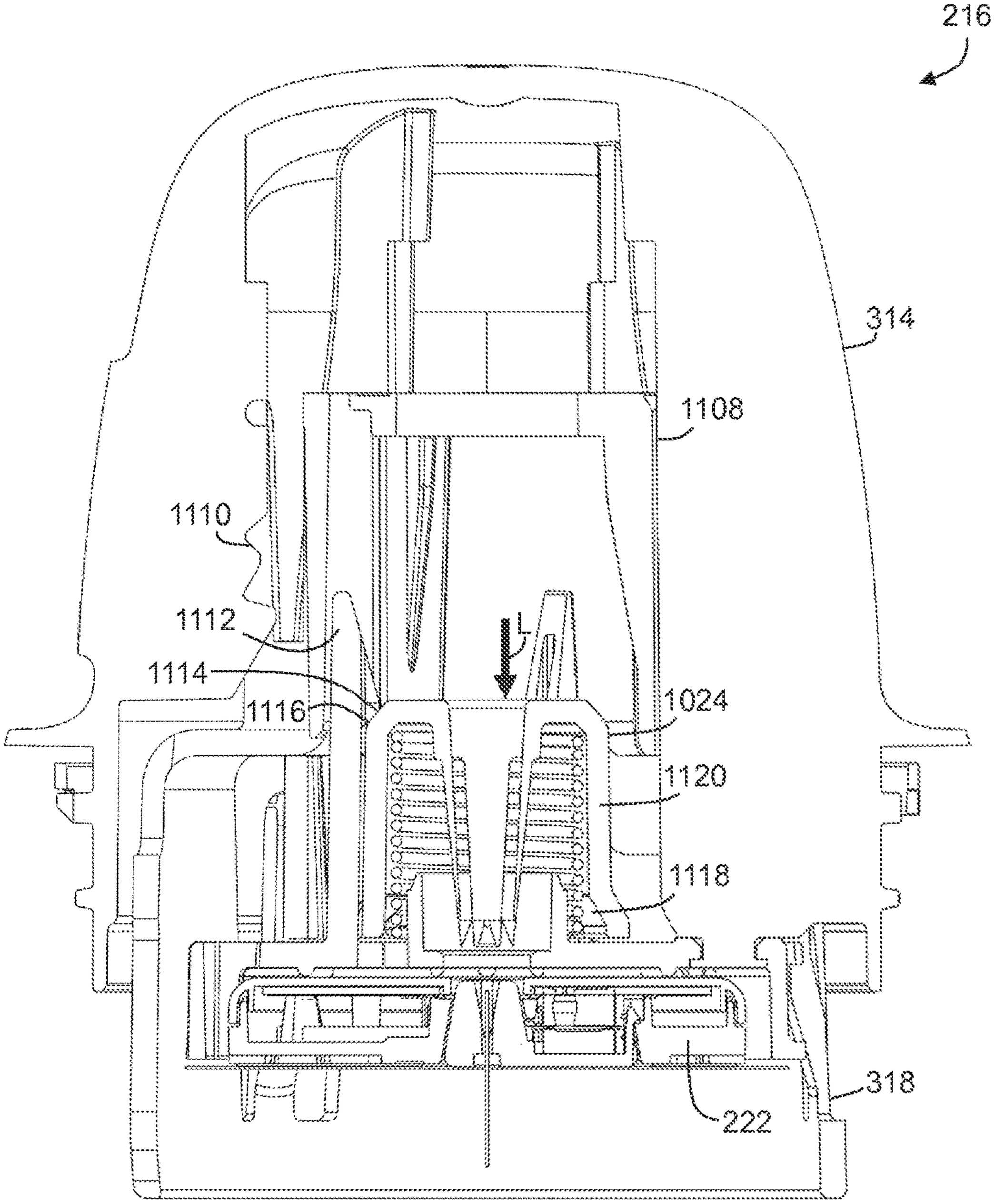

In FIG. 13B, user force is applied to overcome or override detent features 1110 and sheath 318 collapses into housing 314 driving the sensor control device 222 (with associated parts) to translate down as indicated by the arrow L along the longitudinal axis. An inner diameter of the upper guide section 1108 of the sheath 318 constrains the position of carrier arms 1112 through the full stroke of the sensor/sharp insertion process. The retention of the stop surfaces 1114 of carrier arms 1112 against the complimentary faces 1116 of the sharp retraction assembly 1024 maintains the position of the members with return spring 1118 fully energized. According to embodiments, rather than employing user force to drive the sensor control device 222 to translate down as indicated by the arrow L along the longitudinal axis, housing 314 can include a button (for example, not limitation, a push button) which activates a drive spring (for example, not limitation, a coil spring) to drive the sensor control device 222.

Figure 13C:
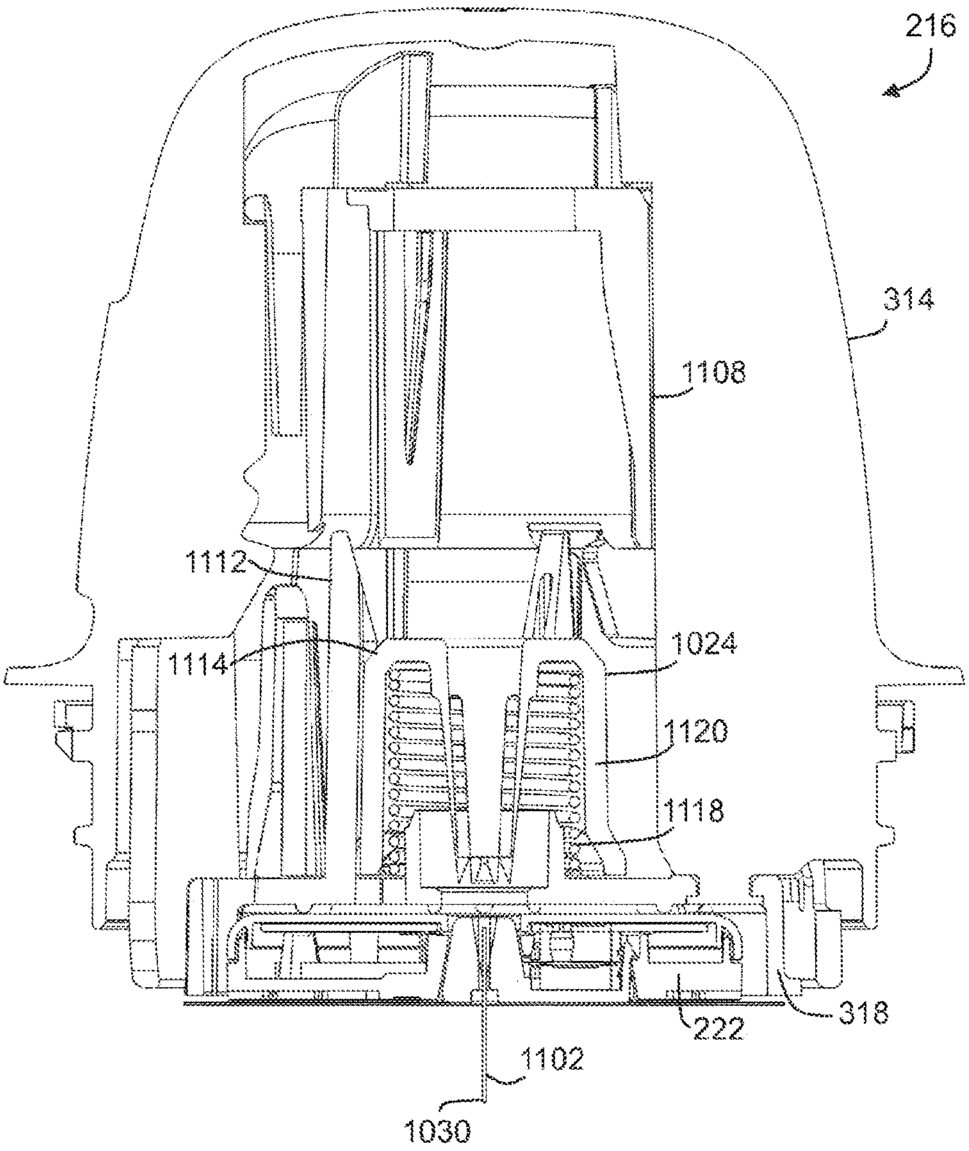
Figure 13D:
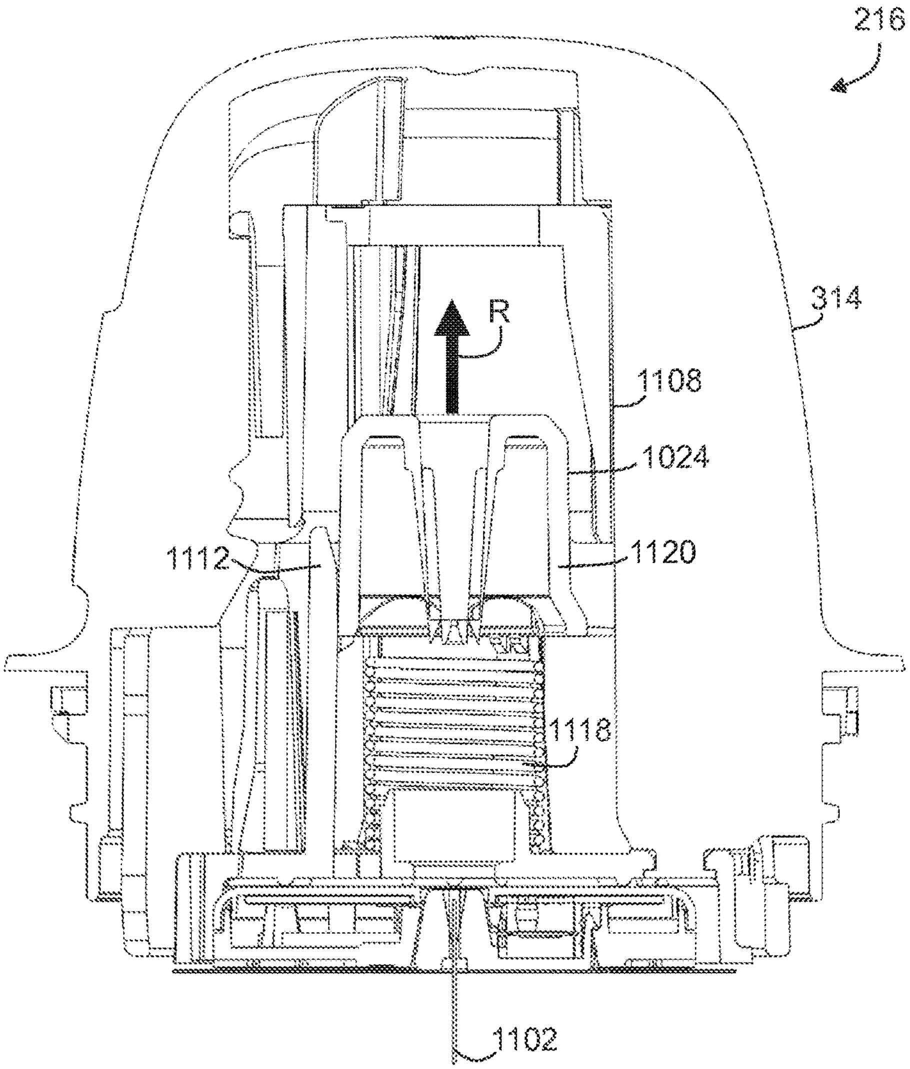

In FIG. 13C, sensor 1102 and sharp 1030 have reached full insertion depth. In so doing, the carrier arms 1112 clear the upper guide section 1108 inner diameter. Then, the compressed force of the coil return spring 1118 drives angled stop surfaces 1114 radially outward, releasing force to drive the sharp carrier 1102 of the sharp retraction assembly 1024 to pull the (slotted or otherwise configured) sharp 1030 out of the user and off of the sensor 1102 as indicated by the arrow R in FIG. 13D.

Figure 13E:
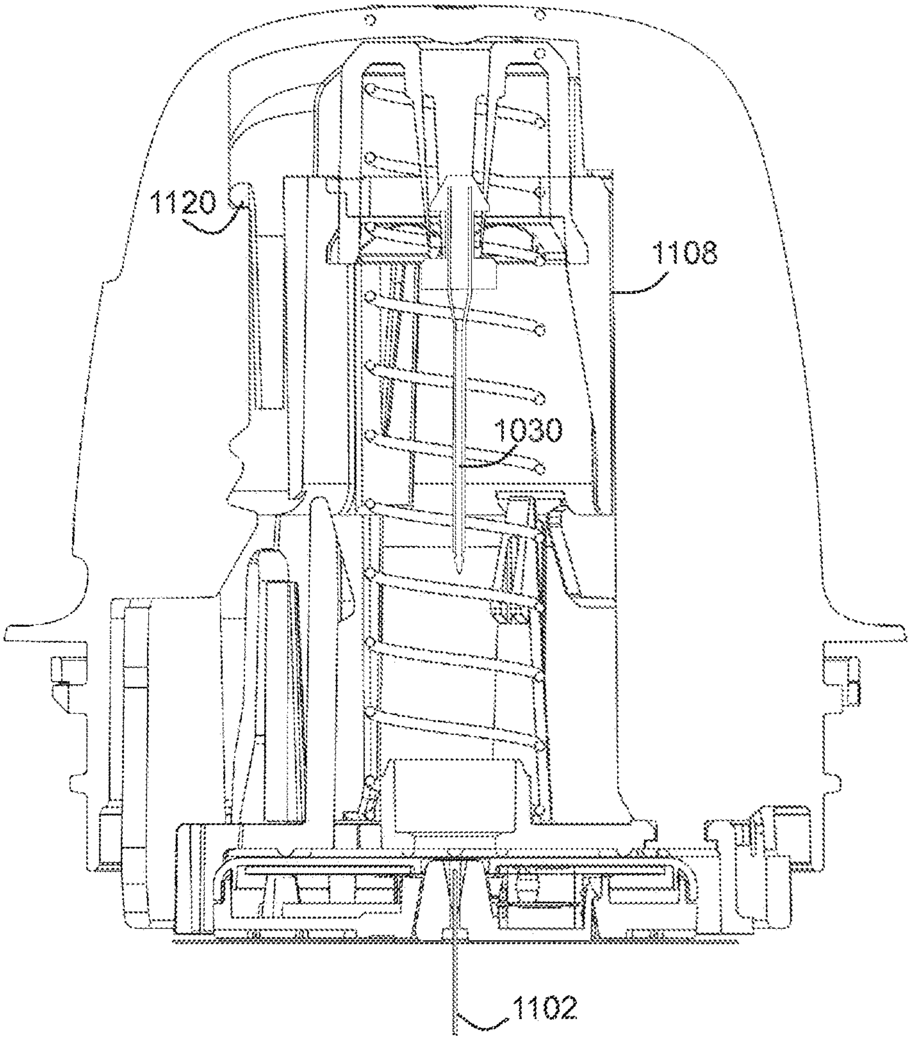
Figure 13F:
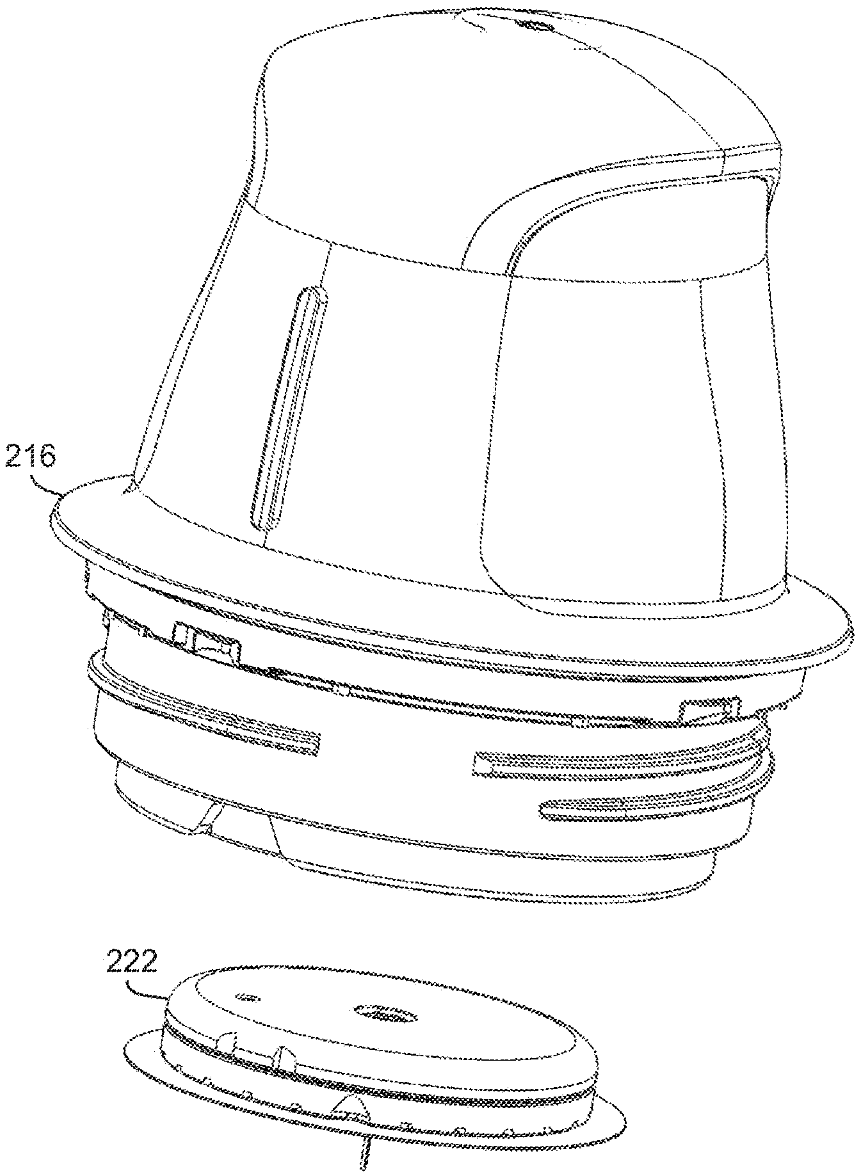

With the sharp 1030 fully retracted as shown in FIG. 13E, the upper guide section 1108 of the sheath 318 is set with a final locking feature 1120. As shown in FIG. 13F, the spent applicator assembly 216 is removed from the insertion site, leaving behind the sensor control device 222, and with the sharp 1030 secured safely inside the applicator assembly 216. The spent applicator assembly 216 is now ready for disposal.

Operation of the applicator 216 when applying the sensor control device 222 is designed to provide the user with a sensation that both the insertion and retraction of the sharp 1030 is performed automatically by the internal mechanisms of the applicator 216. In other words, the present invention avoids the user experiencing the sensation that he is manually driving the sharp 1030 into his skin. Thus, once the user applies sufficient force to overcome the resistance from the detent features of the applicator 216, the resulting actions of the applicator 216 are perceived to be an automated response to the applicator being "triggered." The user does not perceive that he is supplying additional force to drive the sharp 1030 to pierce his skin despite that all the driving force is provided by the user and no additional biasing/driving means are used to insert the sharp 1030. As detailed above in FIG. 13C, the retraction of the sharp 1030 is automated by the coil return spring 1118 of the applicator 216.

With respect to any of the applicator embodiments described herein, as well as any of the components thereof, including but not limited to the sharp, sharp module and sensor module embodiments, those of skill in the art will understand that said embodiments can be dimensioned and configured for use with sensors configured to sense an analyte level in a bodily fluid in the epidermis, dermis, or subcutaneous tissue of a subject. In some embodiments, for example, sharps and distal portions of analyte sensors disclosed herein can both be dimensioned and configured to be positioned at a particular end-depth (i.e., the furthest point of penetration in a tissue or layer of the subject's body, e.g., in the epidermis, dermis, or subcutaneous tissue). With respect to some applicator embodiments, those of skill in the art will appreciate that certain embodiments of sharps can be dimensioned and configured to be positioned at a different end-depth in the subject's body relative to the final end-depth of the analyte sensor. In some embodiments, for example, a sharp can be positioned at a first end-depth in the subject's epidermis prior to retraction, while a distal portion of an analyte sensor can be positioned at a second end-depth in the subject's dermis. In other embodiments, a sharp can be positioned at a first end-depth in the subject's dermis prior to retraction, while a distal portion of an analyte sensor can be positioned at a second end-depth in the subject's subcutaneous tissue. In still other embodiments, a sharp can be positioned at a first end-depth prior to retraction and the analyte sensor can be positioned at a second end-depth, wherein the first end-depth and second end-depths are both in the same layer or tissue of the subject's body.

Additionally, with respect to any of the applicator embodiments described herein, those of skill in the art will understand that an analyte sensor, as well as one or more structural components coupled thereto, including but not limited to one or more spring-mechanisms, can be disposed within the applicator in an off-center position relative to one or more axes of the applicator. In some applicator embodiments, for example, an analyte sensor and a spring mechanism can be disposed in a first off-center position relative to an axis of the applicator on a first side of the applicator, and the sensor electronics can be disposed in a second off-center position relative to the axis of the applicator on a second side of the applicator. In other applicator embodiments, the analyte sensor, spring mechanism, and sensor electronics can be disposed in an off-center position relative to an axis of the applicator on the same side. Those of skill in the art will appreciate that other permutations and configurations in which any or all of the analyte sensor, spring mechanism, sensor electronics, and other components of the applicator are disposed in a centered or off-centered position relative to one or more axes of the applicator are possible and fully within the scope of the present disclosure.

Additional details of suitable devices, systems, methods, components and the operation thereof along with related features are set forth in International Publication No. WO 2018/136898 to Rao et al., International Publication No. WO 2019/236850 to Thomas et al., International Publication No. WO 2019/236859 to Thomas et al., International Publication No. WO 2019/236876 to Thomas et al., and U.S. Patent Publication No. 2020/0196919, filed Jun. 6, 2019, each of which is incorporated by reference in its entirety herein. Further details regarding embodiments of applicators, their components, and variants thereof, are described in U.S. Patent Publication Nos. 2013/0150691, 2016/0331283, and 2018/0235520, all of which are incorporated by reference herein in their entireties and for all purposes. Further details regarding embodiments of sharp modules, sharps, their components, and variants thereof, are described in U.S. Patent Publication No. 2014/0171771, which is incorporated by reference herein in its entirety and for all purposes.

J. Exemplary Methods of Calibrating Analyte Sensors

Biochemical sensors can be described by one or more sensing characteristics. A common sensing characteristic is referred to as the biochemical sensor's sensitivity, which is a measure of the sensor's responsiveness to the concentration of the chemical or composition it is designed to detect. For electrochemical sensors, this response can be in the form of an electrical current (amperometric) or electrical charge (coulometric). For other types of sensors, the response can be in a different form, such as a photonic intensity (e.g., optical light). The sensitivity of a biochemical analyte sensor can vary depending on a number of factors, including whether the sensor is in an in vitro state or an in vivo state.

Figure 14:
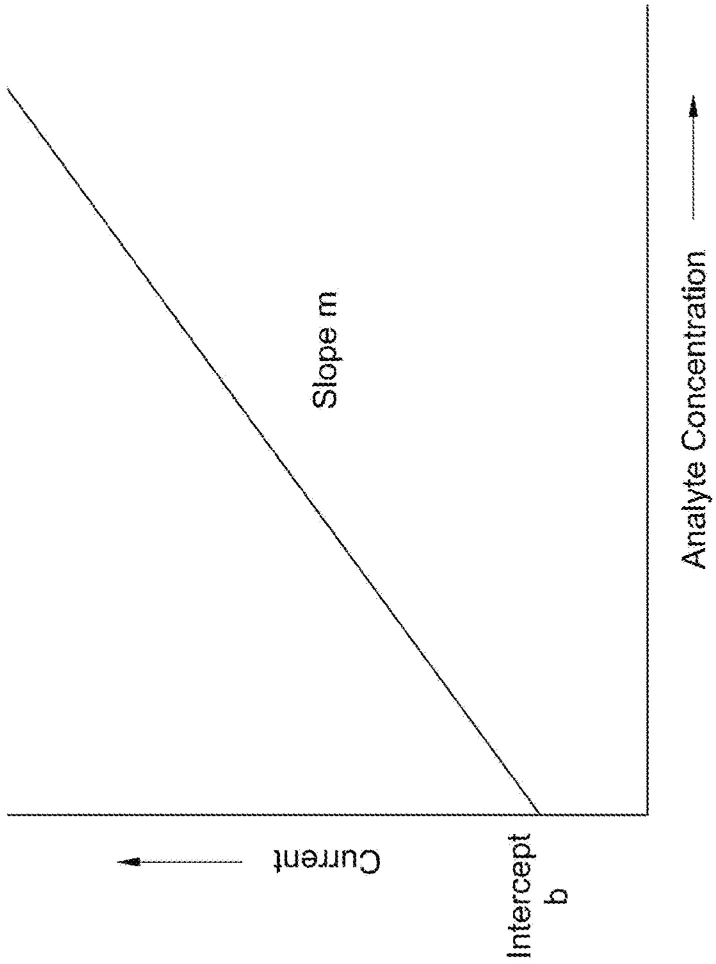
FIG. 14 is a graph depicting an example of an in vitro sensitivity of an analyte sensor.

FIG. 14 is a graph depicting the in vitro sensitivity of an amperometric analyte sensor. The in vitro sensitivity can be obtained by in vitro testing the sensor at various analyte concentrations and then performing a regression (e.g., linear or non-linear) or other curve fitting on the resulting data. In this example, the analyte sensor's sensitivity is linear, or substantially linear, and can be modeled according to the equation $y=mx+b$, where y is the sensor's electrical output current, x is the analyte level (or concentration), m is the slope of the sensitivity and b is the intercept of the sensitivity, where the intercept generally corresponds to a background signal (e.g., noise). For sensors with a linear or substantially linear response, the analyte level that corresponds to a given current can be determined from the slope and intercept of the sensitivity. Sensors with a non-linear sensitivity require additional information to determine the analyte level resulting from the sensor's output current, and those of ordinary skill in the art are familiar with manners by which to model non-linear sensitivities. In certain embodiments of in vivo sensors, the in vitro sensitivity can be the same as the in vivo sensitivity, but in other embodiments a transfer (or conversion) function is used to translate the in vitro sensitivity into the in vivo sensitivity that is applicable to the sensor's intended in vivo use.

Calibration is a technique for improving or maintaining accuracy by adjusting a sensor's measured output to reduce the differences with the sensor's expected output. One or more parameters that describe the sensor's sensing characteristics, like its sensitivity, are established for use in the calibration adjustment.

Certain in vivo analyte monitoring systems require calibration to occur after implantation of the sensor into the user or patient, either by user interaction or by the system itself in an automated fashion. For example, when user interaction is required, the user performs an in vitro measurement (e.g., a blood glucose (BG) measurement using a finger stick and an in vitro test strip) and enters this into the system, while the analyte sensor is implanted. The system then compares the in vitro measurement with the in vivo signal and, using the differential, determines an estimate of the sensor's in vivo sensitivity. The in vivo sensitivity can then be used in an algorithmic process to transform the data collected with the sensor to a value that indicates the user's analyte level. This and other processes that require user action to perform calibration are referred to as "user calibration." Systems can require user calibration due to instability of the sensor's sensitivity, such that the sensitivity drifts or changes over time. Thus, multiple user calibrations (e.g., according to a periodic (e.g., daily) schedule, variable schedule, or on an as-needed basis) can be required to maintain accuracy. While the embodiments described herein can incorporate a degree of user calibration for a particular implementation, generally this is not preferred as it requires the user to perform a painful or otherwise burdensome BG measurement, and can introduce user error.

Some in vivo analyte monitoring systems can regularly adjust the calibration parameters through the use of automated measurements of characteristics of the sensor made by the system itself (e.g., processing circuitry executing software). The repeated adjustment of the sensor's sensitivity based on a variable measured by the system (and not the user) is referred to generally as "system" (or automated) calibration, and can be performed with user calibration, such as an early BG measurement, or without user calibration. Like the case with repeated user calibrations, repeated system calibrations are typically necessitated by drift in the sensor's sensitivity over time. Thus, while the embodiments described herein can be used with a degree of automated system calibration, preferably the sensor's sensitivity is relatively stable over time such that post-implantation calibration is not required.

Some in vivo analyte monitoring systems operate with a sensor that is factory calibrated. Factory calibration refers to the determination or estimation of the one or more calibration parameters prior to distribution to the user or healthcare professional (HCP). The calibration parameter can be determined by the sensor manufacturer (or the manufacturer of the other components of the sensor control device if the two entities are different). Many in vivo sensor manufacturing processes fabricate the sensors in groups or batches referred to as production lots, manufacturing stage lots, or simply lots. A single lot can include thousands of sensors.

Sensors can include a calibration code or parameter which can be derived or determined during one or more sensor manufacturing processes and coded or programmed, as part of the manufacturing process, in the data processing device of the analyte monitoring system or provided on the sensor itself, for example, as a bar code, a laser tag, an RFID tag, or other machine readable information provided on the sensor. User calibration during in vivo use of the sensor can be obviated, or the frequency of in vivo calibrations during sensor wear can be reduced if the code is provided to a receiver (or other data processing device). In embodiments where the calibration code or parameter is provided on the sensor itself, prior to or at the start of the sensor use, the calibration code or parameter can be automatically transmitted or provided to the data processing device in the analyte monitoring system.

Some in vivo analyte monitoring system operate with a sensor that can be one or more of factory calibrated, system calibrated, and/or user calibrated. For example, the sensor can be provided with a calibration code or parameter which can allow for factory calibration. If the information is provided to a receiver (for example, entered by a user), the sensor can operate as a factory calibrated sensor. If the information is not provided to a receiver, the sensor can operate as a user calibrated sensor and/or a system calibrated sensor.

In a further aspect, programming or executable instructions can be provided or stored in the data processing device of the analyte monitoring system, and/or the receiver/controller unit, to provide a time varying adjustment algorithm to the in vivo sensor during use. For example, based on a retrospective statistical analysis of analyte sensors used in vivo and the corresponding glucose level feedback, a predetermined or analytical curve or a database can be generated which is time based, and configured to provide additional adjustment to the one or more in vivo sensor parameters to compensate for potential sensor drift in stability profile, or other factors.

In accordance with the disclosed subject matter, the analyte monitoring system can be configured to compensate or adjust for the sensor sensitivity based on a sensor drift profile. A time varying parameter β(t) can be defined or determined based on analysis of sensor behavior during in vivo use, and a time varying drift profile can be determined. In certain aspects, the compensation or adjustment to the sensor sensitivity can be programmed in the receiver unit, the controller or data processor of the analyte monitoring system such that the compensation or the adjustment or both can be performed automatically and/or iteratively when sensor data is received from the analyte sensor. In accordance with the disclosed subject matter, the adjustment or compensation algorithm can be initiated or executed by the user (rather than self-initiating or executing) such that the adjustment or the compensation to the analyte sensor sensitivity profile is performed or executed upon user initiation or activation of the corresponding function or routine, or upon the user entering the sensor calibration code.

In accordance with the disclosed subject matter, each sensor in the sensor lot (in some instances not including sample sensors used for in vitro testing) can be examined non-destructively to determine or measure its characteristics such as membrane thickness at one or more points of the sensor, and other characteristics including physical characteristics such as the surface area/volume of the active area can be measured or determined. Such measurement or determination can be performed in an automated manner using, for example, optical scanners or other suitable measurement devices or systems, and the determined sensor characteristics for each sensor in the sensor lot is compared to the corresponding mean values based on the sample sensors for possible correction of the calibration parameter or code assigned to each sensor. For example, for a calibration parameter defined as the sensor sensitivity, the sensitivity is approximately inversely proportional to the membrane thickness, such that, for example, a sensor having a measured membrane thickness of approximately 4% greater than the mean membrane thickness for the sampled sensors from the same sensor lot as the sensor, the sensitivity assigned to that sensor in one embodiment is the mean sensitivity determined from the sampled sensors divided by 1.04. Likewise, since the sensitivity is approximately proportional to active area of the sensor, a sensor having measured active area of approximately 3% lower than the mean active area for the sampled sensors from the same sensor lot, the sensitivity assigned to that sensor is the mean sensitivity multiplied by 0.97. The assigned sensitivity can be determined from the mean sensitivity from the sampled sensors, by multiple successive adjustments for each examination or measurement of the sensor. In certain embodiments, examination or measurement of each sensor can additionally include measurement of membrane consistency or texture in addition to the membrane thickness and/or surface are or volume of the active sensing area.

Additional information regarding sensor calibration is provided in U.S. Publication No. 2010/00230285 and U.S. Publication No. 2019/0274598, each of which is incorporated by reference herein in its entirety.

K. Exemplary Bluetooth Communication Protocols

The storage memory 5030 of the sensor 110 can include the software blocks related to communication protocols of the communication module. For example, the storage memory 5030 can include a BLE services software block with functions to provide interfaces to make the BLE module 5041 available to the computing hardware of the sensor 110. These software functions can include a BLE logical interface and interface parser. BLE services offered by the communication module 5040 can include the generic access profile service, the generic attribute service, generic access service, device information service, data transmission services, and security services. The data transmission service can be a primary service used for transmitting data such as sensor control data, sensor status data, analyte measurement data (historical and current), and event log data. The sensor status data can include error data, current time active, and software state. The analyte measurement data can include information such as current and historical raw measurement values, current and historical values after processing using an appropriate algorithm or model, projections and trends of measurement levels, comparisons of other values to patient-specific averages, calls to action as determined by the algorithms or models and other similar types of data.

According to aspects of the disclosed subject matter, and as embodied herein, a sensor 110 can be configured to communicate with multiple devices concurrently by adapting the features of a communication protocol or medium supported by the hardware and radios of the sensor 110. As an example, the BLE module 5041 of the communication module 5040 can be provided with software or firmware to enable multiple concurrent connections between the sensor 110 as a central device and the other devices as peripheral devices, or as a peripheral device where another device is a central device.

Connections, and ensuing communication sessions, between two devices using a communication protocol such as BLE can be characterized by a similar physical channel operated between the two devices (e.g., a sensor 110 and data receiving device 120). The physical channel can include a single channel or a series of channels, including for example and without limitation using an agreed upon series of channels determined by a common clock and channel- or frequency-hopping sequence. Communication sessions can use a similar amount of the available communication spectrum, and multiple such communication sessions can exist in proximity. In certain embodiment, each collection of devices in a communication session uses a different physical channel or series of channels, to manage interference of devices in the same proximity.

For purpose of illustration and not limitation, reference is made to an exemplary embodiment of a procedure for a sensor-receiver connection for use with the disclosed subject matter. First, the sensor 110 repeatedly advertises its connection information to its environment in a search for a data receiving device 120. The sensor 110 can repeat advertising on a regular basis until a connection established. The data receiving device 120 detects the advertising packet and scans and filters for the sensor 120 to connect to through the data provided in the advertising packet. Next, data receiving device 120 sends a scan request command and the sensor 110 responds with a scan response packet providing additional details. Then, the data receiving device 120 sends a connection request using the Bluetooth device address associated with the data receiving device 120. The data receiving device 120 can also continuously request to establish a connection to a sensor 110 with a specific Bluetooth device address. Then, the devices establish an initial connection allowing them to begin to exchange data. The devices begin a process to initialize data exchange services and perform a mutual authentication procedure.

During a first connection between the sensor 110 and data receiving device 120, the data receiving device 120 can initialize a service, characteristic, and attribute discovery procedure. The data receiving device 120 can evaluate these features of the sensor 110 and store them for use during subsequent connections. Next, the devices enable a notification for a customized security service used for mutual authentication of the sensor 110 and data receiving device 120. The mutual authentication procedure can be automated and require no user interaction. Following the successful completion of the mutual authentication procedure, the sensor 110 sends a connection parameter update to request the data receiving device 120 to use connection parameter settings preferred by the sensor 110 and configured to maximum longevity.

The data receiving device 120 then performs sensor control procedures to backfill historical data, current data, event log, and factory data. As an example, for each type of data, the data receiving device 120 sends a request to initiate a backfill process. The request can specify a range of records defined based on, for example, the measurement value, timestamp, or similar, as appropriate. The sensor 110 responds with requested data until all previously unsent data in the memory of the sensor 110 is delivered to the data receiving device 120. The sensor 110 can respond to a backfill request from the data receiving device 120 that all data has already been sent. Once backfill is completed, the data receiving device 120 can notify sensor 110 that it is ready to receive regular measurement readings. The sensor 110 can send readings across multiple notifications result on a repeating basis. As embodied herein, the multiple notifications can be redundant notifications to ensure that data is transmitted correctly. Alternatively, multiple notifications can make up a single payload.

For purpose of illustration and not limitation, reference is made to an exemplary embodiment of a procedure to send a shutdown command to the sensor 110. The shutdown operation is executed if the sensor 110 is in, for example, an error state, insertion failed state, or sensor expired state. If the sensor 110 is not in those states, the sensor 110 can log the command and execute the shutdown when sensor 110 transitions into the error state or sensor expired state. The data receiving device 120 sends a properly formatted shutdown command to the sensor 110. If the sensor 110 is actively processing another command, the sensor 110 will respond with a standard error response indicating that the sensor 110 is busy. Otherwise, the sensor 110 sends a response as the command is received. Additionally, the sensor 110 sends a success notification through the sensor control characteristic to acknowledge the sensor 110 has received the command. The sensor 110 registers the shutdown command. At the next appropriate opportunity (e.g., depending on the current sensor state, as described herein), the sensor 110 will shut down.

L. Exemplary Sensor States and Activation

Figure 15:
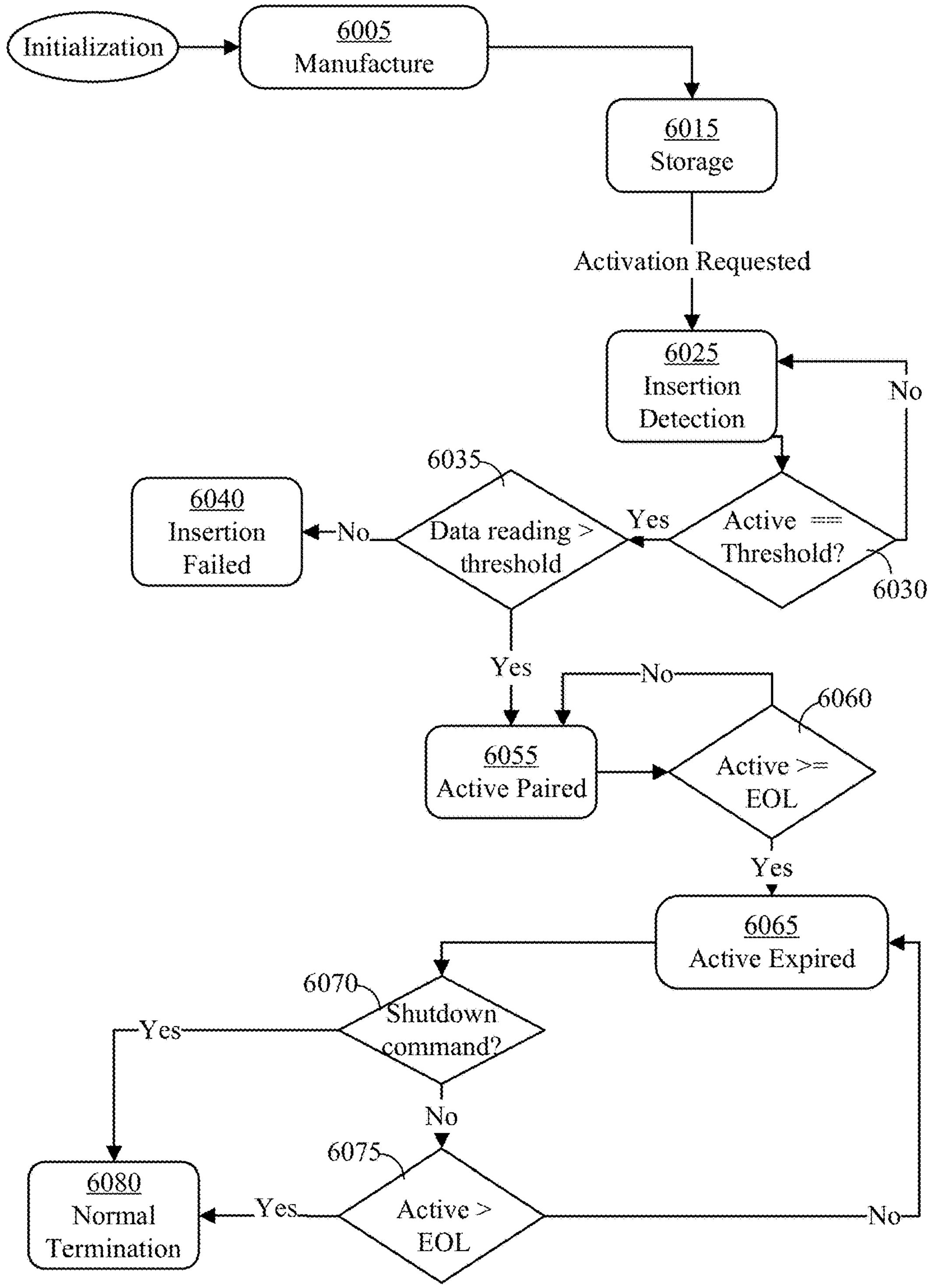
FIG. 15 is a diagram illustrating example operational states of the sensor according to exemplary embodiments of the disclosed subject matter.

For purpose of illustration and not limitation, reference is made to the exemplary embodiment of a high-level depiction of a state machine representation 6000 of the actions that can be taken by the sensor 110 as shown in FIG. 15. After initialization, the sensor enters state 6005, which relates to the manufacture of the sensor 110. In the manufacture state 6005 the sensor 110 can be configured for operation, for example, the storage memory 5030 can be written. At various times while in state 6005, the sensor 110 checks for a received command to go to the storage state 6015. Upon entry to the storage state 6015, the sensor performs a software integrity check. While in the storage state 6015, the sensor can also receive an activation request command before advancing to the insertion detection state 6025.

Upon entry to state 6025, the sensor 110 can store information relating to devices authenticated to communicate with the sensor as set during activation or initialize algorithms related to conducting and interpreting measurements from the sensing hardware 5060. The sensor 110 can also initialize a lifecycle timer, responsible for maintaining an active count of the time of operation of the sensor 110 and begin communication with authenticated devices to transmit recorded data. While in the insertion detection state 6025, the sensor can enter state 6030, where the sensor 110 checks whether the time of operation is equal to a predetermined threshold. This time of operation threshold can correspond to a timeout function for determining whether an insertion has been successful. If the time of operation has reached the threshold, the sensor 110 advances to state 6035, in which the sensor 110 checks whether the average data reading is greater than a threshold amount corresponding to an expected data reading volume for triggering detection of a successful insertion. If the data reading volume is lower than the threshold while in state 6035, the sensor advances to state 6040, corresponding to a failed insertion. If the data reading volume satisfies the threshold, the sensor advances to the active paired state 6055.

The active paired state 6055 of the sensor 110 reflects the state while the sensor 110 is operating as normal by recording measurements, processing the measurements, and reporting them as appropriate. While in the active paired state 6055, the sensor 110 sends measurement results or attempts to establish a connection with a receiving device 120. The sensor 110 also increments the time of operation. Once the sensor 110 reaches a predetermined threshold time of operation (e.g., once the time of operation reaches a predetermined threshold), the sensor 110 transitions to the active expired state 6065. The active expired state 6065 of the sensor 110 reflects the state while the sensor 110 has operated for its maximum predetermined amount of time.

While in the active expired state 6065, the sensor 110 can generally perform operations relating to winding down operation and ensuring that the collected measurements have been securely transmitted to receiving devices as needed. For example, while in the active expired state 6065, the sensor 110 can transmit collected data and, if no connection is available, can increase efforts to discover authenticated devices nearby and establish and connection therewith. While in the active expired state 6065, the sensor 110 can receive a shutdown command at state 6070. If no shutdown command is received, the sensor 110 can also, at state 6075, check if the time of operation has exceeded a final operation threshold. The final operation threshold can be based on the battery life of the sensor 110. The normal termination state 6080 corresponds to the final operations of the sensor 110 and ultimately shutting down the sensor 110.

Before a sensor is activated, the ASIC 5000 resides in a low power storage mode state. The activation process can begin, for example, when an incoming RF field (e.g., NFC field) drives the voltage of the power supply to the ASIC 5000 above a reset threshold, which causes the sensor 110 to enter a wake-up state. While in the wake-up state, the ASIC 5000 enters an activation sequence state. The ASIC 5000 then wakes the communication module 5040. The communication module 5040 is initialized, triggering a power on self-test. The power on self-test can include the ASIC 5000 communicating with the communication module 5040 using a prescribed sequence of reading and writing data to verify the memory and one-time programmable memory are not corrupted.

When the ASIC 5000 enters the measurement mode for the first time, an insertion detection sequence is performed to verify that the sensor 110 has been properly installed onto the patient's body before a proper measurement can take place. First, the sensor 110 interprets a command to activate the measurement configuration process, causing the ASIC 5000 to enter measurement command mode. The sensor 110 then temporarily enters the measurement lifecycle state to run a number of consecutive measurements to test whether the insertion has been successful. The communication module 5040 or ASIC 5000 evaluates the measurement results to determine insertion success. When insertion is deemed successful, the sensor 110 enters a measurement state, in which the sensor 110 begins taking regular measurements using sensing hardware 5060. If the sensor 110 determines that the insertion was not successful, sensor 110 is triggered into an insertion failure mode, in which the ASIC 5000 is commanded back to storage mode while the communication module 5040 disables itself.

M. Exemplary Over-the-Air Updates

FIG. 1B further illustrates an example operating environment for providing over-the-air ("OTA") updates for use with the techniques described herein. An operator of the analyte monitoring system 100 can bundle updates for the data receiving device 120 or sensor 110 into updates for an application executing on the multi-purpose data receiving device 130. Using available communication channels between the data receiving device 120, the multi-purpose data receiving device 130, and the sensor 110, the multi-purpose data receiving device 130 can receive regular updates for the data receiving device 120 or sensor 110 and initiate installation of the updates on the data receiving device 120 or sensor 110. The multi-purpose data receiving device 130 acts as an installation or update platform for the data receiving device 120 or sensor 110 because the application that enables the multi-purpose data receiving device 130 to communicate with an analyte sensor 110, data receiving device 120 and/or remote application server 150 can update software or firmware on a data receiving device 120 or sensor 110 without wide-area networking capabilities.

As embodied herein, a remote application server 150 operated by the manufacturer of the analyte sensor 110 and/or the operator of the analyte monitoring system 100 can provide software and firmware updates to the devices of the analyte monitoring system 100. In particular embodiments, the remote application server 150 can provides the updated software and firmware to a user device 140 or directly to a multi-purpose data receiving device. As embodied herein, the remote application server 150 can also provide application software updates to an application storefront server 160 using interfaces provided by the application storefront. The multi-purpose data receiving device 130 can contact the application storefront server 160 periodically to download and install the updates.

After the multi-purpose data receiving device 130 downloads an application update including a firmware or software update for a data receiving device 120 or sensor 110, the data receiving device 120 or sensor 110 and multi-purpose data receiving device 130 establish a connection. The multi-purpose data receiving device 130 determines that a firmware or software update is available for the data receiving device 120 or sensor 110. The multi-purpose data receiving device 130 can prepare the software or firmware update for delivery to the data receiving device 120 or sensor 110. As an example, the multi-purpose data receiving device 130 can compress or segment the data associated with the software or firmware update, can encrypt or decrypt the firmware or software update, or can perform an integrity check of the firmware or software update. The multi-purpose data receiving device 130 sends the data for the firmware or software update to the data receiving device 120 or sensor 110. The multi-purpose data receiving device 130 can also send a command to the data receiving device 120 or sensor 110 to initiate the update. Additionally or alternatively, the multi-purpose data receiving device 130 can provide a notification to the user of the multi-purpose data receiving device 130 and include instructions for facilitating the update, such as instructions to keep the data receiving device 120 and the multi-purpose data receiving device 130 connected to a power source and in close proximity until the update is complete.

The data receiving device 120 or sensor 110 receives the data for the update and the command to initiate the update from the multi-purpose data receiving device 130. The data receiving device 120 can then install the firmware or software update. To install the update, the data receiving device 120 or sensor 110 can place or restart itself in a so-called "safe" mode with limited operational capabilities. Once the update is completed, the data receiving device 120 or sensor 110 re-enters or resets into a standard operational mode. The data receiving device 120 or sensor 110 can perform one or more self-tests to determine that the firmware or software update was installed successfully. The multi-purpose data receiving device 130 can receive the notification of the successful update. The multi-purpose data receiving device 130 can then report a confirmation of the successful update to the remote application server 150.

In particular embodiments, the storage memory 5030 of the sensor 110 includes one-time programmable (OTP) memory. The term OTP memory can refer to memory that includes access restrictions and security to facilitate writing to particular addresses or segments in the memory a predetermined number of times. The memory 5030 can be prearranged into multiple pre-allocated memory blocks or containers. The containers are pre-allocated into a fixed size. If storage memory 5030 is one-time programming memory, the containers can be considered to be in a non-programmable state. Additional containers which have not yet been written to can be placed into a programmable or writable state. Containerizing the storage memory 5030 in this fashion can improve the transportability of code and data to be written to the storage memory 5030. Updating the software of a device (e.g., the sensor device described herein) stored in an OTP memory can be performed by superseding only the code in a particular previously-written container or containers with updated code written to a new container or containers, rather than replacing the entire code in the memory. In a second embodiment, the memory is not prearranged. Instead, the space allocated for data is dynamically allocated or determined as needed. Incremental updates can be issued, as containers of varying sizes can be defined where updates are anticipated.

Figure 16:
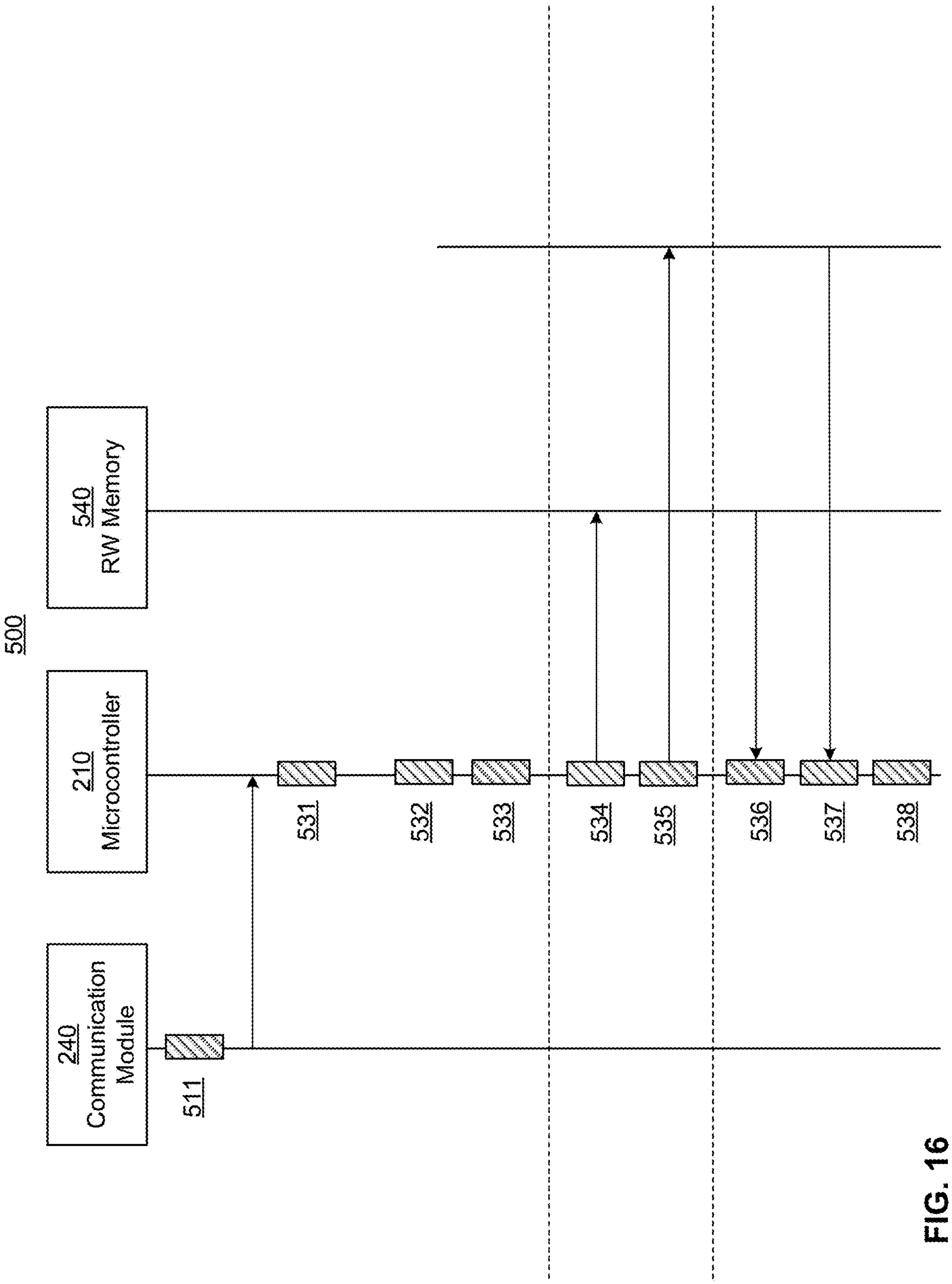
FIG. 16 is a diagram illustrating an example operational and data flow for over-the-air programming of a sensor according to the disclosed subject matter.

FIG. 16 is a diagram illustrating an example operational and data flow for over-the-air (OTA) programming of a storage memory 5030 in a sensor device 100 as well as use of the memory after the OTA programming in execution of processes by the sensor device 110 according to the disclosed subject matter. In the example OTA programming 500 illustrated in FIG. 5, a request is sent from an external device (e.g., the data receiving device 130) to initiate OTA programming (or re-programming). At 511, a communication module 5040 of a sensor device 110 receives an OTA programming command. The communication module 5040 sends the OTA programming command to the microcontroller 5010 of the sensor device 110.

At 531, after receiving the OTA programming command, the microcontroller 5010 validates the OTA programming command. The microcontroller 5010 can determine, for example, whether the OTA programming command is signed with an appropriate digital signature token. Upon determining that the OTA programming command is valid, the microcontroller 5010 can set the sensor device into an OTA programming mode. At 532, the microcontroller 5010 can validate the OTA programming data. At 533, The microcontroller 5010 can reset the sensor device 110 to re-initialize the sensor device 110 in a programming state. Once the sensor device 110 has transitioned into the OTA programming state, the microcontroller 5010 can begin to write data to the rewriteable memory 540 (e.g., memory 5020) of the sensor device at 534 and write data to the OTP memory 550 of the sensor device at 535 (e.g., storage memory 5030). The data written by the microcontroller 5010 can be based on the validated OTA programming data. The microcontroller 5010 can write data to cause one or more programming blocks or regions of the OTP memory 550 to be marked invalid or inaccessible. The data written to the free or unused portion of the OTP memory can be used to replace invalidated or inaccessible programming blocks of the OTP memory 550. After the microcontroller 5010 writes the data to the respective memories at 534 and 535, the microcontroller 5010 can perform one or more software integrity checks to ensure that errors were not introduced into the programming blocks during the writing process. Once the microcontroller 5010 is able to determine that the data has been written without errors, the microcontroller 5010 can resume standard operations of the sensor device.

In execution mode, at 536, the microcontroller 5010 can retrieve a programming manifest or profile from the rewriteable memory 540. The programming manifest or profile can include a listing of the valid software programming blocks and can include a guide to program execution for the sensor 110. By following the programming manifest or profile, the microcontroller 5010 can determine which memory blocks of the OTP memory 550 are appropriate to execute and avoid execution of out-of-date or invalidated programming blocks or reference to out-of-date data. At 537, the microcontroller 5010 can selectively retrieve memory blocks from the OTP memory 550. At 538, the microcontroller 5010 can use the retrieved memory blocks, by executing programming code stored or using variable stored in the memory.

N. Exemplary Security and Other Architecture Features

As embodied herein a first layer of security for communications between the analyte sensor 110 and other devices can be established based on security protocols specified by and integrated in the communication protocols used for the communication. Another layer of security can be based on communication protocols that necessitate close proximity of communicating devices. Furthermore certain packets and/or certain data included within packets can be encrypted while other packets and/or data within packets is otherwise encrypted or not encrypted. Additionally or alternatively, application layer encryption can be used with one or more block ciphers or stream ciphers to establish mutual authentication and communication encryption with other devices in the analyte monitoring system 100.

The ASIC 5000 of the analyte sensor 110 can be configured to dynamically generate authentication and encryption keys using data retained within the storage memory 5030. The storage memory 5030 can also be pre-programmed with a set of valid authentication and encryption keys to use with particular classes of devices. The ASIC 5000 can be further configured to perform authentication procedures with other devices using received data and apply the generated key to sensitive data prior to transmitting the sensitive data. The generated key can be unique to the analyte sensor 110, unique to a pair of devices, unique to a communication session between an analyte sensor 110 and other device, unique to a message sent during a communication session, or unique to a block of data contained within a message.

Both the sensor 110 and a data receiving device 120 can ensure the authorization of the other party in a communication session to, for example, issue a command or receive data. In particular embodiments, identity authentication can be performed through two features. First, the party asserting its identity provides a validated certificate signed by the manufacturer of the device or the operator of the analyte monitoring system 100. Second, authentication can be enforced through the use of public keys and private keys, and shared secrets derived therefrom, established by the devices of the analyte monitoring system 100 or established by the operator of the analyte monitoring system 100. To confirm the identity of the other party, the party can provide proof that the party has control of its private key.

The manufacturer of the analyte sensor 110, data receiving device 120, or provider of the application for multi-purpose data receiving device 130 can provide information and programming necessary for the devices to securely communicate through secured programming and updates. For example, the manufacturer can provide information that can be used to generate encryption keys for each device, including secured root keys for the analyte sensor 110 and optionally for the data receiving device 120 that can be used in combination with device-specific information and operational data (e.g., entropy-based random values) to generate encryption values unique to the device, session, or data transmission as need.

Analyte data associated with a user is sensitive data at least in part because this information can be used for a variety of purposes, including for health monitoring and medication dosing decisions. In addition to user data, the analyte monitoring system 100 can enforce security hardening against efforts by outside parties to reverse-engineering. Communication connections can be encrypted using a device-unique or session-unique encryption key. Encrypted communications or unencrypted communications between any two devices can be verified with transmission integrity checks built into the communications. Analyte sensor 110 operations can be protected from tampering by restricting access to read and write functions to the memory 5020 via a communication interface. The sensor can be configured to grant access only to known or "trusted" devices, provided in a "whitelist" or only to devices that can provide a predetermined code associated with the manufacturer or an otherwise authenticated user. A whitelist can represent an exclusive range, meaning that no connection identifiers besides those included in the whitelist will be used, or a preferred range, in which the whitelist is searched first, but other devices can still be used. The sensor 110 can further deny and shut down connection requests if the requestor cannot complete a login procedure over a communication interface within a predetermined period of time (e.g., within four seconds). These characteristics safeguard against specific denial of service attacks, and in particular against denial of service attacks on a BLE interface.

As embodied herein, the analyte monitoring system 100 can employ periodic key rotation to further reduce the likelihood of key compromise and exploitation. A key rotation strategy employed by the analyte monitoring system 100 can be designed to support backward compatibility of field-deployed or distributed devices. As an example, the analyte monitoring system 100 can employ keys for downstream devices (e.g., devices that are in the field or cannot be feasibly provided updates) that are designed to be compatible with multiple generations of keys used by upstream devices.

Figure 17:
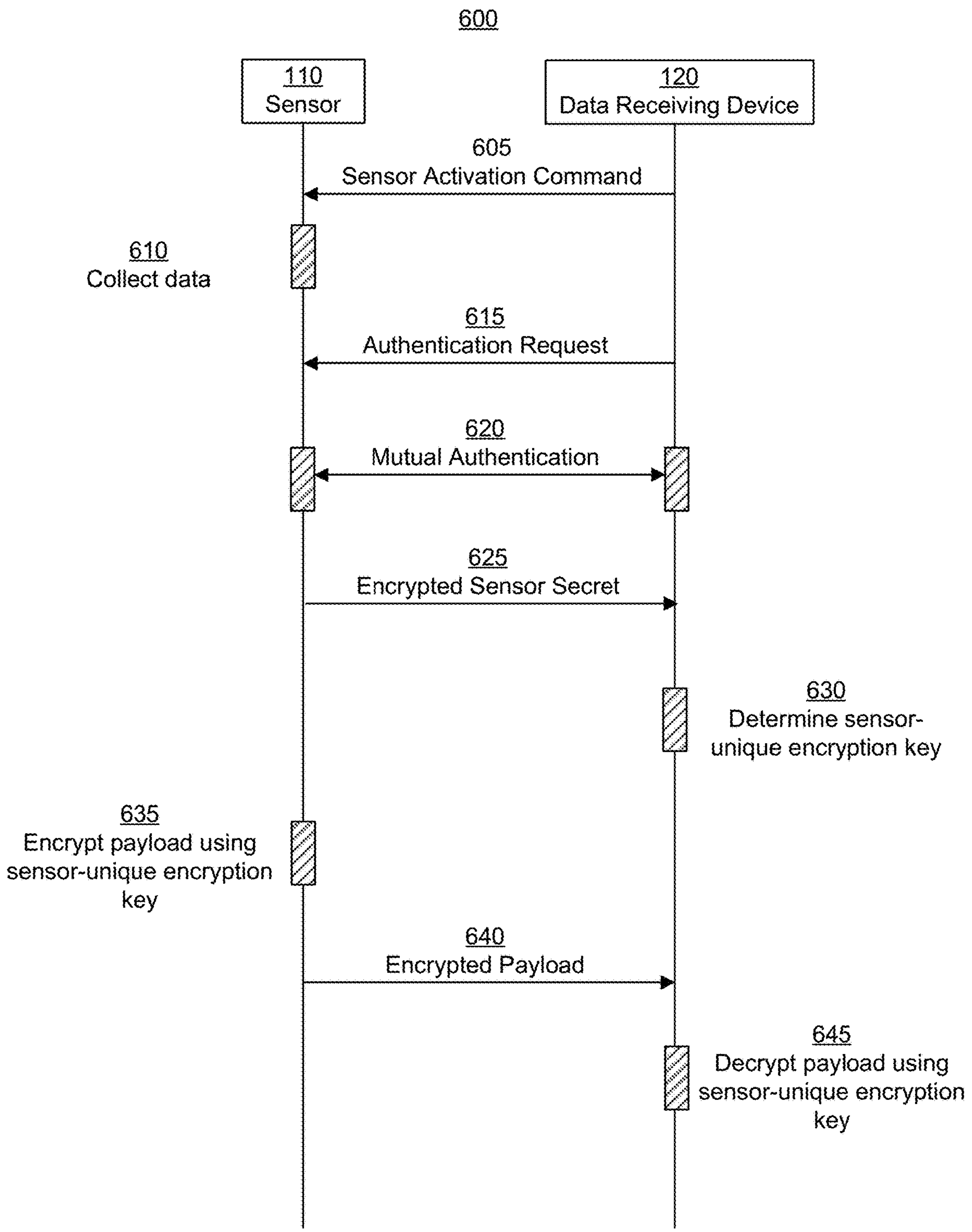
FIG. 17 is a diagram illustrating an example data flow for secure exchange of data between two devices according to the disclosed subject matter.

For purpose of illustration and not limitation, reference is made to the exemplary embodiment of a message sequence diagram 600 for use with the disclosed subject matter as shown in FIG. 17 and demonstrating an example exchange of data between a pair of devices, particularly a sensor 110 and a data receiving device 120. The data receiving device 120 can, as embodied herein, be a data receiving device 120 or a multi-purpose data receiving device 130. At step 605, the data receiving device 120 can transmit a sensor activation command 605 to the sensor 110, for example via a short-range communication protocol. The sensor 110 can, prior to step 605 be in a primarily dormant state, preserving its battery until full activation is needed. After activation during step 610, the sensor 110 can collect data or perform other operations as appropriate to the sensing hardware 5060 of the sensor 110. At step 615 the data receiving device 120 can initiate an authentication request command 615. In response to the authentication request command 615, both the sensor 110 and data receiving device 120 can engage in a mutual authentication process 620. The mutual authentication process 620 can involve the transfer of data, including challenge parameters that allow the sensor 110 and data receiving device 120 to ensure that the other device is sufficiently capable of adhering to an agreed-upon security framework described herein. Mutual authentication can be based on mechanisms for authentication of two or more entities to each other with or without on-line trusted third parties to verify establishment of a secret key via challenge-response. Mutual authentication can be performed using two-, three-, four-, or five-pass authentication, or similar versions thereof.

Following a successful mutual authentication process 620, at step 625 the sensor 110 can provide the data receiving device 120 with a sensor secret 625. The sensor secret can contain sensor-unique values and be derived from random values generated during manufacture. The sensor secret can be encrypted prior to or during transmission to prevent third-parties from accessing the secret. The sensor secret 625 can be encrypted via one or more of the keys generated by or in response to the mutual authentication process 620. At step 630, the data receiving device 120 can derive a sensor-unique encryption key from the sensor secret. The sensor-unique encryption key can further be session-unique. As such, the sensor-unique encryption key can be determined by each device without being transmitted between the sensor 110 or data receiving device 120. At step 635, the sensor 110 can encrypt data to be included in payload. At step 640, the sensor 110 can transmit the encrypted payload 640 to the data receiving device 120 using the communication link established between the appropriate communication models of the sensor 110 and data receiving device 120. At step 645, the data receiving device 120 can decrypt the payload using the sensor-unique encryption key derived during step 630. Following step 645, the sensor 110 can deliver additional (including newly collected) data and the data receiving device 120 can process the received data appropriately.

As discussed herein, the sensor 110 can be a device with restricted processing power, battery supply, and storage. The encryption techniques used by the sensor 110 (e.g., the cipher algorithm or the choice of implementation of the algorithm) can be selected based at least in part on these restrictions. The data receiving device 120 can be a more powerful device with fewer restrictions of this nature. Therefore, the data receiving device 120 can employ more sophisticated, computationally intense encryption techniques, such as cipher algorithms and implementations.

O. Exemplary Payload/Communication Frequencies

The analyte sensor 110 can be configured to alter its discoverability behavior to attempt to increase the probability of the receiving device receiving an appropriate data packet and/or provide an acknowledgement signal or otherwise reduce restrictions that can be causing an inability to receive an acknowledgement signal. Altering the discoverability behavior of the analyte sensor 110 can include, for example and without limitation, altering the frequency at which connection data is included in a data packet, altering how frequently data packets are transmitted generally, lengthening or shortening the broadcast window for data packets, altering the amount of time that the analyte sensor 110 listens for acknowledgement or scan signals after broadcasting, including directed transmissions to one or more devices (e.g., through one or more attempted transmissions) that have previously communicated with the analyte sensor 110 and/or to one or more devices on a whitelist, altering a transmission power associated with the communication module when broadcasting the data packets (e.g., to increase the range of the broadcast or decrease energy consumed and extend the life of the battery of the analyte sensor), altering the rate of preparing and broadcasting data packets, or a combination of one or more other alterations. Additionally, or alternatively, the receiving device can similarly adjust parameters relating to the listening behavior of the device to increase the likelihood of receiving a data packet including connection data.

As embodied herein, the analyte sensor 110 can be configured to broadcast data packets using two types of windows. The first window refers to the rate at which the analyte sensor 110 is configured to operate the communication hardware. The second window refers to the rate at which the analyte sensor 110 is configured to be actively transmitting data packets (e.g., broadcasting). As an example, the first window can indicate that the analyte sensor 110 operates the communication hardware to send and/or receive data packets (including connection data) during the first 2 seconds of each 60 second period. The second window can indicate that, during each 2 second window, the analyte sensor 110 transmits a data packet every 60 milliseconds. The rest of the time during the 2 second window, the analyte sensor 110 is scanning. The analyte sensor 110 can lengthen or shorten either window to modify the discoverability behavior of the analyte sensor 110.

In particular embodiments, the discoverability behavior of the analyte sensor can be stored in a discoverability profile, and alterations can be made based on one or more factors, such as the status of the analyte sensor 110 and/or by applying rules based on the status of the analyte sensor 110. For example, when the battery level of the analyte sensor 110 is below a certain amount, the rules can cause the analyte sensor 110 to decrease the power consumed by the broadcast process. As another example, configuration settings associated with broadcasting or otherwise transmitting packets can be adjusted based on the ambient temperature, the temperature of the analyte sensor 110, or the temperature of certain components of communication hardware of the analyte sensor 110. In addition to modifying the transmission power, other parameters associated with the transmission capabilities or processes of the communication hardware of the analyte sensor 110 can be modified, including, but not limited to, transmission rate, frequency, and timing. As another example, when the analyte data indicates that the subject is, or is about to be, experiencing a negative health event, the rules can cause the analyte sensor 110 to increase its discoverability to alert the receiving device of the negative health event.

P. Exemplary Sensor Sensitivity Initialization/Adjustment Features

As embodied herein, certain calibration features for the sensing hardware 5060 of the analyte sensor 110 can be adjusted based on external or interval environment features as well as to compensate for the decay of the sensing hardware 5060 during expended period of disuse (e.g., a "shelf time" prior to use). The calibration features of the sensing hardware 5060 can be autonomously adjusted by the sensor 110 (e.g., by operation of the ASIC 5000 to modify features in the memory 5020 or storage 5030) or can be adjusted by other devices of the analyte monitoring system 100.

As an example, sensor sensitivity of the sensing hardware 5060 can be adjusted based on external temperature data or the time since manufacture. When external temperatures are monitored during the storage of the sensors, the disclosed subject matter can adaptively change the compensation to sensor sensitivity over time when the device experiences changing storage conditions. For purpose of illustration not limitations, adaptive sensitivity adjustment can be performed in an "active" storage mode where the analyte sensor 110 wakes up periodically to measure temperature. These features can save the battery of the analyte device and extend the lifespan of the analyte sensors. At each temperature measurement, the analyte sensor 110 can calculate a sensitivity adjustment for that time period based on the measured temperature. Then, the temperature-weighted adjustments can be accumulated over the active storage mode period to calculate a total sensor sensitivity adjustment value at the end of the active storage mode (e.g., at insertion). Similarly, at insertion, the sensor 110 can determine the time difference between manufacture of the sensor 110 (which can be written to the storage 5030 of the ASIC 5000) or the sensing hardware 5060 and modify sensor sensitivity or other calibration features according to one or more known decay rates or formulas.

Additionally, for purpose of illustration and not limitation, as embodied herein, sensor sensitivity adjustments can account for other sensor conditions, such as sensor drift. Sensor sensitivity adjustments can be hardcoded into the sensor 110 during manufacture, for example in the case of sensor drift, based on an estimate of how much an average sensor would drift. Sensor 110 can use a calibration function that has time-varying functions for sensor offset and gain, which can account for drift over a wear period of the sensor. Thus, sensor 110 can utilize a function used to transform an interstitial current to interstitial glucose utilizing device-dependent functions describing sensor 110 drift over time, and which can represent sensor sensitivity, and can be device specific, combined with a baseline of the glucose profile. Such functions to account for sensor sensitivity and drift can improve sensor 110 accuracy over a wear period and without involving user calibration.

Q. Exemplary Model-Based Analyte Measurements

The sensor 110 detects raw measurement values from sensing hardware 5060. On-sensor processing can be performed, such as by one or more models trained to interpret the raw measurement values. Models can be machine learned models trained off-device to detect, predict, or interpret the raw measurement values to detect, predict, or interpret the levels of one or more analytes. Additional trained models can operate on the output of the machine learning models trained to interact with raw measurement values. As an example, models can be used to detect, predict, or recommend events based on the raw measurements and type of analyte(s) detected by the sensing hardware 5060. Events can include, initiation or completion of physical activity, meals, application of medical treatment or medication, emergent health events, and other events of a similar nature.

Models can be provided to the sensor 110, data receiving device 120, or multi-purpose data receiving device 130 during manufacture or during firmware or software updates. Models can be periodically refined, such as by the manufacturer of the sensor 110 or the operator of the analyte monitoring system 100, based on data received from the sensor 110 and data receiving devices of an individual user or multiple users collectively. In certain embodiments, the sensor 110 includes sufficient computational components to assist with further training or refinement of the machine learned models, such as based on unique features of the user to which the sensor 110 is attached. Machine learning models can include, by way of example and not limitation, models trained using or encompassing decision tree analysis, gradient boosting, ada boosting, artificial neural networks or variants thereof, linear discriminant analysis, nearest neighbor analysis, support vector machines, supervised or unsupervised classification, and others. The models can also include algorithmic or rules-based models in addition to machine learned models. Model-based processing can be performed by other devices, including the data receiving device 120 or multi-purpose data receiving device 130, upon receiving data from the sensor 110 (or other downstream devices).

R. Exemplary Alarm Features

Data transmitted between the sensor 110 and a data receiving device 120 can include raw or processed measurement values. Data transmitted between the sensor 110 and data receiving device 120 can further include alarms or notification for display to a user. The data receiving device 120 can display or otherwise convey notifications to the user based on the raw or processed measurement values or can display alarms when received from the sensor 110. Alarms that may be triggered for display to the user include alarms based on direct analyte values (e.g., one-time reading exceeding a threshold or failing to satisfy a threshold), analyte value trends (e.g., average reading over a set period of time exceeding a threshold or failing to satisfy a threshold; slope); analyte value predictions (e.g., algorithmic calculation based on analyte values exceeds a threshold or fails to satisfy a threshold), sensor alerts (e.g., suspected malfunction detected), communication alerts (e.g., no communication between sensor 110 and data receiving device 120 for a threshold period of time; unknown device attempting or failing to initiate a communication session with the sensor 110), reminders (e.g., reminder to charge data receiving device 120; reminder to take a medication or perform other activity), and other alerts of a similar nature. For purpose of illustration and not limitation, as embodied herein, the alarm parameters described herein can be configurable by a user or can be fixed during manufacture, or combinations of user-settable and non-user-settable parameters.

S. Exemplary Electrode Configurations

Figure 18A:
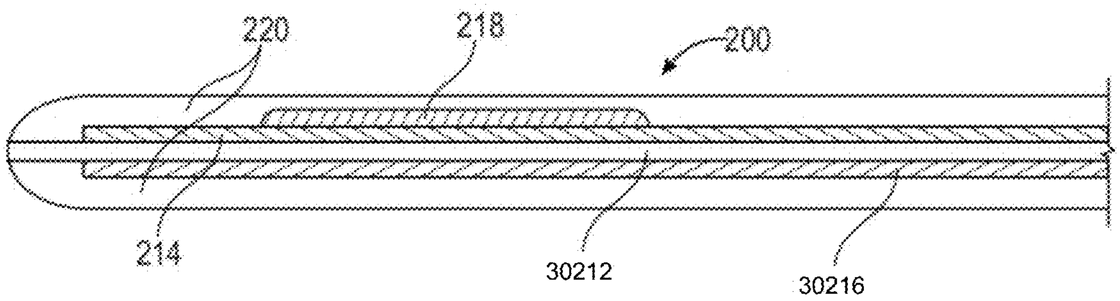
FIGS. 18A-18C show cross-sectional diagrams of analyte sensors including a single active area.
Figure 18B:
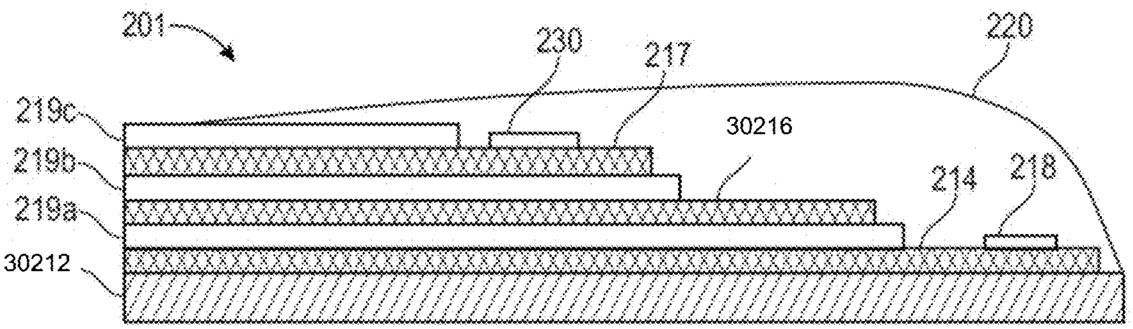
Figure 18C:
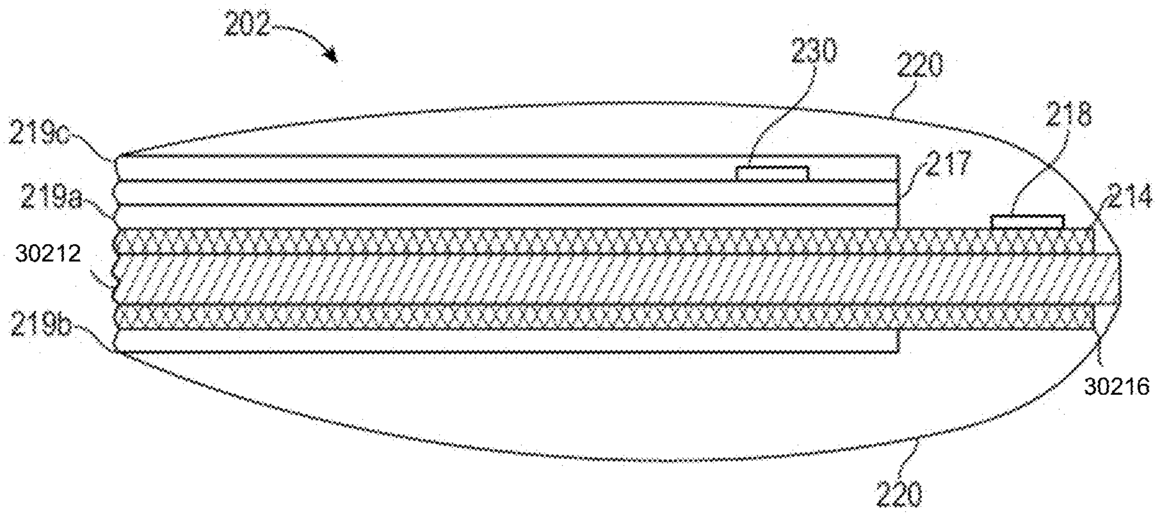

Sensor configurations featuring a single active area that is configured for detection of a corresponding single analyte can employ two-electrode or three-electrode detection motifs, as described further herein in reference to FIGS. 18A-18C. Sensor configurations featuring two different active areas for detection of the same or separate analytes, either upon separate working electrodes or upon the same working electrode, are described separately thereafter in reference to FIGS. 19A-21C. Sensor configurations having multiple working electrodes can be particularly advantageous for incorporating two different active areas within the same sensor tail, since the signal contribution from each active area can be determined more readily.

When a single working electrode is present in an analyte sensor, three-electrode sensor configurations can include a working electrode, a counter electrode, and a reference electrode. Related two-electrode sensor configurations can include a working electrode and a second electrode, in which the second electrode can function as both a counter electrode and a reference electrode (i.e., a counter/reference electrode). The various electrodes can be at least partially stacked (layered) upon one another and/or laterally spaced apart from one another upon the sensor tail. Suitable sensor configurations can be substantially flat in shape, substantially cylindrical in shape or any suitable shape. In any of the sensor configurations disclosed herein, the various electrodes can be electrically isolated from one another by a dielectric material or similar insulator.

Analyte sensors featuring multiple working electrodes can similarly include at least one additional electrode. When one additional electrode is present, the one additional electrode can function as a counter/reference electrode for each of the multiple working electrodes. When two additional electrodes are present, one of the additional electrodes can function as a counter electrode for each of the multiple working electrodes and the other of the additional electrodes can function as a reference electrode for each of the multiple working electrodes.

FIG. 18A shows a diagram of an illustrative two-electrode analyte sensor configuration, which is compatible for use in the disclosure herein. As shown, analyte sensor 200 includes substrate 30212 disposed between working electrode 214 and counter/reference electrode 30216. Alternately, working electrode 214 and counter/reference electrode 30216 can be located upon the same side of substrate 30212 with a dielectric material interposed in between (configuration not shown). Active area 218 is disposed as at least one layer upon at least a portion of working electrode 214. Active area 218 can include multiple spots or a single spot configured for detection of an analyte at a low working electrode potential, as discussed further herein. In certain embodiments, active area 218 can comprise an electron transfer agent described herein.

Referring still to FIG. 18A, membrane 220 overcoats at least active area 218. In certain embodiments, membrane 220 can also overcoat some or all of working electrode 214 and/or counter/reference electrode 30216, or the entirety of analyte sensor 200. One or both faces of analyte sensor 200 can be overcoated with membrane 220. Membrane 220 can include one or more polymeric membrane materials having capabilities of limiting analyte flux to active area 218 (i.e., membrane 220 is a mass transport limiting membrane having some permeability for the analyte of interest). According to the disclosure herein, membrane 220 can be crosslinked with a branched crosslinker in certain particular sensor configurations. For example, but not by way of limitation, membrane 220 is crosslinked with a crosslinking agent, e.g., a branched glycidyl ether, such as polyethylene glycol tetraglycidyl ether. The composition and thickness of membrane 220 can vary to promote a desired analyte flux to active area 218, thereby providing a desired signal intensity and stability. Analyte sensor 200 can be operable for assaying an analyte by any of coulometric, amperometric, voltammetric, or potentiometric electrochemical detection techniques.

FIGS. 18B and 18C show diagrams of illustrative three-electrode analyte sensor configurations, which are also compatible for use in the disclosure herein. Three-electrode analyte sensor configurations can be similar to that shown for analyte sensor 200 in FIG. 18A, except for the inclusion of additional electrode 217 in analyte sensors 201 and 202 (FIGS. 18B and 18C). With additional electrode 217, counter/reference electrode 30216 can then function as either a counter electrode or a reference electrode, and additional electrode 217 fulfills the other electrode function not otherwise accounted for. Working electrode 214 continues to fulfill its original function. Additional electrode 217 can be disposed upon either working electrode 214 or electrode 30216, with a separating layer of dielectric material in between. For example, and not by the way of limitation, as depicted in FIG. 18B, dielectric layers 219*a*, 219*b* and 219*c* separate electrodes 214, 30216 and 217 from one another and provide electrical isolation. Alternatively, at least one of electrodes 214, 30216 and 217 can be located upon opposite faces of substrate 30212, as shown in FIG. 18C. Thus, in certain embodiments, electrode 214 (working electrode) and electrode 30216 (counter electrode) can be located upon opposite faces of substrate 30212, with electrode 217 (reference electrode) being located upon one of electrodes 214 or 30216 and spaced apart therefrom with a dielectric material. Reference material layer 230 (e.g., Ag/AgCl) can be present upon electrode 217, with the location of reference material layer 230 not being limited to that depicted in FIGS. 18B and 18C. As with sensor 200 shown in FIG. 18A, active area 218 in analyte sensors 201 and 202 can include multiple spots or a single spot. In certain embodiments, active area 218 can include a redox mediator disclosed herein. Additionally, analyte sensors 201 and 202 can be operable for assaying an analyte by any of coulometric, amperometric, voltammetric, or potentiometric electrochemical detection techniques.

Like analyte sensor 200, membrane 220 can also overcoat active area 218, as well as other sensor components, in analyte sensors 201 and 202, thereby serving as a mass transport limiting membrane. In certain embodiments, the additional electrode 217 can be overcoated with membrane 220. Although FIGS. 18B and 18C have depicted electrodes 214, 30216 and 217 as being overcoated with membrane 220, it is to be recognized that in certain embodiments only working electrode 214 is overcoated. Moreover, the thickness of membrane 220 at each of electrodes 214, 30216 and 217 can be the same or different. As in two-electrode analyte sensor configurations (FIG. 18A), one or both faces of analyte sensors 201 and 202 can be overcoated with membrane 220 in the sensor configurations of FIGS. 18B and 18C, or the entirety of analyte sensors 201 and 202 can be overcoated. Accordingly, the three-electrode sensor configurations shown in FIGS. 18B and 18C should be understood as being non-limiting of the embodiments disclosed herein, with alternative electrode and/or layer configurations remaining within the scope of the present disclosure.

Figure 19A:
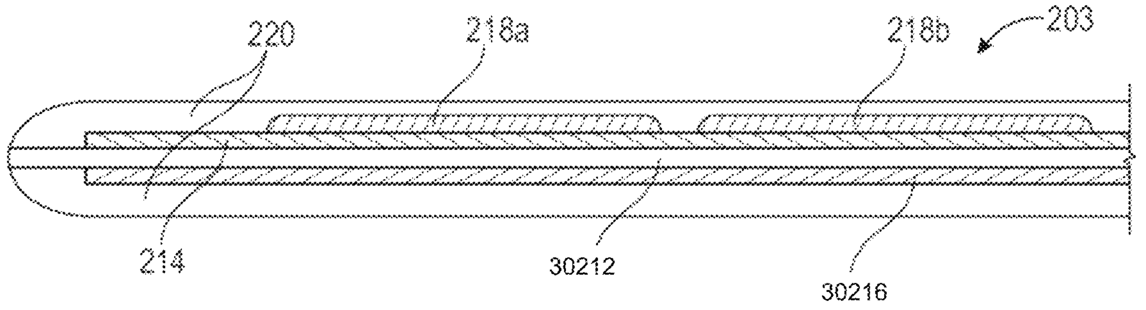
FIGS. 19A-19C show cross-sectional diagrams of analyte sensors including two active areas.

FIG. 19A shows an illustrative configuration for sensor 203 having a single working electrode with two different active areas disposed thereon. FIG. 19A is similar to FIG. 18A, except for the presence of two active areas upon working electrode 214: first active area 218*a* and second active area 218*b*, which are responsive to the same or different analytes and are laterally spaced apart from one another upon the surface of working electrode 214. Active areas 218*a* and 218*b* can include multiple spots or a single spot configured for detection of each analyte. The composition of membrane 220 can vary or be compositionally the same at active areas 218*a* and 218*b*. First active area 218*a* and second active area 218*b* can be configured to detect their corresponding analytes at working electrode potentials that differ from one another, as discussed further below.

Figure 19B:
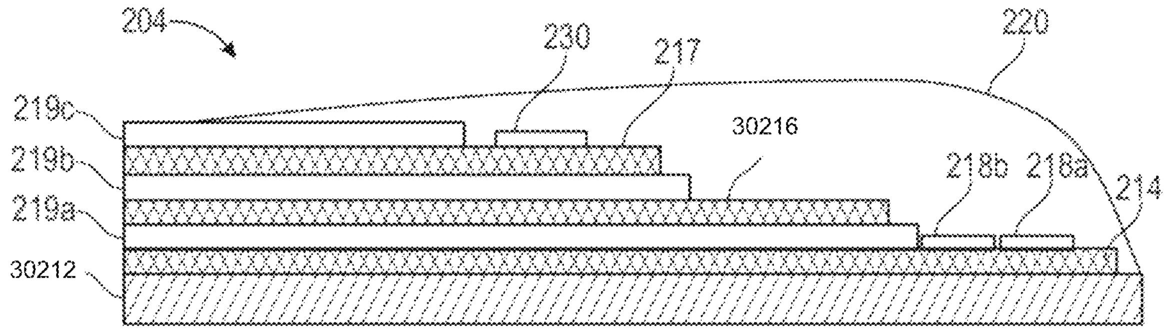
Figure 19C:
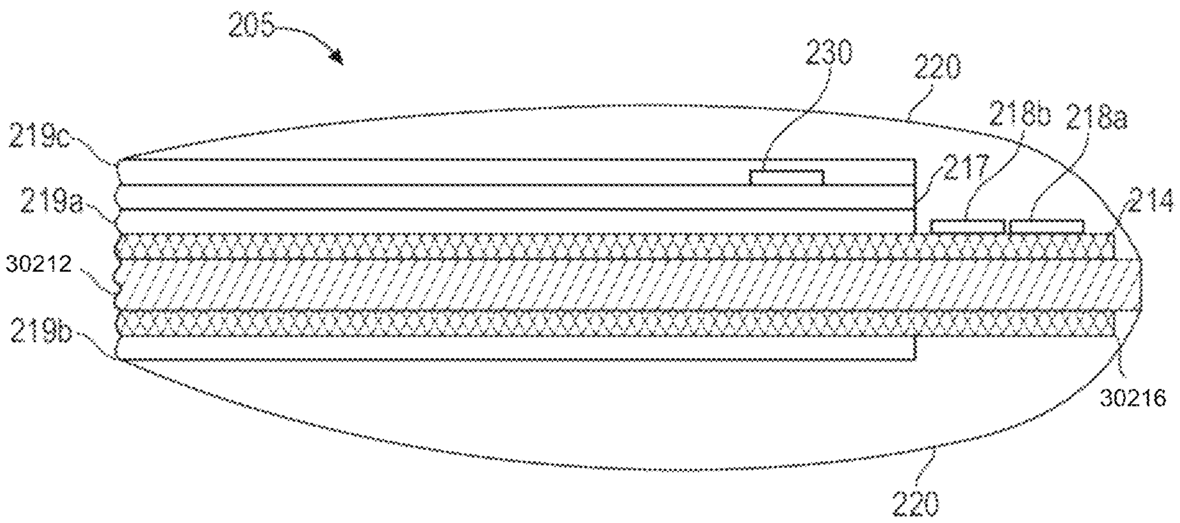

FIGS. 19B and 19C show cross-sectional diagrams of illustrative three-electrode sensor configurations for sensors 204 and 205, respectively, each featuring a single working electrode having first active area 218*a* and second active area 218*b* disposed thereon. FIGS. 19B and 19C are otherwise similar to FIGS. 18B and 18C and can be better understood by reference thereto. As with FIG. 19A, the composition of membrane 220 can vary or be compositionally the same at active areas 218*a* and 218*b*. In certain embodiments, any one of active areas 218*a* and 218*b* can comprise a redox mediator described herein. In certain embodiments, only one of active areas 218*a* and 218*b* can comprise a redox mediator described herein. For example, but not by way of limitation, only active area 218*a* includes a redox mediator described herein. In certain embodiments, only active area 218*b* includes a redox mediator described herein. In certain embodiments, both active areas 218*a* and 218*b* comprise a redox mediator described herein. In certain embodiments, the electron transfer agent present in active area 218*a* is different from the redox mediator present in 218*b*. Alternatively, the electron transfer agent present in active area 218*a* is the same redox mediator present in 218*b*.

Figure 20:
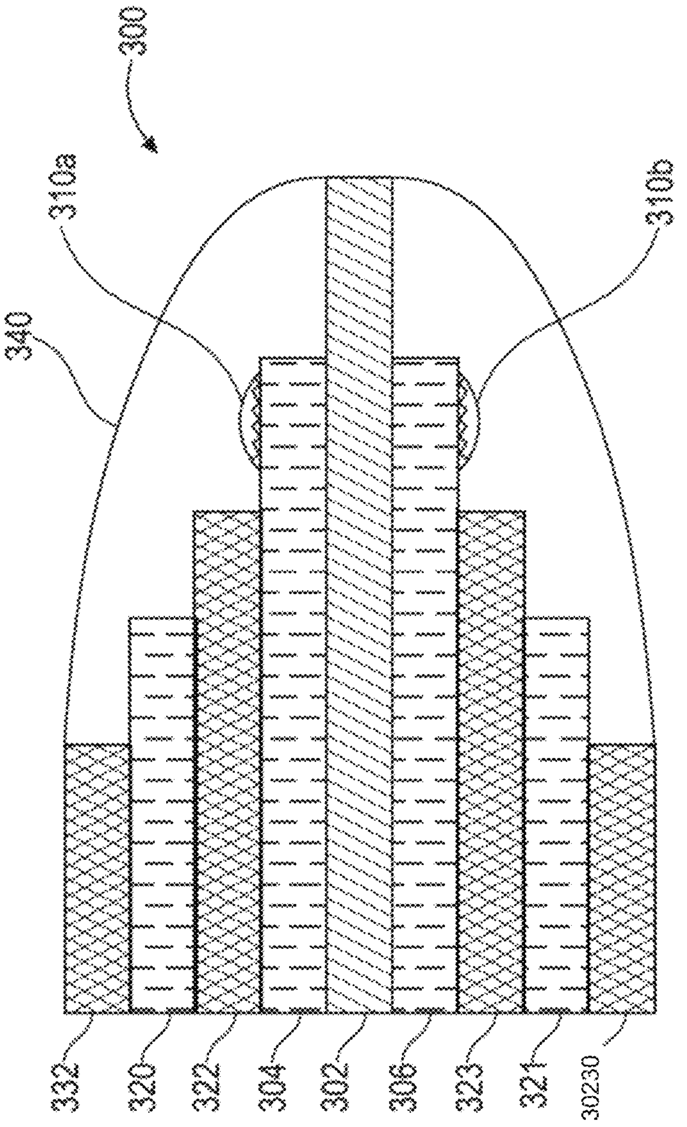
FIG. 20 shows a cross-sectional diagram of an analyte sensor including two active areas.
Figure 21A:
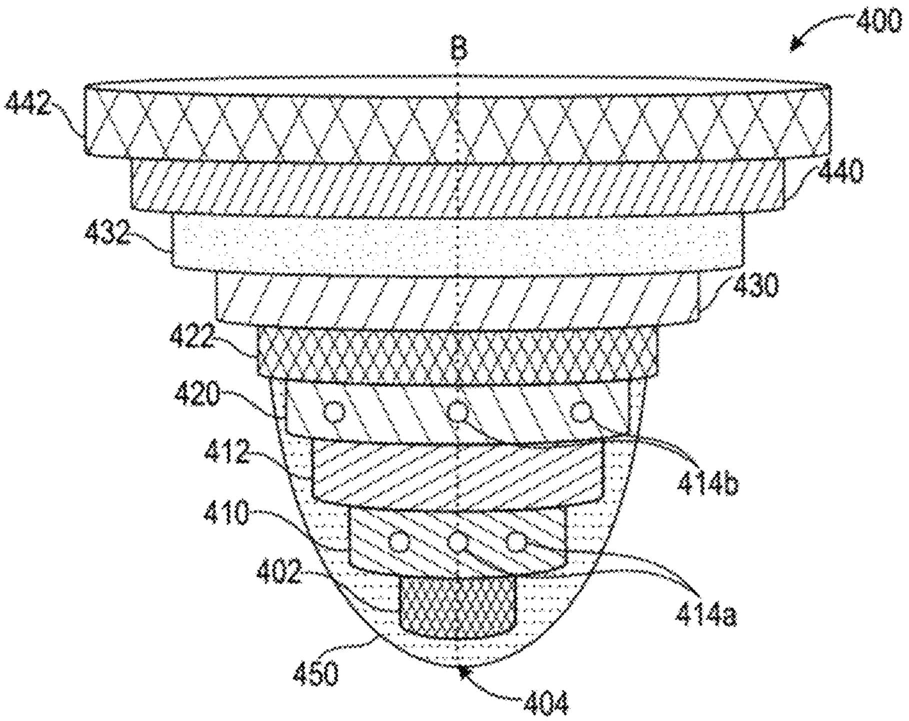
FIGS. 21A-21C show perspective views of analyte sensors including two active areas upon separate working electrodes.
Figure 21B:
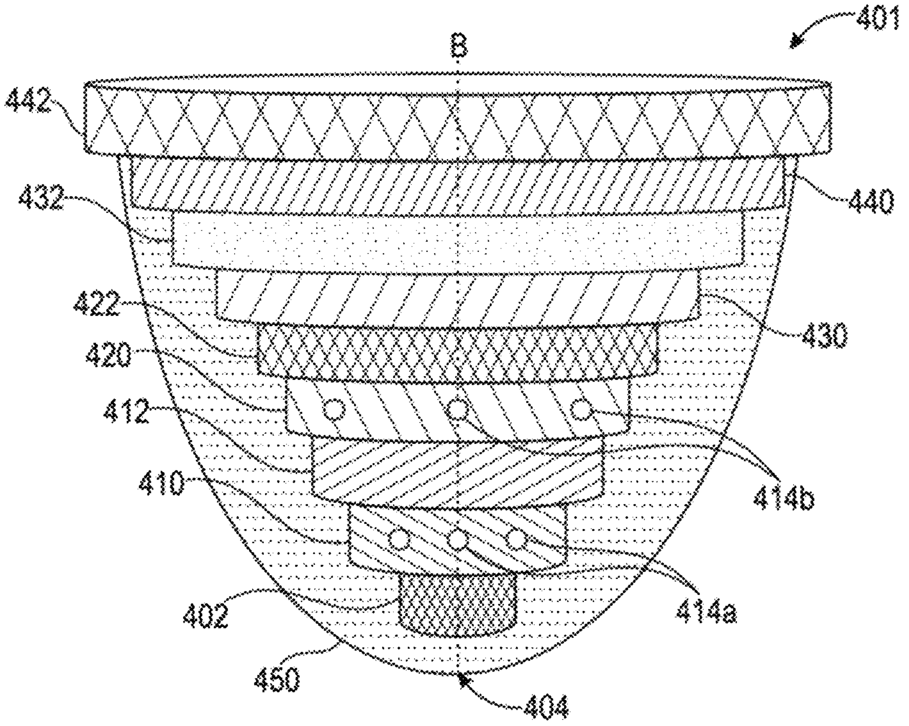
Figure 21C:
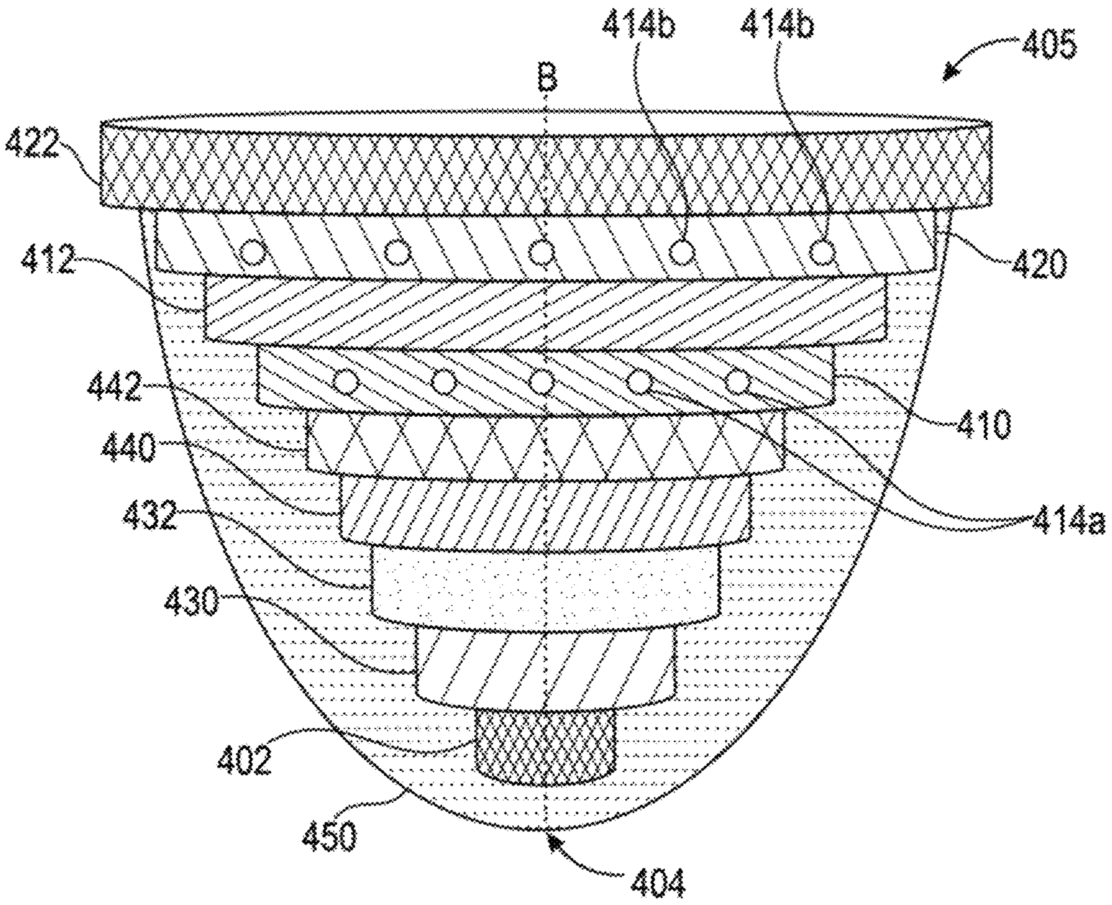

Illustrative sensor configurations having multiple working electrodes, specifically two working electrodes, are described in further detail in reference to FIGS. 20-21C. Although the following description is primarily directed to sensor configurations having two working electrodes, it is to be appreciated that more than two working electrodes can be incorporated through extension of the disclosure herein. Additional working electrodes can be used to impart additional sensing capabilities to the analyte sensors beyond just a first analyte and a second analyte.

FIG. 20 shows a cross-sectional diagram of an illustrative analyte sensor configuration having two working electrodes, a reference electrode and a counter electrode, which is compatible for use in the disclosure herein. As shown, analyte sensor 300 includes working electrodes 304 and 306 disposed upon opposite faces of substrate 302. First active area 310*a* is disposed upon the surface of working electrode 304, and second active area 310*b* is disposed upon the surface of working electrode 306. Counter electrode 320 is electrically isolated from working electrode 304 by dielectric layer 322, and reference electrode 321 is electrically isolated from working electrode 306 by dielectric layer 323. Outer dielectric layers 30230 and 332 are positioned upon reference electrode 321 and counter electrode 320, respectively. Membrane 340 can overcoat at least active areas 310*a* and 310*b*, according to various embodiments, with other components of analyte sensor 300 or the entirety of analyte sensor 300.

In certain embodiments, membrane 340 can be continuous but vary compositionally upon active area 310*a* and/or upon active area 310*b* in order to afford different permeability values for differentially regulating the analyte flux at each location. For example, but not by way of limitation, the one or more electrodes can be overcoated with a first membrane portion 340*a* and/or a second membrane portion 340*b*. In certain embodiments, different membrane formulations can be sprayed and/or printed onto the opposing faces of analyte sensor 300. Dip coating techniques can also be appropriate, particularly for depositing at least a portion of a bilayer membrane upon one of active areas 310*a* and 310*b*. In certain embodiments, membrane 340 can be the same or vary compositionally at active areas 310*a* and 310*b*. For example, but not by way of limitation, membrane 340 can include a bilayer overcoating active area 310*a* and be a homogeneous membrane overcoating active area 310*b*, or membrane 340 can include a bilayer overcoating active areas 310*b* and be a homogeneous membrane overcoating active area 310*a*. In certain embodiments, one of the first membrane portion 340*a* and the second membrane portion 340*b* can comprise a bilayer membrane and the other of the first membrane portion 340*a* and the second membrane portion 340*b* can comprise a single membrane polymer, according to particular embodiments of the present disclosure. In certain embodiments, an analyte sensor can include more than one membrane 340, e.g., two or more membranes. For example, but not by way of limitation, an analyte sensor can include a membrane that overcoats the one or more active areas, e.g., 310*a* and 310*b*, and an additional membrane that overcoats the entire sensor as shown in FIG. 20. In such configurations, a bilayer membrane can be formed over the one or more active areas, e.g., 310*a* and 310*b*. In certain embodiments, any one of active areas 310*a* and 310*b* can comprise an electron transfer agent described herein. In certain embodiments, only one of active areas 310*a* and 310*b* can comprise a redox mediator described herein. For example, but not by way of limitation, only active area 310*a* includes a redox mediator described herein. In certain embodiments, only active area 310*b* includes a redox mediator described herein. In certain embodiments, both active areas 310*a* and 310*b* comprise a redox mediator described herein. In certain embodiments, the redox mediator present in active area 310*a* is different from the electron transfer agent present in 310*b*. Alternatively, the redox mediator present in active area 310*a* is the same electron transfer agent present in 310*b*.

Like analyte sensors 200, 201 and 202, analyte sensor 300 can be operable for assaying ketones (and/or a second analyte) by any of coulometric, amperometric, voltammetric, or potentiometric electrochemical detection techniques. In certain embodiments, an analyte sensor can include more than one membrane 340, e.g., two or more membranes.

Alternative sensor configurations having multiple working electrodes and differing from the configuration shown in FIG. 20 can feature a counter/reference electrode instead of separate counter and reference electrodes 320, 321, and/or feature layer and/or membrane arrangements varying from those expressly depicted. For example, and not by the way of limitation, the positioning of counter electrode 320 and reference electrode 321 can be reversed from that depicted in FIG. 20. In addition, working electrodes 304 and 306 need not necessarily reside upon opposing faces of substrate 302 in the manner shown in FIG. 20.

Although suitable sensor configurations can feature electrodes that are substantially planar in character, it is to be appreciated that sensor configurations featuring non-planar electrodes can be advantageous and particularly suitable for use in the disclosure herein. In particular, substantially cylindrical electrodes that are disposed concentrically with respect to one another can facilitate deposition of a mass transport limiting membrane, as described hereinbelow. For example, but not by way of limitation, concentric working electrodes that are spaced apart along the length of a sensor tail can facilitate membrane deposition through sequential dip coating operations, in a similar manner to that described above for substantially planar sensor configurations. FIGS. 21A-21C show perspective views of analyte sensors featuring two working electrodes that are disposed concentrically with respect to one another. It is to be appreciated that sensor configurations having a concentric electrode disposition but lacking a second working electrode are also possible in the present disclosure.

FIG. 21A shows a perspective view of an illustrative sensor configuration in which multiple electrodes are substantially cylindrical and are disposed concentrically with respect to one another about a central substrate. As shown, analyte sensor 400 includes central substrate 402 about which all electrodes and dielectric layers are disposed concentrically with respect to one another. In particular, working electrode 410 is disposed upon the surface of central substrate 402, and dielectric layer 412 is disposed upon a portion of working electrode 410 distal to sensor tip 404. Working electrode 420 is disposed upon dielectric layer 412, and dielectric layer 422 is disposed upon a portion of working electrode 420 distal to sensor tip 404. Counter electrode 430 is disposed upon dielectric layer 422, and dielectric layer 432 is disposed upon a portion of counter electrode 430 distal to sensor tip 404. Reference electrode 440 is disposed upon dielectric layer 432, and dielectric layer 442 is disposed upon a portion of reference electrode 440 distal to sensor tip 404. As such, exposed surfaces of working electrode 410, working electrode 420, counter electrode 430, and reference electrode 440 are spaced apart from one another along longitudinal axis B of analyte sensor 400.

Referring still to FIG. 21A, first active areas 414*a* and second active areas 414*b*, which are responsive to different analytes, are disposed upon the exposed surfaces of working electrodes 410 and 420, respectively, thereby allowing contact with a fluid to take place for sensing. Although active areas 414*a* and 414*b* have been depicted as three discrete spots in FIG. 21A, it is to be appreciated that fewer or greater than three spots, including a continuous layer of active area, can be present in alternative sensor configurations. In certain embodiments, any one of active areas 414*a* and 414*b* can comprise an electron transfer agent described herein. In certain embodiments, only one of active areas 414*a* and 414*b* can comprise a redox mediator described herein. For example, but not by way of limitation, only active area 414*a* includes a redox mediator described herein. In certain embodiments, only active area 414*b* includes a redox mediator described herein. In certain embodiments, both active areas 414*a* and 414*b* comprise a redox mediator described herein. In certain embodiments, the redox mediator present in active area 414*a* is different from the electron transfer agent present in 414*b*. Alternatively, the redox mediator present in active area 414*a* is the same electron transfer agent present in 414*b*.

In FIG. 21A, sensor 400 is partially coated with membrane 450 upon working electrodes 410 and 420 and active areas 414*a* and 414*b* disposed thereon. FIG. 21B shows an alternative sensor configuration in which the substantial entirety of sensor 401 is overcoated with membrane 450. Membrane 450 can be the same or vary compositionally at active areas 414*a* and 414*b*. For example, membrane 450 can include a bilayer overcoating active area 414*a* and be a homogeneous membrane overcoating active area 414*b*.

It is to be further appreciated that the positioning of the various electrodes in FIGS. 21A and 21B can differ from that expressly depicted. For example, the positions of counter electrode 430 and reference electrode 440 can be reversed from the depicted configurations in FIGS. 21A and 21B. Similarly, the positions of working electrodes 410 and 420 are not limited to those that are expressly depicted in FIGS. 21A and 21B. FIG. 21C shows an alternative sensor configuration to that shown in FIG. 21B, in which sensor 405 contains counter electrode 430 and reference electrode 440 that are located more proximal to sensor tip 404 and working electrodes 410 and 420 that are located more distal to sensor tip 404. Sensor configurations in which working electrodes 410 and 420 are located more distal to sensor tip 404 can be advantageous by providing a larger surface area for deposition of active areas 414*a* and 414*b* (five discrete sensing spots illustratively shown in FIG. 21C), thereby facilitating an increased signal strength in some cases. Similarly, central substrate 402 can be omitted in any concentric sensor configuration disclosed herein, wherein the innermost electrode can instead support subsequently deposited layers.

In certain embodiments, one or more electrodes of an analyte sensor described herein is a wire electrode, e.g., a permeable wire electrode. In certain embodiments, the sensor tail comprises a working electrode and a reference electrode helically wound around the working electrode. In certain embodiments, an insulator is disposed between the working and reference electrodes. In certain embodiments, portions of the electrodes are exposed to allow reaction of the one or more enzymes with an analyte on the electrode. In certain embodiments, each electrode is formed from a fine wire with a diameter of from about 0.001 inches or less to about 0.010 inches or more. In certain embodiments, the working electrode has a diameter of from about 0.001 inches or less to about 0.010 inches or more, e.g., from about 0.002 inches to about 0.008 inches or from about 0.004 inches to about 0.005 inches. In certain embodiments, an electrode is formed from a plated insulator, a plated wire or bulk electrically conductive material. In certain embodiments, the working electrode comprises a wire formed from a conductive material, such as platinum, platinum-iridium, palladium, graphite, gold, carbon, conductive polymer, alloys or the like. In certain embodiments, the conductive material is a permeable conductive material. In certain embodiments, the electrodes can be formed by a variety of manufacturing techniques (e.g., bulk metal processing, deposition of metal onto a substrate or the like), the electrodes can be formed from plated wire (e.g., platinum on steel wire) or bulk metal (e.g., platinum wire). In certain embodiments, the electrode is formed from tantalum wire, e.g., covered with platinum.

In certain embodiments, the reference electrode, which can function as a reference electrode alone, or as a dual reference and counter electrode, is formed from silver, silver/silver chloride or the like. In certain embodiments, the reference electrode is juxtaposed and/or twisted with or around the working electrode. In certain embodiments, the reference electrode is helically wound around the working electrode. In certain embodiments, the assembly of wires can be coated or adhered together with an insulating material so as to provide an insulating attachment.

In certain embodiments, additional electrodes can be included in the sensor tail. For example, but not by way of limitation, a three-electrode system (a working electrode, a reference electrode and a counter electrode) and/or an additional working electrode (e.g., an electrode for detecting a second analyte). In certain embodiments where the sensor comprises two working electrodes, the two working electrodes can be juxtaposed around which the reference electrode is disposed upon (e.g., helically wound around the two or more working electrodes). In certain embodiments, the two or more working electrodes can extend parallel to each other. In certain embodiments, the reference electrode is coiled around the working electrode and extends towards the distal end (i.e., in vivo end) of the sensor tail. In certain embodiments, the reference electrode extends (e.g., helically) to the exposed region of the working electrode.

In certain embodiments, one or more working electrodes are helically wound around a reference electrode. In certain embodiments where two or more working electrodes are provided, the working electrodes can be formed in a double-, triple-, quad- or greater helix configuration along the length of the sensor tail (for example, surrounding a reference electrode, insulated rod or other support structure). In certain embodiments, the electrodes, e.g., two or more working electrodes, are coaxially formed. For example, but not by way limitation, the electrodes all share the same central axis.

In certain embodiments, the working electrode comprises a tube with a reference electrode disposed or coiled inside, including an insulator therebetween. Alternatively, the reference electrode comprises a tube with a working electrode disposed or coiled inside, including an insulator therebetween. In certain embodiments, a polymer (e.g., insulating) rod is provided, wherein the one or more electrodes (e.g., one or more electrode layers) are disposed upon (e.g., by electro-plating). In certain embodiments, a metallic (e.g., steel or tantalum) rod or wire is provided, coated with an insulating material (described herein), onto which the one or more working and reference electrodes are disposed upon. For example, but not by way of limitation, the present disclosure provides a sensor, e.g., a sensor tail, that comprises one or more tantalum wires, where a conductive material is disposed upon a portion of the one or more tantalum wires to function as a working electrode. In certain embodiments, the platinum-clad tantalum wire is covered with an insulating material, where the insulating material is partially covered with a silver/silver chloride composition to function as a reference and/or counter electrode.

In certain embodiments where an insulator is disposed upon the working electrode (e.g., upon the platinum surface of the electrode), a portion of the insulator can be stripped or otherwise removed to expose the electroactive surface of the working electrode. For example, but not by way of limitation, a portion of the insulator can be removed by hand, excimer lasing, chemical etching, laser ablation, grit-blasting or the like. Alternatively, a portion of the electrode can be masked prior to depositing the insulator to maintain an exposed electroactive surface area. In certain embodiments, the portion of the insulator that is stripped and/or removed can be from about 0.1 mm or less to about 2 mm or more in length, e.g., from about 0.5 mm to about 0.75 mm in length. In certain embodiments, the insulator is a non-conductive polymer. In certain embodiments, the insulator comprises parylene, fluorinated polymers, polyethylene terephthalate, polyvinylpyrrolidone, polyurethane, polyimide and other non-conducting polymers. In certain embodiments, glass or ceramic materials can also be used in the insulator layer. In certain embodiments, the insulator comprises parylene. In certain embodiments, the insulator comprises a polyurethane. In certain embodiments, the insulator comprises a polyurethane and polyvinylpyrrolidone.

Several parts of the sensor, including the active areas, are further described below.

2. Redox Mediators

The present disclosure provides transition metal complexes suitable for use as redox mediators. In certain embodiments, the transition metal complexes described herein include a metal center surrounded by one or more tridentate ligands, e.g., two tridentate ligands.

In certain embodiments, a tridentate ligand of the present disclosure comprises at least one pyridine, imidazole or a combination thereof. For example, but not by way a limitation, a tridentate ligand of the present disclosure has an imidazole-pyridine-imidazole structure. In certain embodiments, the tridentate ligand has a pyridine-pyridine-pyridine structure. In certain embodiments, the tridentate ligand has a pyridine-pyridine-imidazole structure. In certain embodiments, the tridentate ligand has a pyridine-imidazole-imidazole structure. In certain embodiments, the tridentate ligand has an imidazole-imidazole-imidazole structure. In certain embodiments, the tridentate ligand has a pyridine-imidazole-pyridine structure.

In certain embodiments, a tridentate ligand having an imidazole-pyridine-imidazole structure is represented by Formula I:

Formula I

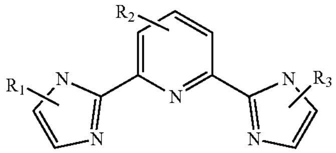

In certain embodiments, a tridentate ligand having an imidazole-pyridine-imidazole structure is represented by Formula II:

Formula II

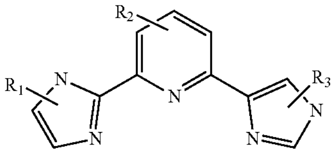

In certain embodiments, a tridentate ligand having an imidazole-pyridine-imidazole structure is represented by Formula III:

Formula III

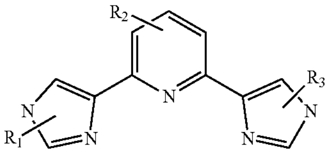

In certain embodiments, a tridentate ligand having an imidazole-pyridine-imidazole structure is represented by Formula IV:

Formula IV

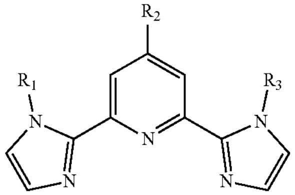

In certain embodiments, a tridentate ligand having a pyridine-pyridine-pyridine structure is represented by Formula V:

Formula V

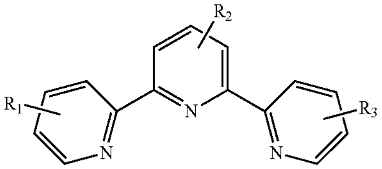

In certain embodiments, a tridentate ligand having a pyridine-pyridine-pyridine structure is represented by Formula VI:

Formula VI

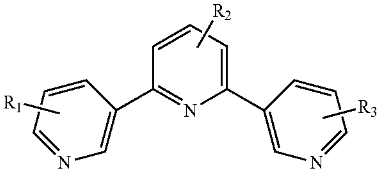

In certain embodiments, a tridentate ligand having a pyridine-pyridine-pyridine structure is represented by Formula VII:

Formula VI

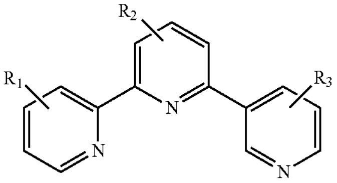

In certain embodiments, a tridentate ligand having a pyridine-pyridine-imidazole structure is represented by Formula VIII:

Formula VIII

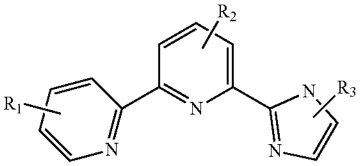

In certain embodiments, a tridentate ligand having a pyridine-pyridine-imidazole structure is represented by Formula IX:

Formula IX

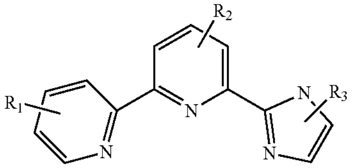

In certain embodiments, a tridentate ligand having a pyridine-imidazole-imidazole structure is represented by Formula X-A:

Formula X-A

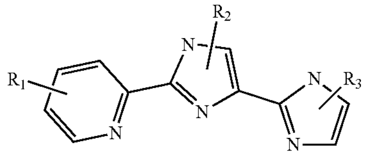

In certain embodiments, a tridentate ligand having a pyridine-imidazole-imidazole structure is represented by Formula X-B:

Formula X-B

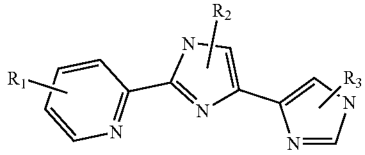

In certain embodiments, a tridentate ligand having a pyridine-imidazole-imidazole structure is represented by Formula XI-A:

Formula XI-A

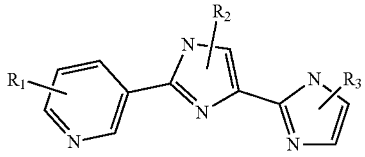

In certain embodiments, a tridentate ligand having a pyridine-imidazole-imidazole structure is represented by Formula XI-B:

Formula XI-B

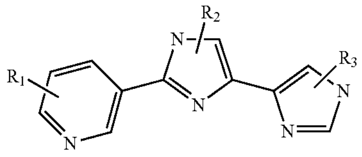

In certain embodiments, a tridentate ligand having a pyridine-imidazole-imidazole structure is represented by Formula XII-A:

Formula XII-A

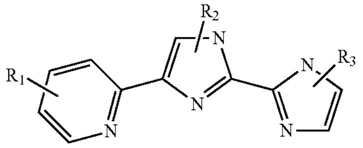

In certain embodiments, a tridentate ligand having a pyridine-imidazole-imidazole structure is represented by Formula XII-B:

Formula XII-B

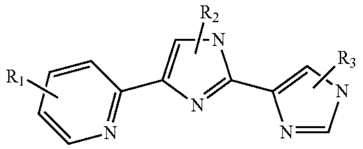

In certain embodiments, a tridentate ligand having a pyridine-imidazole-imidazole structure is represented by Formula XIII-A:

Formula XIII-A

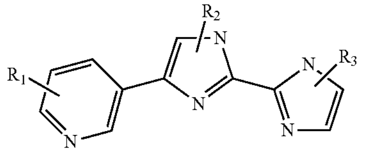

In certain embodiments, a tridentate ligand having a pyridine-imidazole-imidazole structure is represented by Formula XIII-B:

Formula XIII-B

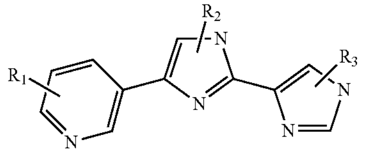

In certain embodiments, a tridentate ligand having an imidazole-imidazole-imidazole structure is represented by Formula XIV:

Formula XIV

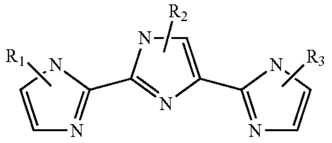

In certain embodiments, a tridentate ligand having an imidazole-imidazole-imidazole structure is represented by Formula XV:

Formula XV

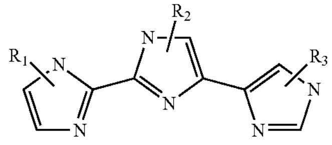

In certain embodiments, a tridentate ligand having an imidazole-imidazole-imidazole structure is represented by Formula XVI:

Formula XVI

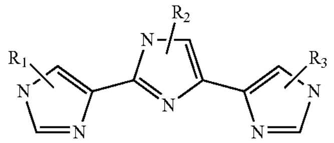

In certain embodiments, a tridentate ligand having an imidazole-imidazole-imidazole structure is represented by Formula XVII:

Formula XVII

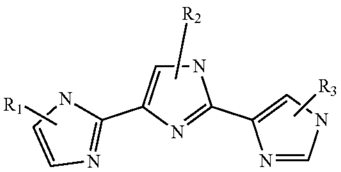

In certain embodiments, a tridentate ligand having a pyridine-imidazole-pyridine structure is represented by Formula XVIII:

Formula XVIII

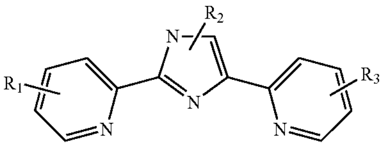

In certain embodiments, a tridentate ligand having a pyridine-imidazole-pyridine structure is represented by Formula XIX:

Formula XIX

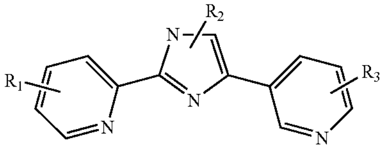

In certain embodiments, a tridentate ligand having a pyridine-imidazole-pyridine structure is represented by Formula XX:

Formula XX

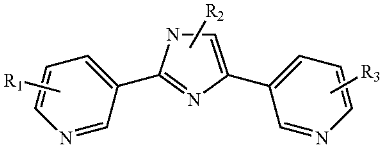

In certain embodiments, a tridentate ligand having a pyridine-imidazole-pyridine structure is represented by Formula XXI:

Formula XXI

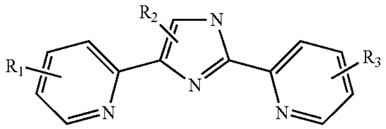

In certain embodiments, $R_1$ and $R_3$ of Formulas I-XXI are independently selected from H, an alkoxy group, an alkyl group, an alkylamido group, an alkylamino or a linking group. In certain embodiments, the linking group is capable of bonding the redox mediator to a polymer. In certain embodiments, the linking group is capable of linking two ligands, e.g., two ligands of Formula I, together. In certain embodiments, $R_1$ and/or $R_3$ can be alkyl groups. Non-limiting examples of alkyl groups include methyl or ethyl groups. In certain embodiments, the alkyl group is a $C_1$-$C_{12}$ straight or branched chain alkyl group. In certain embodiments, $R_1$ and/or $R_3$ can be polyether groups, e.g., polyethylene oxide groups. In certain embodiments, $R_1$ and/or $R_3$ can be alkoxy groups. Non-limiting examples of alkoxy groups include methoxy and ethoxy groups.

In certain embodiments, $R_2$ of Formulas I-XXI is selected from H, an electron donating group or a linking group capable of bonding the redox mediator to a polymer.

In certain embodiments, $R_2$ of Formulas I-XXI is an electron donating group. An electron donating group is an atom or a group that release electron density to neighboring atoms from itself by resonance or inductive effects. In certain embodiments, the electron donating group is a hydroxy, alkoxy, amino, alkyl, acetamido, alkylamido, alkylamino or polyether group. Non-limiting examples of alkoxy groups include methoxy and ethoxy groups, and non-limiting examples of alkylamino groups include methylamino, ethylamino and dialkylamino, e.g., dimethylamino and diethylamino, groups. In certain embodiments, the electron donating group is $NR_7R_8$, wherein $R_7$ and $R_8$ are independently selected from H or an alkyl group. In certain embodiments, the alkyl group is a $C_1$-$C_6$ alkyl group. In certain embodiments, the alkyl group is a methyl group. In certain embodiments, $R_2$ is a dimethylamino group.

In certain embodiments, $R_2$ of Formulas I-XXI is a linking group capable of bonding the redox mediator to a polymer. In certain embodiments, the linking group can contain a functional group capable of promoting covalent bonding to the polymer either by a reaction with a functional group disposed on the polymer or within a precursor to the polymer. In certain embodiments, the linking group can include an amide group, a substituted amine group or a urea group. In certain embodiments, the linking group is a linking group that is compatible with click chemistry reactions, such as an alkyne or an azide group.

In certain embodiments, the tridentate ligand has the structure represented by Formula XXII:

Formula XXII

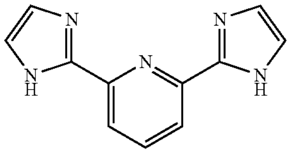

In certain embodiments, the tridentate ligand has the structure represented by Formula XXIII:

Formula XXIII

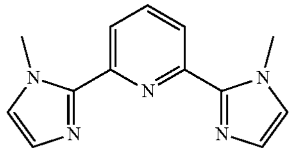

In certain embodiments, the tridentate ligand has the structure represented by Formula XXIV:

Formula XXIV

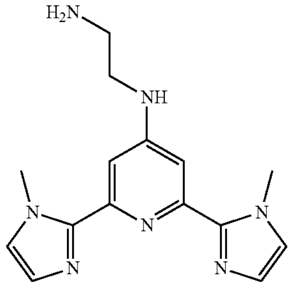

In certain embodiments, the tridentate ligand has the structure represented by Formula XXV:

Formula XXV

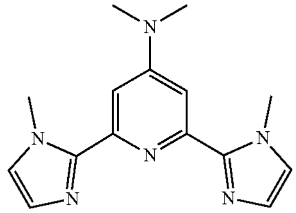

In certain embodiments, the tridentate ligand has the structure represented by Formula XXVI:

Formula XXVI

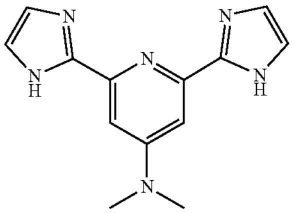

In certain embodiments, the tridentate ligand has the structure represented by Formula XXVII:

Formula XXVII

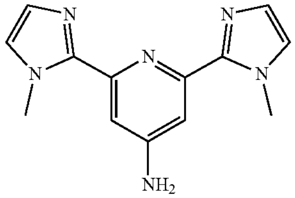

In certain embodiments, the tridentate ligand has the structure represented by Formula XXVIII:

Formula XXVIII

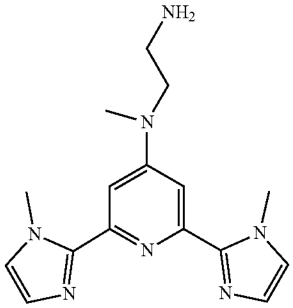

In certain embodiments, the tridentate ligand has the structure represented by Formula XXIX:

Formula XXIX

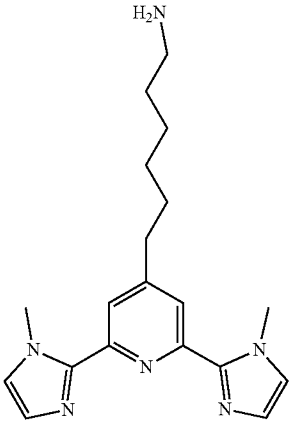

In certain embodiments, the tridentate ligand has the structure represented by Formula XXX:

Formula XXX

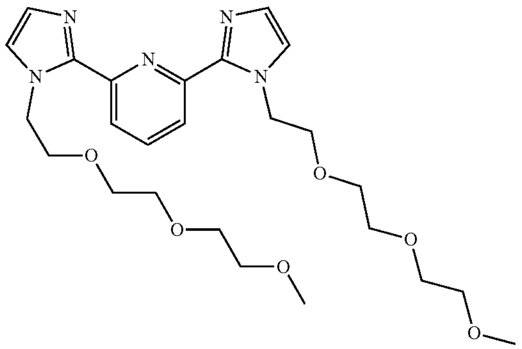

In certain embodiments, the tridentate ligand has the structure represented by Formula XXXI:

Formula XXXI

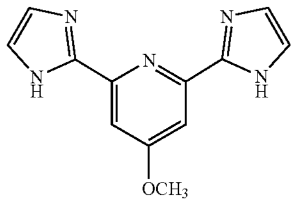

In certain embodiments, the tridentate ligand has the structure represented by Formula XXXII:

Formula XXXII

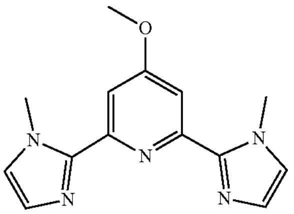

In certain embodiments, the tridentate ligand has the structure represented by Formula XXXIII:

Formula XXXIII

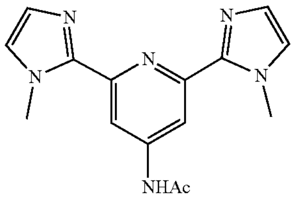

In certain embodiments, the tridentate ligand has the structure represented by Formula XXXIV:

Formula XXXIV

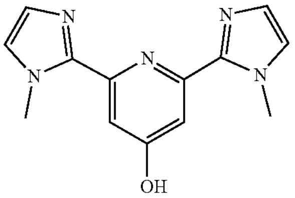

In certain embodiments, the tridentate ligand has the structure represented by Formula XXXV:

Formula XXXV

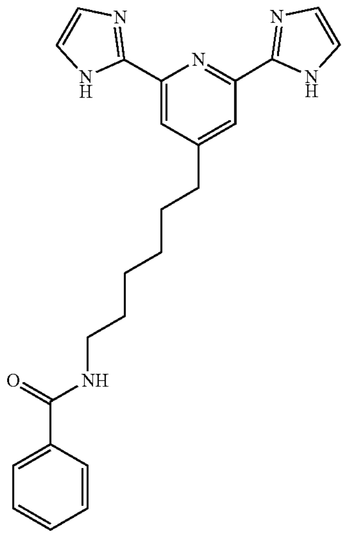

In certain embodiments, the tridentate ligand has the structure represented by Formula XXXVI:

Formula XXXVI

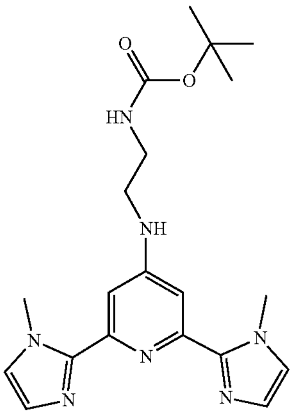

In certain embodiments, the tridentate ligand has the structure represented by Formula XXXVII:

Formula XXXVII

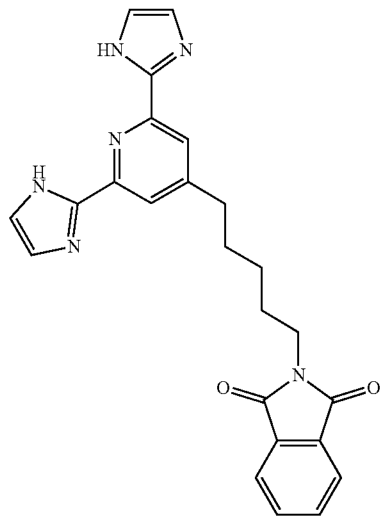

In certain embodiments, the tridentate ligand has the structure represented by Formula XXXVIII:

Formula XXXVIII

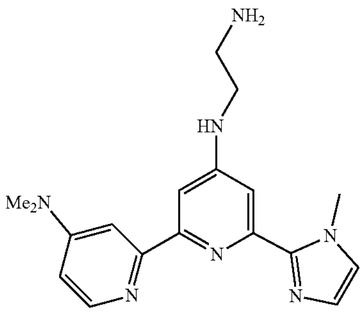

In certain embodiments, the tridentate ligand has the structure represented by Formula XXXIX:

Formula XXXIX

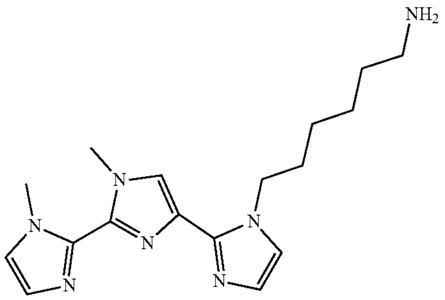

In certain embodiments, the tridentate ligand has the structure represented by Formula XL:

Formula XL

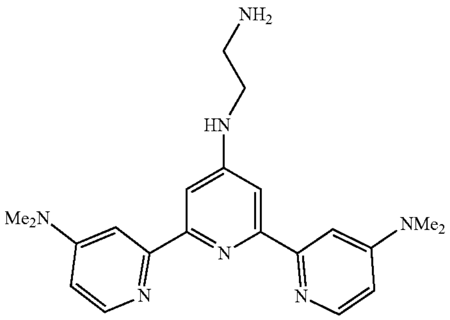

In certain embodiments, a redox mediator of the present disclosure can comprise one or more tridentate ligands of Formulas I-XXI. In certain embodiments, a redox mediator of the present disclosure can comprise two tridentate ligands of Formulas I-XXI.

In certain embodiments, a redox mediator of the present disclosure can comprise two tridentate ligands of Formula I. In certain embodiments, a redox mediator of the present disclosure can comprise a tridentate ligand of Formula I and a tridentate ligand of Formula II. In certain embodiments, a redox mediator of the present disclosure can comprise a tridentate ligand of Formula I and a tridentate ligand of Formula III. In certain embodiments, a redox mediator of the present disclosure can comprise a tridentate ligand of Formula I and a tridentate ligand of Formula IV. In certain embodiments, a redox mediator of the present disclosure can comprise a tridentate ligand of Formula I and a tridentate ligand of Formula V. In certain embodiments, a redox mediator of the present disclosure can comprise a tridentate ligand of Formula I and a tridentate ligand of Formula VI. In certain embodiments, a redox mediator of the present disclosure can comprise a tridentate ligand of Formula I and a tridentate ligand of Formula VII. In certain embodiments, a redox mediator of the present disclosure can comprise a tridentate ligand of Formula I and a tridentate ligand of Formula VIII. In certain embodiments, a redox mediator of the present disclosure can comprise a tridentate ligand of Formula I and a tridentate ligand of Formula IX. In certain embodiments, a redox mediator of the present disclosure can comprise a tridentate ligand of Formula I and a tridentate ligand of Formula X. In certain embodiments, a redox mediator of the present disclosure can comprise a tridentate ligand of Formula I and a tridentate ligand of Formula XI. In certain embodiments, a redox mediator of the present disclosure can comprise a tridentate ligand of Formula I and a tridentate ligand of Formula XII. In certain embodiments, a redox mediator of the present disclosure can comprise a tridentate ligand of Formula I and a tridentate ligand of Formula XIII. In certain embodiments, a redox mediator of the present disclosure can comprise a tridentate ligand of Formula I and a tridentate ligand of Formula XIV. In certain embodiments, a redox mediator of the present disclosure can comprise a tridentate ligand of Formula I and a tridentate ligand of Formula XV. In certain embodiments, a redox mediator of the present disclosure can comprise a tridentate ligand of Formula I and a tridentate ligand of Formula XVI. In certain embodiments, a redox mediator of the present disclosure can comprise a tridentate ligand of Formula I and a tridentate ligand of Formula XVII. In certain embodiments, a redox mediator of the present disclosure can comprise a tridentate ligand of Formula I and a tridentate ligand of Formula XVIII. In certain embodiments, a redox mediator of the present disclosure can comprise a tridentate ligand of Formula I and a tridentate ligand of Formula XIX. In certain embodiments, a redox mediator of the present disclosure can comprise a tridentate ligand of Formula I and a tridentate ligand of Formula XX. In certain embodiments, a redox mediator of the present disclosure can comprise a tridentate ligand of Formula I and a tridentate ligand of Formula XXI.

In certain embodiments, a redox mediator of the present disclosure can comprise two tridentate ligands of Formula II. In certain embodiments, a redox mediator of the present disclosure can comprise a tridentate ligand of Formula II and a tridentate ligand of Formula III. In certain embodiments, a redox mediator of the present disclosure can comprise a tridentate ligand of Formula II and a tridentate ligand of Formula IV. In certain embodiments, a redox mediator of the present disclosure can comprise a tridentate ligand of Formula II and a tridentate ligand of Formula V. In certain embodiments, a redox mediator of the present disclosure can comprise a tridentate ligand of Formula II and a tridentate ligand of Formula VI. In certain embodiments, a redox mediator of the present disclosure can comprise a tridentate ligand of Formula II and a tridentate ligand of Formula VII. In certain embodiments, a redox mediator of the present disclosure can comprise a tridentate ligand of Formula II and a tridentate ligand of Formula VIII. In certain embodiments, a redox mediator of the present disclosure can comprise a tridentate ligand of Formula II and a tridentate ligand of Formula IX. In certain embodiments, a redox mediator of the present disclosure can comprise a tridentate ligand of Formula II and a tridentate ligand of Formula X. In certain embodiments, a redox mediator of the present disclosure can comprise a tridentate ligand of Formula II and a tridentate ligand of Formula XI. In certain embodiments, a redox mediator of the present disclosure can comprise a tridentate ligand of Formula II and a tridentate ligand of Formula XII. In certain embodiments, a redox mediator of the present disclosure can comprise a tridentate ligand of Formula II and a tridentate ligand of Formula XIII In certain embodiments, a redox mediator of the present disclosure can comprise a tridentate ligand of Formula II and a tridentate ligand of Formula XIV. In certain embodiments, a redox mediator of the present disclosure can comprise a tridentate ligand of Formula II and a tridentate ligand of Formula XV. In certain embodiments, a redox mediator of the present disclosure can comprise a tridentate ligand of Formula II and a tridentate ligand of Formula XVI. In certain embodiments, a redox mediator of the present disclosure can comprise a tridentate ligand of Formula II and a tridentate ligand of Formula XVII. In certain embodiments, a redox mediator of the present disclosure can comprise a tridentate ligand of Formula II and a tridentate ligand of Formula XVIII. In certain embodiments, a redox mediator of the present disclosure can comprise a tridentate ligand of Formula II and a tridentate ligand of Formula XIX. In certain embodiments, a redox mediator of the present disclosure can comprise a tridentate ligand of Formula II and a tridentate ligand of Formula XX. In certain embodiments, a redox mediator of the present disclosure can comprise a tridentate ligand of Formula II and a tridentate ligand of Formula XXI.

In certain embodiments, a redox mediator of the present disclosure can comprise two tridentate ligands of Formula III. In certain embodiments, a redox mediator of the present disclosure can comprise a tridentate ligand of Formula III and a tridentate ligand of Formula IV. In certain embodiments, a redox mediator of the present disclosure can comprise a tridentate ligand of Formula III and a tridentate ligand of Formula V. In certain embodiments, a redox mediator of the present disclosure can comprise a tridentate ligand of Formula III and a tridentate ligand of Formula VI. In certain embodiments, a redox mediator of the present disclosure can comprise a tridentate ligand of Formula III and a tridentate ligand of Formula VII. In certain embodiments, a redox mediator of the present disclosure can comprise a tridentate ligand of Formula III and a tridentate ligand of Formula VIII. In certain embodiments, a redox mediator of the present disclosure can comprise a tridentate ligand of Formula III and a tridentate ligand of Formula IX. In certain embodiments, a redox mediator of the present disclosure can comprise a tridentate ligand of Formula III and a tridentate ligand of Formula X. In certain embodiments, a redox mediator of the present disclosure can comprise a tridentate ligand of Formula III and a tridentate ligand of Formula XI. In certain embodiments, a redox mediator of the present disclosure can comprise a tridentate ligand of Formula III and a tridentate ligand of Formula XII. In certain embodiments, a redox mediator of the present disclosure can comprise a tridentate ligand of Formula III and a tridentate ligand of Formula XIII. In certain embodiments, a redox mediator of the present disclosure can comprise a tridentate ligand of Formula III and a tridentate ligand of Formula XIV. In certain embodiments, a redox mediator of the present disclosure can comprise a tridentate ligand of Formula III and a tridentate ligand of Formula XV. In certain embodiments, a redox mediator of the present disclosure can comprise a tridentate ligand of Formula III and a tridentate ligand of Formula XVI. In certain embodiments, a redox mediator of the present disclosure can comprise a tridentate ligand of Formula III and a tridentate ligand of Formula XVII. In certain embodiments, a redox mediator of the present disclosure can comprise a tridentate ligand of Formula III and a tridentate ligand of Formula XVIII. In certain embodiments, a redox mediator of the present disclosure can comprise a tridentate ligand of Formula III and a tridentate ligand of Formula XIX. In certain embodiments, a redox mediator of the present disclosure can comprise a tridentate ligand of Formula III and a tridentate ligand of Formula XX. In certain embodiments, a redox mediator of the present disclosure can comprise a tridentate ligand of Formula III and a tridentate ligand of Formula XXI.

In certain embodiments, a redox mediator of the present disclosure can comprise two tridentate ligands of Formula IV. In certain embodiments, a redox mediator of the present disclosure can comprise a tridentate ligand of Formula IV and a tridentate ligand of Formula V. In certain embodiments, a redox mediator of the present disclosure can comprise a tridentate ligand of Formula IV and a tridentate ligand of Formula VI. In certain embodiments, a redox mediator of the present disclosure can comprise a tridentate ligand of Formula IV and a tridentate ligand of Formula VII. In certain embodiments, a redox mediator of the present disclosure can comprise a tridentate ligand of Formula IV and a tridentate ligand of Formula VIII. In certain embodiments, a redox mediator of the present disclosure can comprise a tridentate ligand of Formula IV and a tridentate ligand of Formula IX. In certain embodiments, a redox mediator of the present disclosure can comprise a tridentate ligand of Formula IV and a tridentate ligand of Formula X. In certain embodiments, a redox mediator of the present disclosure can comprise a tridentate ligand of Formula IV and a tridentate ligand of Formula XI. In certain embodiments, a redox mediator of the present disclosure can comprise a tridentate ligand of Formula IV and a tridentate ligand of Formula XII. In certain embodiments, a redox mediator of the present disclosure can comprise a tridentate ligand of Formula IV and a tridentate ligand of Formula XIII. In certain embodiments, a redox mediator of the present disclosure can comprise a tridentate ligand of Formula IV and a tridentate ligand of Formula XIV. In certain embodiments, a redox mediator of the present disclosure can comprise a tridentate ligand of Formula IV and a tridentate ligand of Formula XV. In certain embodiments, a redox mediator of the present disclosure can comprise a tridentate ligand of Formula IV and a tridentate ligand of Formula XVI. In certain embodiments, a redox mediator of the present disclosure can comprise a tridentate ligand of Formula IV and a tridentate ligand of Formula XVII. In certain embodiments, a redox mediator of the present disclosure can comprise a tridentate ligand of Formula IV and a tridentate ligand of Formula XVIII. In certain embodiments, a redox mediator of the present disclosure can comprise a tridentate ligand of Formula IV and a tridentate ligand of Formula XIX. In certain embodiments, a redox mediator of the present disclosure can comprise a tridentate ligand of Formula IV and a tridentate ligand of Formula XX. In certain embodiments, a redox mediator of the present disclosure can comprise a tridentate ligand of Formula IV and a tridentate ligand of Formula XXI.

In certain embodiments, a redox mediator of the present disclosure can comprise two tridentate ligands of Formula V. In certain embodiments, a redox mediator of the present disclosure can comprise a tridentate ligand of Formula V and a tridentate ligand of Formula VI. In certain embodiments, a redox mediator of the present disclosure can comprise a tridentate ligand of Formula V and a tridentate ligand of Formula VII. In certain embodiments, a redox mediator of the present disclosure can comprise a tridentate ligand of Formula V and a tridentate ligand of Formula VIII. In certain embodiments, a redox mediator of the present disclosure can comprise a tridentate ligand of Formula V and a tridentate ligand of Formula IX. In certain embodiments, a redox mediator of the present disclosure can comprise a tridentate ligand of Formula V and a tridentate ligand of Formula X. In certain embodiments, a redox mediator of the present disclosure can comprise a tridentate ligand of Formula V and a tridentate ligand of Formula XI. In certain embodiments, a redox mediator of the present disclosure can comprise a tridentate ligand of Formula V and a tridentate ligand of Formula XII. In certain embodiments, a redox mediator of the present disclosure can comprise a tridentate ligand of Formula V and a tridentate ligand of Formula XIII In certain embodiments, a redox mediator of the present disclosure can comprise a tridentate ligand of Formula V and a tridentate ligand of Formula XIV. In certain embodiments, a redox mediator of the present disclosure can comprise a tridentate ligand of Formula V and a tridentate ligand of Formula XV. In certain embodiments, a redox mediator of the present disclosure can comprise a tridentate ligand of Formula V and a tridentate ligand of Formula XVI. In certain embodiments, a redox mediator of the present disclosure can comprise a tridentate ligand of Formula V and a tridentate ligand of Formula XVII. In certain embodiments, a redox mediator of the present disclosure can comprise a tridentate ligand of Formula V and a tridentate ligand of Formula XVIII. In certain embodiments, a redox mediator of the present disclosure can comprise a tridentate ligand of Formula V and a tridentate ligand of Formula XIX. In certain embodiments, a redox mediator of the present disclosure can comprise a tridentate ligand of Formula V and a tridentate ligand of Formula XX. In certain embodiments, a redox mediator of the present disclosure can comprise a tridentate ligand of Formula V and a tridentate ligand of Formula XXI.

In certain embodiments, a redox mediator of the present disclosure can comprise two tridentate ligands of Formula VI. In certain embodiments, a redox mediator of the present disclosure can comprise a tridentate ligand of Formula VI and a tridentate ligand of Formula VII. In certain embodiments, a redox mediator of the present disclosure can comprise a tridentate ligand of Formula VI and a tridentate ligand of Formula VIII. In certain embodiments, a redox mediator of the present disclosure can comprise a tridentate ligand of Formula VI and a tridentate ligand of Formula IX. In certain embodiments, a redox mediator of the present disclosure can comprise a tridentate ligand of Formula VI and a tridentate ligand of Formula X. In certain embodiments, a redox mediator of the present disclosure can comprise a tridentate ligand of Formula VI and a tridentate ligand of Formula XI. In certain embodiments, a redox mediator of the present disclosure can comprise a tridentate ligand of Formula VI and a tridentate ligand of Formula XII. In certain embodiments, a redox mediator of the present disclosure can comprise a tridentate ligand of Formula VI and a tridentate ligand of Formula XIII In certain embodiments, a redox mediator of the present disclosure can comprise a tridentate ligand of Formula VI and a tridentate ligand of Formula XIV. In certain embodiments, a redox mediator of the present disclosure can comprise a tridentate ligand of Formula VI and a tridentate ligand of Formula XV. In certain embodiments, a redox mediator of the present disclosure can comprise a tridentate ligand of Formula VI and a tridentate ligand of Formula XVI. In certain embodiments, a redox mediator of the present disclosure can comprise a tridentate ligand of Formula VI and a tridentate ligand of Formula XVII. In certain embodiments, a redox mediator of the present disclosure can comprise a tridentate ligand of Formula VI and a tridentate ligand of Formula XVIII. In certain embodiments, a redox mediator of the present disclosure can comprise a tridentate ligand of Formula VI and a tridentate ligand of Formula XIX. In certain embodiments, a redox mediator of the present disclosure can comprise a tridentate ligand of Formula VI and a tridentate ligand of Formula XX. In certain embodiments, a redox mediator of the present disclosure can comprise a tridentate ligand of Formula VI and a tridentate ligand of Formula XXI.

In certain embodiments, a redox mediator of the present disclosure can comprise two tridentate ligands of Formula VII. In certain embodiments, a redox mediator of the present disclosure can comprise a tridentate ligand of Formula VII and a tridentate ligand of Formula VIII. In certain embodiments, a redox mediator of the present disclosure can comprise a tridentate ligand of Formula VII and a tridentate ligand of Formula IX. In certain embodiments, a redox mediator of the present disclosure can comprise a tridentate ligand of Formula VII and a tridentate ligand of Formula X. In certain embodiments, a redox mediator of the present disclosure can comprise a tridentate ligand of Formula VII and a tridentate ligand of Formula XI. In certain embodiments, a redox mediator of the present disclosure can comprise a tridentate ligand of Formula VII and a tridentate ligand of Formula XII. In certain embodiments, a redox mediator of the present disclosure can comprise a tridentate ligand of Formula VII and a tridentate ligand of Formula XIII In certain embodiments, a redox mediator of the present disclosure can comprise a tridentate ligand of Formula VII and a tridentate ligand of Formula XIV. In certain embodiments, a redox mediator of the present disclosure can comprise a tridentate ligand of Formula VII and a tridentate ligand of Formula XV. In certain embodiments, a redox mediator of the present disclosure can comprise a tridentate ligand of Formula VII and a tridentate ligand of Formula XVI. In certain embodiments, a redox mediator of the present disclosure can comprise a tridentate ligand of Formula VII and a tridentate ligand of Formula XVII. In certain embodiments, a redox mediator of the present disclosure can comprise a tridentate ligand of Formula VII and a tridentate ligand of Formula XVIII. In certain embodiments, a redox mediator of the present disclosure can comprise a tridentate ligand of Formula VII and a tridentate ligand of Formula XIX. In certain embodiments, a redox mediator of the present disclosure can comprise a tridentate ligand of Formula VII and a tridentate ligand of Formula XX. In certain embodiments, a redox mediator of the present disclosure can comprise a tridentate ligand of Formula VII and a tridentate ligand of Formula XXI.

In certain embodiments, a redox mediator of the present disclosure can comprise two tridentate ligands of Formula VIII. In certain embodiments, a redox mediator of the present disclosure can comprise a tridentate ligand of Formula VIII and a tridentate ligand of Formula IX. In certain embodiments, a redox mediator of the present disclosure can comprise a tridentate ligand of Formula VIII and a tridentate ligand of Formula X. In certain embodiments, a redox mediator of the present disclosure can comprise a tridentate ligand of Formula VIII and a tridentate ligand of Formula XI. In certain embodiments, a redox mediator of the present disclosure can comprise a tridentate ligand of Formula VIII and a tridentate ligand of Formula XII. In certain embodiments, a redox mediator of the present disclosure can comprise a tridentate ligand of Formula VIII and a tridentate ligand of Formula XIII. In certain embodiments, a redox mediator of the present disclosure can comprise a tridentate ligand of Formula VIII and a tridentate ligand of Formula XIV. In certain embodiments, a redox mediator of the present disclosure can comprise a tridentate ligand of Formula VIII and a tridentate ligand of Formula XV. In certain embodiments, a redox mediator of the present disclosure can comprise a tridentate ligand of Formula VIII and a tridentate ligand of Formula XVI. In certain embodiments, a redox mediator of the present disclosure can comprise a tridentate ligand of Formula VIII and a tridentate ligand of Formula XVII. In certain embodiments, a redox mediator of the present disclosure can comprise a tridentate ligand of Formula VIII and a tridentate ligand of Formula XVIII. In certain embodiments, a redox mediator of the present disclosure can comprise a tridentate ligand of Formula VIII and a tridentate ligand of Formula XIX. In certain embodiments, a redox mediator of the present disclosure can comprise a tridentate ligand of Formula VIII and a tridentate ligand of Formula XX. In certain embodiments, a redox mediator of the present disclosure can comprise a tridentate ligand of Formula VIII and a tridentate ligand of Formula XXI.

In certain embodiments, a redox mediator of the present disclosure can comprise two tridentate ligands of Formula IX. In certain embodiments, a redox mediator of the present disclosure can comprise a tridentate ligand of Formula IX and a tridentate ligand of Formula X. In certain embodiments, a redox mediator of the present disclosure can comprise a tridentate ligand of Formula IX and a tridentate ligand of Formula XI. In certain embodiments, a redox mediator of the present disclosure can comprise a tridentate ligand of Formula IX and a tridentate ligand of Formula XII. In certain embodiments, a redox mediator of the present disclosure can comprise a tridentate ligand of Formula IX and a tridentate ligand of Formula XIII. In certain embodiments, a redox mediator of the present disclosure can comprise a tridentate ligand of Formula IX and a tridentate ligand of Formula XIV. In certain embodiments, a redox mediator of the present disclosure can comprise a tridentate ligand of Formula IX and a tridentate ligand of Formula XV. In certain embodiments, a redox mediator of the present disclosure can comprise a tridentate ligand of Formula IX and a tridentate ligand of Formula XVI. In certain embodiments, a redox mediator of the present disclosure can comprise a tridentate ligand of Formula IX and a tridentate ligand of Formula XVII. In certain embodiments, a redox mediator of the present disclosure can comprise a tridentate ligand of Formula IX and a tridentate ligand of Formula XVIII. In certain embodiments, a redox mediator of the present disclosure can comprise a tridentate ligand of Formula IX and a tridentate ligand of Formula XIX. In certain embodiments, a redox mediator of the present disclosure can comprise a tridentate ligand of Formula IX and a tridentate ligand of Formula XX. In certain embodiments, a redox mediator of the present disclosure can comprise a tridentate ligand of Formula IX and a tridentate ligand of Formula XXI.

In certain embodiments, a redox mediator of the present disclosure can comprise two tridentate ligands of Formula X. In certain embodiments, a redox mediator of the present disclosure can comprise a tridentate ligand of Formula X and a tridentate ligand of Formula XI. In certain embodiments, a redox mediator of the present disclosure can comprise a tridentate ligand of Formula X and a tridentate ligand of Formula XII. In certain embodiments, a redox mediator of the present disclosure can comprise a tridentate ligand of Formula X and a tridentate ligand of Formula XIII In certain embodiments, a redox mediator of the present disclosure can comprise a tridentate ligand of Formula X and a tridentate ligand of Formula XIV. In certain embodiments, a redox mediator of the present disclosure can comprise a tridentate ligand of Formula X and a tridentate ligand of Formula XV. In certain embodiments, a redox mediator of the present disclosure can comprise a tridentate ligand of Formula X and a tridentate ligand of Formula XVI. In certain embodiments, a redox mediator of the present disclosure can comprise a tridentate ligand of Formula X and a tridentate ligand of Formula XVII. In certain embodiments, a redox mediator of the present disclosure can comprise a tridentate ligand of Formula X and a tridentate ligand of Formula XVIII. In certain embodiments, a redox mediator of the present disclosure can comprise a tridentate ligand of Formula X and a tridentate ligand of Formula XIX. In certain embodiments, a redox mediator of the present disclosure can comprise a tridentate ligand of Formula X and a tridentate ligand of Formula XX. In certain embodiments, a redox mediator of the present disclosure can comprise a tridentate ligand of Formula X and a tridentate ligand of Formula XXI.

In certain embodiments, a redox mediator of the present disclosure can comprise two tridentate ligands of Formula XI. In certain embodiments, a redox mediator of the present disclosure can comprise a tridentate ligand of Formula XI and a tridentate ligand of Formula XII. In certain embodiments, a redox mediator of the present disclosure can comprise a tridentate ligand of Formula XI and a tridentate ligand of Formula XIII In certain embodiments, a redox mediator of the present disclosure can comprise a tridentate ligand of Formula XI and a tridentate ligand of Formula XIV. In certain embodiments, a redox mediator of the present disclosure can comprise a tridentate ligand of Formula XI and a tridentate ligand of Formula XV. In certain embodiments, a redox mediator of the present disclosure can comprise a tridentate ligand of Formula XI and a tridentate ligand of Formula XVI. In certain embodiments, a redox mediator of the present disclosure can comprise a tridentate ligand of Formula XI and a tridentate ligand of Formula XVII. In certain embodiments, a redox mediator of the present disclosure can comprise a tridentate ligand of Formula XI and a tridentate ligand of Formula XVIII. In certain embodiments, a redox mediator of the present disclosure can comprise a tridentate ligand of Formula XI and a tridentate ligand of Formula XIX. In certain embodiments, a redox mediator of the present disclosure can comprise a tridentate ligand of Formula XI and a tridentate ligand of Formula XX. In certain embodiments, a redox mediator of the present disclosure can comprise a tridentate ligand of Formula XI and a tridentate ligand of Formula XXI.

In certain embodiments, a redox mediator of the present disclosure can comprise two tridentate ligands of Formula XII. In certain embodiments, a redox mediator of the present disclosure can comprise a tridentate ligand of Formula XII and a tridentate ligand of Formula XIII In certain embodiments, a redox mediator of the present disclosure can comprise a tridentate ligand of Formula XII and a tridentate ligand of Formula XIV. In certain embodiments, a redox mediator of the present disclosure can comprise a tridentate ligand of Formula XII and a tridentate ligand of Formula XV. In certain embodiments, a redox mediator of the present disclosure can comprise a tridentate ligand of Formula XII and a tridentate ligand of Formula XVI. In certain embodiments, a redox mediator of the present disclosure can comprise a tridentate ligand of Formula XII and a tridentate ligand of Formula XVII. In certain embodiments, a redox mediator of the present disclosure can comprise a tridentate ligand of Formula XII and a tridentate ligand of Formula XVIII. In certain embodiments, a redox mediator of the present disclosure can comprise a tridentate ligand of Formula XII and a tridentate ligand of Formula XIX. In certain embodiments, a redox mediator of the present disclosure can comprise a tridentate ligand of Formula XII and a tridentate ligand of Formula XX. In certain embodiments, a redox mediator of the present disclosure can comprise a tridentate ligand of Formula XII and a tridentate ligand of Formula XXI.

In certain embodiments, a redox mediator of the present disclosure can comprise two tridentate ligands of Formula XIII. In certain embodiments, a redox mediator of the present disclosure can comprise a tridentate ligand of Formula XIII and a tridentate ligand of Formula XIV. In certain embodiments, a redox mediator of the present disclosure can comprise a tridentate ligand of Formula XIIIXIII and a tridentate ligand of Formula XV. In certain embodiments, a redox mediator of the present disclosure can comprise a tridentate ligand of Formula XIII and a tridentate ligand of Formula XVI. In certain embodiments, a redox mediator of the present disclosure can comprise a tridentate ligand of Formula XIII and a tridentate ligand of Formula XVII. In certain embodiments, a redox mediator of the present disclosure can comprise a tridentate ligand of Formula XIII and a tridentate ligand of Formula XVIII. In certain embodiments, a redox mediator of the present disclosure can comprise a tridentate ligand of Formula XIII and a tridentate ligand of Formula XIX. In certain embodiments, a redox mediator of the present disclosure can comprise a tridentate ligand of Formula XIII and a tridentate ligand of Formula XX. In certain embodiments, a redox mediator of the present disclosure can comprise a tridentate ligand of Formula XIII and a tridentate ligand of Formula XXI.

In certain embodiments, a redox mediator of the present disclosure can comprise two tridentate ligands of Formula XIV. In certain embodiments, a redox mediator of the present disclosure can comprise a tridentate ligand of Formula XIV and a tridentate ligand of Formula XV. In certain embodiments, a redox mediator of the present disclosure can comprise a tridentate ligand of Formula XIV and a tridentate ligand of Formula XVI. In certain embodiments, a redox mediator of the present disclosure can comprise a tridentate ligand of Formula XIV and a tridentate ligand of Formula XVII. In certain embodiments, a redox mediator of the present disclosure can comprise a tridentate ligand of Formula XIV and a tridentate ligand of Formula XVIII. In certain embodiments, a redox mediator of the present disclosure can comprise a tridentate ligand of Formula XIV and a tridentate ligand of Formula XIX. In certain embodiments, a redox mediator of the present disclosure can comprise a tridentate ligand of Formula XIV and a tridentate ligand of Formula XX. In certain embodiments, a redox mediator of the present disclosure can comprise a tridentate ligand of Formula XIV and a tridentate ligand of Formula XXI.

In certain embodiments, a redox mediator of the present disclosure can comprise two tridentate ligands of Formula XV. In certain embodiments, a redox mediator of the present disclosure can comprise a tridentate ligand of Formula XV and a tridentate ligand of Formula XVI. In certain embodiments, a redox mediator of the present disclosure can comprise a tridentate ligand of Formula XV and a tridentate ligand of Formula XVII. In certain embodiments, a redox mediator of the present disclosure can comprise a tridentate ligand of Formula XV and a tridentate ligand of Formula XVIII. In certain embodiments, a redox mediator of the present disclosure can comprise a tridentate ligand of Formula XV and a tridentate ligand of Formula XIX. In certain embodiments, a redox mediator of the present disclosure can comprise a tridentate ligand of Formula XV and a tridentate ligand of Formula XX. In certain embodiments, a redox mediator of the present disclosure can comprise a tridentate ligand of Formula XV and a tridentate ligand of Formula XXI.

In certain embodiments, a redox mediator of the present disclosure can comprise two tridentate ligands of Formula XVI. In certain embodiments, a redox mediator of the present disclosure can comprise a tridentate ligand of Formula XVI and a tridentate ligand of Formula XVII. In certain embodiments, a redox mediator of the present disclosure can comprise a tridentate ligand of Formula XVI and a tridentate ligand of Formula XVIII. In certain embodiments, a redox mediator of the present disclosure can comprise a tridentate ligand of Formula XVI and a tridentate ligand of Formula XIX. In certain embodiments, a redox mediator of the present disclosure can comprise a tridentate ligand of Formula XVI and a tridentate ligand of Formula XX. In certain embodiments, a redox mediator of the present disclosure can comprise a tridentate ligand of Formula XVI and a tridentate ligand of Formula XXI.

In certain embodiments, a redox mediator of the present disclosure can comprise two tridentate ligands of Formula XVII. In certain embodiments, a redox mediator of the present disclosure can comprise a tridentate ligand of Formula XVII and a tridentate ligand of Formula XVIII. In certain embodiments, a redox mediator of the present disclosure can comprise a tridentate ligand of Formula XVII and a tridentate ligand of Formula XIX. In certain embodiments, a redox mediator of the present disclosure can comprise a tridentate ligand of Formula XVII and a tridentate ligand of Formula XX. In certain embodiments, a redox mediator of the present disclosure can comprise a tridentate ligand of Formula XVII and a tridentate ligand of Formula XXI.

In certain embodiments, a redox mediator of the present disclosure can comprise two tridentate ligands of Formula XVIII. In certain embodiments, a redox mediator of the present disclosure can comprise a tridentate ligand of Formula XVIII and a tridentate ligand of Formula XIX. In certain embodiments, a redox mediator of the present disclosure can comprise a tridentate ligand of Formula XVIII and a tridentate ligand of Formula XX. In certain embodiments, a redox mediator of the present disclosure can comprise a tridentate ligand of Formula XVIII and a tridentate ligand of Formula XXI.

In certain embodiments, a redox mediator of the present disclosure can comprise two tridentate ligands of Formula XIX. In certain embodiments, a redox mediator of the present disclosure can comprise a tridentate ligand of Formula XIX and a tridentate ligand of Formula XX. In certain embodiments, a redox mediator of the present disclosure can comprise a tridentate ligand of Formula XIX and a tridentate ligand of Formula XXI.

In certain embodiments, a redox mediator of the present disclosure can comprise two tridentate ligands of Formula XX. In certain embodiments, a redox mediator of the present disclosure can comprise a tridentate ligand of Formula XX and a tridentate ligand of Formula XXI.

In certain embodiments, a redox mediator of the present disclosure can comprise two tridentate ligands of Formula XXI.

In certain embodiments, a redox mediator of the present disclosure can comprise one or more tridentate ligands of Formulas I-XL. In certain embodiments, a redox mediator of the present disclosure can comprise two tridentate ligands of Formulas I-XL. In certain embodiments, a redox mediator of the present disclosure can comprise one or more tridentate ligands of Formulas XXII-XL. For example, but not by way of limitation, a redox mediator of the present disclosure can comprise at least one tridentate ligand, e.g., two tridentate ligands, having the structure of Formula I. In certain embodiments, a redox mediator of the present disclosure can comprise at least one tridentate ligand, e.g., two tridentate ligands, having the structure of Formula II. In certain embodiments, a redox mediator of the present disclosure can comprise at least one tridentate ligand, e.g., two tridentate ligands, having the structure of Formula III. In certain embodiments, a redox mediator of the present disclosure can comprise at least one tridentate ligand, e.g., two tridentate ligands, having the structure of Formula IV. In certain embodiments, a redox mediator of the present disclosure can comprise at least one tridentate ligand, e.g., two tridentate ligands, having the structure of Formula V. In certain embodiments, a redox mediator of the present disclosure can comprise at least one tridentate ligand, e.g., two tridentate ligands, having the structure of Formula VI. In certain embodiments, a redox mediator of the present disclosure can comprise at least one tridentate ligand, e.g., two tridentate ligands, having the structure of Formula VII. In certain embodiments, a redox mediator of the present disclosure can comprise at least one tridentate ligand, e.g., two tridentate ligands, having the structure of Formula VIII. In certain embodiments, a redox mediator of the present disclosure can comprise at least one tridentate ligand, e.g., two tridentate ligands, having the structure of Formula IX. In certain embodiments, a redox mediator of the present disclosure can comprise at least one tridentate ligand, e.g., two tridentate ligands, having the structure of Formula X. In certain embodiments, a redox mediator of the present disclosure can comprise at least one tridentate ligand, e.g., two tridentate ligands, having the structure of Formula XI. In certain embodiments, a redox mediator of the present disclosure can comprise at least one tridentate ligand, e.g., two tridentate ligands, having the structure of Formula XII. In certain embodiments, a redox mediator of the present disclosure can comprise at least one tridentate ligand, e.g., two tridentate ligands, having the structure of Formula XIII In certain embodiments, a redox mediator of the present disclosure can comprise at least one tridentate ligand, e.g., two tridentate ligands, having the structure of Formula XIV. In certain embodiments, a redox mediator of the present disclosure can comprise at least one tridentate ligand, e.g., two tridentate ligands, having the structure of Formula XV. In certain embodiments, a redox mediator of the present disclosure can comprise at least one tridentate ligand, e.g., two tridentate ligands, having the structure of Formula XVI. In certain embodiments, a redox mediator of the present disclosure can comprise at least one tridentate ligand, e.g., two tridentate ligands, having the structure of Formula XVII. In certain embodiments, a redox mediator of the present disclosure can comprise at least one tridentate ligand, e.g., two tridentate ligands, having the structure of Formula XVIII. In certain embodiments, a redox mediator of the present disclosure can comprise at least one tridentate ligand, e.g., two tridentate ligands, having the structure of Formula XIX. In certain embodiments, a redox mediator of the present disclosure can comprise at least one tridentate ligand, e.g., two tridentate ligands, having the structure of Formula XX. In certain embodiments, a redox mediator of the present disclosure can comprise at least one tridentate ligand, e.g., two tridentate ligands, having the structure of Formula XXI. In certain embodiments, a redox mediator of the present disclosure can comprise at least one tridentate ligand, e.g., two tridentate ligands, having the structure of Formula XXII. In certain embodiments, a redox mediator of the present disclosure can comprise at least one tridentate ligand, e.g., two tridentate ligands, having the structure of Formula XXIII In certain embodiments, a redox mediator of the present disclosure can comprise at least one tridentate ligand, e.g., two tridentate ligands, having the structure of Formula XXIV. In certain embodiments, a redox mediator of the present disclosure can comprise at least one tridentate ligand, e.g., two tridentate ligands, having the structure of Formula XXV. In certain embodiments, a redox mediator of the present disclosure can comprise at least one tridentate ligand, e.g., two tridentate ligands, having the structure of Formula XXVI. In certain embodiments, a redox mediator of the present disclosure can comprise at least one tridentate ligand, e.g., two tridentate ligands, having the structure of Formula XXVII. In certain embodiments, a redox mediator of the present disclosure can comprise at least one tridentate ligand, e.g., two tridentate ligands, having the structure of Formula XXVIII. In certain embodiments, a redox mediator of the present disclosure can comprise at least one tridentate ligand, e.g., two tridentate ligands, having the structure of Formula XXIX. In certain embodiments, a redox mediator of the present disclosure can comprise at least one tridentate ligand, e.g., two tridentate ligands, having the structure of Formula XXX. In certain embodiments, a redox mediator of the present disclosure can comprise at least one tridentate ligand, e.g., two tridentate ligands, having the structure of Formula XXXI. In certain embodiments, a redox mediator of the present disclosure can comprise at least one tridentate ligand, e.g., two tridentate ligands, having the structure of Formula XXXII. In certain embodiments, a redox mediator of the present disclosure can comprise at least one tridentate ligand, e.g., two tridentate ligands, having the structure of Formula XXXIII In certain embodiments, a redox mediator of the present disclosure can comprise at least one tridentate ligand, e.g., two tridentate ligands, having the structure of Formula XXXIV. In certain embodiments, a redox mediator of the present disclosure can comprise at least one tridentate ligand, e.g., two tridentate ligands, having the structure of Formula XXXV. In certain embodiments, a redox mediator of the present disclosure can comprise at least one tridentate ligand, e.g., two tridentate ligands, having the structure of Formula XXXVI. In certain embodiments, a redox mediator of the present disclosure can comprise at least one tridentate ligand, e.g., two tridentate ligands, having the structure of Formula XXXVII. In certain embodiments, a redox mediator of the present disclosure can comprise at least one tridentate ligand, e.g., two tridentate ligands, having the structure of Formula XXXVIII. In certain embodiments, a redox mediator of the present disclosure can comprise at least one tridentate ligand, e.g., two tridentate ligands, having the structure of Formula XXXIX. In certain embodiments, a redox mediator of the present disclosure can comprise at least one tridentate ligand, e.g., two tridentate ligands, having the structure of Formula XL.

In certain embodiments, the redox mediator disclosed herein can have the structure represented by Formula XLI:

Formula XLI

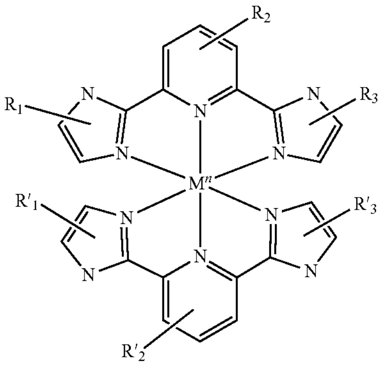

In certain embodiments, $R_1$, $R_3$, $R'_1$ and $R'_3$ of Formula XLI are independently selected from H, an alkoxy group, an alkyl group, an alkylamido group, an alkylamino or a linking group. In certain embodiments, the alkyl group is a $C_1$-$C_{12}$ straight or branched chain alkyl group. In certain embodiments, $R_1$, $R_3$, $R'_1$ and $R'_3$ are methyl groups. In certain embodiments, $R_1$, $R_3$, $R'_1$ and/or $R'_3$ can be alkyl groups. Non-limiting examples of alkyl groups include methyl or ethyl groups. In certain embodiments, the alkyl group is a $C_1$-$C_{12}$ straight or branched chain alkyl group. In certain embodiments, $R_1$, $R_3$, $R'_1$ and/or $R'_3$ can be alkoxy groups. Non-limiting examples of alkoxy groups include methoxy and ethoxy groups. In certain embodiments, $R_1$, $R_3$, $R'_1$ and/or $R'_3$ can be polyether groups, e.g., polyethylene oxide groups.

In certain embodiments, $R_2$ and $R'_2$ of Formula XLI are independently selected from H, an electron donating group or a linking group capable of bonding the redox mediator to a polymer.

In certain embodiments, $R_2$ and/or $R'_2$ of Formula XLI is an electron donating group. In certain embodiments, the electron donating group is a hydroxy, alkoxy, amino, alkyl, acetamido, alkylamido, alkylamino or polyether group. Non-limiting examples of alkoxy groups include methoxy and ethoxy groups, and non-limiting examples of alkylamino groups include methylamino, ethylamino and dialkylamino, e.g., dimethylamino and diethylamino, groups. In certain embodiments, the electron donating group is $NR_7R_8$, wherein $R_7$ and $R_8$ are independently selected from H or an alkyl group. In certain embodiments, the alkyl group is a $C_1$-$C_6$ alkyl group. In certain embodiments, the alkyl group is a methyl group. In certain embodiments, $R_2$ and/or $R'_2$ of Formula XLI is a dimethylamino group.

In certain embodiments, $R_2$ and/or $R'_2$ of Formula XLI is a linking group capable of bonding the redox mediator to a polymer. In certain embodiments, the linking group can contain a functional group capable of promoting covalent bonding to the polymer either by a reaction with a functional group disposed on the polymer or within a precursor to the polymer. In certain embodiments, the linking group can include an amide group, a substituted amine group or a urea group. In certain embodiments, the linking group is a linking group that is compatible with click chemistry reactions, such as an alkyne or an azide group.

In certain embodiments, $R_2$ is an electron donating group, e.g., a dimethylamino group, and $R'_2$ is a linking group.

"M" in Formula XLI represents a transition metal. The transition metal is not particularly limited, as long as it features at least two stable and (electro)chemically reversible redox states. In certain embodiments, the transition metal is iron, ruthenium, osmium, cobalt, or vanadium. In certain particular embodiments, the transition metal is osmium. In certain embodiments, the transition metal of a redox mediator of the present disclosure can be positively charged, as indicated by "n" on Formula XLI. In certain embodiments, n is I, II, III, IV, or V.

In certain embodiments, the redox mediator disclosed herein can have the structure represented by Formula XLII:

Formula XLII

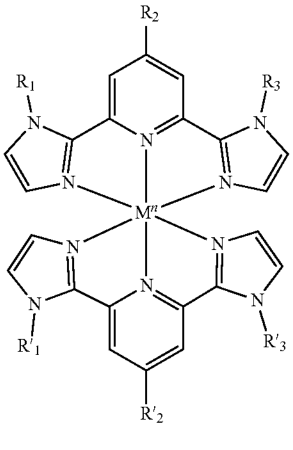

$R_1$, $R'_1$, $R_2$, $R'_2$, $R_3$, $R'_3$, M and n can be defined as described for Formula XLI.

In certain embodiments, the redox mediator can have the structure represented by Formula XLIII.

Formula XLIII

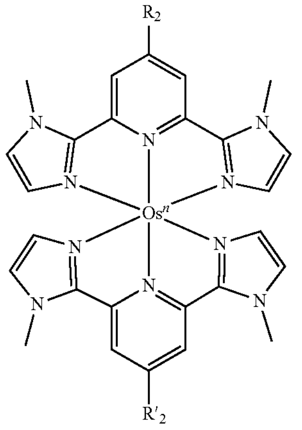

$R_2$, $R'_2$ and n can be defined as described for Formula XLI. For example, but not by way of limitation, $R_2$ and $R'_2$ are independently selected from H, an electron donating group or a linking group capable of bonding the redox mediator to a polymer. In certain embodiments, $R_2$ is an electron donating group, e.g., dimethylamino group, and $R'_2$ is a linking group.

In certain embodiments, the redox mediator can have the structure represented by Formula XLIV.

Formula XLIV

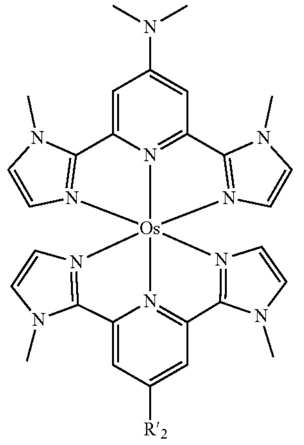

$R'_2$ can be defined as described for Formula XLI. In certain embodiments, $R'_2$ is selected from H, an electron donating group or a linking group capable of bonding the redox mediator to a polymer. In certain embodiments, $R'_2$ is a linking group capable of bonding the redox mediator to a polymer, e.g., a polymer of an active area of the sensor. For example, but not by way of limitation, $R'_2$ can contain an amide group. Non-limiting examples of polymers to be covalently bonded to the redox mediator are disclosed below (also referred to herein as a "polymeric backbone").

In certain embodiments, the redox mediator can have the structure represented by Formula XLV.

Formula XLV

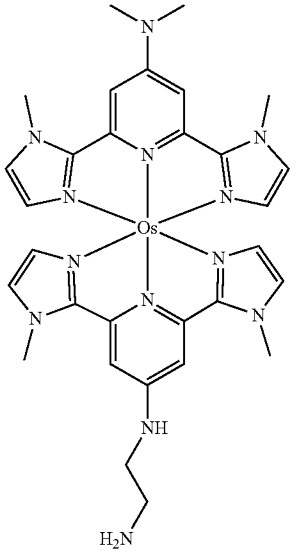

In certain embodiments, the redox mediator can have the structure represented by Formula XLVI.

Formula XLVI

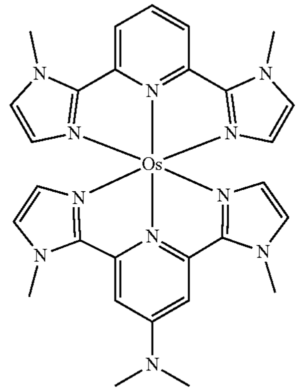

In certain embodiments, the redox mediator can have the structure represented by Formula XLVII.

Formula XLVII

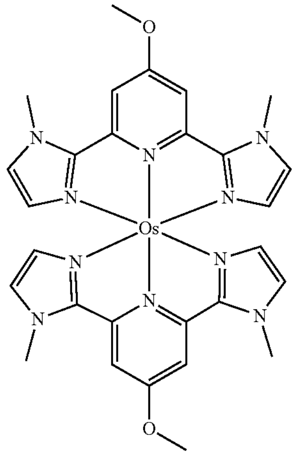

In certain embodiments, the redox mediator can have the structure represented by Formula XLVIII.

Formula XLVIII

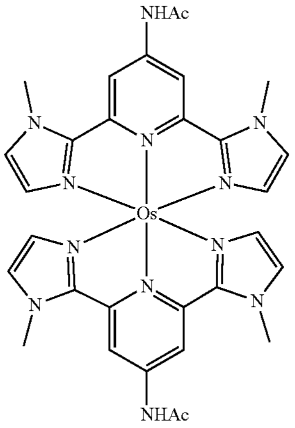

In certain embodiments, the redox mediator can have the structure represented by Formula XLIX.

Formula XLIX

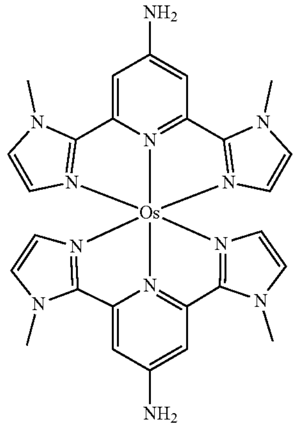

In certain embodiments, the redox mediator can have the structure represented by Formula L.

Formula L

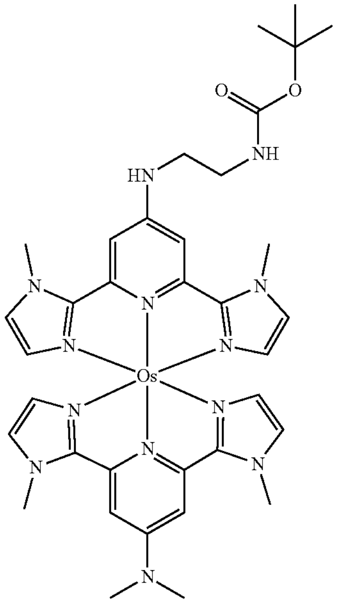

In certain embodiments, the redox mediator can have the structure represented by Formula LI.

Formula LI

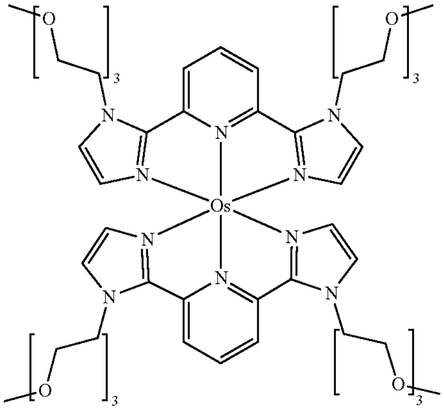

In certain embodiments, the redox mediator can have the structure represented by Formula LII.

Formula LII

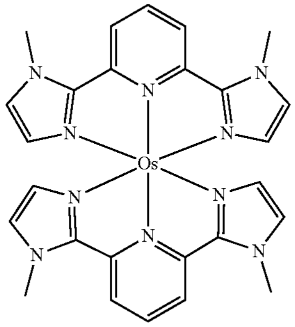

In certain embodiments, the redox mediator can have the structure represented by Formula LIII.

Formula LIII

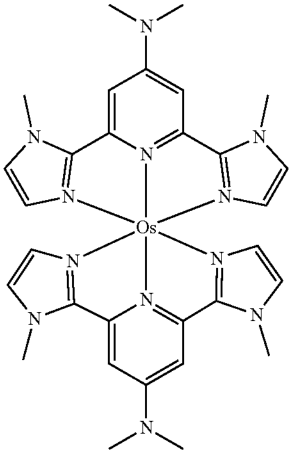

In certain embodiments, the redox mediator can have the structure represented by Formula LIV.

Formula LIV

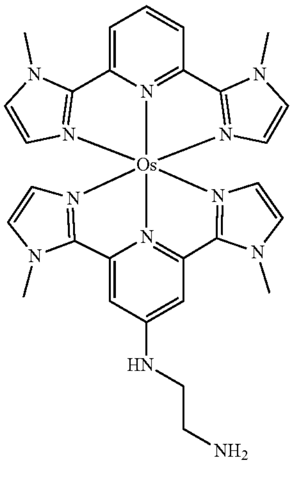

In certain embodiments, the redox mediator can have the structure represented by Formula LV.

Formula LV

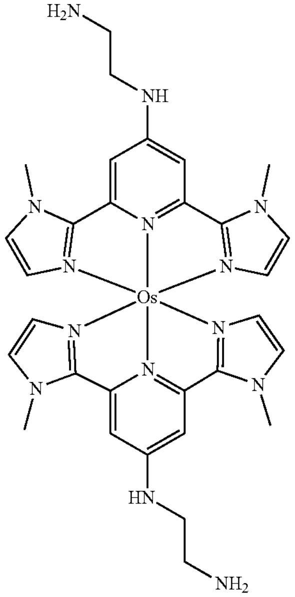

In certain embodiments, the redox mediator can have an overall positive charge. In certain embodiments, the redox mediator has an overall charge from +1 to +5. In certain other embodiments, the redox mediator has an overall negative charge if the ligands or the backbone are derivatized with a sufficient number of negatively charged functional groups, such as but not limited to carboxylate, phosphate, or sulfonate groups. In certain embodiments, the redox mediator has an overall negative charge from −1 to −5.

In certain embodiments, when the redox mediator has an overall positive charge, a counter anion can be present to balance the charge. A large variety of anions can be incorporated to balance the charge. In certain particular embodiments, the anion is a halide (fluoride, chloride, bromide, or iodide), sulfate, phosphate, hexafluorophosphate, acetate, trifluoroacetate or tetrafluoroborate.

In certain embodiments, when the redox mediator has an overall negative charge, a counter cation can be present to balance the charge. A large variety of cations can be incorporated to balance the charge. In certain particular embodiments, the cation is lithium, sodium, potassium, tetralkylammonium or ammonium.

The present disclosure provides analyte sensors including one or more redox mediators comprising a structure of any one of Formulas I-LV. In certain embodiments, an analyte sensor of the present disclosure includes one or more redox mediators of Formulas XLI-LV. In certain embodiments, an analyte sensor of the present disclosure includes one or more redox mediators of Formula XLI. In certain embodiments, an analyte sensor of the present disclosure includes one or more redox mediators of Formula XLII. In certain embodiments, an analyte sensor of the present disclosure includes one or more redox mediators of Formula XLIII. In certain embodiments, an analyte sensor of the present disclosure includes one or more redox mediators of Formula XLIV. In certain embodiments, an analyte sensor of the present disclosure includes one or more redox mediators of Formula XLV. In certain embodiments, an analyte sensor of the present disclosure includes one or more redox mediators of Formula XLVI. In certain embodiments, an analyte sensor of the present disclosure includes one or more redox mediators of Formula XLVII. In certain embodiments, an analyte sensor of the present disclosure includes one or more redox mediators of Formula XLVIII. In certain embodiments, an analyte sensor of the present disclosure includes one or more redox mediators of Formula XLIX. In certain embodiments, an analyte sensor of the present disclosure includes one or more redox mediators of Formula L. In certain embodiments, an analyte sensor of the present disclosure includes one or more redox mediators of Formula LI. In certain embodiments, an analyte sensor of the present disclosure includes one or more redox mediators of Formula LII. In certain embodiments, an analyte sensor of the present disclosure includes one or more redox mediators of Formula LIII. In certain embodiments, an analyte sensor of the present disclosure includes one or more redox mediators of Formula LIV. In certain embodiments, an analyte sensor of the present disclosure includes one or more redox mediators of Formula LV.

In certain embodiments, an analyte sensor of the present disclosure includes one or more redox mediators comprising a structure of any one of Formulas I-LV, wherein the redox mediator is coupled to a polymer. In certain embodiments, an analyte sensor of the present disclosure includes one or more redox mediators of Formulas XLI-LV, wherein the redox mediator is coupled to a polymer. For example, but not by way of limitation, the redox mediator can be covalently bonded to a polymer.

In certain embodiments, a redox mediator of the present disclosure, e.g., a redox mediator comprising a structure of any one of Formulas I-LV, is disposed on or in proximity to (e.g., in a solution surrounding) a working electrode. The redox mediator transfers electrons between the working electrode and an analyte, and in certain embodiments, an enzyme is also included to facilitate the transfer. For example, and not by the way of limitation, the redox mediator transfers electrons between the working electrode and glucose (typically via an enzyme) in an enzyme-catalyzed reaction of glucose. In certain embodiments, a redox mediator of the present disclosure is disposed on a working electrode within a composition comprising an enzyme responsive to an analyte.

In certain embodiments, the transition metal complexes disclosed herein can enable accurate, reproducible and quick or continuous assays. Transition metal complex redox mediators accept electrons from, or transfer electrons to, enzymes or analytes at a high rate and also exchange electrons rapidly with an electrode. Typically, the rate of self-exchange, the process in which a reduced redox mediator transfers an electron to an oxidized redox mediator, is rapid. At a defined redox mediator concentration, this provides for more rapid transport of electrons between the enzyme (or analyte) and electrode, and thereby shortens the response time of the sensor. Additionally, the novel transition metal complex redox mediators of the present disclosure are stable under ambient light and at the temperatures encountered in use, storage and transportation. In certain embodiments, the transition metal complex redox mediators do not undergo chemical change, other than oxidation and reduction, in the period of use or under the conditions of storage, though the redox mediators can be designed to be activated by reacting, for example, with water or the analyte. The properties of the disclosed redox mediators can allow extended wear of an analyte sensor incorporating these redox mediators and extended storage/shelf-life of such analyte sensors. For example, but not by way of limitation, an analyte sensor of the present disclosure can be used for a wear period greater than about 5 days, greater than about 6 days, greater than about 7 days, greater than about 8 days, greater than about 9 days, greater than about 10 days, greater than about 11 days, greater than about 12 days, greater than about 13 days, greater than about 14 days, greater than about 15 days, greater than about 16 days, greater than about 17 days, greater than about 18 days, greater than about 19 days, greater than about 20 days, greater than about 21 days, greater than about 22 days, greater than about 23 days, greater than about 24 days, greater than about 25 days, greater than about 26 days, greater than about 27 days, greater than about 28 days, greater than about 29 days or greater than about 30 days.

Other redox mediators can also be used in the analyte sensor systems disclosed herein. For example, but not by way of limitation, one or more additional redox mediators can be included in a second active site, e.g., in sensors configured to detect two or more analytes. In certain embodiments, redox mediators for inclusion in a second active site can include osmium complexes and other transition metal complexes, such as those described in U.S. Pat. Nos. 6,134,461 and 6,605,200, which are incorporated herein by reference in their entirety. Additional examples of suitable redox mediators include those described in U.S. Pat. Nos. 6,736,957, 7,501,053 and 7,754,093, the disclosures of each of which are also incorporated herein by reference in their entirety. Other examples of suitable redox mediators include metal compounds or complexes of ruthenium, osmium, iron (e.g., polyvinylferrocene or hexacyanoferrate) or cobalt, including metallocene compounds thereof, for example. Suitable ligands for the metal complexes can also include, for example, bidentate or higher denticity ligands such as, for example, bipyridine, biimidazole, phenanthroline, or pyridyl(imidazole). Other suitable bidentate ligands can include, for example, amino acids, oxalic acid, acetylacetone, diaminoalkanes or o-diaminoarenes. Any combination of monodentate, bidentate, tridentate, tetradentate or higher denticity ligands can be present in a metal complex, e.g., osmium complex, to achieve a full coordination sphere. In certain embodiments, the redox mediator is an osmium complex. In certain embodiments, the redox mediator is osmium complexed with bidentate ligands. In certain embodiments, the redox mediator is osmium complexed with tridentate ligands. In certain embodiments, the redox mediator is a bidentate osmium complex bound to a polymer described herein, e.g., a polymeric backbone described herein. Suitable non-limiting examples of polymer-bound redox mediators include those described in U.S. Pat. Nos. 8,444,834, 8,268,143 and 6,605,201, the disclosures of which are incorporated herein by reference in their entirety. In certain embodiments, the polymer-bound redox mediator shown in FIG. 3 of U.S. Pat. No. 8,444,834 can be used in a sensor of the present disclosure, e.g., in a second active site.

In certain embodiments, when a sensor includes two or more active areas, at least one of the active sites includes a redox mediator comprising a structure of any one of Formulas I-LV. In certain embodiments, when a sensor includes two or more active areas, at least one of the active sites includes a redox mediator of any one of Formulas XLI-LV. For example, but not by way of limitation, when a sensor includes two or more active areas, at least one of the active sites includes a redox mediator of Formula XLI, XLII, XLIII, XLIV, XLV, XLVI, XLVII, XLVIII, XLIX, L, LI, LII, LIII, LIV, LV or a combination thereof. In certain embodiments, both active sites include a redox mediator of Formula XLI, XLII, XLIII, XLIV, XLV, XLVI, XLVII, XLVIII, XLIX, L, LI, LII, LIII, LIV, LV or a combination thereof.

In certain embodiments, an analyte of the present disclosure can include (i) a sensor tail including at least a first working electrode; (ii) a first active area disposed upon a surface of the first working electrode and responsive, e.g., at low potential, to a first analyte; and (iii) a mass transport limiting membrane permeable to the first analyte that overcoats at least the first active area. In certain embodiments, the first active area includes a first redox mediator and at least one enzyme responsive to the first analyte. In certain embodiments, the first active area includes a first polymer, a first redox mediator covalently bonded to the first polymer and at least one enzyme responsive to the first analyte covalently bonded to the first polymer. In certain embodiments, the at least one enzyme responsive to the first analyte can include an enzyme system including multiple enzymes that are collectively responsive to the first analyte.

In certain embodiments, analyte sensors of the present disclosure can be further configured to analyze a second or subsequent analyte in addition to the analyte detectable in a first active area, e.g., at low potential. To facilitate detection of a second analyte, the analyte sensors of the present disclosure can further include (iv) a second working electrode, and (v) a second active area disposed upon a surface of the second working electrode and responsive to a second analyte differing from the first analyte. In certain embodiments, the second active area includes a second redox mediator differing from the first redox mediator and at least one enzyme responsive to the second analyte. Alternatively, the second active area includes a second redox mediator that is the same as the first redox mediator. In certain embodiments, the second active area includes a second polymer, a second redox mediator differing from the first redox mediator covalently bonded to the second polymer, and at least one enzyme responsive to the second analyte covalently bonded to the second polymer. In certain embodiments, the at least one enzyme responsive to the second analyte can include an enzyme system including multiple enzymes that are collectively responsive to the second analyte. The second redox mediator in the second active area need not necessarily be capable of promoting electron transfer at a low potential, although it can be. In certain embodiments, a second portion of the mass transport limiting membrane can overcoat the second active area. Alternatively or additionally, a second mass transport limiting membrane can overcoat the second active area or a second mass transport limiting membrane can overcoat the second active area and the first active area. In certain embodiments, the second mass transport limiting membrane comprises different polymers than the first mass transport limiting membrane. In certain embodiments, the second mass transport limiting membrane comprises the same polymers as the first mass transport limiting membrane but comprises a different crosslinking agent.

In certain embodiments, an analyte-responsive active area of the present disclosure can include a ratio of an enzyme to redox mediator from about 100:1 to about 1:100, e.g., from about 95:1 to about 1:95, from about 90:1 to about 1:90, from about 85:1 to about 1:85, from about 80:1 to about 1:80, from about 75:1 to about 1:75, from about 60:1 to about 1:60, from about 55:1 to about 1:55, from about 50:1 to about 1:50, from about 45:1 to about 1:45, from about 40:1 to about 1:40, from about 35:1 to about 1:35, from about 30:1 to about 1:30, from about 25:1 to about 1:25, from about 20:1 to about 1:20, from about 15:1 to about 1:15, from about 10:1 to about 1:10, from about 9:1 to about 1:9, from about 8:1 to about 1:8, from about 7:1 to about 1:7, from about 6:1 to about 1:6, from about 5:1 to about 1:5, from about 4:1 to about 1:4, from about 3:1 to about 1:3 or from about 2:1 to about 1:2. In certain embodiments, an analyte-responsive active area can include a ratio of an enzyme to redox mediator from about 10:1 to about 1:10. In certain embodiments, an analyte-responsive active area can include a ratio of an enzyme to redox mediator from about 9:1 to about 1:9. In certain embodiments, an analyte-responsive active area can include a ratio of an enzyme to redox mediator from about 8:1 to about 1:8. In certain embodiments, an analyte-responsive active area can include a ratio of an enzyme to redox mediator from about 7:1 to about 1:7. In certain embodiments, an analyte-responsive active area can include a ratio of an enzyme to redox mediator from about 6:1 to about 1:6. In certain embodiments, an analyte-responsive active area can include a ratio of an enzyme to redox mediator from about 5:1 to about 1:5. In certain embodiments, an analyte-responsive active area can include a ratio of an enzyme to redox mediator from about 4:1 to about 1:4. In certain embodiments, an analyte-responsive active area can include a ratio of an enzyme to redox mediator from about 3:1 to about 1:3. In certain embodiments, an analyte-responsive active area can include a ratio of an enzyme from about 2:1 to about 1:2. In certain embodiments, an analyte-responsive active area can include a ratio of an enzyme to redox mediator of about 1:1.

In certain embodiments, the analyte-responsive active area can include by weight from about 10% to about 50% of the redox mediator, e.g., from about 15% to about 45%, from about 20% to about 40%, from about 20% to about 35% or from about 20% to about 30% of the redox mediator. In certain embodiments, the analyte-responsive active area can include from about 5% to about 35% by weight of the redox mediator. In certain embodiments, the analyte-responsive active area can include from about 10% to about 35% by weight of the redox mediator. In certain embodiments, the analyte-responsive active area can include from about 10% to about 30% by weight of the redox mediator. In certain embodiments, the analyte-responsive active area can include from about 15% to about 35% by weight of the redox mediator.

3. Polymeric Backbone

In certain embodiments, one or more active sites for promoting analyte detection can include a polymer to which the redox mediator of the present disclosure are covalently bound. Any suitable polymeric backbone can be present in the active area for facilitating detection of an analyte through covalent bonding of the redox mediator and the enzyme thereto. Non-limiting examples of suitable polymers within the active area include polyvinylpyridines, e.g., poly(4-vinylpyridine) and/or poly(2-vinylpyridine), and polyvinylimidazoles, e.g., poly(N-vinylimidazole) and poly(1-vinylimidazole), or a copolymer thereof, for example, in which quaternized pyridine groups serve as a point of attachment for the redox mediator or enzyme thereto. Illustrative copolymers that can be suitable for inclusion in the active areas include those containing monomer units such as styrene, acrylamide, methacrylamide, or acrylonitrile, for example. In certain embodiments, the polymer is a copolymer of vinylpyridine and styrene. In certain embodiments, polymers that can be present in an active area include a polyurethane or a copolymer thereof, and/or polyvinylpyrrolidone. Additional non-limiting examples of polymers that can be present in the active area include those described in U.S. Pat. No. 6,605,200, incorporated herein by reference in its entirety, such as poly(acrylic acid), styrene/maleic anhydride copolymer, methylvinylether/maleic anhydride copolymer (GANTREZ polymer), poly(vinylbenzylchloride), poly(allylamine), polylysine, poly(4-vinylpyridine) quaternized with carboxypentyl groups, and poly(sodium 4-styrene sulfonate). In certain embodiments, polymers that can be present in the active area include those described in U.S. Pat. Nos. 8,444,834, 8,268,143 and 6,605,201, the disclosures of which are incorporated herein by reference in their entirety. In certain embodiments, the polymer within each active area can be the same or different.

In certain embodiments, the polymer is a polyvinylpyridine-based polymer. In certain embodiments, the polymer is polyvinylpyridine or polyvinylimidazole. In certain embodiments, the polymer is a co-polymer of vinylpyridine and styrene or a co-polymer of polyvinylpyridine and polystyrenesulfonate.

In certain embodiments, a polymer disclosed herein is covalently bonded to a redox mediator, e.g., by the linking group ($R_2$ and/or R' 2) of the redox mediator, of the present disclosure.

4. Enzymes

The sensors of the present disclosure include one or more enzymes, e.g., covalently bound to a polymer, for detecting one or more analytes. Suitable enzymes for use in a sensor of the present disclosure include, but are not limited to, enzymes for use in detecting glutamate, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, aspartate, asparagine, magnesium, oxygen, pH, phosphorus, potassium, sodium, total protein and uric acid. In certain embodiments, enzymes for use in detecting glucose, lactate, ketones, creatinine, alcohol, e.g., ethanol, or the like can be included in an active area of an analyte sensor disclosed herein. In certain embodiments, the one or more enzymes covalently bound to the polymer can include multiple enzymes, e.g., an enzyme system, that are collectively responsive to the analyte, e.g., at low potential.

In certain embodiments, the active area can further include a redox mediator of the present disclosure. For example, but not by way of limitation, an active area for detecting an analyte, e.g., glutamate, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, aspartate, asparagine, magnesium, oxygen, pH, phosphorus, potassium, sodium, total protein or uric acid, includes a redox mediator comprising a structure of any one of Formulas I-LV. In certain embodiments, an active area for detecting an analyte, e.g., glutamate, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, aspartate, asparagine, magnesium, oxygen, pH, phosphorus, potassium, sodium, total protein or uric acid, includes a redox mediator comprising a structure of any one of Formulas XLI-LV.

In certain embodiments, a sensor of the present disclosure can include one or more enzymes that can be used to detect glucose, e.g., in a first active area. For example, but not by way of limitation, the sensor can include a glucose-responsive enzyme such as a glucose oxidase or a glucose dehydrogenase. In certain embodiments, a glucose-responsive area can include glucose oxidase. In certain embodiments, a glucose-responsive area can include glucose dehydrogenase. In certain embodiments, a glucose-responsive area can further include a redox mediator of the present disclosure.

In certain particular embodiments, a sensor of the present disclosure can include one or more enzymes that can be used to detect creatinine. For example, but not by way of limitation, the sensor can include amidohydrolase, creatine amidinohydrolase, and/or sarcosine oxidase. In certain embodiments, a creatinine-responsive area can further include a redox mediator of the present disclosure.

In certain particular embodiments, a sensor of the present disclosure can include one or more enzymes that can be used to detect lactate. For example, but not by way of limitation, the sensor can include lactate oxidase and/or lactate dehydrogenase. In certain embodiments, a lactate-responsive area can further include a redox mediator of the present disclosure.

Figure 22A:
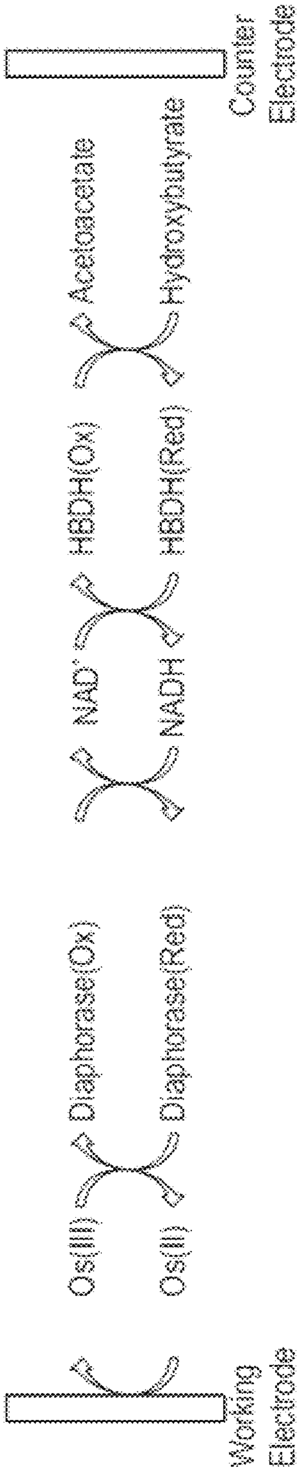
FIGS. 22A-22C show diagrams of enzyme systems that can be used for detecting ketones in an analyte sensor.
Figure 24A:
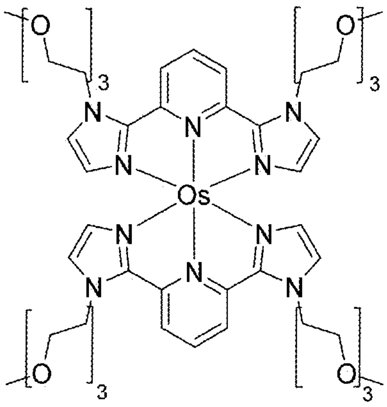
FIG. 24A provides the chemical structure of an exemplary redox mediator of the present disclosure in free form.
Figure 24B:
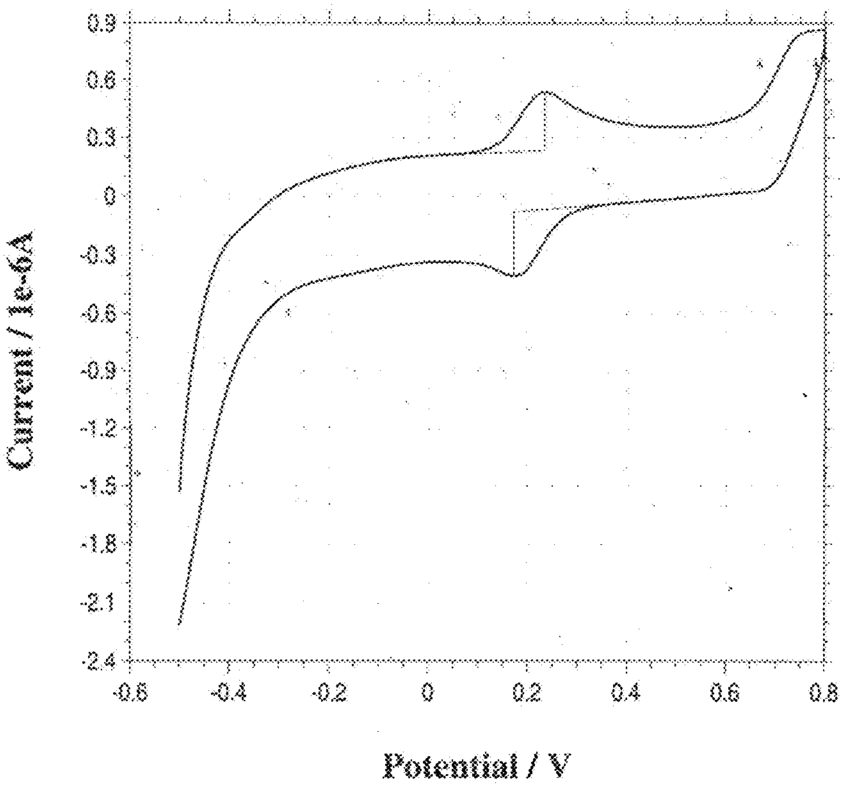
FIG. 24B shows a cyclic voltammogram for the exemplary redox mediator of FIG. 24A.

In certain particular embodiments, a sensor of the present disclosure can include one or more enzymes that that can be used to detect ketones, e.g., in a first active area or a second active area. As referenced previously, ketones are usually present in low biological abundance and can benefit from detection at low potential in accordance with the disclosure herein. Referring now to FIGS. 24A-24C, particular enzyme systems that can be used for detecting ketones will be described in further detail. In the depicted enzymatic reactions, β-hydroxybutyrate serves as a surrogate for ketones formed in vivo. As shown in FIG. 22A, one pair of concerted enzymes that can be used for detecting ketones according to the disclosure herein is β-hydroxybutyrate dehydrogenase (HBDH) and diaphorase, which can be deposited within a ketones-responsive active area upon the surface of at least one working electrode, as described further herein. When a ketones-responsive active area contains this pair of concerted enzymes, β-hydroxybutyrate dehydrogenase can convert β-hydroxybutyrate and oxidized nicotinamide adenine dinucleotide ($NAD^+$) into acetoacetate and reduced nicotinamide adenine dinucleotide (NADH), respectively. The enzyme cofactors $NAD^+$ and NADH aid in promoting the concerted enzymatic reactions disclosed herein. The NADH can then undergo reduction under diaphorase mediation, with the electrons transferred during this process providing the basis for ketone detection at the working electrode. Thus, there is a 1:1 molar correspondence between the number of electrons transferred to the working electrode and β-hydroxybutyrate converted, thereby providing the basis for ketone detection and quantification based upon the measured amount of current at the working electrode. Transfer of the electrons resulting from NADH reduction to the working electrode can take place through the redox mediator capable of promoting operation at low potential. In certain embodiments, the redox mediator comprises a structure of any one of Formulas I-LV. In certain embodiments, albumin can be present as a stabilizer with this pair of concerted enzymes.

In certain particular embodiments, the β-hydroxybutyrate dehydrogenase and the diaphorase can be covalently bonded to a polymer within the ketones-responsive active area of the analyte sensors. The $NAD^+$ can be covalently bonded to the polymer. In certain embodiments, when the $NAD^+$ is not covalently bonded, it can be physically retained within the ketones-responsive active area. A membrane overcoating the ketones-responsive active area can aid in retaining the $NAD^+$ within the ketones-responsive active area while still permitting sufficient inward diffusion of ketones to permit detection thereof.

Other suitable chemistries for enzymatically detecting ketones are shown in FIGS. 24B and 24C. In both instances, there is again a 1:1 molar correspondence between the number of electrons transferred to the working electrode and the amount of β-hydroxybutyrate converted, thereby providing the basis for ketones detection.

Figure 22B:
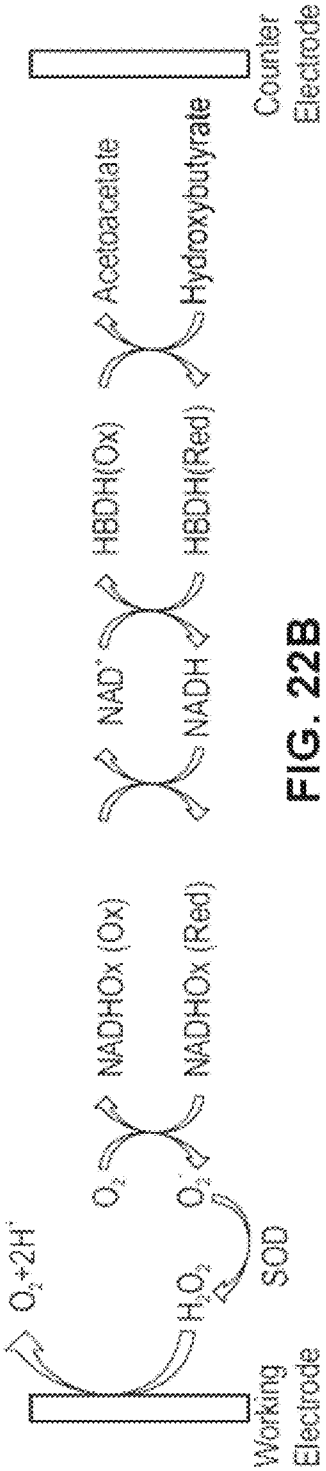

As shown in FIG. 22B, β-hydroxybutyrate dehydrogenase (HBDH) can convert β-hydroxybutyrate and $NAD^+$ into acetoacetate and NADH, respectively. Instead of electron transfer to the working electrode being completed by diaphorase (see FIG. 22A) and a suitable redox mediator, the reduced form of NADH oxidase (NADHOx (Red)) undergoes a reaction to form the corresponding oxidized form (NADHOx (Ox)). NADHOx (Red) can then reform through a reaction with molecular oxygen to produce superoxide, which can undergo subsequent conversion to hydrogen peroxide under superoxide dismutase (SOD) mediation. The hydrogen peroxide can then undergo reduction at the working electrode to provide a signal that can be correlated to the amount of ketones that were initially present. The SOD can be covalently bonded to a polymer in the ketones-responsive active area, according to various embodiments. Like the enzyme system shown in FIG. 22A, the β-hydroxybutyrate dehydrogenase and the NADH oxidase can be covalently bonded to a polymer in the ketones-responsive active area. In certain embodiments, the NAD can be covalently bonded to a polymer in the ketones-responsive active area. In certain other embodiments, the NAD can be present without being covalently bonded to a polymer in the ketones-responsive active area. If the $NAD^+$ is not covalently bonded, it can be physically retained within the ketones-responsive active area, with a membrane polymer promoting retention of the $NAD^+$ within the ketones-responsive active area. In certain embodiments, SOD is not included in the enzyme system for detecting ketones. For example, but not by way of limitation, an enzyme system for use in an analyte sensor of the present disclosure is provided in International Patent Application No. PCT/US21/62968, the contents of which are incorporated by reference herein in its entirety.

Figure 22C:
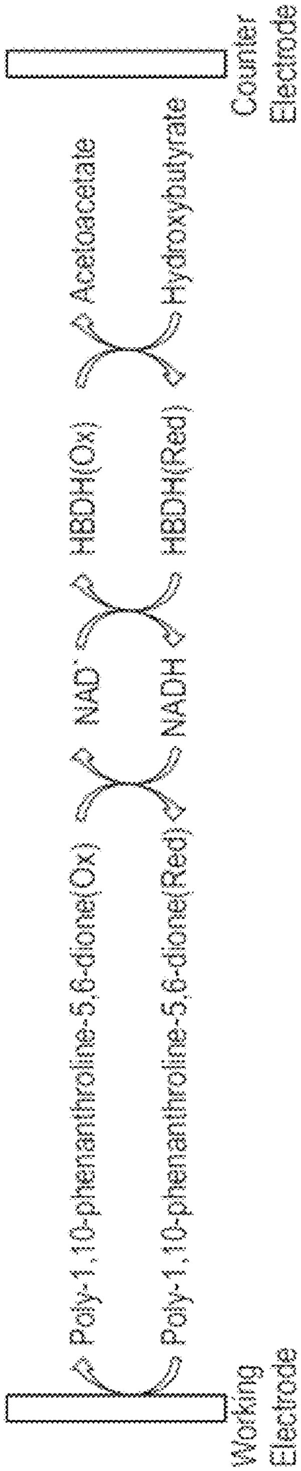
Figure 23A:
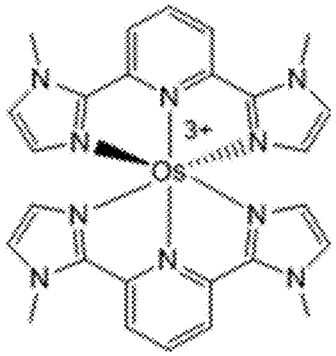
FIG. 23A provides the chemical structure of an exemplary redox mediator of the present disclosure in free form.
Figure 23B:
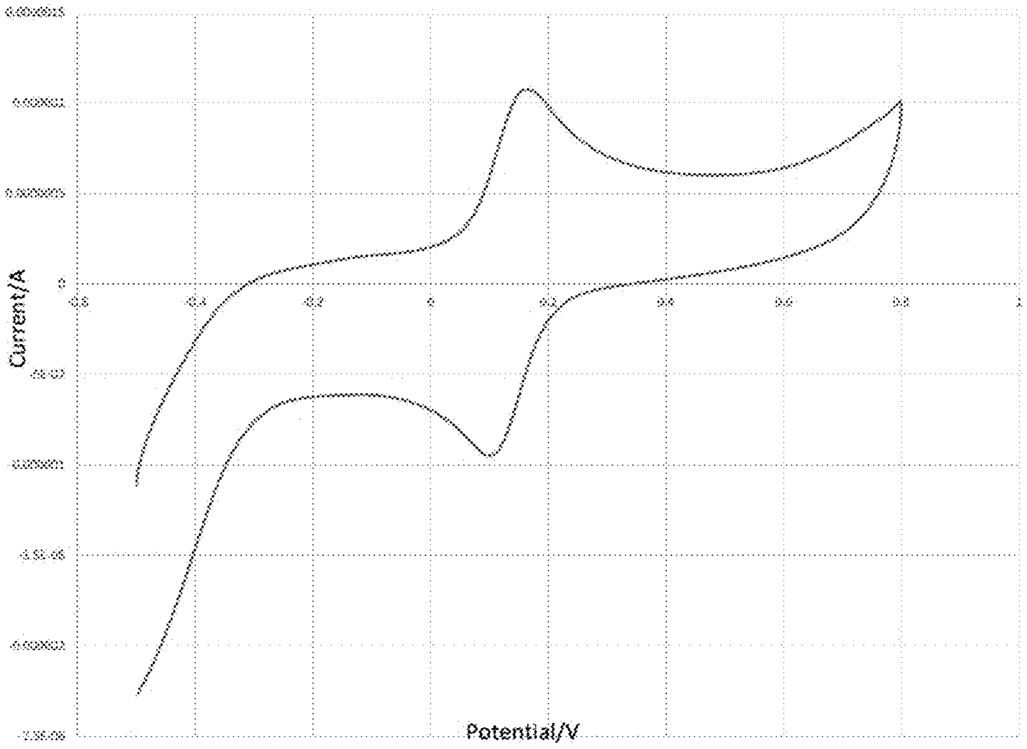
FIG. 23B shows a cyclic voltammogram the exemplary redox mediator of FIG. 23A.

As shown in FIG. 22C, another enzymatic detection chemistry for ketones can utilize β-hydroxybutyrate dehydrogenase (HBDH) to convert β-hydroxybutyrate and $NAD^+$ into acetoacetate and NADH, respectively. The electron transfer cycle in this case is completed by oxidation of poly-1,10-phenanthroline-5,6-dione at the working electrode to reform NAD. The poly-1,10-phenanthroline-5,6-dione can be covalently bonded to a polymer within the ketones-responsive active area or otherwise retained in or near the active area. Like the enzyme system shown in FIG. 22A, the β-hydroxybutyrate dehydrogenase can be covalently bonded to a polymer in the ketones-responsive active area, and the NAD can be covalently bonded to a polymer in the ketones-responsive active area or otherwise retained in or near the ketones-responsive area. Inclusion of an albumin in the active area can provide a surprising improvement in response stability. A suitable membrane polymer can promote retention of the $NAD^+$ within the ketones-responsive active area.

In certain embodiments, an analyte sensor disclosed herein can include one active site that includes one or more enzymes for detecting an analyte, e.g., one or more enzymes for use in detecting glucose. In certain embodiments, an analyte sensor disclosed herein can include one active site that includes one or more enzymes for detecting an analyte, e.g., one or more enzymes for use in detecting ketones. Alternatively, an analyte sensor disclosed herein can include two or more active sites, with each active site containing one or more enzymes. For example, but not by way of limitation, an analyte sensor of the present disclosure can include a first active area that comprises a first enzyme (or enzyme system) for use in detecting a first analyte, e.g., glucose, and a second active site that includes a second enzyme (or second enzyme system) for detecting a second analyte, e.g., a ketone.

In certain embodiments, when more than one active area is present in a sensor, the enzymes can be the same or different. For example, but not by the way of limitation, when the sensor includes a first and a second active area, the enzyme in the first active area and the enzyme in the second active area can be the same. In certain other embodiments, when the sensor includes a first active area and a second active area, the one or more enzymes of the first active area and the one or more enzymes in the second active area can be different. For example, but not by way of limitation, the second active area can be configured to detect glucose in combination with a different analyte detectable in the first active area, e.g., at low potential. As such, in certain embodiments, the second enzyme can be glucose oxidase.

In certain embodiments, the first analyte is glucose, detectable by an enzyme system comprising glucose oxidase (e.g., glucose oxidase or glucose oxidase and diaphorase), and the second analyte is a ketone, detectable by an enzyme system as described herein (e.g., β-hydroxybutyrate dehydrogenase and diaphorase). Alternatively, the first analyte is a ketone, detectable by an enzyme system as described herein (e.g., β-hydroxybutyrate dehydrogenase and diaphorase), and the second analyte is glucose, detectable by a glucose-responsive enzyme, e.g., glucose oxidase (e.g., glucose oxidase or glucose oxidase and diaphorase).

In certain embodiments, an analyte-responsive active area of the present disclosure can include from about 10% to about 80% by weight, e.g., from about 15% to about 75%, from about 20% to about 70%, from about 25% to about 65%, from about 30% to about 60% or from about 20% to about 50%, of one or more enzymes disclosed herein. In certain embodiments, the analyte-responsive active area can include from about 20% to about 70% by weight of one or more enzymes disclosed herein. In certain embodiments, the analyte-responsive active area can include from about 30% to about 60% by weight of one or more enzymes disclosed herein. In certain embodiments, the analyte-responsive active area can include from about 30% to about 50% by weight of one or more enzymes disclosed herein. In certain embodiments, the analyte-responsive active area can include from about 20% to about 50% by weight of one or more enzymes disclosed herein. In certain embodiments, the analyte-responsive active area can include from about 20% to about 40% by weight of one or more enzymes disclosed herein.

In certain embodiments, an analyte-responsive active area can further include a stabilizing agent, e.g., for stabilizing the one or more enzymes. For example, but not by way of limitation, the stabilizing agent can be an albumin, e.g., a serum albumin. Non-limiting examples of serum albumins include bovine serum albumin and human serum albumin. In certain embodiments, the stabilizing agent is a human serum albumin. In certain embodiments, the stabilizing agent is a bovine serum albumin. In certain embodiments, an analyte-responsive active area of the present disclosure can include a ratio of stabilizing agent, e.g., a serum albumin, to one or more enzymes present in the active area from about 100:1 to about 1:100, e.g., from about 95:1 to about 1:95, from about 90:1 to about 1:90, from about 85:1 to about 1:85, from about 80:1 to about 1:80, from about 75:1 to about 1:75, from about 60:1 to about 1:60, from about 55:1 to about 1:55, from about 50:1 to about 1:50, from about 45:1 to about 1:45, from about 40:1 to about 1:40, from about 35:1 to about 1:35, from about 30:1 to about 1:30, from about 25:1 to about 1:25, from about 20:1 to about 1:20, from about 15:1 to about 1:15, from about 10:1 to about 1:10, from about 9:1 to about 1:9, from about 8:1 to about 1:8, from about 7:1 to about 1:7, from about 6:1 to about 1:6, from about 5:1 to about 1:5, from about 4:1 to about 1:4, from about 3:1 to about 1:3 or from about 2:1 to about 1:2. In certain embodiments, an analyte-responsive active area can include a ratio of stabilizing agent to one or more enzymes present in the active area from about 50:1 to about 1:50. In certain embodiments, an analyte-responsive active area can include a ratio of stabilizing agent to one or more enzymes present in the active area from about 10:1 to about 1:10. In certain embodiments, an analyte-responsive active area can include a ratio of stabilizing agent to one or more enzymes present in the active area from about 7:1 to about 1:7. In certain embodiments, an analyte-responsive active area can include a ratio of stabilizing agent to one or more enzymes present in the active area from about 6:1 to about 1:6. In certain embodiments, an analyte-responsive active area can include a ratio of stabilizing agent to one or more enzymes present in the active area from about 5:1 to about 1:5. In certain embodiments, an analyte-responsive active area can include a ratio of stabilizing agent to one or more enzymes present in the active area from about 4:1 to about 1:4. In certain embodiments, an analyte-responsive active area can include a ratio of stabilizing agent to one or more enzymes present in the active area from about 3:1 to about 1:3. In certain embodiments, an analyte-responsive active area can include a ratio of stabilizing agent to one or more enzymes present in the active area from about 2:1 to about 1:2. In certain embodiments, an analyte-responsive active area can include a ratio of stabilizing agent to one or more enzymes present in the active area of about 1:1. In certain embodiments, an analyte-responsive active area can include by weight from about 5% to about 50%, e.g., from about 10% to about 50%, from about 15% to about 45%, from about 20% to about 40%, from about 20% to about 35% or from about 20% to about 30%, of the stabilizer. In certain embodiments, the analyte-responsive active area can include from about 5% to about 40% of the stabilizing agent by weight. In certain embodiments, the analyte-responsive active area can include from about 5% to about 35% of the stabilizing agent by weight. In certain embodiments, the analyte-responsive active area can include from about 5% to about 30% of the stabilizing agent by weight. In certain embodiments, the analyte-responsive active area can include from about 10% to about 30% of the stabilizing agent by weight. In certain embodiments, the analyte-responsive active area can include from about 15% to about 35% of the stabilizing agent by weight.

In certain embodiments, an analyte-responsive active area, e.g., an analyte-responsive active area, can further include a cofactor or coenzyme for one or more enzymes present in the analyte-responsive active area. In certain embodiments, the cofactor is nicotinamide adenine dinucleotide (NAD) or nicotinamide adenine dinucleotide phosphate (NADP) (referred to herein collectively as "NAD(P)"). In certain embodiments, the coenzyme is FAD. In certain embodiments, the analyte-responsive active area can include a ratio of cofactor to enzyme from about 40:1 to about 1:40, e.g., from about 35:1 to about 1:35, from about 30:1 to about 1:30, from about 25:1 to about 1:25, from about 20:1 to about 1:20, from about 15:1 to about 1:15, from about 10:1 to about 1:10, from about 9:1 to about 1:9, from about 8:1 to about 1:8, from about 7:1 to about 1:7, from about 6:1 to about 1:6, from about 5:1 to about 1:5, from about 4:1 to about 1:4, from about 3:1 to about 1:3, from about 2:1 to about 1:2 or about 1:1. In certain embodiments, the analyte-responsive active area can include a ratio of cofactor to enzyme from about 5:1 to about 1:5. In certain embodiments, the analyte-responsive active area can include a ratio of cofactor to enzyme from about 4:1 to about 1:4. In certain embodiments, the analyte-responsive active area can include a ratio of cofactor to enzyme from about 3:1 to about 1:3. In certain embodiments, the analyte-responsive active area can include a ratio of cofactor to enzyme from about 2:1 to about 1:2. In certain embodiments, the analyte-responsive active area can include a ratio of cofactor to enzyme of about 1:1. In certain embodiments, the analyte-responsive active area can include from about 10% to about 50% by weight, e.g., from about 15% to about 45%, from about 20% to about 40%, from about 20% to about 35% or from about 20% to about 30% by weight, of the cofactor. In certain embodiments, the analyte-responsive active area can include from about 20% to about 40% by weight of the cofactor. In certain embodiments, the analyte-responsive active area can include from about 20% to about 30% by weight of the cofactor. In certain embodiments, the analyte-responsive active area can include from about 15% to about 35% by weight of the cofactor. In certain embodiments, the cofactor, e.g., NAD(P), can be physically retained within the analyte-responsive active area. For example, but not by way of limitation, a membrane overcoating the analyte-responsive active area can aid in retaining the cofactor within the analyte-responsive active area while still permitting sufficient inward diffusion of the analyte to permit detection thereof.

In certain embodiments, one or more enzymes of an analyte-responsive active area can be covalently bonded to the polymer, e.g., polymeric backbone as described in Section 3, present in the active area. In certain embodiments, when an enzyme system with multiple enzymes is present in a given active area, all of the multiple enzymes can be covalently bonded to the polymer. In certain other embodiments, only a portion of the multiple enzymes is covalently bonded to the polymer. For example, and not by the way of limitation, one or more enzymes within an enzyme system can be covalently bonded to the polymer and at least one enzyme can be non-covalently associated with the polymer, such that the non-covalently bonded enzyme is physically retained within the polymer. In certain embodiments, a membrane overcoating the analyte-responsive active area can aid in retaining the one or more enzymes within the analyte-responsive active area while still permitting sufficient inward diffusion of the analyte to permit detection thereof. Suitable membrane polymers for overcoating the analyte-responsive active area are discussed further herein.

In certain embodiments, when a stabilizer is present in an active area, one or more enzymes within the area can be covalently bonded to the stabilizer. For example, and not by the way of limitation, one or more enzymes can be covalently bonded to the stabilizer, e.g., albumin, present in the active area.

In certain particular embodiments, covalent bonding of the one or more enzymes and/or redox mediators to the polymer and/or stabilizer in a given active area can take place via crosslinking introduced by a suitable crosslinking agent. In certain embodiments, crosslinking of the polymer and/or stabilizer to the one or more enzymes and/or redox mediators can reduce the occurrence of delamination of the enzyme compositions from an electrode. Suitable crosslinking agents can include one or more crosslinkable functionalities such as, but not limited to, vinyl, alkoxy, acetoxy, enoxy, oxime, amino, hydroxyl, cyano, halo, acrylate, epoxide and isocyanato groups. In certain embodiments, the crosslinking agent comprises one or more, two or more, three or more or four or more epoxide groups. For example, but not by way of limitation, a crosslinker for use in the present disclosure can include mono-, di-, tri- and tetra-ethylene oxides. In certain embodiments, crosslinking agents for reaction with free amino groups in the enzyme (e.g., with the free side chain amine in lysine) can include crosslinking agents such as, for example, polyethylene glycol dibutyl ethers, polypropylene glycol dimethyl ethers, polyalkylene glycol allyl methyl ethers, polyethylene glycol diglycidyl ether (PEGDGE) or other polyepoxides, cyanuric chloride, N-hydroxysuccinimide, imidoesters, epichlorohydrin, or derivatized variants thereof. In certain embodiments, the crosslinking agent is PEGDGE, e.g., having an average molecular weight (Me) from about 200 to 1,000, e.g., about 400. In certain embodiments, the crosslinking agent is PEGDGE 400. In certain embodiments, the crosslinking agent can be glutaraldehyde. In certain embodiments, the crosslinking of the enzyme to the polymer is generally intermolecular. In certain embodiments, the crosslinking of the enzyme to the polymer is generally intramolecular.

In certain embodiments, an analyte-responsive active area can include a ratio of crosslinking agent to one or more enzymes of the active area from about 100:1 to about 1:100. In certain embodiments, an analyte-responsive active area can include a ratio of crosslinking agent to one or more enzymes of the active area from about 40:1 to about 1:40, e.g., from about 35:1 to about 1:35, from about 30:1 to about 1:30, from about 25:1 to about 1:25, from about 20:1 to about 1:20, from about 15:1 to about 1:15, from about 10:1 to about 1:10, from about 9:1 to about 1:9, from about 8:1 to about 1:8, from about 7:1 to about 1:7, from about 6:1 to about 1:6, from about 5:1 to about 1:5, from about 4:1 to about 1:4, from about 3:1 to about 1:3, from about 2:1 to about 1:2 or about 1:1. In certain embodiments, an analyte-responsive active area can include a ratio of crosslinking agent to one or more enzymes of the active area from about 5:1 to about 1:5. In certain embodiments, an analyte-responsive active area can include a ratio of crosslinking agent to one or more enzymes of the active area from about 4:1 to about 1:4. In certain embodiments, an analyte-responsive active area can include a ratio of crosslinking agent to one or more enzymes of the active area from about 3:1 to about 1:3. In certain embodiments, an analyte-responsive active area can include a ratio of crosslinking agent to one or more enzymes of the active area from about 2:1 to about 1:2. In certain embodiments, an analyte-responsive active area can include a ratio of crosslinking agent to one or more enzymes of the active area of about 1:1. In certain embodiments, an analyte-responsive active area can include by weight from about 5% to about 50%, e.g., from about 5% to about 45%, from about 5% to about 40%, from about 5% to about 35%, from about 10% to about 30% or from about 10% to about 25%, of the crosslinking agent. In certain embodiments, an analyte-responsive active area can include by weight from about 5% to about 35% of the crosslinking agent. In certain embodiments, an analyte-responsive active area can include by weight from about 10% to about 30% of the crosslinking agent. In certain embodiments, an analyte-responsive active area can include by weight from about 10% to about 25% of the crosslinking agent.

In certain embodiments, an active area of the present disclosure can have a thickness from about 0.1 μm to about 100 μm, e.g., from about 1 μm to about 90 μm, from about 1 μm to about 80 μm, from about 1 μm to about 70 μm, from about 1 μm to about 60 μm, from about 1 μm to about 50 μm, from about 1 μm to about 40 μm, from about 1 μm to about 30 μm, from about 1 μm to about 20 μm, from about 0.5 μm to about 10 μm, from about 1 μm to about 10 μm, from about 1 μm to about 5 μm or from about 0.1 μm to about 5 μm. In certain embodiments, a series of droplets can be applied atop of one another to achieve the desired thickness of the active area, without substantially increasing the diameter of the applied droplets (i.e., maintaining the desired diameter or range thereof).

5. Mass Transport Limiting Membranes

In certain embodiments, the analyte sensors disclosed herein further include a mass transport limiting membrane permeable to an analyte that overcoats at least one active area, e.g., a first active area. In certain embodiments, when multiple active areas are present, the mass transport limiting membrane can overcoat each active area. Alternatively, a first membrane overcoats one of the active areas and a second membrane overcoats the second active area. In certain embodiments, a first membrane overcoats one of the active areas and a second membrane overcoats both the first and second active areas.

In certain embodiments, a membrane overcoating an analyte-responsive active area can function as a mass transport limiting membrane and/or to improve biocompatibility. A mass transport limiting membrane can act as a diffusion-limiting barrier to reduce the rate of mass transport of the analyte. For example, but not by way of limitation, limiting access of an analyte, e.g., glucose or ketones, to the analyte-responsive active area with a mass transport limiting membrane can aid in avoiding sensor overload (saturation), thereby improving detection performance and accuracy.

In certain embodiments, the mass transport limiting membrane can be homogeneous and can be single-component (contain a single membrane polymer). Alternatively, the mass transport limiting membrane can be multi-component (contain two or more different membrane polymers). In certain embodiments, the multi-component membrane can be present as a bilayer membrane or as a homogeneous admixture of two or more membrane polymers. A homogeneous admixture can be deposited by combining the two or more membrane polymers in a solution and then depositing the solution upon a working electrode, e.g., dip coating.

In certain embodiments, the mass transport limiting membrane can include two or more layers, e.g., a bilayer or trilayer membrane. In certain embodiments, each layer can comprise a different polymer or the same polymer at different concentrations or thicknesses. In certain embodiments, the first analyte-responsive active area can be covered by a multi-layered membrane, e.g., a bilayer membrane, and the second analyte-responsive active area can be covered by a single membrane. In certain embodiments, the first analyte-responsive active area can be covered by a multi-layered membrane, e.g., a bilayer membrane, and the second analyte-responsive active area can be covered by a multi-layered membrane, e.g., a bilayer membrane. In certain embodiments, the first analyte-responsive active area can be covered by a single membrane and the second analyte-responsive active area can be covered by a multi-layered membrane, e.g., a bilayer membrane. In certain embodiments, the first analyte-responsive active area can be covered by a single membrane and the second analyte-responsive active area can be covered by a single membrane.

In certain embodiments, a mass transport limiting membrane can include polymers containing heterocyclic nitrogen groups. In certain embodiments, a mass transport limiting membrane can include a polyvinylpyridine-based polymer. Non-limiting examples of polyvinylpyridine-based polymers are disclosed in U.S. Patent Publication No. 2003/0042137 (e.g., Formula 2b), the contents of which are incorporated by reference herein in its entirety. In certain embodiments, the polyvinylpyridine-based polymer has a molecular weight from about 50 Da to about 500 kDa.

In certain embodiments, a mass transport limiting membrane can include a polyvinylpyridine (e.g., poly(4-vinylpyridine) or poly(4-vinylpyridine)), a polyvinylimidazole, a polyvinylpyridine copolymer (e.g., a copolymer of vinylpyridine and styrene), a polyacrylate, a polyurethane, a polyether urethane, a silicone, a polytetrafluoroethylene, a polyethylene-co-tetrafluoroethylene, a polyolefin, a polyester, a polycarbonate, a biostable polytetrafluoroethylene, homopolymers, copolymers or terpolymers of polyurethanes, a polypropylene, a polyvinylchloride, a polyvinylidene difluoride, a polybutylene terephthalate, a polymethylmethacrylate, a polyether ether ketone, cellulosic polymers, polysulfones and block copolymers thereof including, for example, di-block, tri-block, alternating, random and graft copolymers or a chemically related material and the like.

In certain embodiments, a membrane for use in the present disclosure, e.g., a single-component membrane, can include a polyvinylpyridine (e.g., poly(4-vinylpyridine) and/or poly(2-vinylpyridine)). In certain embodiments, a membrane for use in the present disclosure, e.g., a single-component membrane, can include poly(4-vinylpyridine). In certain embodiments, a membrane for use in the present disclosure, e.g., a single-component membrane, can include a copolymer of vinylpyridine and styrene. In certain embodiments, the membrane can comprise a polyvinylpyridine-co-styrene copolymer. For example, but not by way of limitation, a polyvinylpyridine-co-styrene copolymer for use in the present disclosure can include a polyvinylpyridine-co-styrene copolymer in which a portion of the pyridine nitrogen atoms were functionalized with a non-crosslinked polyethylene glycol tail and a portion of the pyridine nitrogen atoms were functionalized with an alkylsulfonic acid, e.g., a propylsulfonic acid, group. In certain embodiments, a derivatized polyvinylpyridine-co-styrene copolymer for use as a membrane polymer can be the 10Q5 polymer as described in U.S. Pat. No. 8,761,857, the contents of which are incorporated by reference herein in its entirety.

A suitable copolymer of vinylpyridine and styrene can have a styrene content ranging from about 0.01% to about 50% mole percent, or from about 0.05% to about 45% mole percent, or from about 0.1% to about 40% mole percent, or from about 0.5% to about 35% mole percent, or from about 1% to about 30% mole percent, or from about 2% to about 25% mole percent, or from about 5% to about 20% mole percent. Substituted styrenes can be used similarly and in similar amounts. A suitable copolymer of vinylpyridine and styrene can have a molecular weight of 5 kDa or more, or about 10 kDa or more, or about 15 kDa or more, or about 20 kDa or more, or about 25 kDa or more, or about 30 kDa or more, or about 40 kDa or more, or about 50 kDa or more, or about 75 kDa or more, or about 90 kDa or more, or about 100 kDa or more. In non-limiting examples, a suitable copolymer of vinylpyridine and styrene can have a molecular weight ranging from about 5 kDa to about 150 kDa, or from about 10 kDa to about 125 kDa, or from about 15 kDa to about 100 kDa, or from about 20 kDa to about 80 kDa, or from about 25 kDa to about 75 kDa, or from about 30 kDa to about 60 kDa.

In certain embodiments, the membrane includes a polyurethane membrane that includes both hydrophilic and hydrophobic regions. In certain embodiments, a hydrophobic polymer component is a polyurethane, a polyurethane urea or poly(ether-urethane-urea). In certain embodiments, a polyurethane is a polymer produced by the condensation reaction of a diisocyanate and a difunctional hydroxyl-containing material. In certain embodiments, a polyurethane urea is a polymer produced by the condensation reaction of a diisocyanate and a difunctional amine-containing material. In certain embodiments, diisocyanates for use herein include aliphatic diisocyanates, e.g., containing from about 4 to about 8 methylene units, or diisocyanates containing cycloaliphatic moieties. Additional non-limiting examples of polymers that can be used for the generation of a membrane of a presently disclosed sensor include vinyl polymers, polyethers, polyesters, polyamides, inorganic polymers (e.g., polysiloxanes and polycarbosiloxanes), natural polymers (e.g., cellulosic and protein based materials) and mixtures (e.g., admixtures or layered structures) or combinations thereof. In certain embodiments, the hydrophilic polymer component is polyethylene oxide and/or polyethylene glycol. In certain embodiments, the hydrophilic polymer component is a polyurethane copolymer. For example, but not by way of limitation, a hydrophobic-hydrophilic copolymer component for use in the present disclosure is a polyurethane polymer that comprises about 10% to about 50%, e.g., about 20%, hydrophilic polyethylene oxide.

In certain embodiments, the membrane includes a silicone polymer/hydrophobic-hydrophilic polymer blend. In certain embodiments, the hydrophobic-hydrophilic polymer for use in the blend can be any suitable hydrophobic-hydrophilic polymer such as, but not limited to, polyvinylpyrrolidone, polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic and graft copolymers. In certain embodiments, the hydrophobic-hydrophilic polymer is a copolymer of polyethylene oxide (PEO) and polypropylene oxide (PPO). Non-limiting examples of PEO and PPO copolymers include PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide and blends thereof. In certain embodiments, the copolymers can be substituted with hydroxy substituents.

In certain embodiments, hydrophilic or hydrophobic modifiers can be used to “fine-tune” the permeability of the resulting membrane to an analyte of interest. In certain embodiments, hydrophilic modifiers such as poly(ethylene) glycol, hydroxyl or polyhydroxyl modifiers and the like, and any combinations thereof, can be used to enhance the biocompatibility of the polymer or the resulting membrane.

In certain embodiments, the mass transport limiting membrane can include a membrane polymer, such as a polyvinylpyridine or polyvinylimidazole homopolymer or copolymer, which can be further crosslinked with a suitable crosslinking agent. In certain particular embodiments, the membrane polymer can include a copolymer of vinylpyridine and styrene, e.g., further crosslinked with a suitable crosslinking agent.

In certain embodiments, the mass transport limiting membrane can comprise a membrane polymer crosslinked with a crosslinking agent disclosed herein and above in Section 4. In certain embodiments where there are two mass transport limiting membranes, e.g., a first mass transport limiting membrane and a second mass transport limiting membrane, each membrane can be crosslinked with a different crosslinking agent. For example, but not by way of limitation, the crosslinking agent can result in a membrane that is more restrictive to diffusion of certain compounds, e.g., analytes within the membrane, or less restrictive to diffusion of certain compounds, e.g., by affecting the size of the pores within the membrane.

In certain embodiments, crosslinking agents for use in the present disclosure can include polyepoxides, carbodiimide, cyanuric chloride, triglycidyl glycerol (Gly3), N-hydroxysuccinimide, imidoesters, epichlorohydrin or derivatized variants thereof. In certain embodiments, a membrane polymer overcoating one or more active areas can be crosslinked with a branched crosslinker, e.g., which can decrease the amount of extractables obtainable from the mass transport limiting membrane. Non-limiting examples of a branched crosslinker include branched glycidyl ether crosslinkers, e.g., including branched glycidyl ether crosslinkers that include two or three or more crosslinkable groups. In certain embodiments, the branched crosslinker can include two or more crosslinkable groups, such as polyethylene glycol diglycidyl ether. In certain embodiments, the branched crosslinker can include three or more crosslinkable groups, such as polyethylene glycol tetraglycidyl ether. In certain embodiments, the mass transport limiting membrane can include polyvinylpyridine or a copolymer of vinylpyridine and styrene crosslinked with a branched glycidyl ether crosslinker including two or three crosslinkable groups, such as polyethylene glycol tetraglycidyl ether or polyethylene glycol diglycidyl ether. In certain embodiments, the epoxide groups of a polyepoxides, e.g., polyethylene glycol tetraglycidyl ether or polyethylene glycol diglycidyl ether, can form a covalent bond with pyridine or an imidazole via epoxide ring opening resulting in a hydroxyalkyl group bridging a body of the crosslinker to the heterocycle of the membrane polymer.

In certain embodiments, the crosslinking agent is polyethylene glycol diglycidyl ether (PEGDGE). In certain embodiments, the PEGDGE used to promote crosslinking (e.g., intermolecular crosslinking) between two or more membrane polymer backbones can exhibit a broad range of suitable molecular weights. In certain embodiments, the molecular weight of the PEGDGE can range from about 100 g/mol to about 5,000 g/mol. The number of ethylene glycol repeat units in each arm of the PEGDGE can be the same or different, and can typically vary over a range within a given sample to afford an average molecular weight. In certain embodiments, the PEGDGE for use in the present disclosure has an average molecular weight ($M_n$) from about 200 to 1,000, e.g., about 400. In certain embodiments, the crosslinking agent is PEGDGE 400.

In certain embodiments, the crosslinking can be intermolecular. The polyethylene glycol tetraglycidyl ether used to promote crosslinking (e.g., intermolecular crosslinking) between two or more membrane polymer backbones can exhibit a broad range of suitable molecular weights. Up to four polymer backbones can crosslinked with a single molecule of the polyethylene glycol tetraglycidyl ether crosslinker. In certain particular embodiments, the molecular weight of the polyethylene glycol tetraglycidyl ether can range from about 1,000 g/mol to about 5,000 g/mol. The number of ethylene glycol repeat units in each arm of the polyethylene glycol tetraglycidyl ether can be the same or different, and can typically vary over a range within a given sample to afford an average molecular weight. The structure of the polyethylene glycol tetraglycidyl ether prior to crosslinking can be represented by Formula LVI below:

Formula LVI

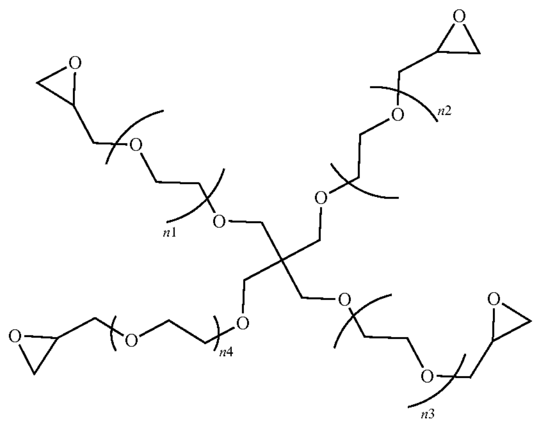

wherein n1, n2, n3 and n4 are each an integer greater than or equal to 0. In certain embodiments, each of n1, n2, n3 and n4 are 1 or greater, and n1, n2, n3 and n4 can be the same or different. A sum of n1, n2, n3 and n4 can be selected such that the molecular weight of the polyethylene glycol tetraglycidyl ether falls within the foregoing range. In other words, to produce a polyethylene glycol tetraglycidyl ether having a molecular weight within the foregoing range, a sum of n1, n2, n3 and n4 can range from about 14 to about 110, or about 15 to about 104, including any sub-range in between these values, wherein n1, n2, n3 and n4 can independently be any integer greater than or equal to 0 or greater than or equal to 1.

Crosslinking density, as used herein, refers to the number of membrane polymer side chains that have a crosslinker attached thereto. Membrane polymers crosslinked with a branched glycidyl ether, such as polyethylene glycol tetraglycidyl ether or a similar polyethylene oxide crosslinker having three or more crosslinkable groups, can have a crosslinking density varying over a wide range. In particular examples, the fraction of side chains that can have a crosslinker appended thereto can be about 0.1% or above of the available heterocycles in the membrane polymer, or about 0.2% or above of the available heterocycles in the membrane polymer, or about 0.3% or above of the available heterocycles in the membrane polymer, or about 0.4% or above of the available heterocycles in the membrane polymer, or about 0.5% or above of the available heterocycles in the membrane polymer, or about 0.6% or above of the available heterocycles in the membrane polymer, or about 0.7% or above of the available heterocycles in the membrane polymer, or about 0.8% or above of the available heterocycles in the membrane polymer, or about 0.9% or above of the available heterocycles in the membrane polymer, or about 1.0% or above of the available heterocycles in the membrane polymer, or about 1.2% or above of the available heterocycles in the membrane polymer, or about 1.4% or above of the available heterocycles in the membrane polymer, or about 1.6% or above of the available heterocycles in the membrane polymer, or about 1.8% or above of the available heterocycles in the membrane polymer, or about 2.0% or above of the available heterocycles in the membrane polymer, or about 2.2% or above of the available heterocycles in the membrane polymer, or about 2.4% or above of the available heterocycles in the membrane polymer, or about 2.6% or above of the available heterocycles in the membrane polymer, or about 2.8% or above of the available heterocycles in the membrane polymer, or about 3.0% or above of the available heterocycles in the membrane polymer, or about 3.5% or above of the available heterocycles in the membrane polymer, or about 4.0% or above of the available heterocycles in the membrane polymer, or about 4.5% or above of the available heterocycles in the membrane polymer, or about 5.0% or above of the available heterocycles in the membrane polymer, or about 5.5% or above of the available heterocycles in the membrane polymer, or about 6.0% or above of the available heterocycles in the membrane polymer, or about 6.5% or above of the available heterocycles in the membrane polymer, or about 7.0% or above of the available heterocycles in the membrane polymer, or about 7.5% or above of the available heterocycles in the membrane polymer, or about 8.0% or above of the available heterocycles in the membrane polymer, or about 8.5% or above of the available heterocycles in the membrane polymer, or about 9.0% or above of the available heterocycles in the membrane polymer, or about 9.5% or above of the available heterocycles in the membrane polymer, or about 10% or above of the available heterocycles in the heterocyclic polymer. In certain embodiments, the crosslinker can be appended to between about 1% and about 20% of the available heterocycles in the membrane polymer, or between about 2% and about 10% of the available heterocycles in the membrane polymer, or between about 3% and about 8% of the available heterocycles in the membrane polymer, or between about 4% and about 9% of the available heterocycles in the membrane polymer, or between about 5% and about 12% of the available heterocycles in the membrane polymer.

Suitable membrane polymers can further include one or more polyether arms (side chains) that are bonded to the nitrogen atom of the pyridine or imidazole monomer units. Any of the membrane polymers disclosed herein can further include one or more polyether arms. Polyether arms are distinguished from the crosslinking group formed from polyethylene glycol tetraglycidyl ether or a similar crosslinker in that the polyether arm does not extend between separate polymer chains or terminate intramolecularly within a single polymer chain. Thus, polyether arms are separate and distinct from the crosslinking group formed from the crosslinker. Polyether arms can include a polyethylene oxide (PEO) block and a polypropylene oxide (PPO) block, particularly a polyether arm having a polypropylene oxide block inserted between two polyethylene oxide blocks. Bonding of the polyether arm to a heterocyclic nitrogen atom can occur through any reactive functional group capable of forming a bond to the nitrogen atom of the heterocycle in the membrane polymer. Bonding of the polyether arm to the heterocyclic nitrogen atom can be through an alkyl group, a hydroxyl-functionalized alkyl group, or a carbonyl. The polyether arm can also contain an amine group remote from the heterocyclic nitrogen atom or be amine-free in other particular instances.

The polyether arms of the membrane polymer can include at least one polyethylene oxide block and at least one polypropylene oxide block, thereby affording at least a diblock arrangement of polyethylene oxide and polypropylene oxide monomer units bound via a spacer to a heterocyclic nitrogen atom. Either the polyethylene oxide block or the polypropylene oxide block can be bound to the spacer. In other certain embodiments, the polyether arms can include, in order, a spacer, a first polyethylene oxide block, a polypropylene oxide block, and a second polyethylene oxide block (i.e., an A-B-A repeat pattern) or, in order, a spacer, a first polypropylene oxide block, a polyethylene oxide block, and a second polypropylene oxide block (i.e., a B-A-B repeat pattern). An amine group can intercede between a polyethylene oxide block and a polypropylene oxide block in amine-containing polyether arms.

In certain embodiments, the polyether arms in the membrane polymers described herein can have a structure generally defined by Formulas LVII-LX below:

Formula LVII

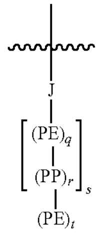

Formula LVIII

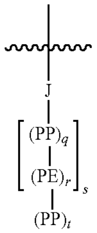

Formula LIX

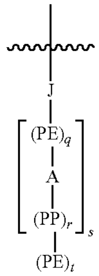

Formula LX

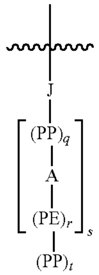

wherein PE represents a polyethylene oxide block, PP represents a polypropylene oxide block, A is an amine group, and J is a spacer group. Spacer group J can become bonded to a heterocycle of the membrane polymer. Suitable spacer groups J can include, but are not limited to, alkyl, hydroxy-functionalized alkyl, carbonyl, carboxylic ester, carboxamide, and the like. Variables q, r, s, and t are positive integers defining the number of monomer units in each block and the number of times the blocks are repeated, with the proviso that in diblock arrangements, variable t can be 0 and variable s can be 1. In certain embodiments, variable q is an integer ranging between about 2 and about 50 or between about 6 and about 20, variable r is an integer ranging between about 2 and about 60 or between about 10 and about 40, and variable t is an integer ranging between about 2 and about 50 or between about 10 and about 30. In certain other embodiments, variable s is an integer ranging between 1 and about 20 or between 1 and about 10. In certain particular embodiments, variable s is equal to 1.

In certain particular embodiments of the present disclosure, amine-free polyether arms having a triblock arrangement of polyethylene oxide, polypropylene oxide, and polyethylene oxide (corresponding to Formula LVII) arm can have a structure defined by Formula LXI:

Formula LXI

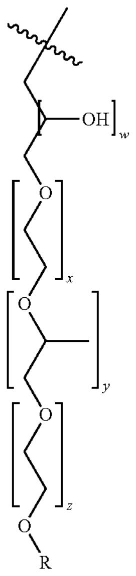

wherein R is an alkyl group, (such as but not limited to a methyl group), variable w is 0 or 1, variable x is an integer ranging between about 4 and about 24 or between about 6 and about 20, variable y is an integer ranging between about 8 and about 60 or between about 10 and about 40, and variable z is an integer ranging between about 6 and about 36 or between about 10 and about 30. In more specific embodiments, variable x can range between about 8 and about 16 or between about 9 and about 12, variable y can range between about 10 and about 32, or between about 16 and about 30, or between about 12 and about 20, and variable z can range between about 10 and about 20 or between about 14 and about 18. In certain embodiments, variable x can be less than variable z, such that the second polyethylene oxide block is longer (larger) than the first polyethylene oxide block. If variable w is 0, the amine-free polyether arm is directly bonded to the membrane polymer by a two-carbon alkyl group, although longer alkyl groups are also contemplated by the present disclosure.

In certain particular embodiments of the present disclosure, polyether arms having a triblock arrangement of polyethylene oxide, polypropylene oxide, and polyethylene oxide and having an amine group interceding between a polyethylene oxide block and the polypropylene oxide block (corresponding to Formula LIX) can have a structure defined by Formula LXIII:

Formula LXII

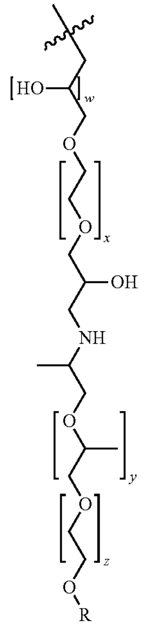

wherein w, x, y, z and R are defined as above for Formula LXI. If variable w is 0, the polyether arm is directly bonded to the membrane polymer by a two-carbon alkyl group, although longer alkyl groups are also contemplated by the present disclosure.

The polyether arms described herein can become bonded to a heterocyclic nitrogen atom by way of a reactive functionality in a polyether arm precursor. Suitable reactive functionalities can include a halogen or an epoxide, for example. Epoxides, for example, lead to formation of a hydroxyalkyl spacer group connecting the polyether arm to a heterocyclic nitrogen atom of the membrane polymer, as exemplified in Formulas LXI and LXII above (n=1 in Formulas LXI and LXII). Halogen-functionalized polyether arm precursors, in contrast, can lead to an alkyl spacer (n=0 in Formulas LXI and LXII), wherein suitable alkyl groups can be straight- or branched-chain $C_2$-$C_{20}$ alkyl groups.

In certain embodiments, a sulfonate-containing arm can be appended as a side chain in at least a portion of the membrane polymers disclosed herein. The sulfonate-containing arm can be present in combination with the polyether arms and/or a crosslinker in any suitable ratio. Any of the membrane polymers disclosed herein can include a higher quantity of polyether arms or crosslinking groups than sulfonate-containing arms. A sulfonate-containing arm can be appended to the membrane polymer via an alkyl group. The alkyl group can contain between 1 and about 6 carbon atoms, or between 2 and about 4 carbon atoms, according to various embodiments. Suitable reagents for introducing a sulfonate-containing arm to the membrane polymers disclosed herein can include halosulfonic acid compounds such as chloromethanesulfonic acid, bromoethanesulfonic acid, or the like, or cyclic sulfonates (sultones).

Polydimethylsiloxane (PDMS) can be incorporated in any of the mass transport limiting membranes disclosed herein.

Accordingly, at least some of the analyte sensors described herein can comprise a sensor tail comprising at least a first working electrode, a first active area disposed upon a surface of the first working electrode, and a mass transport limiting membrane permeable to the first analyte that overcoats at least the first active area. The first active area comprises a first polymer and at least one enzyme covalently bonded to the first polymer and responsive to a first analyte. In certain embodiments, the mass transport limiting membrane comprises a membrane polymer cross-linked with a branched glycidyl ether crosslinker comprising two or more or three or more crosslinkable groups, e.g., polyethylene glycol diglycidyl ether or polyethylene glycol tetraglycidyl ether.

In certain embodiments when a first active area and a second active area configured for assaying different analytes are disposed on separate working electrodes, the mass transport limiting membrane can have differing permeability values for the first analyte and the second analyte. Although the membrane thickness at each working electrode and/or the sizes of the active areas can be varied to levelize the sensitivity for each analyte, this approach can significantly complicate manufacturing of the analyte sensors. As a solution, the mass transport limiting membrane overcoating at least one of the active areas can include an admixture of a first membrane polymer and a second membrane polymer or a bilayer of the first membrane polymer and the second membrane polymer. A homogeneous membrane can overcoat the active area not overcoated with the admixture or the bilayer, wherein the homogeneous membrane includes only one of the first membrane polymer or the second membrane polymer. Advantageously, the architectures of the analyte sensors disclosed herein readily allow a continuous membrane having a homogenous membrane portion to be disposed upon a first active area and a multi-component membrane portion to be disposed upon a second active area of the analyte sensors, thereby levelizing the permeability values for each analyte concurrently to afford improved sensitivity and detection accuracy. Continuous membrane deposition can take place through sequential dip coating operations in particular embodiments.

Generally, the thickness of the membrane is controlled by the concentration of the membrane solution, by the number of droplets of the membrane solution applied, by the number of times the sensor is dipped in or sprayed with the membrane solution, by the volume of membrane solution sprayed on the sensor, and the like, and by any combination of these factors. In certain embodiments, the membrane described herein can have a thickness ranging from about 0.1 micrometers (μm) to about 1,000 μm, e.g., from about 1 μm to and about 500 μm, about 10 μm to about 100 μm or about 10 μm to about 100 μm. In certain embodiments, the sensor can be dipped in the membrane solution more than once. For example, but not by way of limitation, a sensor (or working electrode) of the present disclosure can be dipped in a membrane solution at least twice, at least three times, at least four times or at least five times to obtain the desired membrane thickness.

6. Interference Domain

In certain embodiments, the sensor of the present disclosure, e.g., sensor tail, can further comprise an interference domain. In certain embodiments, the interference domain can include a polymer domain that restricts the flow of one or more interferants, e.g., to the surface of the working electrode. In certain embodiments, the interference domain can function as a molecular sieve that allows analytes and other substances that are to be measured by the working electrode to pass through, while preventing passage of other substances such as interferents. In certain embodiments, the interferents can affect the signal obtained at the working electrode. Non-limiting examples of interferents include acetaminophen, ascorbate, ascorbic acid, bilirubin, cholesterol, creatinine, dopamine, ephedrine, ibuprofen, L-dopa, methyldopa, salicylate, tetracycline, tolazamide, tolbutamide, triglycerides, urea and uric acid.

In certain embodiments, the interference domain is located between the working electrode and one or more active areas. In certain embodiments, non-limiting examples of polymers that can be used in the interference domain include polyurethanes, polymers having pendant ionic groups and polymers having controlled pore size. In certain embodiments, the interference domain is formed from one or more cellulosic derivatives. Non-limiting examples of cellulosic derivatives include polymers such as cellulose acetate, cellulose acetate butyrate, 2-hydroxyethyl cellulose, cellulose acetate phthalate, cellulose acetate propionate, cellulose acetate trimellitate and the like.

In certain embodiments, the interference domain is part of the mass transport limiting membrane and not a separate membrane. In certain embodiments, the interference domain is located between the one or more active areas and the mass transport limiting membrane.

In certain embodiments, the interference domain includes a thin, hydrophobic membrane that is non-swellable and restricts diffusion of high molecular weight species. For example, but not by way of limitation, the interference domain can be permeable to relatively low molecular weight substances, such as hydrogen peroxide, while restricting the passage of higher molecular weight substances, such as ketones, glucose, acetaminophen and/or ascorbic acid.

In certain embodiments, the interference domain can be deposited directly onto the working electrode, e.g., onto the surface of the permeable working electrode. In certain embodiments, the interference domain has a thickness, e.g., dry thickness, ranging from about 0.1 μm to about 1,000 μm, e.g., from about 1 μm to about 500 μm, about 10 μm to about 100 μm or about 10 μm to about 100 μm. In certain embodiments, the interference domain can have a thickness from about 0.1 μm to about 10 μm, e.g., from about 0.5 μm to about 10 μm, from about 1 μm to about 10 μm, from about 1 μm to about 5 μm or from about 0.1 μm to about 5 μm. In certain embodiments, the sensor can be dipped in the interference domain solution more than once. For example, but not by way of limitation, a sensor (or working electrode) of the present disclosure can be dipped in an interference domain solution at least twice, at least three times, at least four times or at least five times to obtain the desired interference domain thickness.

III. METHODS OF USE

The present disclosure further provides methods of using the analyte sensors and redox mediators disclosed herein. In certain embodiments, the present disclosure provides methods for detecting an analyte. For example, but not by way of limitation, the present disclosure provides methods for detecting one or more analytes including glutamate, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, aspartate, asparagine, magnesium, oxygen, pH, phosphorus, potassium, sodium, total protein or uric acid.

In certain embodiments, the analyte is glucose, ketones, lactate, alcohol and/or creatinine. In certain embodiments, the present disclosure provides methods for detecting glucose, e.g., as a first analyte. In certain embodiments, the present disclosure provides methods for detecting one or more ketones. In certain embodiments, the present disclosure provides methods for detecting glucose and ketones.

In certain embodiments, the present disclosure provides methods for detecting an analyte in a subject in need thereof. In certain embodiments, the subject has a disease or disorder that is associated with the dysregulation of an analyte.

In certain embodiments, the subject is in need of monitoring glucose levels. For example, but not by way of limitation, a subject in need thereof is a subject that is at risk of having or has diabetes. Alternatively, glucose levels in a subject can be monitored for wellness. Wellness data can generally include any type of data associated with a person's health, such as their weight, heart rate, blood pressure, blood glucose level or the like. In certain embodiments, glucose levels in a subject can be monitored for weight management, to obtain better sleep and/or to help the subject feel better and think clearer.

In certain embodiments, a subject in need of monitoring ketone levels is a subject that is on a ketogenic diet. In certain embodiments, the present disclosure provides methods for detecting ketone levels in a subject in a state of ketosis or detecting ketone levels in a subject to maintain a state of ketosis. In certain embodiments, an analyte sensor of the present disclosure can be used to ensure a subject adheres to a ketogenic diet. For example, but not by way of limitation, an analyte sensor of the present disclosure can be used to measure the level of ketones in a sample to inform the subject to adjust or make modifications to their diet to maintain ketosis. In certain embodiments, the present disclosure provides methods for detecting ketone levels in a subject at risk of developing ketoacidosis. In certain embodiments, the present disclosure provides methods for detecting ketone levels in a subject at risk of developing diabetic ketoacidosis. In certain embodiments, a sensor of the present disclosure can be used to monitor and/or prevent diabetic ketoacidosis. For example, but not by way of limitation, a sensor of the present disclosure includes sensing chemistry for detecting ketones and glucose for monitoring and/or preventing diabetic ketoacidosis in a subject, e.g., a subject with diabetes. Alternatively or additionally, a sensor of the present disclosure can be used in combination with a glucose sensor (or a glucose-responsive active area) to monitor and/or prevent diabetic ketoacidosis. In certain embodiments, a sensor of the present disclosure can be used with an application for monitoring the ketones level in a subject, e.g., for monitoring adherence to a ketogenic diet, for maintaining a state of ketosis and/or monitoring and/or preventing diabetic ketoacidosis. In certain embodiments, ketogenic diets can be beneficial for promoting weight loss as well as helping epileptic individuals manage their condition.

In certain embodiments, the subject is in need of monitoring lactate levels. In certain embodiments, a subject in need of monitoring lactate levels is an athlete, e.g., a professional athlete. In certain embodiments, monitoring lactate levels during an exercise regimen can be used as an indicator of performance. In certain embodiments, monitoring lactate levels can be useful to diagnose, monitor and/or assess sepsis in its various forms and/or related infections. For example, but not by way of limitation, determining a concentration of lactate according to the present disclosure can allow sepsis and/or infections to be more effectively monitored, assessed, and/or managed. Alternately, the analyte sensors of the present disclosure can be utilized to monitor a subject at risk for sepsis and/or infection but who is not presently exhibiting signs of either condition (e.g., a patient in a hospital).

In certain embodiments, methods of the present disclosure include: (i) providing an analyte sensor including: a sensor tail including at least a first working electrode; a first active area disposed upon a surface of the first working electrode and responsive, e.g., at low potential, to the first analyte, the first active area including a first polymer, a first redox mediator covalently bonded to the first polymer, and at least one enzyme responsive to the first analyte covalently bonded to the first polymer, wherein the redox mediator comprises a structure of any one of Formulas I-LV, e.g., has a structure presented by Formulas XLI-LV; and a mass transport limiting membrane permeable to the first analyte that overcoats at least the first active area; (ii) applying a potential, e.g., low potential, to the first working electrode; (iii) obtaining a first signal at or above an oxidation-reduction potential of the first active area, the first signal being proportional to a concentration of a first analyte in a fluid contacting the first active area; and (iv) correlating the first signal to the concentration of the first analyte in the fluid.

In certain embodiments, methods of the present disclosure can include: (i) exposing an analyte sensor to a fluid comprising a first analyte; wherein the analyte sensor comprises: a sensor tail comprising at least a first working electrode; a first active area disposed upon a surface of the first working electrode and responsive, e.g., at low potential, to the first analyte, the first active area comprising a first polymer, a first redox mediator covalently bonded to the first polymer, and at least one enzyme responsive to the first analyte covalently bonded to the first polymer; wherein the first redox mediator comprises a structure of any one of Formulas I-LV, e.g., has a structure presented by Formulas XLI-LV; and a mass transport limiting membrane permeable to the first analyte that overcoats at least the first active area; (ii) applying a potential, e.g., low potential, to the first working electrode; (iii) obtaining a first signal at or above an oxidation-reduction potential of the first active area, the first signal being proportional to a concentration of the first analyte in the fluid; and (iv) correlating the first signal to the concentration of the first analyte in the fluid.

In certain embodiments, the at least one enzyme responsive to the first analyte comprises an enzyme system comprising multiple enzymes that are collectively responsive to the first analyte. In certain embodiments, the first analyte comprises one or more ketones. In certain embodiments, the first analyte is glucose.

In certain embodiments, the analyte sensor for use in the disclosed methods can further include a second working electrode; and a second active area disposed upon a surface of the second working electrode and responsive to a second analyte differing from the first analyte, the second active area comprising a second polymer, a second redox mediator differing from the first redox mediator covalently bonded to the second polymer, and at least one enzyme responsive to the second analyte covalently bonded to the second polymer; wherein a second portion of the mass transport limiting membrane overcoats the second active area. In certain embodiments, at least one enzyme responsive to the second analyte comprises an enzyme system comprising multiple enzymes that are collectively responsive to the second analyte. In certain embodiments, the second analyte comprises glucose.

In certain embodiments, the mass transport limiting membrane of the analyte sensor comprises a membrane polymer crosslinked with a branched crosslinker comprising three or more crosslinkable groups. In certain embodiments, the membrane polymer comprises a polyvinylpyridine or a polyvinylimidazole. In certain embodiments, the membrane polymer comprises a copolymer of vinylpyridine and styrene. In certain embodiments, the branched crosslinker comprises polyethylene glycol diglycidyl ether or polyethylene glycol tetraglycidyl ether.

IV. EXEMPLARY EMBODIMENTS

A. In certain non-limiting embodiments, the presently disclosed subject matter provides for analyte sensors comprising:

(i) a sensor tail comprising at least a first working electrode;

(ii) a first active area disposed upon a surface of the first working electrode and responsive to a first analyte, wherein the first active area comprises a redox mediator and at least one enzyme responsive to the first analyte;

wherein the first redox mediator comprises at least one tridentate ligand selected from the group consisting of Formulas I-XXI, wherein $R_1$ and $R_3$ are independently selected from H, an alkoxy group, an alkyl group, an alkylamido group, an alkylamino or a linking group, wherein $R_2$ is selected from H, an electron donating group or a linking group capable of bonding the redox mediator to a first polymer; and (iii) a mass transport limiting membrane permeable to the first analyte that overcoats at least the first active area.

A1. The analyte sensor of A, wherein the first active area further comprises the first polymer.

A2. The analyte sensor of A1, wherein the redox mediator is covalently bonded to the first polymer, e.g., via the linking group of $R_2$.

A3. The analyte sensor of A1 or A2, wherein the at least one enzyme responsive to the first analyte is covalently bonded to the first polymer.

A4. The analyte sensor of any one of A1-A3, wherein the linking group is capable of bonding the redox mediator to the first polymer.

A5. The analyte sensor of any one of A-A4, wherein the $R_1$ and/or $R_3$ are alkyl groups.

A6. The analyte sensor of A5, wherein the alkyl groups are selected from the group consisting of a methyl group, an ethyl group, a $C_1$-$C_{12}$ straight chain alkyl group and a branched chain alkyl group.

A7. The analyte sensor of any one of A-A4, wherein the $R_1$ and/or $R_3$ are polyether groups.

A8. The analyte sensor of any one of A-A4, wherein the $R_1$ and/or $R_3$ are alkoxy groups, e.g., a methoxy group or an ethoxy group.

A9. The analyte sensor of any one of A-A8, wherein the first redox mediator comprises two tridentate ligands selected from the group consisting of Formulas I-XXI.

A10. The analyte sensor of any one of A-A9, wherein the first redox mediator comprises two tridentate ligands selected from the group consisting of Formulas I-XXI in a complex (e.g., coordination complex) with a metal.

A11. The analyte sensor of A10, wherein the metal is osmium.

A12. The analyte sensor of any one of A-A11, wherein the tridentate ligand is selected from the group consisting of Formulas XXII-XL.

A13. The analyte sensor of any one of A-A12, wherein the first active area comprises from about 10% to about 80% by weight of the first redox mediator.

A14. The analyte sensor of any one of A-A13, wherein the first active area comprises an enzyme system comprising multiple enzymes that are collectively responsive to the first analyte, e.g., glucose oxidase.

A15. The analyte sensor of any one of A-A14, wherein the first analyte comprises glucose.

A16. The analyte sensor of any one of A-A15, wherein the first active area further comprises a stabilizing agent.

A17. The analyte sensor of any one of A-A16, wherein the first active area further comprises a crosslinking agent.

A18. The analyte sensor of any one of A-A17, wherein the first active area further comprises a cofactor.

A19. The analyte sensor of any one of A-A18, wherein the mass transport limiting membrane comprises a polyvinylpyridine-based polymer, a polyvinylimidazole, a polyacrylate, a polyurethane, a polyether urethane, a silicone or a combination thereof.

A20. The analyte sensor of A19, wherein the mass transport limiting membrane comprises a polyvinylpyridine or a polyvinylimidazole.

A21. The analyte sensor of A19, wherein the mass transport limiting membrane comprises a polyvinylpyridine-based polymer.

A22. The analyte sensor of A19, wherein the membrane polymer comprises a copolymer of vinylpyridine and styrene.

A23. The analyte sensor of any one of A-A22, further comprising:

(iv) a second working electrode; and (v) a second active area disposed upon a surface of the second working electrode and responsive to a second analyte differing from the first analyte, wherein the second active area comprises at least one enzyme responsive to the second analyte.

A24. The analyte sensor of A23, wherein a second portion of the mass transport limiting membrane overcoats the second active area.

A25. The analyte sensor of A23, further comprising a second mass transport limiting membrane overcoating the second active area or further comprising a second mass transport limiting membrane overcoating the second active area and the first active area.

A26. The analyte sensor of any one of A23-A25, wherein the second active area further comprises a second redox mediator.

A27. The analyte sensor of any one of A23-A26, wherein the second analyte is a ketone.

A28. The analyte sensor of any one of A-A27, wherein the analyte sensor is configured to detect a first analyte and/or a second analyte in interstitial fluid from a subject.

A29. The analyte sensor of any one of A-A28, wherein the analyte sensor is implanted in a subject that has diabetes.

A30. The analyte sensor of any one of A-A29, wherein the analyte sensor is implanted in a subject that is undergoing or is at risk of undergoing ketoacidosis.

A31. The analyte sensor of any one of A-A28, wherein the analyte sensor is implanted in a subject that is on a ketogenic diet.

A32. The analyte sensor of any one of A-A31, wherein the analyte sensor is implanted in a subject that is in a state of ketosis or is in need of maintaining a state of ketosis.

A33. The analyte sensor of any one of A-A28, wherein the analyte sensor is implanted in a subject in need of lactate monitoring.

B. In certain non-limiting embodiments, the presently disclosed subject matter provides for analyte sensors comprising:

(i) a sensor tail comprising at least a first working electrode;

(ii) a first active area disposed upon a surface of the first working electrode and responsive to a first analyte, wherein the first active area comprises a first redox mediator and at least one enzyme responsive to the first analyte; and (iii) a mass transport limiting membrane permeable to the first analyte that overcoats at least the first active area, wherein the first redox mediator has a structure selected from the group consisting of Formulas I-XXI.

C. In certain non-limiting embodiments, the presently disclosed subject matter provides for analyte sensors comprising:

(i) a sensor tail comprising at least a first working electrode;

(ii) a first active area disposed upon a surface of the first working electrode and responsive to a first analyte, wherein the first active area comprises a first redox mediator and at least one enzyme responsive to the first analyte;

wherein the first redox mediator has a structure of:

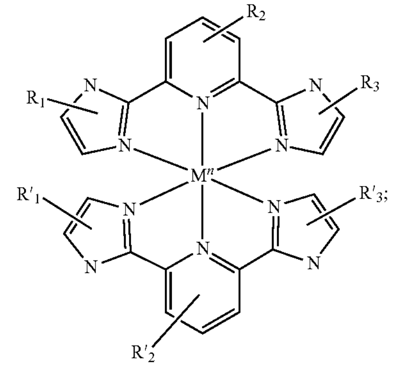

wherein M is iron, ruthenium, osmium, cobalt, or vanadium;

wherein n is I, II, II, IV or V;

wherein $R_1$, $R_3$, $R'_1$, and $R'_3$ are independently selected from H, an alkylamido group, alkylamino group, an alkoxy or an alkyl group;

wherein $R_2$ and $R'_2$ are independently selected from H, an electron donating group or a linking group; and (iii) a mass transport limiting membrane permeable to the first analyte that overcoats at least the first active area.

C1. The analyte sensor of B and C, wherein the first active area further comprises a first polymer.

C2. The analyte sensor of C1, wherein the first redox mediator is covalently bonded to the first polymer.

C3. The analyte sensor of C1 or C2, wherein the at least one enzyme responsive to the first analyte is covalently bonded to the first polymer.

C4. The analyte sensor of any one of C1-C3, wherein the linking group is capable of bonding the first redox mediator to the first polymer.

C5. The analyte sensor of any one of C-C4, wherein the first analyte is glucose.

C6. The analyte sensor of any one of C-C4, wherein the first analyte is a ketone.

D. In certain non-limiting embodiments, the presently disclosed subject matter provides for analyte sensors comprising:

(i) a sensor tail comprising at least a first working electrode;

(ii) a first active area disposed upon a surface of the first working electrode and responsive to a first analyte, wherein the first active area comprises a first polymer, a first redox mediator covalently bonded to the first polymer, and at least one enzyme responsive to the first analyte covalently bonded to the first polymer;

wherein the first redox mediator has a structure of:

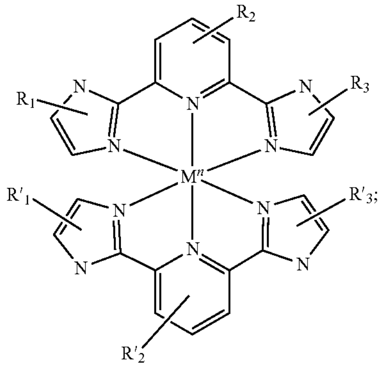

wherein M is iron, ruthenium, osmium, cobalt, or vanadium;

wherein n is I, II, II, IV or V;

wherein $R_1$, $R_3$, $R'_1$, and $R'_3$ are independently selected from H, an alkylamido group, alkylamino group, an alkoxy or an alkyl group;

wherein $R_2$ and $R'_2$ are independently selected from H, an electron donating group or a linking group;

wherein the linking group covalently bonds the first redox mediator to the first polymer; and (iii) a mass transport limiting membrane permeable to the first analyte that overcoats at least the first active area.

D1. The analyte sensor of any one of B-D, wherein the first active area comprises from about 10% to about 80% by weight of the first redox mediator.

D2. The analyte sensor of any one of B-D1, wherein the at least one enzyme comprises an enzyme system comprising multiple enzymes that are collectively responsive to the first analyte.

D3. The analyte sensor of any one of B-D2, wherein the first analyte is glucose.

D4. The analyte sensor of any one of B-D3, wherein the first active area further comprises a stabilizing agent.

D5. The analyte sensor of any one of B-D4, wherein the first active area further comprises a crosslinking agent.

D6. The analyte sensor of any one of B-D5, wherein the first active area further comprises a cofactor.

D7. The analyte sensor of any one of B-D6, wherein the mass transport limiting membrane comprises a polyvinylpyridine-based polymer, a polyvinylimidazole, a polyacrylate, a polyurethane, a polyether urethane, a silicone or a combination thereof.

D8. The analyte sensor of D7, wherein the mass transport limiting membrane comprises a polyvinylpyridine or a polyvinylimidazole.

D9. The analyte sensor of D7, wherein the mass transport limiting membrane comprises a polyvinylpyridine-based polymer.

D10. The analyte sensor of D7, wherein the membrane polymer comprises a copolymer of vinylpyridine and styrene.

D11. The analyte sensor of any one of B-D10, further comprising:

(iv) a second working electrode; and (v) a second active area disposed upon a surface of the second working electrode and responsive to a second analyte differing from the first analyte, wherein the second active area comprises at least one enzyme responsive to the second analyte.

D12. The analyte sensor of D11, wherein a second portion of the mass transport limiting membrane overcoats the second active area.

D13. The analyte sensor of D11, further comprising a second mass transport limiting membrane overcoating the second active area or further comprising a second mass transport limiting membrane overcoating the second active area and the first active area.

D14. The analyte sensor of any one of D11-D13, wherein the second active area further comprises a second redox mediator.

D15. The analyte sensor of any one of D11-D14, wherein the second analyte is a ketone.

D16. The analyte sensor of any one of C-D15, wherein M is Os.

D17. The analyte sensor of any one of C-D16, wherein the first redox mediator has a structure of:

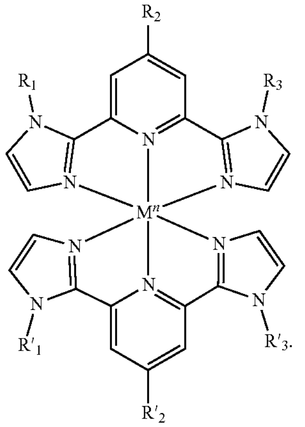

D18. The analyte sensor of any one of C-D17, wherein the first redox mediator has a structure of:

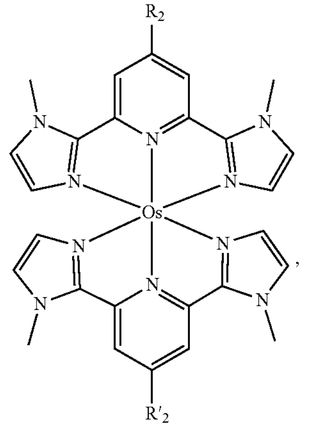

wherein n is II or III.

D19. The analyte sensor of any one of C-D18, wherein the linking group comprises an amide linkage.

D20. The analyte sensor of any one of D-D19, further comprising:

(iv) a second working electrode; and (v) a second active area disposed upon a surface of the second working electrode and responsive to a second analyte differing from the first analyte, wherein the second active area comprising a second polymer, a second redox mediator differing from the first redox mediator covalently bonded to the second polymer, and at least one enzyme responsive to the second analyte covalently bonded to the second polymer;

wherein a second portion of the mass transport limiting membrane overcoats the second active area.

D21. The analyte sensor of D20, wherein the at least one enzyme responsive to the second analyte comprises an enzyme system comprising multiple enzymes that are collectively responsive to the second analyte.

D22. The analyte sensor of D20 or D21, wherein the second analyte comprises one or more ketones.

D23. The analyte sensor of any one of D-D22, wherein the first active area is responsive to the first analyte at a potential above an oxidation-reduction potential of the first redox mediator and below about −80 mV relative to an Ag/AgCl reference.

D24. The analyte sensor of any one of D-D23, wherein the analyte sensor is configured to detect a first analyte and/or a second analyte in interstitial fluid from a subject.

D25. The analyte sensor of any one of D-D24, wherein the analyte sensor is implanted in a subject that has diabetes.

D26. The analyte sensor of any one of D-D25, wherein the analyte sensor is implanted in a subject that is undergoing or is at risk of undergoing ketoacidosis.

D27. The analyte sensor of any one of D-D24, wherein the analyte sensor is implanted in a subject that is on a ketogenic diet.

D28. The analyte sensor of any one of D-D27, wherein the analyte sensor is implanted in a subject that is in a state of ketosis or is in need of maintaining a state of ketosis.

D29. The analyte sensor of any one of D-D24, wherein the analyte sensor is implanted in a subject in need of lactate monitoring.

E. In certain non-limiting embodiments, the presently disclosed subject matter provides methods for detecting a first analyte using an analyte sensor of any one of A-D23.

E1. The method of E, wherein the first analyte is glucose.

E2. The method of E, wherein the first analyte is a ketone.

E3. The method of E, wherein the first analyte is a lactate.

E4. The method of E, wherein the first analyte is an alcohol.

F. In certain non-limiting embodiments, the presently disclosed subject matter provides methods for detecting a first analyte, wherein the method comprises:

(i) providing an analyte sensor comprising:

(a) a sensor tail comprising at least a first working electrode;

(b) a first active area disposed upon a surface of the first working electrode and responsive to the first analyte, wherein the first active area comprises a first polymer, a first redox mediator covalently bonded to the first polymer, and at least one enzyme responsive to the first analyte covalently bonded to the first polymer;

wherein the first redox mediator has a structure of

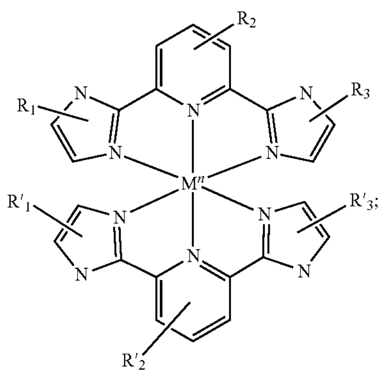

wherein M is iron, ruthenium, osmium, cobalt, or vanadium;

wherein n is I, II, III, IV, or V;

wherein $R_1$, $R_3$, $R'_1$, and $R'_3$ are independently selected from H, an alkylamido group, alkylamino group, an alkoxy or an alkyl group;

wherein $R_2$ and $R'_2$ are independently selected from H, an electron donating group or a linking group;

wherein the linking group covalently bonds the first redox mediator to the first polymer; and (c) a mass transport limiting membrane permeable to the first analyte that overcoats at least the first active area;

(ii) applying a potential to the first working electrode;

(iii) obtaining a first signal at or above an oxidation-reduction potential of the first active area, the first signal being proportional to a concentration of a first analyte in a fluid contacting the first active area; and (iv) correlating the first signal to the concentration of the first analyte in the fluid.

F1. The method of F, wherein the first active area comprises from about 10% to about 80% by weight of the first redox mediator.

F2. The method of F or F1, wherein the at least one enzyme comprises an enzyme system comprising multiple enzymes that are collectively responsive to the first analyte.

F3. The method of any one of F-F2, wherein the first analyte comprises glucose.

F4. The method of any one of F-F3, wherein the first active area further comprises a stabilizing agent.

F5. The method of any one of F-F4, wherein the first active area further comprises a crosslinking agent.

F6. The method of any one of F-F5, wherein the first active area further comprises a cofactor.

F7. The method of any one of F-F6, wherein the mass transport limiting membrane comprises a polyvinylpyridine-based polymer, a polyvinylimidazole, a polyacrylate, a polyurethane, a polyether urethane, a silicone or a combination thereof.

F8. The method of F7, wherein the mass transport limiting membrane comprises a polyvinylpyridine or a polyvinylimidazole.

F9. The method of F7, wherein the mass transport limiting membrane comprises a polyvinylpyridine-based polymer.

F10. The method of F7, wherein the membrane polymer comprises a copolymer of vinylpyridine and styrene.

F11. The method of any one of F-F10, further comprising:

(iv) a second working electrode; and (v) a second active area disposed upon a surface of the second working electrode and responsive to a second analyte differing from the first analyte, wherein the second active area comprises at least one enzyme responsive to the second analyte.

F12. The method of F11, wherein a second portion of the mass transport limiting membrane overcoats the second active area.

F13. The method of F11, further comprising a second mass transport limiting membrane overcoating the second active area or further comprising a second mass transport limiting membrane overcoating the second active area and the first active area.

F14. The method of any one of F11-F13, wherein the second active area further comprises a second redox mediator.

F15. The method of any one of F11-F14, wherein the second analyte is a ketone.

F16. The method of any one of F-F15, wherein the potential is above the oxidation-reduction potential of the first redox mediator and below about −80 mV relative to an Ag/AgCl reference.

F17. The method of any one of F11-F16, wherein the second active area comprises a second polymer, a second redox mediator differing from the first redox mediator covalently bonded to the second polymer, and at least one enzyme responsive to the second analyte covalently bonded to the second polymer.

F18. The method of any one of F-F17, wherein the first redox mediator has a structure of:

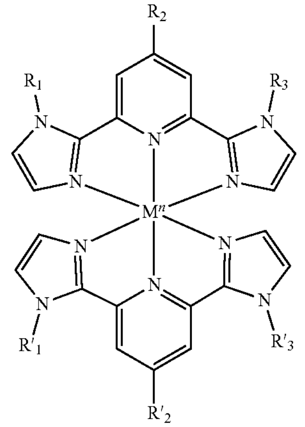

F19. The method of any one of F-F19, wherein the first redox mediator has a structure of:

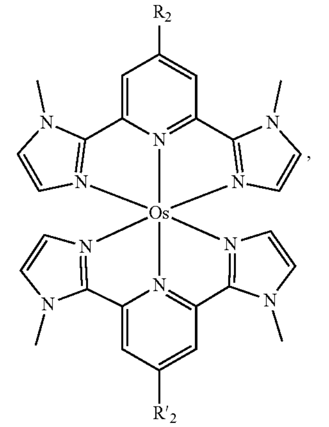

wherein n is II or III.

EXAMPLES

The presently disclosed subject matter will be better understood by reference to the following Examples, which are provided as exemplary of the presently disclosed subject matter, and not by way of limitation.

Example 1: Synthesis of Tridentate Ligands. 2,6-bis(N-methylimidazol-2-yl)-pyridine and 2,6-bis(N-methylimidazol-2-yl)-4-(dimethylamino)-pyridine The present example provides an illustrative method for preparing a tridentate ligand of Formula XXIII (compound (3a)). The ligand can be prepared in three (3) steps as follows:

Scheme Ia

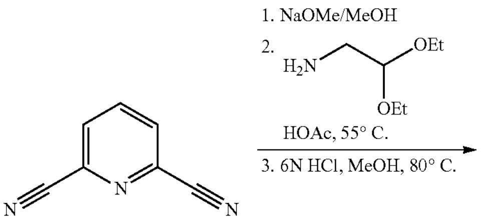

(1a)

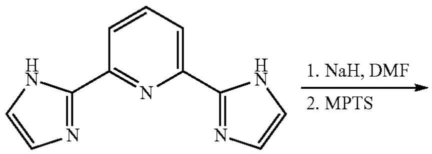

(2a)

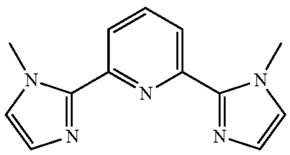

(3a)

To a 2,6-pyridinedicarbonitrile (1a) solution in MeOH, NaOMe/MeOH was added under nitrogen atmosphere and the mixture was stirred for 4 hours at room temperature. Subsequently, 2,2-dimethoxyethanamine and HOAc was added to the reaction mixture. The reaction mixture was then heated in an oil bath to 55° C. for 1 hour and cooled to room temperature. MeOH and 6N HCl (aq) was then sequentially added to the reaction mixture. The reaction flask was fitted with a reflux condenser and the reaction mixture was refluxed overnight at 80° C. The reaction mixture was then allowed to cool to room temperature and the solvent was removed via rotary evaporation. The intermediate product (2a) was isolated by EtOAc/$H_2O$ workup.

The isolated intermediate product (2a) was dissolved in DMF under argon atmosphere. The reaction mixture was then cooled in an ice bath and NaH was added to the reaction mixture slowly, in three portions. After addition of NaH, the reaction mixture was stirred in the ice bath for about an hour. Methyl p-toluenesulfonate (MPTS) was dissolved in DMF and added dropwise to the reaction mixture. The reaction mixture was stirred for 15 minutes before quenching NaH. The product (3a) was isolated by organic $CH_3Cl/H_2O$ work-up.

The present example also provides an illustrative method for preparation of a tridentate ligand of Formula XXV (compound (4b)). The ligand in synthesized in four (4) steps as illustrated by Scheme 1b starting from 4-chloropyridine-2,6-dicarbonitrile (compound (1)):

Scheme Ib

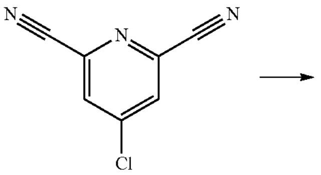

(1b)

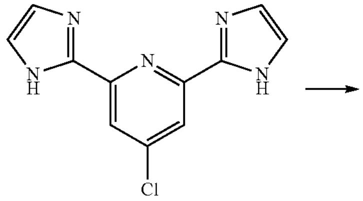

(2b)

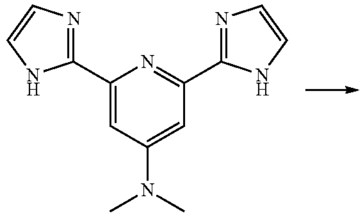

(3b)

-continued

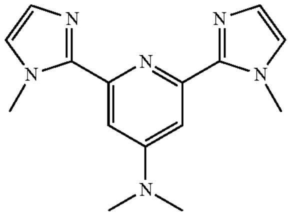

(4b)

To a 4-chloropyridine-2,6-dicarbonitrile solution in MeOH, NaOMe/MeOH was added under nitrogen atmosphere and the mixture was stirred for 4 hours at room temperature. Subsequently, 2,2-dimethoxyethanamine and HOAc was added to the reaction mixture. The reaction mixture was then heated in an oil bath to 55° C. for 1 hour and cooled to room temperature. MeOH and 6N HCl (aq) was then sequentially added to the reaction mixture. The reaction flask was fitted with a reflux condenser and the reaction mixture was refluxed overnight at 80° C. The reaction mixture was then allowed to cool to room temperature and the solvent was removed via rotary evaporation. The intermediate product (2b) was isolated by EtOAc/$H_2O$ workup.

The intermediate product (2b) was then dissolved in DMF, and dimethylamine hydrochloride and DMF/$K_2CO_3$ were added to the reaction mixture. The reaction mixture was placed in a pressure reaction at 110-120° C. for 5 days. After this time and a work-up, the intermediate product (3b) was isolated.

Methylation of the intermediate product (3b) was carried similarly, as described above. Specifically, NaH in mineral oil (2.2 eq) was slowly added to a solution of compound (3b) in DMF under argon and subsequently methyl p-toluenesulfonate (MPTS, 2.2 eq) was added. The reaction mixture was stirred in an ice bath for three days. The reaction mixture was then worked-up to produce ligand (4b).

Example 2: Synthesis of Tridentate 2,6-bis(N-methylimidazol-2-yl)-pyridine Ligand with an Ethylene Diamine Linking Group The present example provides an illustrative method for preparing a tridentate ligand of Formula XXIV (compound (7)) starting from compound (5), as shown by Scheme II:

Scheme II

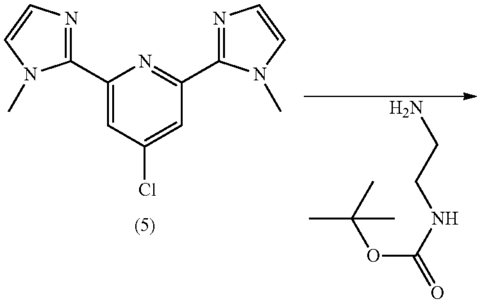

(5)

-continued

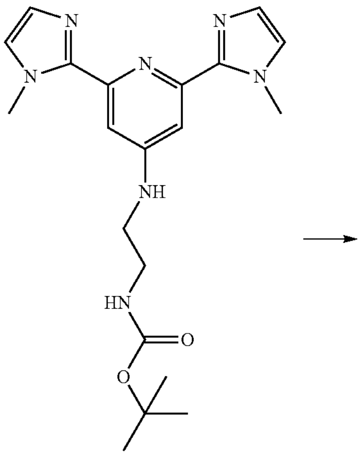

(6)

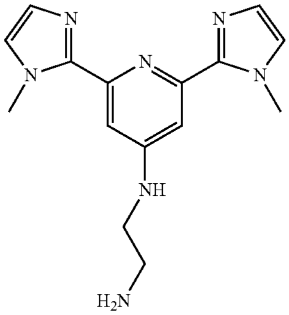

(7)

The present example further provides an illustrative method for preparing a tridentate ligand of Formula XXVIII (compound (11)) starting from compound (8), as shown by Scheme III:

Scheme III

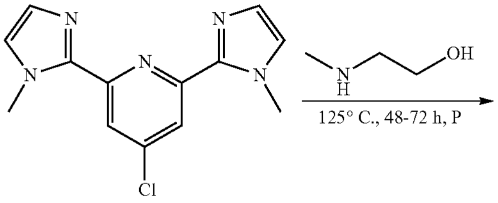

(8)

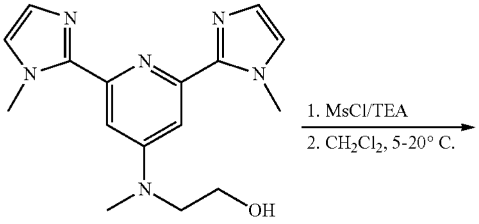

(9)

-continued

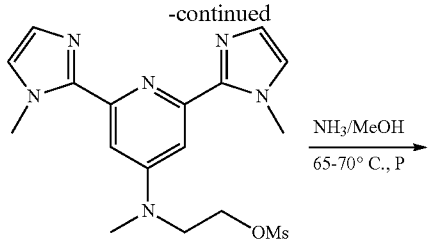

(10)

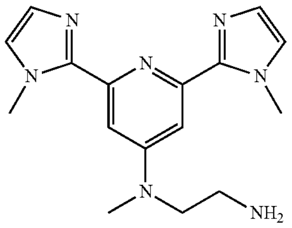

(11)

To 4-chloro-2,6-bis(1-methyl-1H-imidazol-2-yl)pyridine (8) a neat solution of 2-(methylamino)ethan-1-ol was added and the reaction mixture was heated at 125° C. for 48-72 hours in a pressure flask. The resulting product (9) was mesylated using mesyl chloride and triethylamine. The mesylated intermediate (10) was then treated with methanolic ammonia at temperature of 65-70° C. in a pressure flask to obtain ligand (11) (2-((2,6-bis(1-methyl-1H-imidazol-2-yl)pyridin-4-yl)(methyl)amino)ethyl methanesulfonate), which was purified by column chromatography.

Example 3: Synthesis of a Polymeric Tridentate Redox Mediator

The present example provides an illustrative method of generating an exemplary redox mediator of Formula XLV (compound (7)) from tridentate ligands of Formulas XXV and XXIV. The compound is synthesized as shown in Scheme IV using ammonium hexachloroosmate ($(NH_4)_2OsCl_6$), and compounds (4) and (6) (which are denoted as compounds (4a) and (7), respectively, above):

Scheme IV

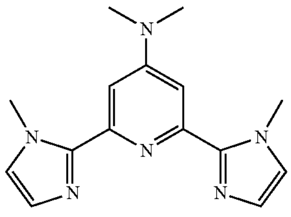

(4)

+

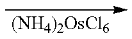

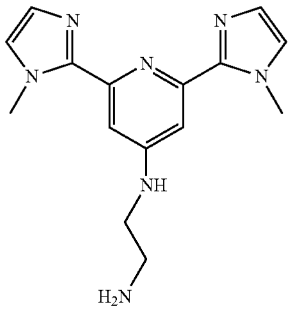

(6)

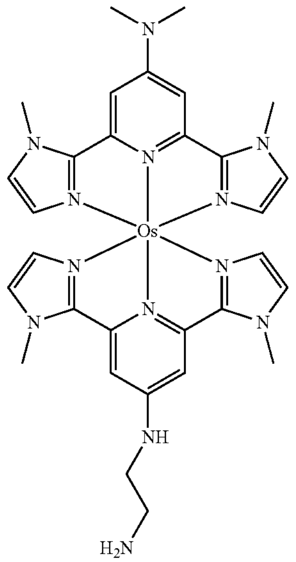

(7)

Compounds (4) and (6) were added sequentially to $(NH_4)_2OsCl_6$ to achieve selectivity for the redox mediator of Formula XLV. Preparative HPLC was performed to isolate the redox mediator of Formula XLV from complexes that included two of the same ligands.

The redox mediator (compound (7)) was further covalently bonded to a polymer via the $NH_2$ group of the linking group. Particularly, as shown in Scheme V, the redox mediator (7) is bonded to polyvinyl pyridine (PVP) though a reaction of the $NH_2$ group of the linking group and COOH group of poly(4-vinyl)pyridine derivatized with bromohexanoic acid (PVP-COOH), which forms an amide bond.

Scheme V

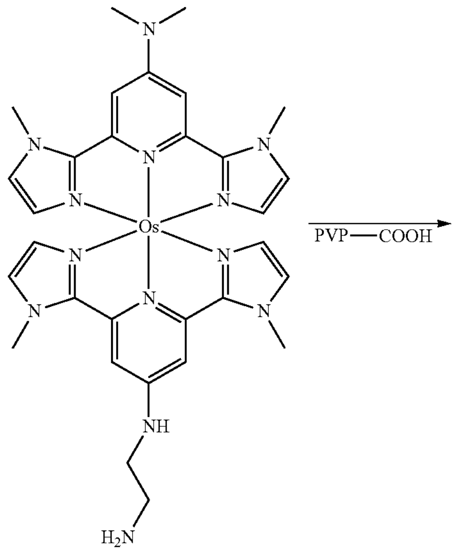

(7)

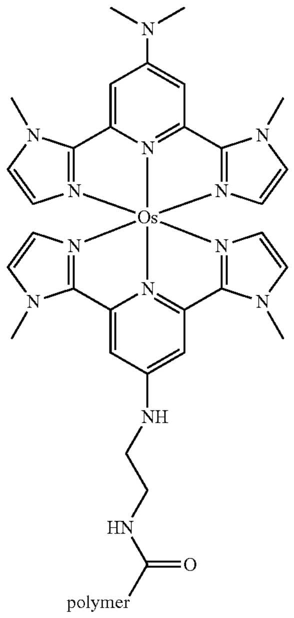

(8)

Example 4: Analysis of Redox Mediators

Figure 29A:
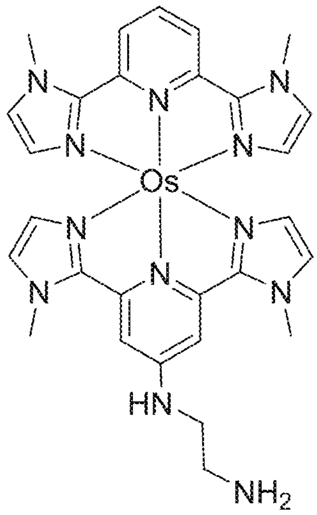
FIG. 29A provides the chemical structure of an exemplary redox mediator of the present disclosure in free form.
Figure 29B:
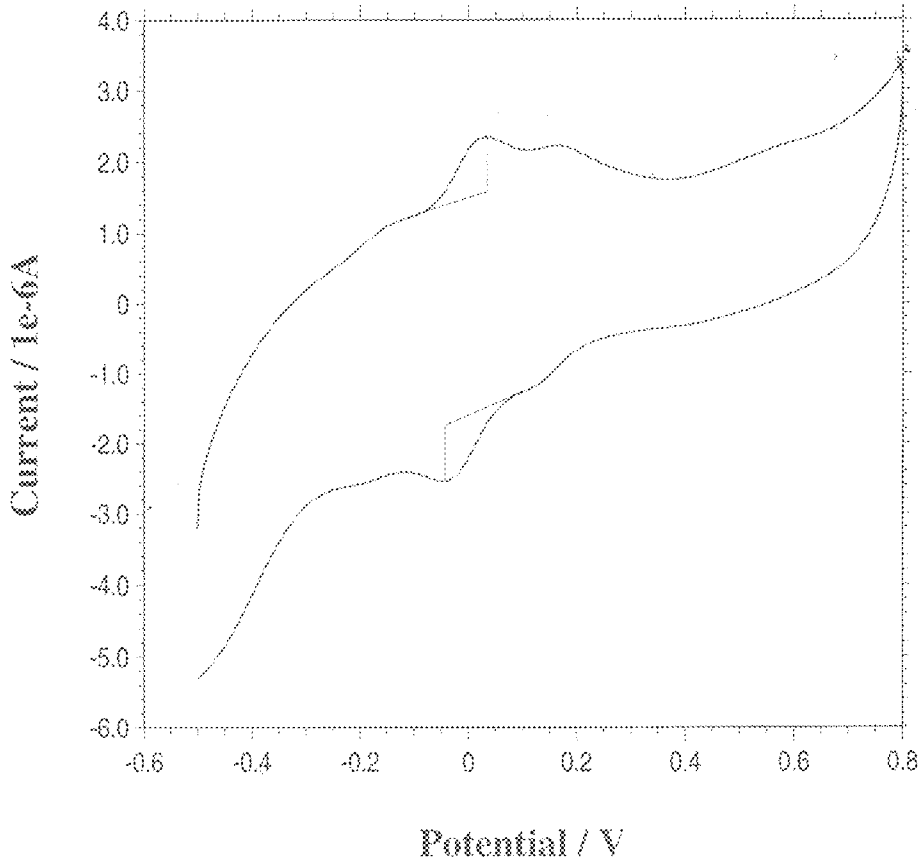
FIG. 29B shows a cyclic voltammogram for the exemplary redox mediator of FIG. 29A.
Figure 30:
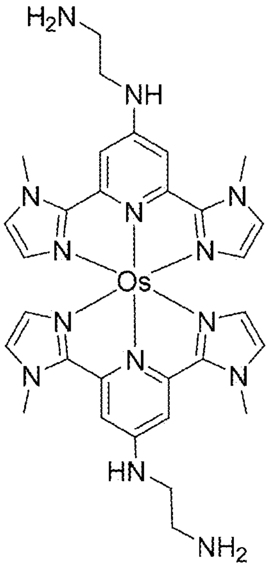
FIG. 30 provides the chemical structure of an exemplary redox mediator of the present disclosure in free form.

The present example provides the cyclic voltammetry of exemplary redox mediators. FIGS. 23A, 24A, 25A, 26A, 27A, 28A, 29A, and 31A provide the chemical structures of the exemplary redox mediators analyzed. FIGS. 23B, 24B, 25B, 26B, 27B, 28B, 29B, and 31B provide cyclic voltammograms of the analyzed redox mediators. Generally, the cyclic voltammetry method was performed as follows: Unit: CH Instruments; working electrode: glassy carbon; counter electrode graphite; reference electrode: Ag/AgCl; scan rate: 0.1 V/s; samples dissolved in PBS buffer. FIG. 25B was run at a scan rate of 0.2 V/s. FIGS. 26B and 29B are crude mixtures which contain the stated compound (heterocomplex) in each case but also contain both homocomplexes.

Figure 31A:
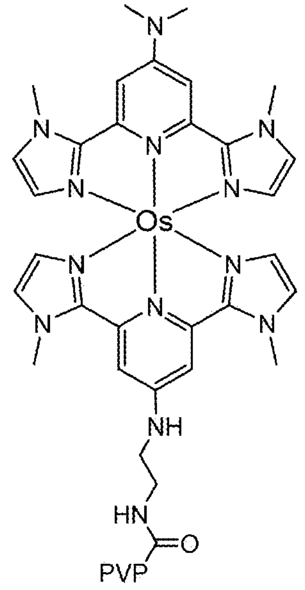
FIG. 31A provides the chemical structure of an exemplary redox mediator of the present disclosure covalently bound to a polymer.
Figure 31B:
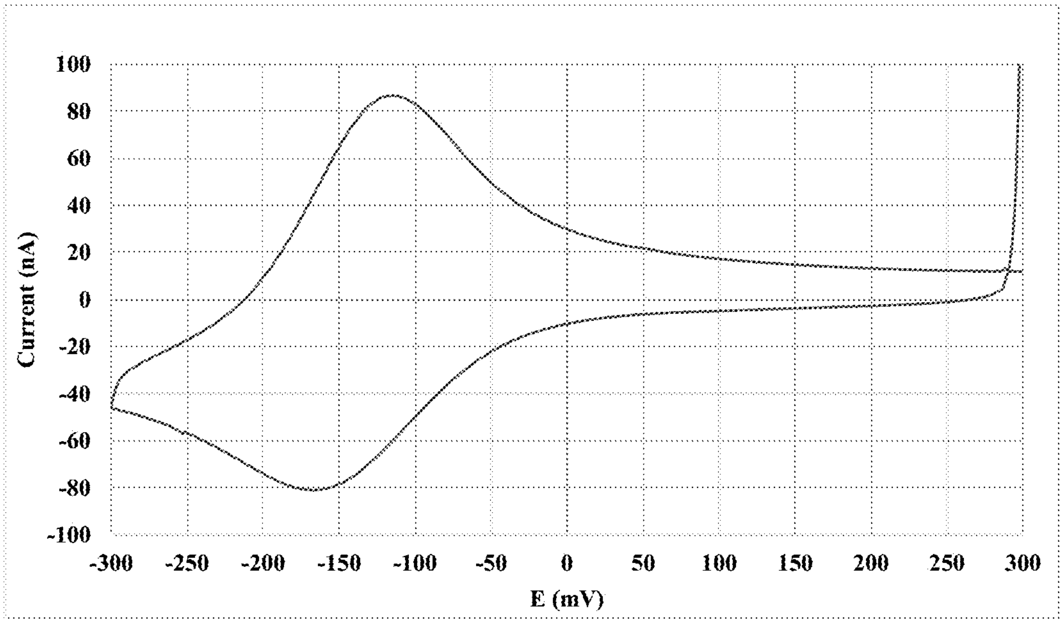
FIG. 31B shows a cyclic voltammogram for the exemplary redox mediator of FIG. 31A.

FIG. 31B shows a cyclic voltammogram of a complete sensor made with the complex in FIG. 31A.

Example 5: Detection of Glucose in Low $O_2$ Conditions

The present example provides the analysis of sensors configured for detecting glucose and include redox mediators of the present disclosure.

Figure 25A:
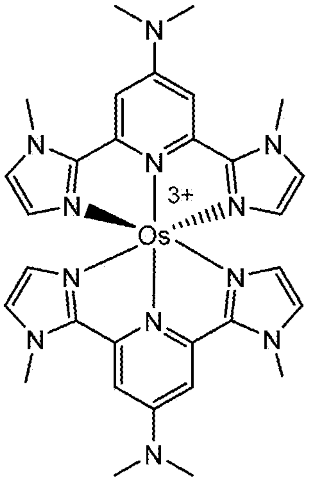
FIG. 25A provides the chemical structure of an exemplary redox mediator of the present disclosure in free form.
Figure 25B:
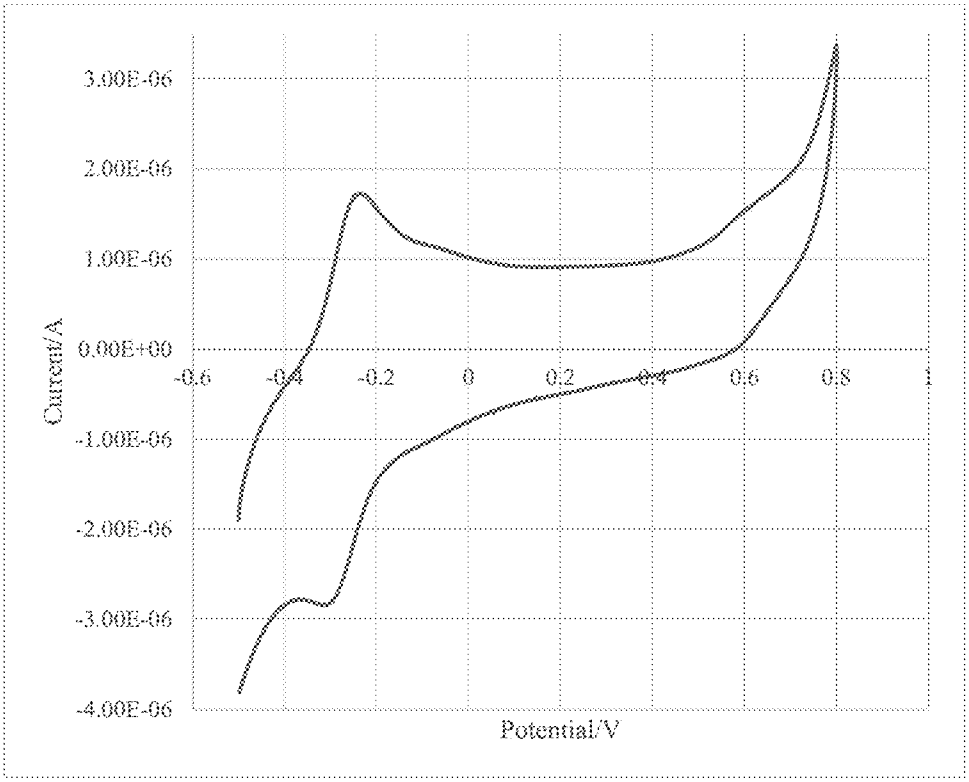
FIG. 25B shows a cyclic voltammogram for the exemplary redox mediator of FIG. 25A.
Figure 26A:
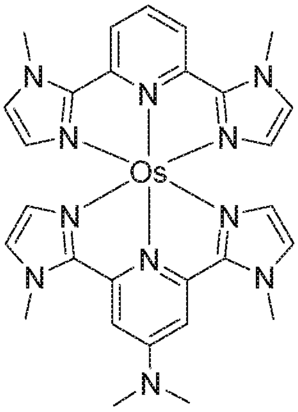
FIG. 26A provides the chemical structure of an exemplary redox mediator of the present disclosure in free form.
Figure 26B:
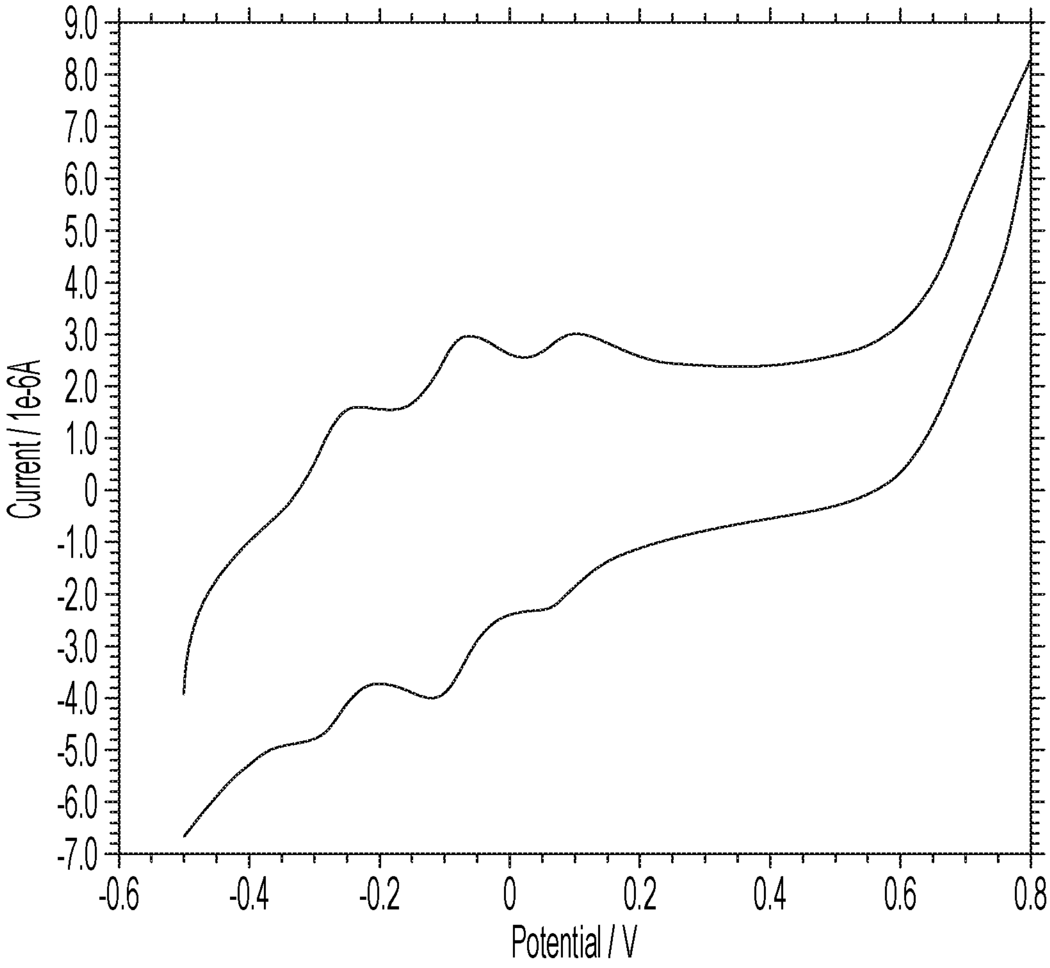
FIG. 26B shows a cyclic voltammogram for the exemplary redox mediator of FIG. 26A.
Figure 27A:
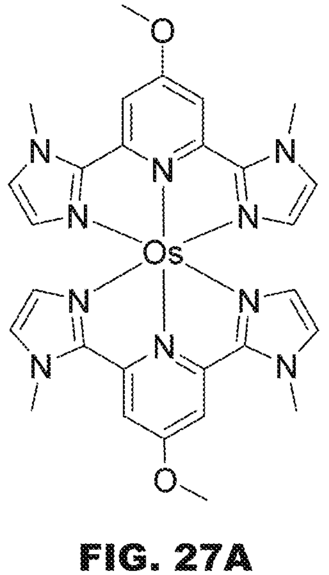
FIG. 27A provides the chemical structure of an exemplary redox mediator of the present disclosure in free form.
Figure 27B:
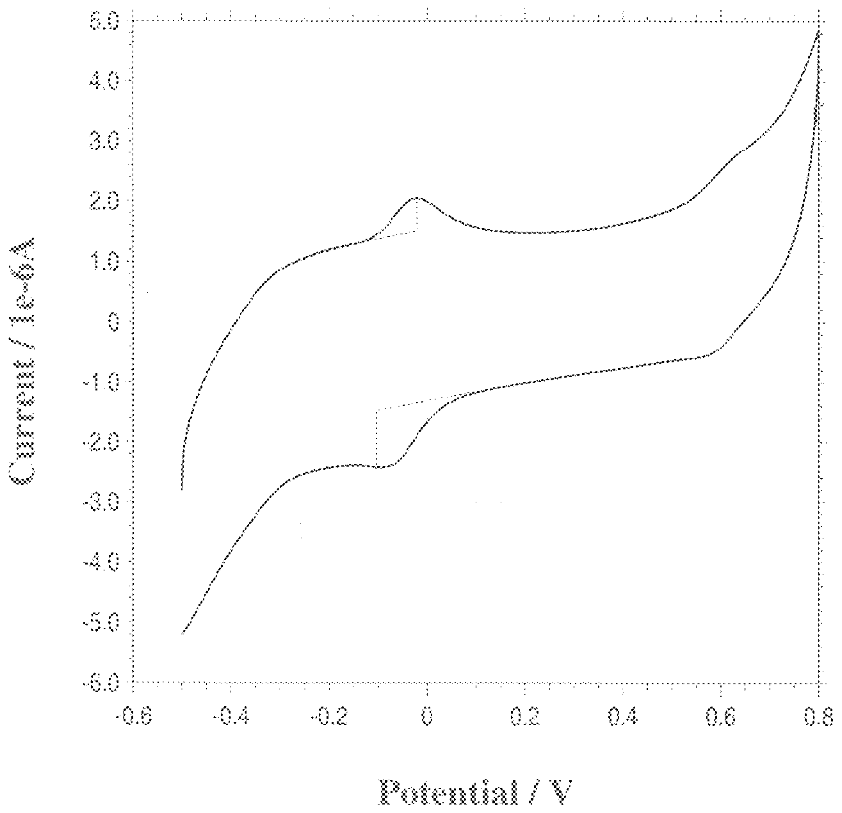
FIG. 27B shows a cyclic voltammogram for the exemplary redox mediator of FIG. 27A.
Figure 28A:
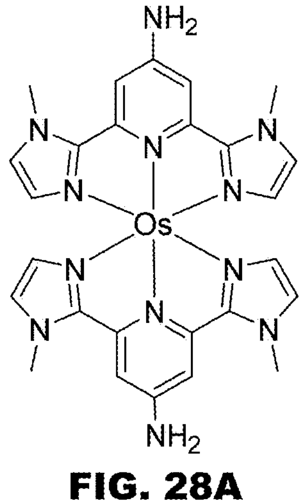
FIG. 28A provides the chemical structure of an exemplary redox mediator of the present disclosure in free form.
Figure 28B:
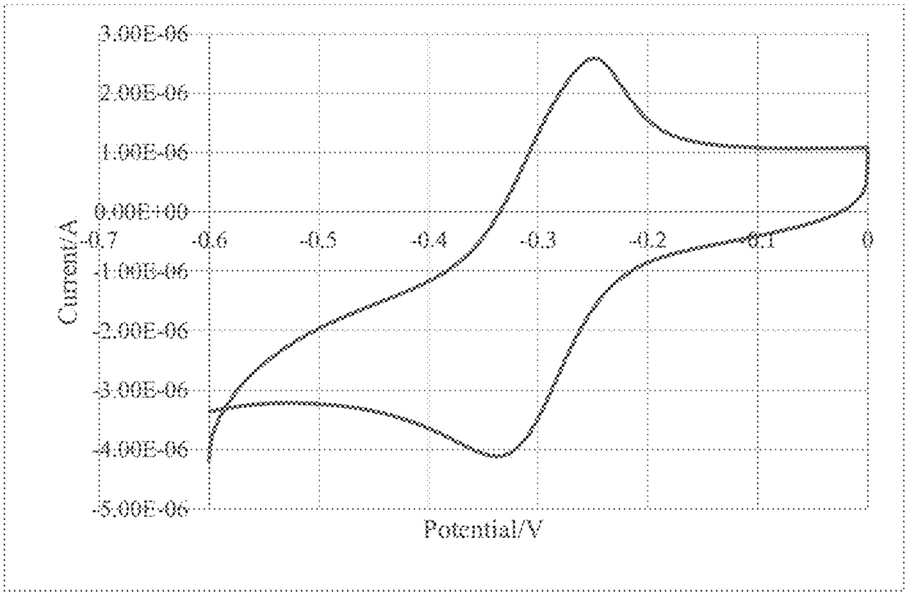
FIG. 28B shows a cyclic voltammogram for the exemplary redox mediator of FIG. 28A.
Figure 32A:
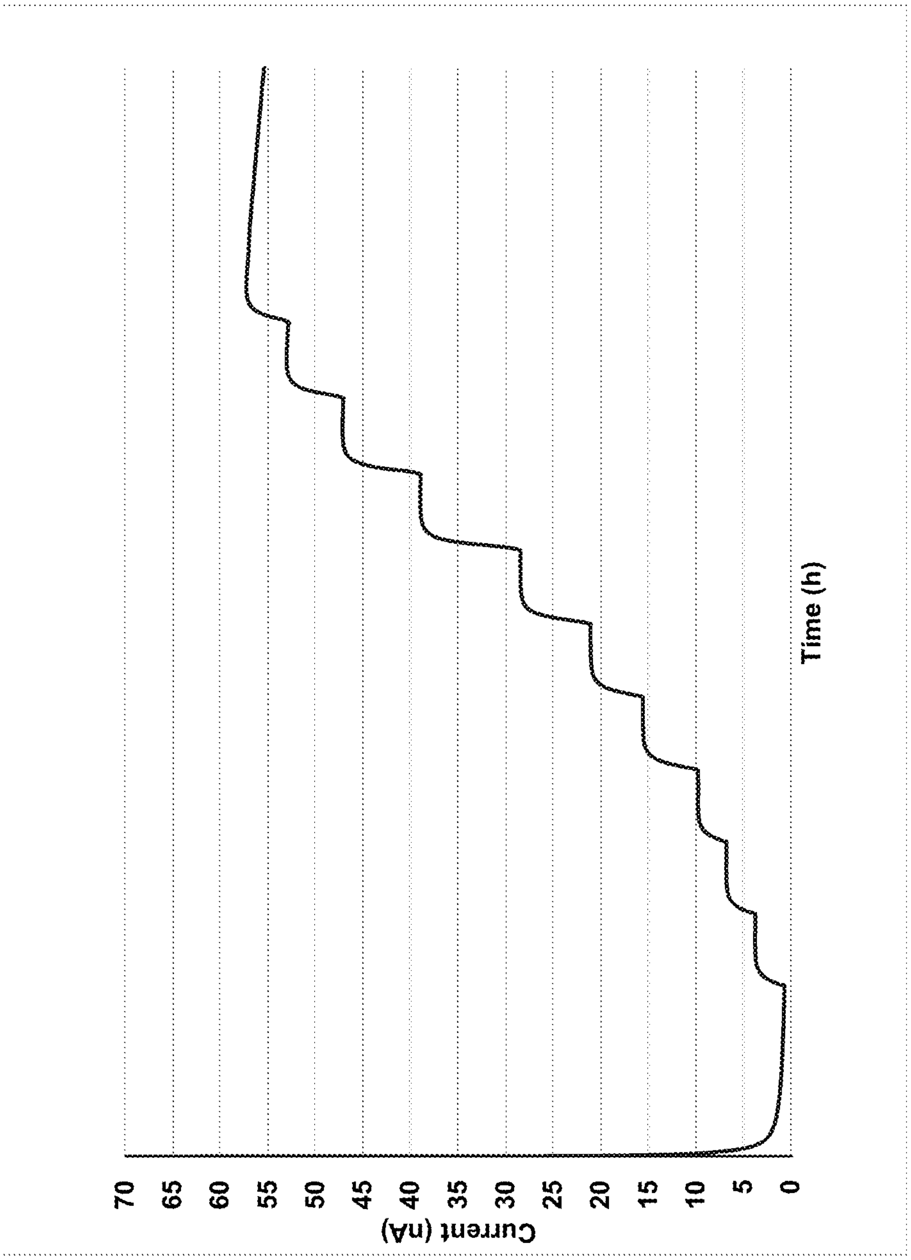
FIG. 32A shows a plot of current versus time at various working electrode potentials for a glucose sensor incorporating the exemplary redox mediator of FIG. 25A.
Figure 32B:
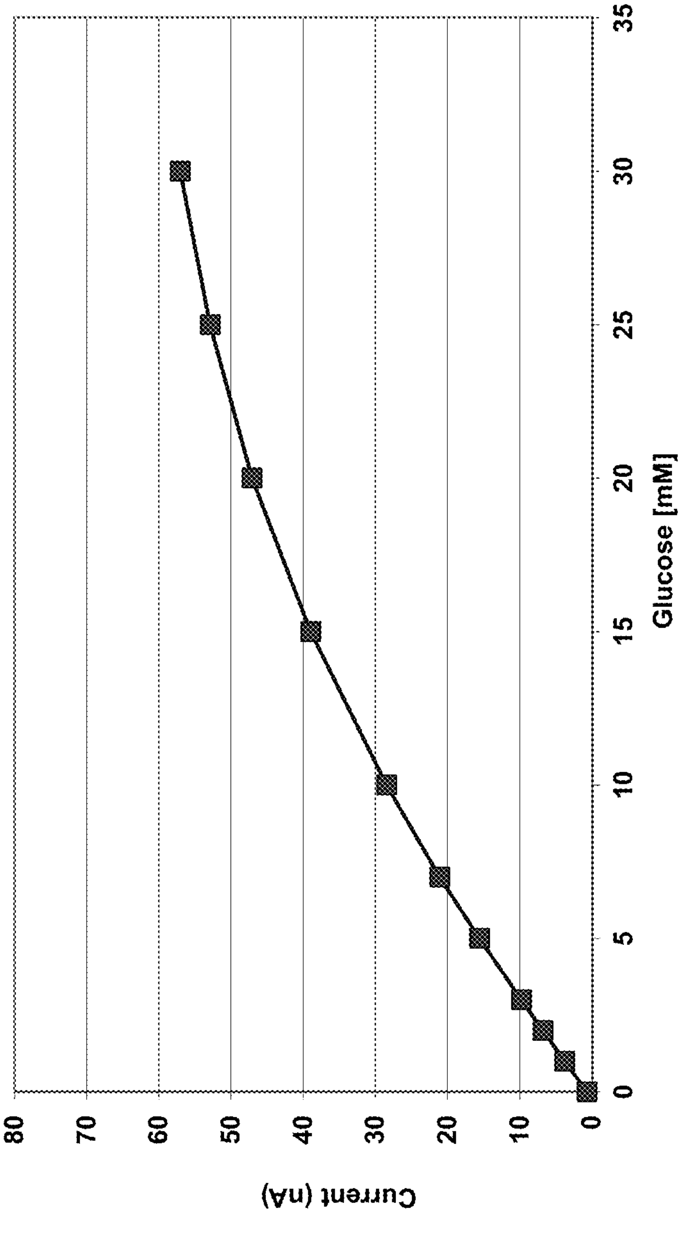
FIG. 32B shows a plot of current versus glucose at various working electrode potentials for a glucose sensor incorporating the exemplary redox mediator of FIG. 25A.

FIG. 32A shows a plot of current versus time for a glucose sensor incorporating the redox mediator shown in FIG. 25A under low oxygen conditions. FIG. 32B shows a plot of current versus glucose for a glucose sensor incorporating the redox mediator shown in FIG. 25A under low oxygen conditions. The redox mediator of FIG. 25A is in free form and not covalently bound to a polymer.

Figure 33A:
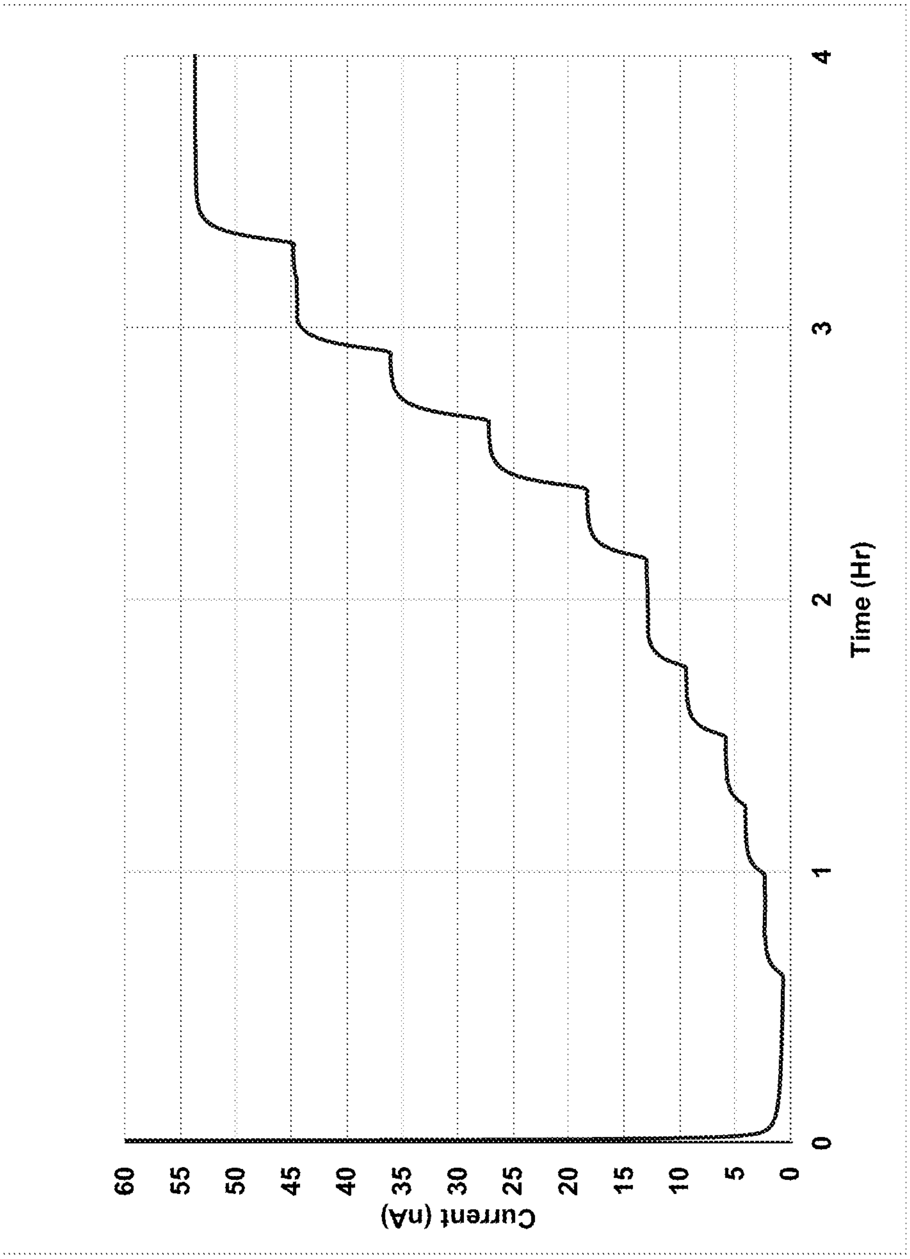
FIG. 33A shows a plot of current versus time at various working electrode potentials for a glucose sensor incorporating the exemplary redox mediator of FIG. 31A.
Figure 33B:
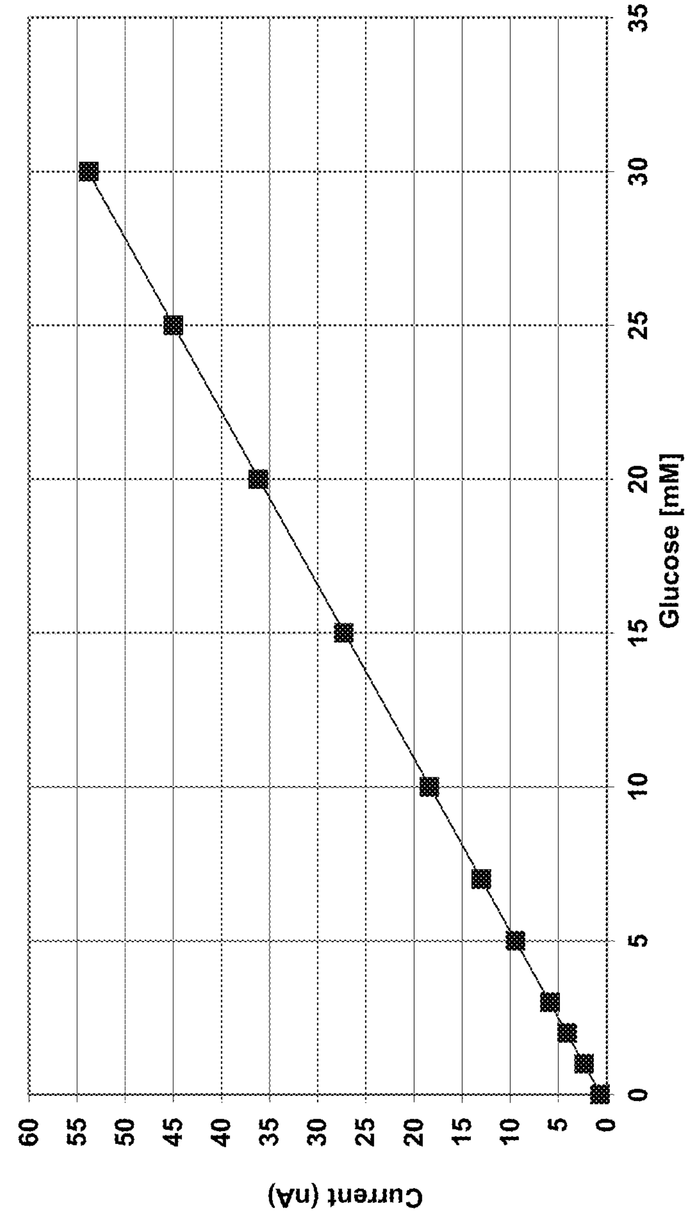
FIG. 33B shows a plot of current versus glucose at various working electrode potentials for a glucose sensor incorporating the exemplary redox mediator of FIG. 31A.

FIG. 33A shows a plot of current versus time for a glucose sensor incorporating the redox mediator shown in FIG. 31A under low oxygen conditions. FIG. 33B shows a plot of current versus glucose for a glucose sensor incorporating the redox mediator shown in FIG. 31A under low oxygen conditions. As shown in FIG. 31A, the redox mediator is covalently bound to the polymer PVP.

In FIGS. 32A-B and 33A-B, sensors were constructed with a sensing layer containing the redox mediators of 25A or 31A, respectively, as the redox mediating component, coated with a membrane layer, and tested in PBS solution in a temperature-controlled beaker under low oxygen conditions. Stepwise increases in current on FIGS. 32A and 33A correspond to addition of glucose in controlled dosages. Linearity of glucose response can be assessed in FIGS. 32B and 33B. Nonlinearity observed in FIG. 32B is likely due to unbound mediator, and is not observed when the mediator is linked to the polymer in FIG. 33B.

Although the presently disclosed subject matter and its advantages have been described in detail, it should be understood that various changes, substitutions and alterations can be made herein without departing from the spirit and scope of the disclosed subject matter. Moreover, the scope of the present application is not intended to be limited to the particular embodiments of the process, machine, manufacture, and composition of matter, methods and processes described in the specification.

As one of ordinary skill in the art will readily appreciate from the disclosed subject matter of the presently disclosed subject matter, processes, machines, manufacture, compositions of matter, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, methods, or steps.

Various patents, patent applications, publications, product descriptions, and protocols are cited throughout this application, the inventions of which are incorporated herein by reference in their entireties for all purposes.

What is claimed is:

1. An analyte sensor comprising:

(i) a distal end comprising at least a first working electrode;

(ii) a first active area disposed upon a surface of the first working electrode and responsive to a first analyte, wherein the first active area comprises a first polymer, a first redox mediator covalently bonded to the first polymer, and at least one enzyme responsive to the first analyte;

wherein the first redox mediator has a structure of:

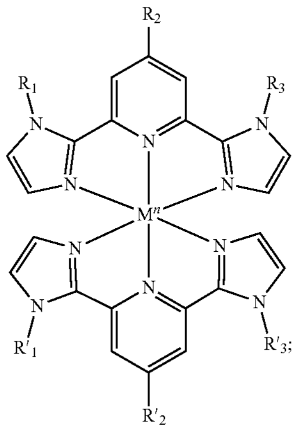

wherein M is iron, ruthenium, osmium, cobalt, or vanadium;

wherein n is I, II, III, IV or V;

wherein $R_1$, $R_3$, $R'_1$, and $R'_3$ are each independently a $C_1$-$C_{12}$ straight or branched chain alkyl group;

wherein $R_2$ is selected from the group consisting of H and an electron donating group;

wherein R'2 is a linking group that covalently bonds the first redox mediator to the first polymer; and (iii) a mass transport limiting membrane permeable to the first analyte that overcoats at least the first active area.

2. The analyte sensor of claim 1, wherein the at least one enzyme comprises an enzyme system comprising multiple enzymes that are collectively responsive to the first analyte.

3. The analyte sensor of claim 1, wherein the first analyte comprises glucose.

4. The analyte sensor of claim 1, wherein the mass transport limiting membrane comprises a membrane polymer crosslinked with a branched crosslinker comprising two or more crosslinkable groups.

5. The analyte sensor of claim 4, wherein the branched crosslinker comprises polyethylene glycol diglycidyl ether or polyethylene glycol tetraglycidyl ether.

6. The analyte sensor of claim 1, wherein the mass transport limiting membrane comprises a polyvinylpyridine-based polymer, a polyvinylimidazole, a polyacrylate, a polyurethane, a polyether urethane, a silicone or a combination thereof.

7. The analyte sensor of claim 1, wherein the first active area further comprises (i) a cofactor, (ii) a stabilizing agent or (iii) a cofactor and a stabilizing agent.

8. The analyte sensor of claim 1, wherein M is osmium.

9. The analyte sensor of claim 1, wherein the first redox mediator has a structure of:

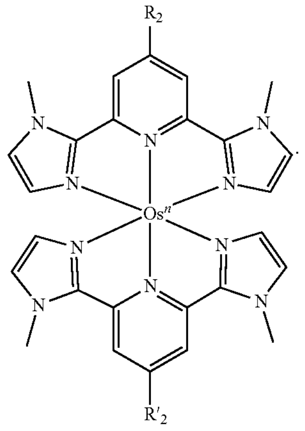

10. The analyte sensor of claim 1, wherein the linking group comprises an amide linkage.

11. The analyte sensor of claim 1, further comprising:

(iv) a second working electrode; and (v) a second active area disposed upon a surface of the second working electrode and responsive to a second analyte differing from the first analyte, wherein the second active area comprises a second polymer, a second redox mediator covalently bonded to the second polymer, and at least one enzyme responsive to the second analyte;

wherein a second portion of the mass transport limiting membrane overcoats the second active area.

12. The analyte sensor of claim 11, wherein the at least one enzyme responsive to the second analyte comprises an enzyme system comprising multiple enzymes that are collectively responsive to the second analyte.

13. The analyte sensor of claim 11, wherein the second analyte comprises one or more ketones.

14. The analyte sensor of claim 11, wherein the second redox mediator differs from the first redox mediator.

15. The analyte sensor of claim 1, wherein the first active area is responsive to the first analyte at a potential above an oxidation-reduction potential of the first redox mediator and below about-80 mV relative to an Ag/AgCl reference.

16. The analyte sensor of claim 1, wherein the mass transport limiting membrane comprises a polyvinylpyridine-based polymer.

17. A method comprising:

(i) providing an analyte sensor comprising:

(a) a distal end comprising at least a first working electrode;

(b) a first active area disposed upon a surface of the first working electrode and responsive to the first analyte, wherein the first active area comprises a first polymer, a first redox mediator covalently bonded to the first polymer, and at least one enzyme responsive to the first analyte;

wherein the first redox mediator has a structure of

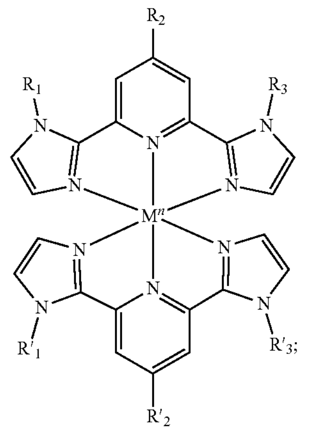

wherein M is iron, ruthenium, osmium, cobalt, or vanadium;

wherein n is I, II, III, IV, or V;

wherein $R_1$, $R_3$, $R'_1$, and $R'_3$ are each independently a $C_1$-$C_{12}$ straight or branched chain alkyl group;

wherein $R_2$ is selected from the group consisting of H and an electron donating group;

wherein R'2 is a linking group that covalently bonds the first redox mediator to the first polymer; and (c) a mass transport limiting membrane permeable to the first analyte that overcoats at least the first active area;

(ii) applying a potential to the first working electrode;

(iii) obtaining a first signal at or above an oxidation-reduction potential of the first active area, the first signal being proportional to a concentration of a first analyte in a fluid contacting the first active area; and (iv) correlating the first signal to the concentration of the first analyte in the fluid.

18. The method of claim 17, wherein the at least one enzyme comprises an enzyme system comprising multiple enzymes that are collectively responsive to the first analyte.

19. The method of claim 17, wherein the first analyte comprises glucose.

20. The method of claim 17, wherein the mass transport limiting membrane comprises a membrane polymer crosslinked with a branched crosslinker comprising two or more crosslinkable groups.

21. The method of claim 20, wherein the branched crosslinker comprises polyethylene glycol diglycidyl ether or polyethylene glycol tetraglycidyl ether.

22. The method of claim 17, wherein the mass transport limiting membrane comprises a polyvinylpyridine-based polymer, a polyvinylimidazole, a polyacrylate, a polyurethane, a polyether urethane, a silicone or a combination thereof.

23. The method of claim 17, wherein first active area further comprises (i) a cofactor, (ii) a stabilizing agent or (iii) a cofactor and a stabilizing agent.

24. The method of claim 17, wherein the potential is above the oxidation-reduction potential of the first redox mediator and below about-80 mV relative to an Ag/AgCl reference.

25. The method of claim 17, wherein the analyte sensor further comprises:

(d) a second working electrode; and (e) a second active area disposed upon a surface of the second working electrode and responsive to a second analyte differing from the first analyte, wherein the second active area comprises a second polymer, a second redox mediator covalently bonded to the second polymer, and at least one enzyme responsive to the second analyte;

wherein a second portion of the mass transport limiting membrane overcoats the second active area.

26. The method of claim 25, wherein the at least one enzyme responsive to the second analyte comprises an enzyme system comprising multiple enzymes that are collectively responsive to the second analyte.

27. The method of claim 25, wherein the second analyte comprises one or more ketones.

28. The method of claim 25, wherein the second redox mediator differs from the first redox mediator.

29. The method of claim 17, wherein the first redox mediator has a structure of:

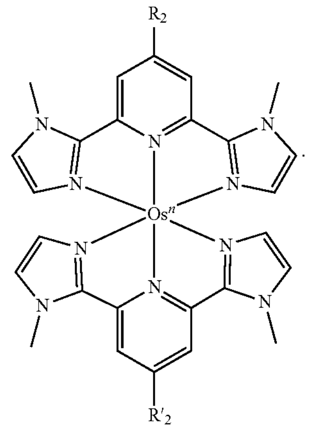

30. The method of claim 17, wherein the mass transport limiting membrane comprises a polyvinylpyridine-based polymer.

31. An analyte sensor comprising:

(i) a distal end comprising at least a first working electrode;

(ii) a first active area disposed upon a surface of the first working electrode and responsive to a first analyte, wherein the first active area comprises a first polymer, a first redox mediator covalently bonded to the first polymer, and at least one enzyme responsive to the first analyte;

wherein the first redox mediator has a structure of:

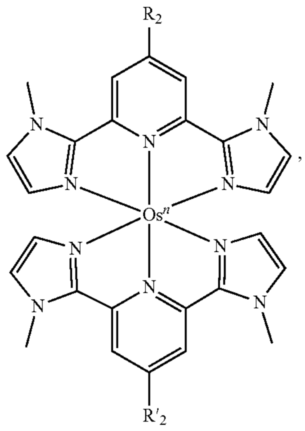

wherein n is I, II, III, IV or V;

wherein $R_2$ is selected from the group consisting of H and an electron donating group;

wherein $R'_2$ is a linking group that covalently bonds the first redox mediator to the first polymer; and (iii) a mass transport limiting membrane permeable to the first analyte that overcoats at least the first active area.

32. The analyte sensor of claim 31, wherein the redox mediator has a structure of:

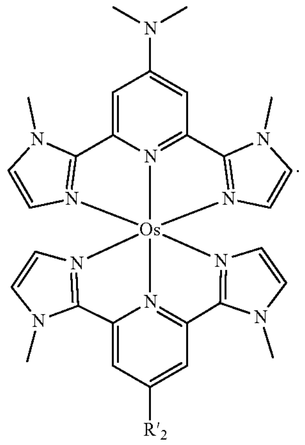

33. A method comprising:

(i) providing the analyte sensor of claim 32;

(ii) applying a potential to the first working electrode;

(iii) obtaining a first signal at or above an oxidation-reduction potential of the first active area, the first signal being proportional to a concentration of a first analyte in a fluid contacting the first active area; and (iv) correlating the first signal to the concentration of the first analyte in the fluid.

34. A method comprising:

(i) providing the analyte sensor of claim 31;

(ii) applying a potential to the first working electrode;

(iii) obtaining a first signal at or above an oxidation-reduction potential of the first active area, the first signal being proportional to a concentration of a first analyte in a fluid contacting the first active area; and (iv) correlating the first signal to the concentration of the first analyte in the fluid.

* * * * *